(12) United States Patent
Messinger et al.

(10) Patent No.: US 8,088,758 B2
(45) Date of Patent: Jan. 3, 2012

(54) 17β-HYDROXYSTEROID DEHYDROGENASE TYPE I INHIBITORS

(75) Inventors: Josef Messinger, Sehnde (DE); Heinrich-Hubert Thole, Hannover (DE); Bettina Husen, Hannover (DE); Bartholomeus Johannes Van Steen, Utrecht (NL); Gyula Schneider, Szeged (HU); Johannes Bernardus Everardus Hulshof, VH Eelde (NL); Pasi Koskimies, Turku (FI); Nina Johansson, Turku (FI); Jerzy Adamski, Munich, DE (US)

(73) Assignee: Abbott Products GmbH, Hannover (DE)

( * ) Notice: Subject to any disclaimer, the term of this patent is extended or adjusted under 35 U.S.C. 154(b) by 1207 days.

(21) Appl. No.: 10/983,887

(22) Filed: Nov. 9, 2004

(65) Prior Publication Data
US 2005/0192263 A1    Sep. 1, 2005

Related U.S. Application Data

(60) Provisional application No. 60/518,847, filed on Nov. 12, 2003, provisional application No. 60/621,644, filed on Oct. 26, 2004.

(30) Foreign Application Priority Data

Nov. 12, 2003  (EP) ..................................... 03104169

(51) Int. Cl.
*A61K 31/58* (2006.01)
*C07J 1/00* (2006.01)
*C07J 43/00* (2006.01)

(52) U.S. Cl. ......... 514/176; 514/178; 540/107; 552/626
(58) Field of Classification Search .................. 552/626; 540/107; 514/176
See application file for complete search history.

(56) References Cited

U.S. PATENT DOCUMENTS

| | | | | |
|---|---|---|---|---|
| 3,125,495 | A * | 3/1964 | Laskin et al. ................... | 435/54 |
| 7,153,844 | B2 * | 12/2006 | Berube ......................... | 514/176 |
| 2003/0170292 | A1 | 9/2003 | Yong et al. | |

FOREIGN PATENT DOCUMENTS

| | | | |
|---|---|---|---|
| EP | 0 367 576 A2 | | 5/1990 |
| WO | WO 97/11162 | * | 3/1997 |
| WO | WO 00/07996 | | 2/2000 |
| WO | WO 03/017973 A1 | | 3/2003 |
| WO | WO 2004/080271 A2 | | 9/2004 |
| WO | WO 2004/085345 A2 | | 10/2004 |
| WO | WO 2004/085457 A2 | | 10/2004 |

OTHER PUBLICATIONS

B. Koffman, et al., "Evidence for Involvement of Tyronsine in Estradiol Binding by Rat Uterus Estrogen Receptor", J. Steroid Biochem. Molec. Biol., 1991, pp. 135-139, vol. 38, No. 2, Pergamon Press PLC, Great Britain.
Fernand Labrie, et al., "The Key Role of 17B-Hydroxysteroid Dehydrongenases in Sex Steroid Biology", Steroids, 1997, pp. 148-158, vol. 62, Elsevier Science Inc., New York, NY.
Monique Linder, et al., "Preparation of Estrone ans Estradiol Antigens through Carbon 15 of these Estrogens", Steroids, Feb. 1977, pp. 161-170, vol. 29, No. 2, XP009024906.
Joelle D. Pelletier, et al., "Synthesis and Evaluation of Estradiol Derivatives with 16α-(Bromoalkylamide), 16α-(Bromoalkyl) or 16α-(Bromoalkynyl) Side Chain as Inhibitors of 17β-Hydroxysteroid Dehydrogenase Type 1 Without Estrogenic Activity", Bioorganic * Medicinal Chemistry, 1996, pp. 1617-1628, vol. 4, No. 10, Elsevier Science Ltd., Great Britain.
Donald Poirier, et al. "Inhibitors of 17β-Hydroxysteroid Dehydrogenases", Current Medicinal Chemistry, 2003, pp. 453-477, vol. 10, Bentham Science Publishers Ltd.
Kay-Mane Sam, et al., "C16 and C17 Derivatives of Estradiol as Inhibitors of 17β-Hydroxysteroid Dehydrogenase Type 1: Chemical Synthesis and Structure-Activity Relationships", Drug Design and Discovery, 1998, pp. 157-180, vol. 15, OPA (Overseas Publishers Association).
Fernand Labrie, et al., "Role of 17β-Hydroxysteroid Dehyrogenases in Sex Steroid Formation in Peripheral Intracrine Tissues", TEM, 2000, pp. 421-427, vol. 11, No. 10,Elsevier Science Ltd.
Donald Poirier, et al., "Synthesis of 17β-Estradiol Derivates with N-Butyl, M-Methyl Alkylamide Side Chain at Position 15", Tetrahedron, 1991, pp. 7751-7766, vol. 47, No. 37, Pergamon Press plc.
T. Tamaya, et al., "Comparison of Cellular Levels of Steroid Receptors in Uterine Leiomyoma and Myometrium", Acta. Obsstet. Gynecol, Scand., 1995, pp. 307-309, vol. 64.
Donald Poirier, et al., a 6β-(Thiaheptanamide) Derivative of Estradiol of 17β-Hydroxysteroid Dehydrogenase Type 1, J. Steroid Biochem. Molec. Biol., 1998, pp. 83-90, vol. 64, No. ½.
Martin R. Tremblay, et al., "Overview of a Rational Approach to Design Type I 17β-Hydroxysteroid Dehydrogenase Inhibitors Without Estrogenic Activity: Chemical Synthesis and Biological Evaluation", J. Steroid Biochem. Molec. Biol., 1998, pp. 170-191, vol. 66, No. 4, Elsevier Science Ltd., Great Britain, PII-S0960-0760(98)00043-0.
Toshio Namara, et al., "Synthesis of Estetrol Monoglucuronides1" Steroids, Jan. 1976, pp. 111-122, vol. 27, No. 1.
Donald Poirier, et al., D-Ring Alkylamide Derivatives of Estradiol: Effect on Er-Binding Affinity and Antiestrongenic Activity, Bioorganic & Medicinal Chemistry Letters, 1996, pp. 2537-2542, Elsevier Science Ltd., Great Britain, PII: S0960-894X(96)00472-6.
Donald Poirier, et al., "Inhibitors of 17β-Hydroxysteroid Dehydrogenases", Current Medical Chemical, 2003, pp. 453-477, vol. 10, Bentham Science Publishers.

(Continued)

*Primary Examiner* — Barbara P Badio
(74) *Attorney, Agent, or Firm* — Crowell & Moring LLP

(57) ABSTRACT

3,15-substituted estrone compounds which act as inhibitors of 17β-hydroxysteroid dehydrogenase type I (17β-HSD1), salts thereof, pharmaceutical preparations containing such compounds, processes for preparing such compounds, and therapeutic uses of such compounds, particularly in the treatment or inhibition of steroid hormone dependent diseases or disorders, such as steroid hormone dependent diseases or disorders requiring the inhibition of 17β-hydroxysteroid dehydrogenase type I enzymes and/or requiring the lowering of the endogenous 17β-estradiol concentration, as well as the general use of selective 17β-hydroxysteroid dehydrogenase type 1 inhibitors which possess in addition no or only pure antagonistic binding affinities to the estrogen receptor for the treatment or inhibition of benign gynecological disorders, particularly endometriosis.

41 Claims, No Drawings

OTHER PUBLICATIONS

Jerzy Adamski, et al., "A Guide to 17β-Hydroxysteroid Dehdrogenases", Molecular and Cellular Endocrinology, 2001, pp. 1-4, vol. 171, Elsevier Science Ireland Ltd.

David C. Labaree, et al., "Synthesis and Evaluation of B-, C- and D-Ring-Substituted Estradiol Carboxylic Acid Esters as Locally Active Estrogens", J. Med. Chem., 2003, pp. 1886-1904, vol. 46, American Chemical Society.

G. S. Chetrite, The selective estrogen enzyme modulator (SEEM) in breast cancer, Journal of Steroid Biochemistry & Molecular Biology 76 (2001), pp. 95-104.

T. M. Penning, Molecular Endocrinology of Hydroxysteroid Dehydrogenases*, Department of Pharmacology, University of Pennsylvania School of Medicine, Philadelphia, PA, 19104-6084, Endocrine Reviews, vol. 18, No. 3, pp. 281-305, 1997.

H. J. Smith et al., Inhibitors of steroidogenesis as agents for the treatment of hormone-dependent cancers, Welsh School of Pharmacy, Cardiff University, Cathays Park, Cardiff, CG10 3XF, UK, pp. 789-824, 2001.

T. M. Penning, 17β-Hydroxysteroid dehydrogenase: inhibitors and inhibitor design, Department of Pharmacology, University of Pennsylvania School of Medicine, Phliadelphia, PA, 19104-6084, Endocrine-Related Cancer (1996) pp. 41-56.

M. R. Tremblay et al., Overview of a Rational Approach to Design Type I 17β-Hydroxysteroid Dehydrogenase Inhibitors Without Estrogenic Activity: Chemical Synthesis and Biological Evaluation, F.Steroid Biochem. Molec. Biol. vol. 66, No. 4, pp. 179-191, 1998.

K. M. Zeitoun et al., Aromatase: a key molecule in the pathophysiology of endometriosis and a therapeutic target, Dept. of Obstetrics and Gynecology, the University of Texas Southwestern Medical Center, Dallas, Texas, Fertility and Sterility, vol. 72, No. 6, Dec. 1999, pp. 961-969.

S. E. Bulun et al., Estrogen biosynthesis in endometriosis: molecular basis and clinical relevance, Journal of Molecular Endocrinology (2000) 25, pp. 35-42.

M. Di Domenico, Estradiol Activation of Human Colon Carcinoma-deprived Caco-2 Cell Growth, American Association of Cancer Research 56, pp. 4516-4521, Oct. 1, 1996.

* cited by examiner

17β-HYDROXYSTEROID DEHYDROGENASE TYPE I INHIBITORS

CROSS REFERENCE TO RELATED APPLICATIONS

This application claims priority from U.S. provisional patent application nos. 60/518,847, filed Nov. 12, 2003, and 60/621,644, filed Oct. 26, 2004, the entire disclosures of which are incorporated herein by reference.

BACKGROUND OF THE INVENTION

The present invention relates to novel 3, 15 substituted estrone derivatives which represent inhibitory compounds of the 17β-hydroxysteroid dehydrogenase type I (17β-HSD1) enzyme, to their salts, to pharmaceutical preparations containing these compounds and to processes for the preparation of these compounds. Furthermore, the invention concerns the therapeutic use of said novel 3, 15 substituted estrone derivatives, particularly their use in the treatment or prevention of steroid hormone dependent diseases or disorders, such as steroid hormone dependent diseases or disorders requiring the inhibition of the 17β-HSD1 enzyme and/or requiring the lowering of the endogenous 17β-estradiol concentration. In addition, the present invention relates to the general use of selective 17β-HSD1 inhibitors which possess in addition no or only pure antagonistic binding affinities to the estrogen receptor for the treatment and prevention of benign gynecological disorders, in particular endometriosis.

The publications and other materials used herein to illuminate the background of the invention, and in particular, cases to provide additional details respecting the practice, are incorporated by reference.

Mammalian 17β-hydroxysteroid dehydrogenases (17β-HSDs) are NAD(H) or NADP(H) dependent enzymes which catalyse—besides other reactions—the final steps in male and female sex hormone biosynthesis. These enzymes convert inactive 17-keto-steroids into their active 17β-hydroxy-forms or catalyse the oxidation of the 17β-hydroxy-forms into the 17-keto-steroids. Because both estrogens and androgens have the highest affinity for their receptors in the 17β-hydroxy form, 17β-HSD enzymes play an essential role in the tissue-selective regulation of the activity of sex steroid hormones.

At present, 10 human members of the 17β-HSD enzyme family have been described (types 1-5, 7, 8, 10-12). The human 17β-HSD family members share less than 30% similarity in their primary structure. The 17β-HSDs are expressed in distinct, though in some cases, overlapping patterns. The different types of 17β-HSDs also differ in their substrate and cofactor specificities. In intact cells in culture, the 17β-HSDs catalyse the reaction in a unidirectional way: types 1, 3, 5 and 7 use NADP(H) as a cofactor and catalyse the reductive reaction (activation), while types 2, 4, 8 and 10 catalyse the oxidative reaction (inactivation) using NAD(H) as a cofactor [see e.g. Labrie et al. (2000) Trends Endocrinol Metab, 11:421-7, and Adamski & Jakob (2001) Mol Cell Endocrinol, 171:1-4].

Due to their essential role in the tissue-selective regulation of the activity of sex steroid hormones 17β-HSDs can be involved in the occurrence and development of estrogen-sensitive pathologies (f. ex. breast, ovarian, and endometrium cancers etc.) and androgen-sensitive pathologies (f. ex. prostate cancer, benign prostatic hyperplasia, acne, hirsutism, etc). Furthermore, many types of 17β-HSD have been shown to be involved in the pathogenesis of particular human disorders. For example, the 17β-HSD3 is known to be involved in the development of pseudohermaphroditism, the 17β-HSD8 plays a role in polycystic kidney disease and the 17β-HSD4 is related to the occurrence of bifunctional enzyme deficiency. Therefore treatment of sex steroid-sensitive diseases by administration of specific inhibitors of the 17β-HSDs enzymes have been suggested, optionally in combination with potent and specific anti-estrogens and anti-androgens [Labrie F et al. (1997) Steroids, 62:148-58].

Due to the fact that each type of 17β-HSD has a selective substrate affinity, directional (reductive or oxidative) activity in intact cells, and a particular tissue distribution, the selectivity of drug action could be achieved by targeting a particular 17β-HSD isozyme. By individual modulation of the particular 17β-HSDs it is possible to influence or even control the local and paracrine concentration of estrogens and androgens in different target tissues.

The best characterized member of the 17β-HSD family is the 17β-HSD1 [EC 1.1.1.62]. This enzyme could be crystallized in different states of functionality (e.g. with and without ligand and/or co-factor). In vitro, the 17β-HSD1 enzyme catalyses the reduction and the oxidation between estrone (E1) and estradiol (E2). However, under physiological in vivo conditions the enzyme only catalyses the reductive reaction from the estrone (E1) to the estradiol (E2). The 17β-HSD1 was found to be expressed in a variety of hormone-dependent tissues, e.g. placenta, mammary gland tissue or uterus and endometrium tissue, respectively. Estradiol itself is, especially in comparison to the significantly less active estrone, a very potent hormone, which regulates the expression of a variety of genes by binding to the nuclear estrogen receptor and plays an essential role in the proliferation and differentiation of the target cell. Physiological as well as pathological cell proliferations can be estradiol dependent. Especially many breast cancer cells are stimulated by a locally raised estradiol concentration. Furthermore, the occurrence or course of benign pathologies such as endometriosis, uterine leiomyomas (fibroids or myomas), adenomyosis, menorrhagia, metrorrhagia and dysmenorrhoea is dependent from the existence of significantly high estradiol levels.

Endometriosis is a well-known gynecological disorder that affects 10 to 15% of women in the reproductive age. It is a benign disease defined as the presence of viable endometrial gland and stroma cells outside the uterine cavity. It is most frequently found in the pelvic area. In women developing endometriosis, the endometrial cells entering the peritoneal cavity by retrograde menstruation (the most likely mechanism) have the capacity to adhere to and invade the peritoneal lining, and are then able to implant and grow. The implants respond to steroid hormones of the menstrual cycle in a similar way as the endometrium in the uterus. The infiltrating lesions and the blood from these lesions which are unable to leave the body cause inflammation of the surrounding tissue. The most common symptoms of endometriosis are dysmenorrhoea, dyspareunia and (chronic) abdominal pain. The occurrence of these symptoms is not related to the extent of the lesions. Some women with severe endometriosis are asymptomatic, while women with mild endometriosis may have severe pain. Up to now, no reliable non-invasive test is available to diagnose endometriosis. Laparoscopy has to be performed to diagnose the disease. Endometriosis is classified according to the 4 stages set up by the American Fertility Society (AFS). Stage I corresponds to minimal disease while stage IV is severe, depending on the location and the extent of the endometriosis. Endometriosis is found in up to 50% of the women with infertility. However, currently no causal relation has been proven between mild endometriosis and infertility.

Moderate to severe endometriosis can cause tubal damage and adhesions leading to infertility. The aims of treatment of endometriosis are pain relief, resolution of the endometriotic tissue and restoration of fertility (if desired). The two common treatments are surgery or anti-inflammatory and/or hormonal therapy or a combination thereof.

Uterine leiomyomas (fibroids or myomas), benign clonal tumours, arise from smooth muscle cells of the human uterus. They are clinically apparent in up to 25% of women and are the single, most common indication for hysterectomy. They cause significant morbidity, including prolonged and heavy menstrual bleeding, pelvic pressure and pain, urinary problems, and, in rare cases, reproductive dysfunction. The pathophysiology of myomas is not well understood. Myomas are found submucosally (beneath the endometrium), intramurally (within the myometrium) and subserosally (projecting out of the serosal compartment of the uterus), but mostly are mixed forms of these 3 different types. The presence of estrogen receptors in leiomyoma cells has been studied by Tamaya et al. [Tamaya et al. (1985) Acta Obstet Gynecol Scand. 64:307-9]. They have shown that the ratios of estrogen receptor compared to progesterone and androgen receptor levels were higher in leiomyomas than in the corresponding normal myometrium. Surgery has long been the main treatment for myomas. Furthermore, medical therapies that have been proposed to treat myomas include administration of a variety of steroids such as the androgenic steroids danazol or gestrinone, GnRH agonists and progestogens, whereby the administration is often associated a variety of serious side-effects.

Everything that has been said above in relation to the treatment of uterine leiomyomas and endometriosis equally applies to other benign gynecological disorders, notably adenomyosis, functional menorrhagia and metrorrhagia. These benign gynecological disorders are all estrogen sensitive and are treated in a comparable way as described herein before in relation to uterine leiomyomas and endometriosis. The available pharmaceutical treatments, however, suffer from the same major drawbacks, i.e. they have to be discontinued once the side-effects become more serious than the symptoms to be treated and symptoms reappear after discontinuation of the therapy.

Since the aforementioned malign and benign pathologies are all 17β-estradiol dependent, a reduction of the endogenous 17β-estradiol concentration in the respective tissue will result in an impaired or reduced proliferation of 17β-estradiol cells in said tissues. Therefore, it may be concluded that selective inhibitors of the 17β-HSD1 enzyme are well suited for their use to impair endogenous productions of estrogens, in particular of 17β-estradiol, in myomas, endometriotic, adenomyotic and endometrial tissue. The application of a compound acting as selective inhibitor on the 17β-HSD1 which preferentially catalyses the reductive reaction will result in a lowered intracellular estradiol-concentration since the reductive conversion of the estrone into the active estradiol is reduced or suppressed. Therefore, reversible or even irreversible inhibitors of the 17β-HSD1 may play a significant role in the prophylaxis and/or treatment of steroid-hormone, in particular 17β-estradiol, dependent disorders or diseases. Furthermore, the reversible or even irreversible inhibitors of the 17β-HSD1 should have no or only pure antagonistic binding activities to the estradiol receptor, in particular to the estrogen receptor a subtype, since agonistic binding of the estrogen receptor would lead to activation and therefore—by regulation of a variety of genes—to the proliferation and differentiation of the target cell. In contrast, antagonists of the estrogen receptor, so called anti-estrogens, bind competitively to the specific receptor protein thus preventing access of endogenous estrogens to their specific binding site.

At present it is described in the literature that several malignant disease as breast cancer, prostate carcinoma, ovarian cancer, uterine cancer, endometrial cancer and endometrial hyperplasia may be treated by the administration of a selective 17β-HSD1 inhibitor. Furthermore, a selective 17β-HSD1 inhibitor may be useful for the prevention of the aforementioned hormone-dependent cancers, especially breast cancer. The international patent application WO 2004/080271 discloses the use of a particular 17β-HSD1 inhibitor, so called compound A, for prevention or treatment of disorders caused by the 17HSD1 enzyme activity, in particular breast cancer. Furthermore, the international patent application WO 03/017973 describes the use of a selective estrogen enzyme modulator (SEEM) in the manufacture of a drug delivery vehicle for use in a method of treating or preventing a benign gynecological disorder in a mammalian female, said benign gynecological disorder being selected from the group consisting of uterine leiomyomas, endometriosis, adenomyosis, functional menorrhagia and metrorrhagia, wherein the method comprises the intravaginal administration of the SEEM to the female suffering from the benign gynecological disorder in a therapeutically effective dosage to prevent or reduce the symptoms of said benign gynecological disorder, said SEEM being selected from the group consisting of aromatase inhibitors, cyclo-oxygenase 2 (COX-2) inhibitors, 17β-HSD1 inhibitors and combinations thereof.

Several reversible or irreversible inhibitors of the 17β-HSD1 enzyme of steroidal and even non-steroidal origin are already known from the literature. The characteristics of these inhibitory molecules, which mainly have a substrate or cofactor-like core structure, have been reported in the literature [reviewed in: Poirier D. (2003) Curr Med Chem. 10:453-77].

For example, Tremblay and Poirier describe an estradiol derivative, 16-[carbamoyl-(bromo-methyl)-alkyl]-estradiol, and tested the same in respect of its inhibition of the estradiol formation catalysed by the enzyme 17β-HSD1 [Tremblay & Poirier (1998) J. Steroid Biochem. Molec. Biol., 66:179-191]. Poirier and colleagues describe a 6β-thiaheptan-butyl-methyl-amide derivative of estradiol as a potent and selective inhibitor of the 17HSD1 enzyme [Poirier et al. (1998) J. Steroid Biochem. Molec. Biol., 64:83-90]. Furthermore, Poirier and colleagues describe new derivatives of 17β-estradiol with N-butyl, N-methyl alkylamide side chains of three different lengths (n=8, 10 or 12) at position 15, which might be potential inhibitors of the 17β-HSD enzyme [Poirier et al. (1991) Tetrahedron, 47(37):7751-7766]. The biological activity of these compounds was only tested with regard to estrogen receptor binding affinity, estrogenic and anti-estrogenic activity [Poirier et al. (1996) Bioorg Med Chem Lett 6(21):2537-2542]. In addition, Pelletier and Poirier describe novel 17β-estradiol derivatives with different bromo-alkyl side chains, which might be potential inhibitors of the 17β-HSD enzyme [Pelletier & Poirier (1996) Bioorg Med Chem, 4(10):1617-1628]. Sam and colleagues describe several estradiol derivatives with a halogenated alkyl side chain in 16α or 17α position of the steroidal D ring which possess 17β-HSD1 inhibiting properties [Sam et al. (1998) Drug Design and Discovery, 15:157-180]. Furthermore, the finding that some anti-estrogens, such as tamoxifen, possess weak 17β-HSD inhibiting properties suggested that it may be possible to develop a potent 17β-HSD1 inhibitor that is also anti-estrogenic [reviewed in: Poirier D. (2003) Curr Med Chem. 10:453-77]. Several of the aforementioned already known compounds also display anti-estrogenic properties (e.g. the 6β-thiaheptan-butyl-methyl-amide derivative of estradiol described by Poirier and colleagues [Poirier et al. (1998) J. Steroid Biochem. Molec. Biol., 64:83-90]). None of the aforementioned compounds has been clinically used so far.

International patent application WO 2004/085457 discloses a variety of estron derivatives with different substituents in C3, C6, C16 and/or C17 position as potent 17β-HSD1 inhibitors.

The synthesis of different B-, C- and D-ring substituted estradiol carboxylic esters was described by Labaree et al. [Labaree et al. (2003) J. Med. Chem. 46:1886-1904]. However, these esters were only analyzed with regard to their estrogenic potential. The related international patent application WO 2004/085345 discloses 15α substituted estradiol compounds bearing a —(CH$_2$)$_m$—CO—O—R side chain, wherein R is H, a C$_1$ to C$_5$ alkyl group, optionally substituted with at least one halogen group, such as CH$_2$CH$_2$F, or other group (e.g. CH$_2$CHF$_2$, CH$_2$CF$_3$ or CF$_3$ group); and m is from 0-5. This 15α estradiol esters are described as locally active estrogens without significant systemic action.

Accordingly, there is a need for the development of compounds which are suited for the treatment and/or prevention of steroid hormone dependent diseases or disorders such as breast cancer, endometriosis and uterine leiomyomas by selectively inhibiting the 17β-HSD1 enzyme, while desirably failing to substantially inhibit other members of the 17β-HSD protein family or other catalysts of sex steroid degradation or activation. In particular, it is an aim of the present invention to develop selective inhibitors of the 17β-HSD1 enzyme, whereby in addition the compounds have no or only pure antagonistic binding affinities to the estrogen receptor (both subtypes α and β). Furthermore, there is still a need to provide a new type of therapy regimen for estrogen dependent benign gynecological disorders, particularly for pre- and peri-menopausal females, whereby the therapy should not cause serious side-effects.

SUMMARY OF THE INVENTION

Therefore, it is an object of the present invention to provide new inhibitors of the enzyme 17β-HSD1, which have valuable pharmacological properties and which are suited for the treatment of estrogen dependent diseases and disorders.

It has now been found that the novel 3, 15 substituted estrone derivatives bearing a side chain of the amide, ester, carbonyl, hydrazone, alcohol, ether, urea, carbamate, "retro"-amide, sulfonyl urea, sulfamide, sulfamate, "retro"-sulfonamide, "retro"-carbamate, "retro"-ester or sulfonylcarbamate type in position 15 would be valuable in therapy, especially in the treatment or prevention of steroid hormone dependent diseases or disorders requiring the inhibition of 17β-HSD enzymes. In particular, compounds of formula (I) represent potent inhibitors of the 17β-HSD1 enzyme and possess valuable pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhoea, menorrhagia, metrorrhagia, prostadynia, benign prostatic hyperplasia, urinary dysfunction or lower urinary tract syndrome. Further estrogen-dependent diseases which may be treated and/or prevented with an effective amount of a compound of the invention are multiple sclerosis, rheumatoid arthritis, colon cancer, tissue wounds, skin wrinkles and cataracts.

It is a further object of the present invention to provide a new therapy regimen for the treatment of estradiol dependent benign gynecological diseases or disorders such as endometriosis, uterine fibroids, uterine leiomyoma, adenomyosis, dysmenorrhoea, menorrhagia, metrorrhagia, or urinary dysfunction by the administration of an effective amount of a selective inhibitor of the 17β-HSD1 enzyme. Preferably the selective inhibitor of the 17β-HSD1 enzyme possesses no or only pure antagonistic binding affinities to the estrogen receptor. In particular, this novel type of therapy regimen for estrogen dependent benign disorders is suited for pre- and peri-menopausal females.

Accordingly, the present invention relates to a compound having the structural formula I

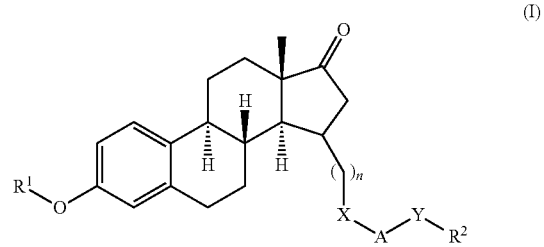

(I)

or a physiologically acceptable salt thereof, wherein
(i) X represents:
  (a) a bond,
  (b) —NR$^3$—, or
  (c) —O—;
A represents:
  (a) —CO—, or
  (b) under the proviso that X represents —NR$^3$—, A represents —SO$_2$—;
Y represents:
  (a) —NR$^4$—,
  (b) —O—, under the proviso that X represents a bond or —NR$^3$—,
  (c) a bond,
  (d) —NH—SO$_2$—, under the proviso that X represents —NR$^3$— and A represents —CO—,
  (e) —NH—SO$_2$—NR$^4$—, under the proviso that X represents —O—, or
  (f) —NH—NR$^4$—, under the proviso that X represents a bond;
or
(ii) —X-A-Y— together represent —O—;
and wherein
R$^1$ and R$^3$ are independently selected from:
  (a) —H,
  (b) —(C$_1$-C$_6$)alkyl, which is optionally substituted with halogen, nitrile, —OR$^6$, —SR$^6$, or —COOR$^6$; the number of said substituents being up to three for halogen, and up to two for any combination of said halogen, nitrile, —OR$^6$, —SR$^6$, or —COOR$^6$ moieties,
  (c) -phenyl, which is optionally substituted with halogen, nitrile, —OR$^6$, —SR$^6$, —R$^6$, or —COOR$^6$, the number of said substituents being up to perhalo for halogen, and up to two for any combination of said halogen, nitrile, —OR$^6$, —SR$^6$, —R$^6$ or —COOR$^6$ moieties,
  (d) —(C$_1$-C$_4$)alkyl-phenyl, in which the alkyl portion is optionally substituted with up to three halogens; and the phenyl portion is optionally substituted with halogen, nitrile, —OR$^6$, —SR$^6$, —R$^6$ or —COOR$^6$, the number of substituents on said phenyl portion being up to perhalo for halogen, and up to two for any combination of said halogen, nitrile, —OR$^6$, —SR$^6$, —R$^6$ or —COOR$^6$ moieties;

R$^2$ and R$^4$ are independently selected from:
  (a) —H, wherein if X represents a bond, A represents —CO— and Y represents —O— or a bond, then R$^2$ is different from —H;
  (b) optionally substituted alkyl,
  (c) optionally substituted acyl, under the proviso that Y represents —NH—NR$^4$—,
  (d) optionally substituted aryl,
  (e) optionally substituted heteroaryl, and
  (f) optionally substituted cycloheteroalkyl,
or, under the proviso that Y represents —NR$^4$—, —NH—NR$^4$— or —NH—SO$_2$—NR$^4$—,
  R$^2$ and R$^4$ form together with the nitrogen atom, where R$^2$ and R$^4$ are attached, a heterocyclic 4-, 5-, 6-, 7- or 8-membered ring, which is optionally saturated, partly unsaturated, or aromatic; which optionally contains up to three additional heteroatoms selected from N, O or S, the number of additional N atoms being 0, 1, 2 or 3 and the number of O and S atoms each being 0, 1 or 2; and which ring is optionally part of a multiple condensed ring-system, wherein the ring or the ring-system is optionally substituted;

R$^6$ represents H, —(C$_1$-C$_4$)alkyl or halogenated —(C$_1$-C$_4$)alkyl; and n represents 0, 1, 2, 3, 4, 5 or 6, wherein, if X represents —NR$^3$— or —O—, then n is different from 0.

Accordingly, the present inventions relates to a compound of the general formula I, wherein —X-A-Y— together represent
  (a) —CO—NR$^4$—,
  (b) —CO—O—,
  (c) —CO—,
  (d) —CO—NH—NR$^4$—,
  (e) —NR$^3$—CO—NR$^4$—,
  (f) —NR$^3$—CO—,
  (g) —NR$^3$—CO—
  (h) —NR$^3$—CO—NH—SO$_2$—,
  (i) —NR$^3$—SO$_2$—NR$^4$—,
  (j) —NR$^3$—SO$_2$—O—,
  (k) —NR$^3$—SO$_2$—
  (l) —O—CO—NR$^4$—,
  (m) —O—CO—,
  (n) —O—CO—NH—SO$_2$—NR$^4$—, or
  (o) —O—.

In a further embodiment, the present invention relates to a compound of the general formula I, which is an optically pure 15α enantiomer having the formula (II)

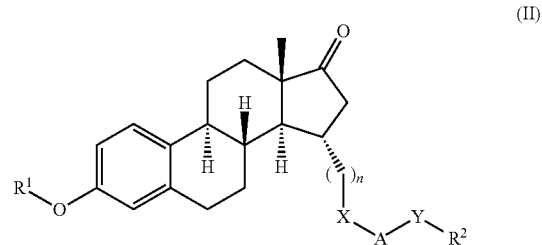

(II)

or a physiologically acceptable salt thereof. In a further embodiment, the present invention relates to the 15α enantiomer having formula (II), wherein n represents 1, 2, 3 or 4, if X represents —NR$^3$— or —O—, or wherein n represents 0, 1, 2, or 3, if X represents a bond.

In another embodiment, the present invention relates to a compound of the general formula I, which is an optically pure 15β enantiomer having the formula (III)

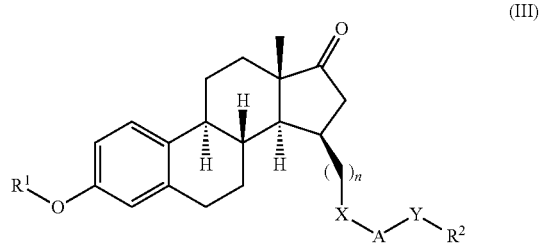

(III)

or a physiologically acceptable salt thereof.

In a further embodiment, the present invention relates to the 15β enantiomer having formula (III), wherein n represents 2, 3, 4, or 5, if X represents a bond, or wherein n represents 3, 4, 5 or 6, if X represents —NR$^3$— or —O—.

One embodiment of the present invention relates to compounds of the general formula I, wherein R$^1$ and R$^3$, if R$^3$ is present, are independently selected from H, (C$_1$-C$_4$)alkyl, preferably methyl, and phenyl(C$_1$-C$_4$)alkyl, preferably benzyl.

A further embodiment of the present invention relates to compounds of the general formula I, wherein R$^1$ and R$^3$, if R$^3$ is present, are independently selected from H and methyl.

A further embodiment of the present invention relates to compounds of the general formula I, wherein, if X represents —NR$^3$— or —O— and Y represents —NR$^2$R$^4$—, then R$^4$ is —H.

A further embodiment of the present invention relates to compounds of the general formula I, in which R$^2$ and R$^4$ are independently selected from:
  (a) —H, wherein if X represents a bond, A represents —CO— and Y represents —O— or a bond, then R$^2$ is different from —H,
  (b) —(C$_1$-C$_{12}$)alkyl, optionally substituted with up to five substituents independently selected from the group consisting of halogen, hydroxyl, thiol, nitrile, alkoxy, aryloxy, arylalkyloxy, amino, amido, alkylthio, arylthio, arylalkylthio, sulfamoyl, sulfonamide, acyl, carboxyl, acylamino,
  aryl, which aryl is optionally substituted with up to three substituents independently selected from the group consisting of halogen, hydroxyl, (C$_1$-C$_6$)alkoxy, (C$_1$-C$_6$)alkyl, halogenated (C$_1$-C$_6$)alkyl, halogenated (C$_1$-C$_6$)alkoxy, carboxyl-(C$_1$-C$_6$)alkyl, thiol, nitrile, sulfamoyl, sulfonamide, carboxyl, aryloxy, arylalkyloxy, (C$_1$-C$_6$)alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2;
  heteroaryl, which heteroaryl is optionally substituted with up to three substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$)alkoxy, carboxyl-($C_1$-$C_6$)alkyl, thiol, nitrile, sulfamoyl, sulfonamide, carboxyl, aryloxy, arylalkyloxy, ($C_1$-$C_6$)alkylthio, arylthio, arylalkylthio, amino, amido, acyl, acylamino, aryl-($C_1$-$C_4$)-alkyl and aryl;

whereby each aryl group is optionally substituted with up to three substituents independently selected from the group consisting of hydroxyl, halogen, ($C_1$-$C_6$)alkoxy, ($C_1$-$C_6$)alkyl, halogenated ($C_1$-$C_6$)alkyl and halogenated ($C_1$-$C_6$) alkoxy; and cycloheteroalkyl, which cycloheteroalkyl group is optionally substituted with up to three substituents independently selected from the group consisting of oxo, ($C_1$-$C_8$)-alkyl, aryl, aryl-($C_1$-$C_4$)-alkyl, hydroxyl, ($C_1$-$C_6$)alkoxy, carboxyl-($C_1$-$C_6$)alkyl, thiol, nitrile, sulfamoyl, sulfonamide, carboxyl, aryloxy, arylalkyloxy, ($C_1$-$C_6$)alkylthio, arylthio, arylalkylthio, amino, amido, acyl, and acylamino, whereby each aryl group is optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, and halogenated ($C_1$-$C_4$)-alkoxy);

(c) acyl —(C=O)—R', wherein R' represents hydrogen, ($C_1$-$C_4$)alkyl, aryl, or aryl-($C_1$-$C_4$)alkyl, or heteroaryl-($C_1$-$C_4$)alkyl;

which aryl is optionally substituted with up to three substituents independently selected from the group consisting of hydroxyl, halogen, ($C_1$-$C_4$)alkoxy, ($C_1$-$C_4$)-alkyl or halogenated ($C_1$-$C_4$)alkyl;

(d) aryl which aryl is optionally substituted with up to three substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$)alkoxy, carboxyl-($C_1$-$C_6$)alkyl, thiol, nitrile, nitro, sulfamoyl, sulfonamide, carboxyl, aryloxy, arylalkyloxy, ($C_1$-$C_6$)alkylsulfonyl, arylsulfonyl, ($C_1$-$C_6$) alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8-membered ring system, optionally containing up to three heteroatoms, such as N, O or S, the number of N atoms being 0-3 and the number of O and S atoms each being 0-2;

(e) heteroaryl, which heteroaryl is optionally substituted with up to three substituents independently selected from the group consisting of halogen, hydroxyl, ($C_1$-$C_6$) alkoxy, ($C_1$-$C_6$)alkyl, halogenated ($C_1$-$C_6$)alkyl, halogenated ($C_1$-$C_6$)alkoxy, carboxyl-($C_1$-$C_6$)alkyl, thiol, nitrile, sulfamoyl, sulfonamide, arylsulfoxy, carboxyl, aryloxy, arylalkyloxy, ($C_1$-$C_6$)alkylsulfonyl, arylsulfonyl, ($C_1$-$C_6$)alkylthio, arylthio, arylalkylthio, amino, amido, acyl, acylamino, aryl-($C_1$-$C_4$)-alkyl and aryl, whereby each aryl group is optionally substituted with up to three substituents independently selected from the group consisting of hydroxyl, halogen, ($C_1$-$C_6$)alkoxy, ($C_1$-$C_6$)alkyl, halogenated ($C_1$-$C_6$)alkyl and halogenated ($C_1$-$C_6$) alkoxy; or (f) cycloheteroalkyl, which cycloheteroalkyl is optionally substituted with up to three substituents independently selected from the group consisting of oxo, ($C_1$-$C_{14}$)-alkyl, aryl, aryl-($C_1$-$C_4$)-alkyl, hydroxyl, ($C_1$-$C_6$)alkoxy, carboxyl-($C_1$-$C_6$)alkyl, thiol, nitrile, sulfamoyl, sulfonamide, carboxyl, aryloxy, arylalkyloxy, ($C_1$-$C_6$)alkylthio, arylthio, arylalkylthio, amino, amido, acyl, and acylamino, whereby each aryl group is optionally further substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, and halogenated ($C_1$-$C_4$)-alkoxy;

or wherein, under the proviso that Y represents —NR⁴—, —NH—NR⁴— or —NH—SO₂—NR⁴—, R² and R⁴ form together with the nitrogen atom, where R² and R⁴ are attached, a heterocyclic 4-, 5-, 6-, 7- or 8-membered ring, which is optionally saturated or partly unsaturated; which optionally contains up to three additional heteroatoms selected from N, O or S, the number of additional N atoms being 0-3 and the number of O and S atoms each being 0-2; and which ring is optionally part of a multiple condensed ring-system, wherein the ring or the ring-system is optionally substituted (i) with up to three substituents independently selected from the group consisting of ($C_1$-$C_8$)-alkyl, halogen, hydroxyl, carboxyl, thiol, nitrile, ($C_1$-$C_6$)-alkoxy, carboxyl-($C_1$-$C_6$)alkyl, aryloxy, arylalkyloxy, amino, amido, alkylthio, arylthio, arylalkylthio, sulfamoyl, sulfonamide, aryl, aryl-($C_1$-$C_4$)-alkyl, heteroaryl, and cycloheteroalkyl, wherein the ($C_1$-$C_8$)-alkyl group is optionally substituted with up to three substituents independently selected among hydroxyl, halogen, ($C_1$-$C_4$)-alkoxy, or halogenated ($C_1$-$C_4$)-alkoxy, whereby the alkyl-chain of the ($C_1$-$C_4$)-alkoxy moiety is optionally substituted with hydroxyl;

wherein the aryl is optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, halogenated ($C_1$-$C_4$)-alkoxy and carboxyl-($C_1$-$C_6$)alkyl, or wherein the aryl moiety is optionally substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2;

wherein the heteroaryl is optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, halogenated ($C_1$-$C_4$)-alkoxy) and carboxyl-($C_1$-$C_6$)alkyl;

wherein the cycloheteroalkyl is optionally substituted with up to three substituents independently selected from the group consisting of oxo, ($C_1$-$C_8$)-alkyl, aryl, aryl-($C_1$-$C_4$)-alkyl, hydroxyl, ($C_1$-$C_6$)alkoxy, carboxyl-($C_1$-$C_6$)alkyl, and carboxyl, whereby each aryl group is optionally further substituted with up to three substituents independently selected from the group consisting of hydroxyl, halogen, $(C_1\text{-}C_4)$-alkyl, $(C_1\text{-}C_4)$-alkoxy, halogenated $(C_1\text{-}C_4)$-alkyl, and halogenated $(C_1\text{-}C_4)$-alkoxy); or (ii) by two groups which are attached to the same carbon atom and are combined into a saturated or partly unsaturated cyclic 4, 5, 6, 7, or 8-membered ring system, optionally containing up to three heteroatoms, such as N, O or S, the number of N atoms being 0-3 and the number of O and S atoms each being 0-2, whereby the cyclic ring system is optionally substituted by up to two substituents independently selected from oxo, $(C_1\text{-}C_6)$-alkyl, aryl and aryl-$(C_1\text{-}C_4)$-alkyl;

and wherein n represents (a) 1, 2, 3, 4, 5 or 6, under the proviso that X represents —$NR^3$— or —O—, or (b) 0, 1, 2, 3, 4, or 5, under the proviso that X represents a bond.

In one embodiment of the present invention, in the compounds of the general formula I the residues $R^2$ and $R^4$ may independently represent —H, wherein if X represents a bond, A represents —CO— and Y represents —O— or a bond, then $R^2$ is different from —H.

In a further embodiment of the present invention, the term "optionally substituted alkyl", wherefrom $R^2$ and/or $R^4$ can be independently selected, refers to (i) —$(C_1\text{-}C_8)$alkyl, optionally substituted with substituents independently selected from the group consisting of
  (a) hydroxyl,
  (b) nitrile,
  (c) —O—$R^{7'}$,
  (d) —O-phenyl,
  (e) —O—$(C_1\text{-}C_4)$alkyl-phenyl,
  (f) alkylamino,
  (g) alkylamido, preferably carbamoyl,
  (h) —S—$R^{7'}$, and
  (i) —(C=O)—$OR^{8'}$;
  the number of substituents on said alkyl portion being up to five for hydroxyl and one, two or three, more preferably up to two for any combination of said other substituents; and wherein
  $R^{7'}$ represents $(C_1\text{-}C_4)$alkyl, preferably $(C_1\text{-}C_2)$alkyl, optionally substituted in the alkyl chain with one or two hydroxyl groups; and
  $R^{8'}$ represents hydrogen, $(C_1\text{-}C_4)$alkyl, preferably methyl, or $(C_1\text{-}C_4)$alkyl-phenyl, preferably benzyl;

(ii) —$(C_1\text{-}C_4)$alkyl, substituted with one or two substituents independently selected from the group consisting of
  (a) aryl, wherein the aryl is preferably selected among phenyl, naphthyl, indanyl, indenyl, and 1,2,3,4-tetrahydro-naphthalen-1-yl, more preferably the aryl is phenyl or naphthyl, and
    which aryl is optionally substituted with halogen, hydroxyl, $(C_1\text{-}C_6)$alkoxy, $(C_1\text{-}C_6)$alkyl, halogenated $(C_1\text{-}C_4)$alkyl, halogenated $(C_1\text{-}C_4)$alkoxy, sulfamoyl, or alkylamido; the number of substituents on said aryl portion being up to five, more preferably up to three, for halogen and up to three, more preferably up to two for any combination of said other substituents; or
    which aryl is optionally substituted by two groups which are attached to adjacent carbon atoms and are combined into a saturated cyclic 5 or 6 membered ring system, optionally containing up to three heteroatoms, such as N or O, the number of N atoms being 0-3 and the number of O atoms each being 0-2;

(b) heteroaryl, wherein the heteroaryl is preferably selected among pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, benzothiazolyl, indolyl, quinolinyl, isoquinolinyl, benzoimidazolyl, benzofuran and benzo[b]thiophene, more preferably the heteroaryl is thienyl, furyl, imidazolyl, pyridinyl, indolyl, or benzoimidazolyl, and
  which heteroaryl is optionally substituted with up to two, preferably one substituent independently selected from the group consisting of $(C_1\text{-}C_4)$alkoxy, preferably methoxy, or $(C_1\text{-}C_4)$alkyl, preferably methyl; and (c) cycloheteroalkyl, wherein the cycloheteroalkyl group is preferably selected from the group consisting of pyrrolidinyl, tetrahydrofuranyl, dihydro-1H-pyrrolyl, tetrahydrothiophenyl, tetrahydropyridinyl, azetidinyl, thiazolidinyl, oxazolidinyl, piperidinyl, morpholinyl, thiomorpholinyl, piperazinyl, 1,3-dihydrobenzoimidazolyl, azepanyl, diazepanyl, oxazepanyl and thiazepanyl, preferably the cycloheteroalkyl group is piperidinyl or morpholinyl; and
  which cycloheteroalkyl is optionally substituted with up to three substituents independently selected from the group consisting of oxo, hydroxyl, $(C_1\text{-}C_4)$-alkyl, phenyl, —$(C_1\text{-}C_4)$alkyl-phenyl, preferably benzyl, —(C=O)—O—$(C_1\text{-}C_4)$alkyl, and alkylamino, preferably the cycloheteroalkyl moiety is not substituted;

(iii) -cyclo$(C_3\text{-}C_8)$alkyl, optionally substituted with hydroxyl;

(iv) —$(C_1\text{-}C_4)$alkyl-cyclo$(C_3\text{-}C_8)$alkyl, optionally substituted with hydroxyl;

(v) a bicyclic ring system of 6 to 10 carbon atoms, preferably Bicyclo[2.1.1]hexyl, Bicyclo[2.2.1]heptyl, Bicyclo[3.2.1]octyl, Bicyclo[2.2.2]octyl, Bicyclo[3.2.2]nonanyl, Bicyclo[3.3.1]nonanyl, Bicyclo[3.3.2]decanyl; or (vi) a fused ring system of up to 10 carbon atoms, preferably adamantly.

In a further embodiment of the present invention, the term "optionally substituted acyl", wherefrom $R^2$ and/or $R^4$ can be independently selected under the proviso that Y represents —NH—$NR^4$—, refers to acyl —(C=O)—R', wherein R' represents hydrogen, $(C_1\text{-}C_4)$alkyl, aryl, or aryl-$(C_1\text{-}C_4)$alkyl, or heteroaryl-$(C_1\text{-}C_4)$alkyl; which aryl or aryl-$(C_1\text{-}C_4)$alkyl is optionally substituted in the aryl, preferably phenyl, moiety with up to three substituents independently selected from the group consisting of hydroxyl, halogen, $(C_1\text{-}C_4)$alkoxy, $(C_1\text{-}C_4)$-alkyl or halogenated $(C_1\text{-}C_4)$alkyl.

In a further embodiment of the present invention, the term "optionally substituted aryl", wherefrom $R^2$ and/or $R^4$ can be independently selected, refers to aryl, which is preferably selected among phenyl, naphthyl, indanyl, indenyl, and 1,2,3,4-tetrahydro-naphthalen-1-yl. According to one aspect of the invention, the aryl is optionally substituted with up to five, more preferably up to three substituents independently selected from the group consisting of (i) hydroxyl,
(ii) halogen, preferably fluorine or chlorine,
(iii) $(C_1\text{-}C_6)$alkoxy, preferably $(C_1\text{-}C_2)$alkoxy
(iv) $(C_1\text{-}C_6)$alkyl, preferably $(C_1\text{-}C_4)$alkyl
(v) halogenated $(C_1\text{-}C_6)$alkyl, preferably halogenated $(C_1\text{-}C_4)$alkyl, more preferably trifluoromethyl,
(vi) halogenated $(C_1\text{-}C_6)$alkoxy, preferably halogenated $(C_1\text{-}C_4)$alkoxy, more preferably trifluoromethoxy;
(vii) —$(C_1\text{-}C_4)$alkyl-(C=O)—$OR^{8'}$ (viii) nitrile,
(ix) nitro,
(x) sulfamoyl,
(xi) —(C=O)—$R^{8'}$
(xii) —(C=O)—$OR^{8'}$,
(xiii) —NH—(C=O)—$R^{8'}$,
(xiv) —S—$R^{8'}$,
(xv) —$SO_2$—$R^{8'}$,
(xvi) alkylamino,
(xvii) alkylamido, preferably carbamoyl,
(xviii) phenyl, and
(xix) a further heteroaryl group, optionally substituted with ($C_1$-$C_4$)alkyl, preferably 6-methyl-benzothiazolyl;
wherein
$R^{8'}$ represents hydrogen, ($C_1$-$C_4$)alkyl, preferably methyl, or ($C_1$-$C_4$)alkyl-phenyl, preferably benzyl;
or which aryl may be optionally substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2.

In a further embodiment, the aryl moiety, wherefrom $R^2$ and/or $R^4$ can be independently selected, is optionally substituted with halogen, ($C_1$-$C_6$)alkoxy, halogenated ($C_1$-$C_4$)alkyl, preferably halogenated methyl, nitro, nitrile, —CO—($C_1$-$C_4$)alkyl, —CO—O—($C_1$-$C_4$)alkyl, —NH—CO—($C_1$-$C_4$)alkyl, ($C_1$-$C_4$)alkyl-sulfonyl, phenyl or heteroaryl, the number of substituents on said aryl portion being up to perhalo for halogen, and up to two for any combination of said ($C_1$-$C_6$)alkoxy or halogenated ($C_1$-$C_4$)alkyl moieties.

In a further embodiment of the present invention, the term "optionally substituted heteroaryl", wherefrom $R^2$ and/or $R^4$ can be independently selected, refers to heteroaryl, which is preferably selected among pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, benzothiazolyl, indolyl, quinolinyl, isoquinolinyl, benzoimidazolyl, benzofuran and benzo[b]thiophene; more preferably heteroaryl is furyl, thiazolyl, pyrazolyl, pyridinyl, quinolinyl, or benzo[b]thiophene. The heteroaryl is optionally substituted with up to three, preferably up to two substituents independently selected from the group consisting of
(i) halogen,
(ii) ($C_1$-$C_4$)alkyl,
(iii) hydroxyl,
(iv) halogenated ($C_1$-$C_4$)alkyl,
(v) —($C_1$-$C_4$)alkoxy,
(vi) —($C_1$-$C_4$)alkyl-(C=O)—$OR^{8'}$,
(vii) —O—$Ar^{1'}$,
(viii) —$SO_2$—$Ar^{1'}$,
(ix) phenyl,
(x) —($C_1$-$C_4$)alkyl-phenyl,
(xi) nitrile,
(xii) alkylamino, and
(xiii) alkylamido, preferably carbamoyl;
wherein
$R^{8'}$ represents hydrogen, ($C_1$-$C_4$)alkyl, preferably methyl, or ($C_1$-$C_4$)alkyl-phenyl, preferably benzyl; and
$Ar^{1'}$ represents phenyl optionally substituted with up to three halogen.

Furthermore, the heteroaryl moiety, from which $R^2$ and/or $R^4$ can be independently selected, is optionally substituted with up to three, preferably up to two substituents independently selected from the group consisting of halogen, ($C_1$-$C_4$)alkyl, preferably methyl, halogenated ($C_1$-$C_4$)alkyl, preferably halogenated methyl, —($C_1$-$C_4$)alkyl-(C=O)—O—($C_1$-$C_4$)alkyl, —$SO_2$-phenyl, —O-phenyl, and phenyl.

In a further embodiment of the present invention, the term "optionally substituted cycloheteroalkyl", wherefrom $R^2$ and/or $R^4$ can be independently selected, refers to cycloheteroalkyl, which is preferably selected among pyrrolidinyl, tetrahydrofuranyl, dihydro-1H-pyrrolyl, tetrahydrothiophenyl, tetrahydropyridinyl, azetidinyl, thiazolidinyl, oxazolidinyl, piperidinyl, morpholinyl, thiomorpholinyl, piperazinyl, 1,3-dihydro-benzoimidazolyl, azepanyl, diazepanyl, oxazepanyl and thiazepanyl; more preferably cycloheteroalkyl is pyrrolidinyl, morpholinyl, tetrahydrofuranyl, piperidinyl or azepanyl, and which cycloheteroalkyl is optionally substituted with up to three, preferably one or two substituents independently selected from the group consisting of
(i) oxo,
(ii) ($C_1$-$C_4$)alkyl,
(iii) phenyl,
(iv) —($C_1$-$C_4$)alkyl-phenyl,
(v) hydroxyl,
(vi) ($C_1$-$C_4$)alkoxy, and
(vii) —($C_1$-$C_4$)alkyl-C=O)—$OR^{8'}$;
wherein
$R^{8'}$ represents hydrogen, ($C_1$-$C_4$)alkyl, preferably methyl, or ($C_1$-$C_4$)alkyl-phenyl, preferably benzyl.

Furthermore, the cycloheteroalkyl group, wherefrom $R^2$ and/or $R^4$ can be independently selected, is optionally substituted with one or two substituents independently selected from the group consisting of oxo, ($C_1$-$C_4$)alkyl, preferably methyl, and ($C_1$-$C_4$)alkyl-phenyl, preferably benzyl.

In a further embodiment, the invention relates to a compound of the general formula I, wherein, under the proviso that Y represents —$NR^4$—, —NH—$NR^4$— or —NH—$SO_2$—$NR^4$—, $R^2$ and $R^4$ can form together with the nitrogen atom, where $R^2$ and $R^4$ are attached, a heterocyclic 4-, 5-, 6-, 7- or 8-membered ring, which can be saturated or partly unsaturated, which can contain up to three additional heteroatoms selected from N, O or S, the number of additional N atoms being 0-3 and the number of O and S atoms each being 0-2, and which ring can be part of a multiple condensed ring-system. According to one embodiment, said ring or ring system is selected from the group consisting of

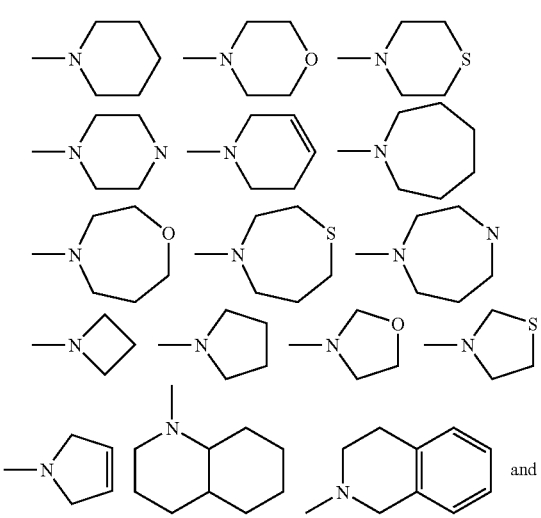

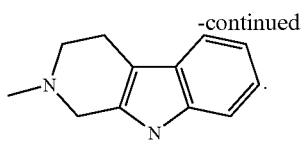

Even more preferred, said ring or ring system is selected from the group consisting of

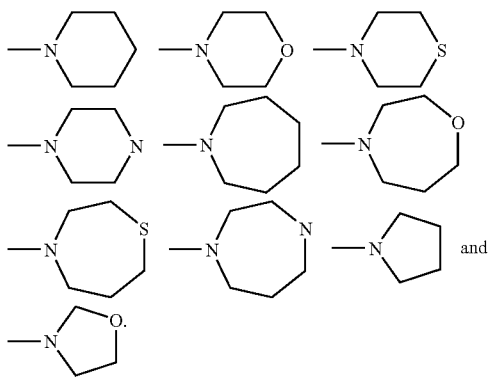

and

The ring or the ring-system may be optionally substituted with up to three substituents independently selected from the group consisting of
(i) hydroxyl,
(ii) $(C_1-C_4)$-alkyl optionally substituted with up to two hydroxyl and/or $(C_1-C_4)$-alkoxy groups, whereby the alkyl-chain of the $(C_1-C_4)$-alkoxy moiety may optionally be further substituted with up to two, preferably one hydroxyl;
(iii) cyclo$(C_3-C_8)$alkyl;
(iv) —(C=O)—O—$(C_1-C_4)$-alkyl;
(v) phenyl optionally substituted with halogen, $(C_1-C_4)$-alkyl, preferably methyl, $(C_1-C_4)$-alkoxy, or halogenated $(C_1-C_4)$-alkyl, preferably halogenated methyl, the number of said substituents on the phenyl moiety being up to three for halogen, and one or two for any combination of said other substituents;
(vi) phenyl-$(C_1-C_4)$alkyl, preferably benzyl, optionally substituted in the phenyl group by up to three halogen, or optionally substituted in the phenyl group by two groups which are attached to adjacent carbon atoms and are combined into a saturated or partly unsaturated cyclic 5 or 6-membered ring system, optionally containing up to two O atoms;
(vii) alkylamido, preferably carbamoyl;
(viii) heteroaryl, wherein the heteroaryl is preferably selected from the group consisting of pyridinyl, furyl, thienyl, thiazolyl, imidazolyl, pyrazolyl, indolyl, quinolinyl, benzoimidazolyl or benzo[b]thiophene, more preferably the heteroaryl is pyridinyl; and
(ix) cycloheteroalkyl, wherein the cycloheteroalkyl is preferably selected from the group consisting of pyrrolidinyl, 1,3-dihydro-benzoimidazolyl, morpholinyl, tetrahydrofuranyl, piperidinyl and azepanyl; more preferably the cycloheteroalkyl group is pyrrolidinyl or 1,3-dihydro-benzoimidazolyl, which cycloheteroalkyl group is optionally substituted with oxo.

Alternatively, said ring or the ring-system may be optionally substituted by two groups which are attached to the same carbon atom and are combined into a saturated or partly unsaturated cyclic 4, 5, 6, 7, or 8-membered ring system, optionally containing up to three heteroatoms, such as N, O or S, the number of N atoms being 0-3 and the number of O and S atoms each being 0-2, whereby the cyclic ring system may optionally be further substituted with up to two substituents independently selected from oxo and phenyl.

In a further embodiment, the invention relates to a compound of the general formula I, wherein $R^4$ represents
(a) —H, under the proviso that X represents —$NR^3$— or that X represents a bond and Y represents —$NR^4$—,
(b) an alkyl group selected from
(i) —$(C_1-C_6)$alkyl, optionally substituted with substituents independently selected from the group consisting of hydroxyl, nitrile, alkylamino —O—$(C_1-C_4)$alkyl, the number of substituents on said alkyl portion being up to five for hydroxyl and up to three, more preferably up to two for any combination of said other substituents;
(ii) —$(C_1-C_4)$alkyl, preferably —$(C_1-C_2)$alkyl, substituted with up to two, preferably one substituent independently selected among aryl and heteroaryl, wherein the aryl is preferably phenyl or naphthyl, and wherein the heteroaryl is preferably pyridinyl;
(iii) cyclo$(C_3-C_8)$alkyl, preferably cyclo$(C_3-C_6)$alkyl;
(iv) cyclo$(C_3-C_8)$alkyl-$(C_1-C_4)$alkyl-, preferably cyclo$(C_3-C_6)$alkyl-$(C_1-C_2)$alkyl-; or
(c) cycloheteroalkyl, wherein the cycloheteroalkyl preferably is piperidinyl, which cycloheteroalkyl group is optionally substituted with one or two, preferably one $(C_1-C_4)$alkyl, preferably methyl, group.

In one embodiment, the invention relates to a compound of the following formula VI

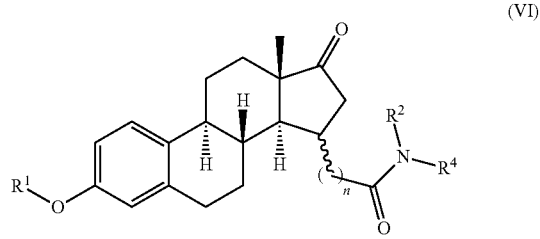

(VI)

wherein
$R^1$ represents H, $(C_1-C_4)$alkyl, preferably methyl, or phenyl $(C_1-C_4)$alkyl, preferably benzyl; and n represents 0, 1, 2, 3, 4, or 5.

In this embodiment, $R^2$ preferably represents
(i) —$(C_1-C_4)$alkyl,
(ii) —$(C_3-C_8)$cycloalkyl
(iii) —$(C_1-C_4)$alkyl-aryl, wherein the aryl is phenyl or naphthyl,
which phenyl is optionally substituted with one or two substituents independently selected from the group consisting of hydroxyl, halogen, and $(C_1-C_4)$alkoxy; or
which phenyl is optionally substituted by two groups which are attached to adjacent carbon atoms and are combined into a saturated cyclic 5 or 6-membered ring system, containing 1 or 2 O atoms; or
(iv) heteroaryl or $C_1-C_4$)alkyl-heteroaryl, wherein the heteroaryl is furyl, thienyl, thiazolyl, pyridinyl, indolyl, or benzoimidazolyl;
which heteroaryl is optionally substituted with one or two substituents independently selected from the group consisting of $(C_1-C_4)$alkyl and —$(C_1-C_4)$alkyl-(C=O)—O—$(C_1-C_4)$alkyl;
and preferably $R^4$ is independently selected from H or —$(C_1-C_4)$-alkyl; or $R^2$ and $R^4$ may form together with the nitrogen atom, where $R^2$ and $R^4$ are attached, a ring or ringsystem, which is selected from the group consisting of morpholine and thiomorpholine.

In a further embodiment the invention relates to a compound of the following formula XL,

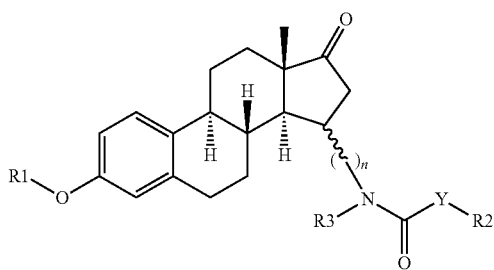

(XL)

wherein
$R^3$ is as defined above; preferably $R^3$ represents H;
Y represents —NH—, a bond, or —O—;
$R^1$ represents H, $(C_1-C_4)$alkyl, preferably methyl, or phenyl $(C_1-C_4)$alkyl, preferably benzyl;
and n represents 1, 2, 3, 4, 5 or 6, preferably 1, 2, 3 or 4.

A further embodiment of the invention relates to a compound of the following formula XVII,

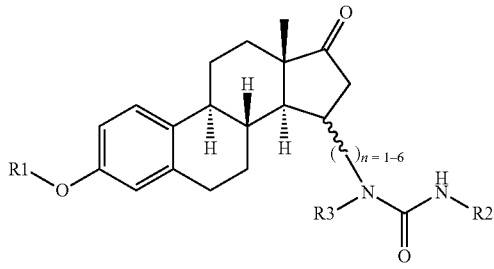

(XVII)

wherein
$R^3$ is as defined above; preferably $R^3$ represents H;
$R^1$ represents H, $(C_1-C_4)$alkyl, preferably methyl, or phenyl $(C_1-C_4)$alkyl, preferably benzyl; and
n represents 1, 2, 3, or 4, preferably 3 or 4.
In this embodiment, $R^2$ preferably represents
(i) —$(C_1-C_4)$alkyl,
(ii) —$(C_3-C_8)$cycloalkyl,
(iii) —$(C_1-C_4)$alkyl$(C_3-C_8)$cycloalkyl,
(iv) aryl, wherein the aryl is phenyl or naphthyl,
which phenyl is optionally substituted with one or two substituents independently selected from the group consisting of hydroxyl, halogen, —CO—O$(C_1-C_4)$alkyl and $(C_1-C_4)$alkoxy; or
which phenyl is optionally substituted by two groups which are attached to adjacent carbon atoms and are combined into a saturated cyclic 5 or 6-membered ring system, containing 1 or 2 O atoms, or
(v) —$(C_1-C_4)$alkyl-phenyl.

A further embodiment of the invention relates to a compound of the following formula XXIII,

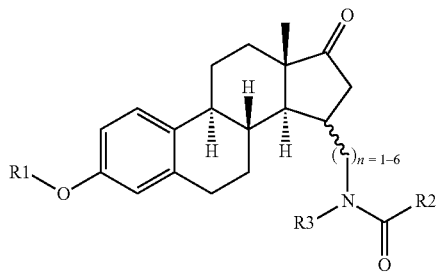

(XXIII)

wherein
$R^3$ is as defined above; preferably $R^3$ represents H;
$R^1$ represents H, $(C_1-C_4)$alkyl, preferably methyl, or phenyl $(C_1-C_4)$alkyl, preferably benzyl; and
n represents 1, 2, 3, or 4.
In this embodiment, $R^2$ preferably represents
(i) —$(C_1-C_4)$alkyl,
(ii) —$(C_3-C_8)$cycloalkyl,
(iii) —$(C_1-C_4)$alkyl-$(C_3-C_8)$cycloalkyl,
(iv) —$(C_1-C_4)$alkyl, substituted with one or two substituents independently selected from the group consisting of —O—$(C_1-C_4)$alkyl and —O—$(C_1-C_4)$alkyl-phenyl,
(v) phenyl,
which phenyl is optionally substituted with one, two or three substituents independently selected from the group consisting of halogen and $(C_1-C_4)$alkoxy;
(vi) —$(C_1-C_4)$alkyl-phenyl; or
(vii) adamantyl.

A further embodiment of the invention relates to a compound of the following formula XXIV,

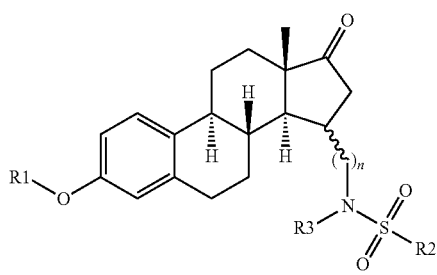

(XXIV)

wherein
$R^3$ is as defined above; preferably $R^3$ represents H or —$(C_1-C_4)$alkyl;
$R^1$ represents H, $(C_1-C_4)$alkyl, preferably methyl, or phenyl $(C_1-C_4)$alkyl, preferably benzyl;
n represents 1, 2, 3, or 4.
In this embodiment, $R^2$ preferably represents
(i) aryl, wherein the aryl is selected among phenyl and naphthyl,
which aryl is optionally substituted with one or two substituents independently selected from the group consisting of halogen, nitro, $(C_1-C_4)$alkoxy, and —$(C_1-C_4)$alkyl; or
(ii) heteroaryl, wherein the heteroaryl is furyl, thienyl, or thiazolyl, or indolyl, which heteroaryl is optionally substituted with one or two substituents independently selected from the group consisting of —SO$_2$-phenyl and (C$_1$-C$_4$)alkyl.

A further embodiment of the invention relates to a compound of the following formula XXVI,

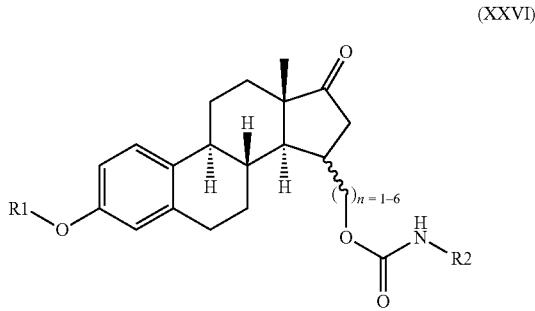

(XXVI)

wherein
R$^1$ represents H, (C$_1$-C$_4$)alkyl, preferably methyl, or phenyl (C$_1$-C$_4$)alkyl, preferably benzyl;
n represents 3, 4, 5 or 6.

In this embodiment, R$^2$ preferably represents phenyl or naphthyl, and the phenyl is optionally substituted with one or two substituents independently selected from the group consisting of hydroxyl, halogen, nitro, —CO—O(C$_1$-C$_4$)alkyl and (C$_1$-C$_4$)alkoxy and halogenated (C$_1$-C$_4$)alkyl; or the phenyl group is optionally substituted by two groups which are attached to adjacent carbon atoms and are combined into a saturated cyclic 5 or 6-membered ring system, containing 1 or 2 O atoms.

A further embodiment of the invention relates to a compound of the following formula XXVIII,

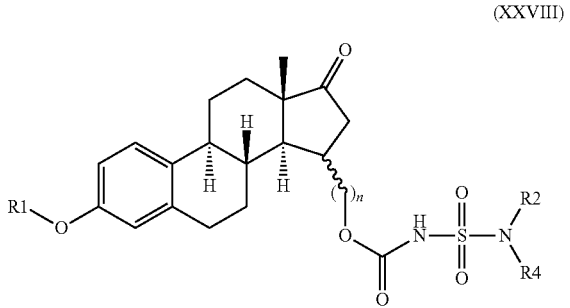

(XXVIII)

wherein
R$^1$ represents H, (C$_1$-C$_4$)alkyl, preferably methyl, or phenyl (C$_1$-C$_4$)alkyl, preferably benzyl;
n represents 3, 4, 5 or 6.
In this embodiment, R$^2$ preferably represents
(i) —(C$_1$-C$_4$)alkyl,
(ii) —(C$_3$-C$_8$)cycloalkyl,
(iii) —(C$_1$-C$_4$)alkyl-phenyl,
(iv) phenyl, or
(v) heteroaryl or —(C$_1$-C$_4$)alkyl-heteroaryl, wherein the heteroaryl is furyl, thienyl, thiazolyl, pyridinyl, indolyl, or benzoimidazolyl;
and preferably R$^4$ is independently selected from H, —(C$_1$-C$_4$)-alkyl and —(C$_1$-C$_4$)alkyl-phenyl; or
R$^2$ and R$^4$ may form together with the nitrogen atom, where R$^2$ and R$^4$ are attached, a ring, which is selected from the group consisting of morpholine, thiomorpholine and piperazyl, and which is optionally substituted with (C$_1$-C$_4$)-alkyl.

A further embodiment of the invention relates to a compound of the following formula XXXI,

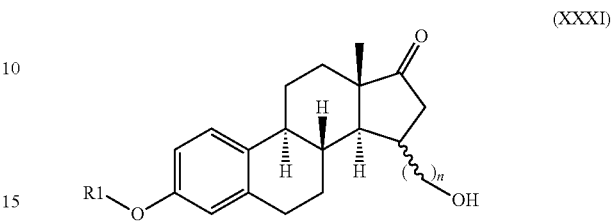

(XXXI)

wherein
R$^1$ represents H, (C$_1$-C$_4$)alkyl, preferably methyl, or phenyl (C$_1$-C$_4$)alkyl, preferably benzyl;
n represents 1, 2, 3, 4, 5 or 6, preferably 3 or 4.

Particularly preferred embodiments of the invention include the following compounds:
No. 1. 3-Hydroxy-15β-(4-morpholin-4-yl-4-oxo-butyl)-estra-1,3,5(10)-trien-17-one
No. 2. 3-Methoxy-15β-(4-morpholin-4-yl-4-oxo-butyl)-estra-1,3,5(10)-trien-17-one
No. 3B. N-Benzyl-4-(3-methoxy-17-oxo-estra-1,3,5(10)-trien-15β-yl)-butyramide
No. 3A. N-Benzyl-4-(3-Hydroxy-17-oxo-estra-1,3,5(10)-trien-15β-yl)-butyramide
No. 31. 4-(3-Methoxy-17-oxo-estra-1,3,5(10)-trien-15β-yl)-N-[2-(7-methyl-1H-indol-3-yl)-ethyl]-butyramide
No. 36. 4-(3-Hydroxy-17-oxo-estra-1,3,5(10)-trien-15β-yl)-N-[2-(7-methyl-1H-indol-3-yl)-ethyl]-butyramide
No. 37. N-(2,4-Difluoro-benzyl)-4-(3-hydroxy-17-oxo-estra-1,3,5(10)-trien-15β-yl)-butyramide
No. 38. N-Benzyl-4-(3-hydroxy-17-oxo-estra-1,3,5(10)-trien-15β-yl)-N-methyl-butyramide
No. 39. N-Benzyl-4-(3-hydroxy-17-oxo-estra-1,3,5(10)-trien-15α-yl)-butyramide
No. 40. 3-Hydroxy-15α-(4-morpholin-4-yl-4-oxo-butyl)-estra-1,3,5(10)-trien-17-one
No. 105. 3-Methoxy-17-oxo-estra-1,3,5(10)-trien-15α-carboxylic acid(5-methyl-thiazol-2-yl)-amide
No. 310. N-Cyclohexyl-3-(3-methoxy-17-oxo-estra-1,3,5 (10)-trien-15β-yl)-propionamide
No. 311. N-Cyclooctyl-3-(3-methoxy-17-oxo-estra-1,3,5 (10)-trien-15β-yl)-propionamide
No. 313. N-Cyclohexyl-3-(3-methoxy-17-oxo-estra-1,3,5 (10)-trien-15β-yl)-N-methyl-propionamide
No. 324. N-[2-(4-Hydroxy-phenyl)-ethyl]-3-(3-methoxy-17-oxo-estra-1,3,5(10)-trien-15β-yl)-propionamide
No. 329. 3-(3-Methoxy-17-oxo-estra-1,3,5(10)-trien-15β-yl)-N-(5-methyl-thiazol-2-yl)-propionamide
No. 331. 5-(3-Methoxy-17-oxo-estra-1,3,5(10)-trien-15β-yl)-pentanoic acid cyclohexylamide
No. 332. 5-(3-Methoxy-17-oxo-estra-1,3,5(10)-trien-15β-yl)-pentanoic acid cyclooctylamide
No. 333. 5-(3-Methoxy-17-oxo-estra-1,3,5(10)-trien-15β-yl)-pentanoic acid (furan-2-ylmethyl)-amide
No. 335. 5-(3-Methoxy-17-oxo-estra-1,3,5(10)-trien-15β-yl)-pentanoic acid (benzo[1,3]dioxol-5-ylmethyl)-amide
No. 338. 5-(3-Methoxy-17-oxo-estra-1,3,5(10)-trien-15β-yl)-pentanoic acid (pyridin-3-ylmethyl)-amide
No. 339. 5-(3-Methoxy-17-oxo-estra-1,3,5(10)-trien-15β-yl)-pentanoic acid (pyridin-4-ylmethyl)-amide No. 340. 5-(3-Methoxy-17-oxo-estra-1,3,5(10)-trien-15β-yl)-pentanoic acid benzylamide
No. 341. 5-(3-Methoxy-17-oxo-estra-1,3,5(10)-trien-15β-yl)-pentanoic acid 2-methoxy-benzylamide
No. 342. 5-(3-Methoxy-17-oxo-estra-1,3,5(10)-trien-15β-yl)-pentanoic acid 3-fluoro-benzylamide
No. 343. 5-(3-Methoxy-17-oxo-estra-1,3,5(10)-trien-15β-yl)-pentanoic acid 4-chloro-benzylamide
No. 344. 5-(3-Methoxy-17-oxo-estra-1,3,5(10)-trien-15β-yl)-pentanoic acid benzyl-methyl-amide
No. 345. 5-(3-Methoxy-17-oxo-estra-1,3,5(10)-trien-15β-yl)-pentanoic acid butylamide
No. 346. 5-(3-Methoxy-17-oxo-estra-1,3,5(10)-trien-15β-yl)-pentanoic acid (2-thiophen-2-yl-ethyl)-amide
No. 347. 5-(3-Methoxy-17-oxo-estra-1,3,5(10)-trien-15β-yl)-pentanoic acid [2-(7-methyl-1H-indol-3-yl)-ethyl]-amide
No. 348. 6-(3-Methoxy-17-oxo-estra-1,3,5(10)-trien-15β-yl)-hexanoic acid cyclohexylamide
No. 350. 6-(3-Methoxy-17-oxo-estra-1,3,5(10)-trien-15β-yl)-hexanoic acid (furan-2-ylmethyl)-amide
No. 353. 6-(3-Methoxy-17-oxo-estra-1,3,5(10)-trien-15β-yl)-hexanoic acid (benzo[1,3]dioxol-5-ylmethyl)-amide
No. 354. 3-Methoxy-15β-(6-morpholin-4-yl-6-oxo-hexyl)-estra-1,3,5(10)-trien-17-one
No. 355. 3-Methoxy-15β-(6-oxo-6-thiomorpholin-4-yl-hexyl)-estra-1,3,5(10)-trien-17-one
No. 356. 6-(3-Methoxy-17-oxo-estra-1,3,5(10)-trien-15β-yl)-hexanoic acid (pyridin-3-ylmethyl)-amide
No. 357. 6-(3-Methoxy-17-oxo-estra-1,3,5(10)-trien-15β-yl)-hexanoic acid (pyridin-4-ylmethyl)-amide
No. 359. 6-(3-Methoxy-17-oxo-estra-1,3,5(10)-trien-15β-yl)-hexanoic acid benzylamide
No. 360. 6-(3-Methoxy-17-oxo-estra-1,3,5(10)-trien-15β-yl)-hexanoic acid 2-methoxy-benzylamide
No. 361. 6-(3-Methoxy-17-oxo-estra-1,3,5(10)-trien-15β-yl)-hexanoic acid 3-fluoro-benzylamide
No. 363. 6-(3-Methoxy-17-oxo-estra-1,3,5(10)-trien-15β-yl)-hexanoic acid [2-(4-hydroxy-phenyl)-ethyl]-amide
No. 364. 6-(3-Methoxy-17-oxo-estra-1,3,5(10)-trien-15β-yl)-hexanoic acid benzyl-methyl-amide
No. 365. 6-(3-Methoxy-17-oxo-estra-1,3,5(10)-trien-15β-yl)-hexanoic acid butylamide
No. 366. 6-(3-Methoxy-17-oxo-estra-1,3,5(10)-trien-15β-yl)-hexanoic acid (2-thiophen-2-yl-ethyl)-amide
No. 443. 1-[3-(3-Methoxy-17-oxo-estra-1,3,5(10)-trien-15β-yl)-propyl]-3-(3-methoxy-phenyl)-urea
No. 446. 1-[3-(3-Methoxy-17-oxo-estra-1,3,5(10)-trien-15β-yl)-propyl]-3-(4-methoxy-phenyl)-urea
No. 449. 1-Isopropyl-3-[3-(3-methoxy-17-oxo-estra-1,3,5(10)-trien-15β-yl)-propyl]-urea
No. 450. 1-Cyclohexyl-3-[3-(3-methoxy-17-oxo-estra-1,3,5(10)-trien-15β-yl)-propyl]-urea
No. 452. 1-Benzyl-3-[3-(3-methoxy-17-oxo-estra-1,3,5(10)-trien-15β-yl )-propyl]-urea
No. 464. 1-(3,4-Dimethoxy-phenyl)-3-[3-(3-methoxy-17-oxo-estra-1,3,5(10)-trien-15β-yl)-propyl]-urea
No. 465. 1-Benzo[1,3]dioxol-5-yl-3-[3-(3-methoxy-17-oxo-estra-1,3,5(10)-trien-15β-yl)-propyl]-urea
No. 477. 1-Benzyl-3-[4-(3-methoxy-17-oxo-estra-1,3,5(10)-trien-15β-yl)-butyl]-urea
No. 488. 1-(3,4-Dimethoxy-phenyl)-3-[4-(3-methoxy-17-oxo-estra-1,3,5(10)-trien-15β-yl)-butyl]-urea
No. 490. 4-{3-[4-(3-Hydroxy-17-oxo-estra-1,3,5(10)-trien-15α-yl)-butyl]-ureido}-benzoic acid ethylester
No. 491. 1-Cyclohexylmethyl-3-[4-(3-hydroxy-17-oxo-estra-1,3,5(10)-trien-15α-yl)-butyl]-urea
No. 661. Naphthalene-2-sulfonic acid (3-hydroxy-17-oxo-estra-1,3,5(10)-trien-15α-ylmethyl)-amide
No. 662. Thiophene-2-sulfonic acid (3-hydroxy-17-oxo-estra-1,3,5(10)-trien-15α-ylmethyl)-amide
No. 664. N-(3-Hydroxy-17-oxo-estra-1,3,5(10)-trien-15α-ylmethyl)-benzenesulfonamide
No. 665. 4-Fluoro-N-(3-hydroxy-17-oxo-estra-1,3,5(10)-trien-15α-ylmethyl)-benzenesulfonamide
No. 668. N-(3-Hydroxy-17-oxo-estra-1,3,5(10)-trien-15α-ylmethyl)-4-methoxy-benzenesulfonamide
No. 677. N-(3-Hydroxy-17-oxo-estra-1,3,5(10)-trien-15α-ylmethyl)-3-methyl-benzenesulfonamide
No. 681. Naphthalene-2-sulfonic acid (3-hydroxy-17-oxo-estra-1,3,5(10)-trien-15α-ylmethyl)-methyl-amide
No. 682. Thiophene-2-sulfonic acid (3-hydroxy-17-oxo-estra-1,3,5(10)-trien-15α-ylmethyl)-methyl-amide
No. 684. N-(3-Hydroxy-17-oxo-estra-1,3,5(10)-trien-15α-ylmethyl)-N-methyl-benzenesulfonamide
No. 685. 4-Fluoro-N-(3-hydroxy-17-oxo-estra-1,3,5(10)-trien-15α-ylmethyl)-N-methyl-benzenesulfonamide
No. 688. N-(3-Hydroxy-17-oxo-estra-1,3,5(10)-trien-15α-ylmethyl)-4-methoxy-N-methyl-benzenesulfonamide
No. 693. 3-Chloro-N-(3-hydroxy-17-oxo-estra-1,3,5(10)-trien-15α-ylmethyl)-N-methyl-benzenesulfonamide
No. 694. N-(3-Hydroxy-17-oxo-estra-1,3,5(10)-trien-15α-ylmethyl)-3,N-dimethyl-benzenesulfonamide
No. 696. 4-Benzenesulfonyl-thiophene-2-sulfonic acid (3-hydroxy-17-oxo-estra-1,3,5(10)-trien-15α-ylmethyl)-methyl-amide
No. 748. Benzo[1,3]dioxol-5-yl-carbamic acid 3-(3-methoxy-17-oxo-estra-1,3,5(10)-trien-15β-yl)-propylester
No. 823. 3-Hydroxy-15β-(3-hydroxypropyl)-estra-1,3,5(10)-trien-17-one and physiologically acceptable salts of any of the foregoing.

Pharmaceutically acceptable salts of the compounds of the invention as well as commonly used pro-drugs and active metabolites of these compounds are also within the scope of the invention.

The invention also relates to pharmaceutical compositions comprising one or more of the compounds of the invention, or their salts or pro-drugs, as active agent in at lease one pharmaceutically acceptable carrier.

Furthermore, the invention relates to the use of an effective amount of a compound of the invention for the treatment or inhibition of a steroid hormone dependent disease or disorder in a mammal, in particular a human. Preferably the steroid hormone dependent disease or disorder is an estradiol dependent disease or disorder.

In addition, the invention relates to the use of a compound of the invention for the manufacture of a medicament for the treatment or inhibition of a steroid hormone dependent disease or disorder in a mammal, in particular a human. Preferably the steroid hormone dependent disease or disorder is an estradiol dependent disease or disorder.

In a further embodiment of the invention, the steroid hormone dependent disease or disorder requires the inhibition of a 17β-HSD enzyme, preferably the human 17β-HSD1 enzyme.

Furthermore, the invention also relates to a method of treating a mammal such as a human having a condition related to 17β-HSD1 activity, comprising administering to the mammal an amount of a compound of this invention, or a salt or a prodrug thereof, which amount is effective to treat the condition. Administration of compounds of this invention in combination with other pharmaceuticals used in treatment of the listed conditions is contemplated.

The conditions to be treated include, but are not limited to, malign estradiol dependent disease or disorder such as breast cancer, ovarian cancer, uterine cancer, endometrial cancer, and endometrial hyperplasia.

According to a further aspect of the invention, the estradiol dependent disease is breast cancer and the mammal is a human post-menopausal female.

Furthermore, the conditions to be treated include but are not limited to benign estradiol dependent diseases or disorders such as endometriosis, uterine fibroids, uterine leiomyoma, adenomyosis, dysmenorrhea, menorrhagia, metrorrhagia, and urinary dysfunction.

In a further embodiment, the invention relates to use of an effective amount of a compound of the invention for the treatment or prevention of one of the aforementioned benign gynecological diseases or disorders in a mammal whereby the mammal is a human, preferably a female and most preferably a pre- or peri-menopausal female.

According to one aspect of the present invention, the steroid hormone dependent disease or disorder is selected from the group consisting of prostate carcinoma, prostadynia, benign prostatic hyperplasia, urinary dysfunction and lower urinary tract syndrome.

According to another aspect of the invention, the steroid hormone dependent disease or disorder to be treated requires the lowering of the endogenous 17β-estradiol concentration in a generalized and/or tissue specific manner.

Therefore, further estrogen-dependent diseases which may be treated with an effective amount of a compound of the invention include rheumatoid arthritis, colon cancer, tissue wounds, skin wrinkles and cataracts.

The disclosed compounds are also useful as diagnostic agents (e.g. in diagnostic kits or for use in clinical laboratories) for screening for the presence or absence of 17β-HSD1 activity.

In addition, the present invention relates to the use of a selective inhibitor of the 17β-HSD1 enzyme for the treatment and/or prophylaxis of a benign estradiol dependent disease or disorder in a mammal, in particular a human, preferably a female and most preferably a pre- or peri-menopausal female.

In a preferred embodiment of the present invention the selective inhibitor of the 17β-HSD1 enzyme used for the treatment and/or prophylaxis of a benign estradiol dependent disease or disorder possesses no or only pure antagonistic binding affinities to the estrogen receptor.

The invention also relates to a method of treating a mammal such as a human having a benign estradiol dependent condition, comprising administering to the mammal an amount of a selective inhibitor of the 17β-HSD1 enzyme, whereby said inhibitor preferably possesses in addition no or only pure antagonistic binding affinities to the estrogen receptor, and which amount is effective to treat the condition. Administration of a selective inhibitor of the 17β-HSD1 enzyme which additionally possesses no or only pure antagonistic binding affinities to the estrogen receptor of this invention in combination with other pharmaceuticals used in treatment of the listed conditions is contemplated.

The benign estradiol dependent conditions to be treated with a selective inhibitor of the 17β-HSD1 enzyme include, but are not limited to, endometriosis, uterine fibroids, uterine leiomyoma, adenomyosis, dysmenorrhea, menorrhagia, metrorrhagia, and urinary dysfunction.

The invention also relates to the use of a selective inhibitor of the 17β-HSD1 enzyme for the manufacture of a pharmaceutical composition for the treatment and/or prevention of a benign estradiol dependent disease or disorder in a mammal. The benign estradiol dependent disease or disorder is preferably endometriosis, uterine fibroids, uterine leiomyoma, adenomyosis, dysmenorrhea, menorrhagia, metrorrhagia, or urinary dysfunction. Furthermore, the inhibitor of the 17β-HSD1 enzyme preferably possesses in addition no or only pure antagonistic binding affinities to the estrogen receptor.

In a preferred embodiment the invention relates to use of an effective amount of a selective inhibitor of the 17β-HSD1 enzyme for the manufacture of a pharmaceutical composition for the treatment and/or prevention of a benign estradiol dependent disease or disorder in a mammal, whereby the mammal is a human, preferably a female and most preferably a pre- or peri-menopausal female.

In addition, the present invention relates to the use of a selective inhibitor of the 17β-HSD1 enzyme showing no or only pure antagonistic binding affinities to the estrogen receptor for the prevention of breast cancer in a post-menopausal female, and to the use of said selective inhibitors for the manufacture of a medicament for the prevention of breast cancer in a post-menopausal female.

DESCRIPTION OF THE INVENTION

Definitions

The following terms are used to describe various constituents of the chemical composition useful in this invention. The terms are defined as follows:

As used herein, the terms "comprising" and "including" are used herein in their open, non-limiting sense.

The word "compound" shall here be understood to cover any and all isomers (e. g., enantiomers, stereoisomers, diastereomers, rotomers, tautomers) or any mixture of isomers, prodrugs, and any pharmaceutically acceptable salt of said compound.

Where the plural form is used for compounds, salts, and the like, this is taken to mean also a single compound, salt, or the like.

The term "substituted" means that the specified group or moiety bears one or more substituents. Where any group may carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents.

Any asymmetric carbon atoms may be present in the (R)-, (S)- or (R,S)-configuration, preferably in the (R)- or (S)-configuration, whichever is most active. Substituents at a double bond or a ring may be present in cis- (=Z-) or trans (=E-) form.

The compounds of the formula I contain at least one chiral (i.e., asymmetric) carbon atom, namely the carbon atom carrying the side chain in the 15-position of the steroide structure. The compounds can thus be present in two optically active stereoisomeric forms or as a racemate. The present invention includes both the racemic mixtures and the isomerically pure compounds of the formula I. The position of the substituents within the C15 position is characterized by α or β. A C15α derivative according to the present invention is represented by a compound of the following formula (II)

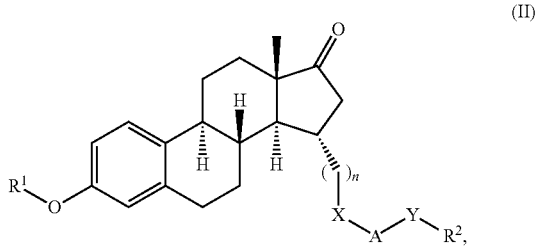

whereas a C15β derivative according to the present invention is represented by a compound of the following formula (III)

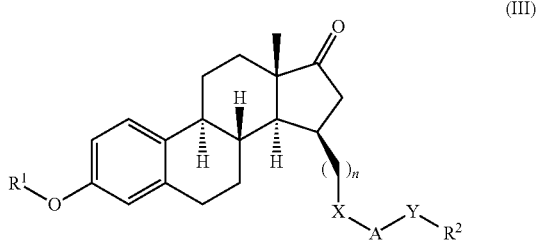

The compounds of the present invention may contain further asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention.

The term "halogen" refers to fluorine (F, Fluoro-), bromine (Br, Bromo-), chlorine (Cl, Chloro), and iodine (J, Iodo-) atoms.

The terms "dihalogen", "trihalogen" and "perhalogen" refer to two, three and four substituents, respectively, each individually selected from the group consisting of fluorine, bromine, chlorine, and iodine atoms.

The term "hydroxyl" refers to the group —OH

The term "oxo" refers to the group =O

The term "carbamoyl" refers to the group —CO—NH$_2$

The term "thio" refers to the group =S

The term "thiol" refers to the group —SH

The term "sulfanyl" refers to the group —S—

The term "sulfoxy" or "sulfonyl" refers to the group —SO$_2$—

The term "sulfamoyl" refers to the group —SO$_2$—NH$_2$

The term "nitro" refers to the group —NO$_2$

The term "nitrile" or "cyano" refers to the group —CN

For the purpose of the present invention, the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus $C_1$-$C_4$-alkyl refers to alkyl of 1-4 carbon atoms, inclusive, or methyl, ethyl, propyl, butyl and isomeric forms thereof.

The term "alkyl" identifies a hydrocarbon radical which may be linear, cyclic or branched, with single or multiple branching, whereby the alkyl group comprises 1 to 12 carbon atoms. In one embodiment, the term "alkyl" stands for a linear or branched (with single or multiple branching) alkyl chain of 1 to 8 carbon atoms, exemplified by the term $(C_1$-$C_8)$alkyl, more preferably of 1 to 6 carbon atoms exemplified by the term $(C_1$-$C_6)$alkyl. The term $(C_1$-$C_8)$alkyl is further exemplified by such groups as methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl, heptyl, octyl and the like. The alkyl or $(C_1$-$C_8)$alkyl group may be partially unsaturated, forming such groups as, for example, vinyl, propenyl (allyl), butenyl, pentenyl, pentinyl, hexenyl, octadienyl, and the like. The term "alkyl" further comprises cycloalkyl groups, preferably cyclo$(C_3$-$C_8)$alkyl which refers to cyclopropyl, cyclobutyl, cyclopentyl, cyclohexyl, cycloheptyl, cyclooctyl and isomeric forms thereof such as methylcyclopropyl; 2- or 3-methylcyclobutyl; 2-, or 3-methylcyclopentyl, and the like. The cycloalkyl group may also be partly unsaturated, forming such groups as, for example, cyclohexenyl, cyclopentenyl, cyclooctadienyl, and the like. Furthermore, the term "alkyl" comprises a cycloalkyl-alkyl group comprising 4 to 12 carbon atoms, preferably "—$(C_1$-$C_4)$alkyl-cyclo$(C_3$-$C_8)$alkyl" which refers to a alkyl group of 1 to 4 carbon atoms as described above substituted with a cyclo$(C_3$-$C_8)$alkyl group as described above, forming such groups as for example cyclopropylmethyl, cyclohexylmethyl, cyclopentylethyl or cyclohexenylethyl. The term "alkyl" further comprises bicyclic ring systems of 6 to 10 carbon atoms, preferably Bicyclo[2.1.1]hexyl, Bicyclo[2.2.1]heptyl, Bicyclo[3.2.1]octyl, Bicyclo[2.2.2]octyl, Bicyclo[3.2.2]nonanyl, Bicyclo[3.3.1]nonanyl, Bicyclo[3.3.2]decanyl; and the like, preferably Bicyclo[2.2.1]heptyl, and fused ring systems of up to 10 carbon atoms such as adamantyl and the like.

The alkyl group may optionally be substituted by up to five, more preferably by up to three substituents independently selected from the group consisting of halogen, hydroxyl, optionally substituted aryl, optionally substituted heteroaryl, optionally substituted cycloheteroalkyl, thiol, nitro, nitrile, alkoxy, aryloxy, arylalkyloxy, amino, amido, alkylthio, arylthio, arylalkylthio, sulfamoyl, sulfonamide, acyl, carboxyl, and acylamino, as defined herein. These groups may be attached to any carbon atom of the alkyl moiety. Substituted alkyl is preferably substituted with halogen, nitrile, hydroxyl, $C_1$-$C_4$-alkoxy (wherein the alkyl chain may be optionally further substituted with up to three hydroxyl groups), phenoxy, benzyloxy, $C_1$-$C_4$-alkylthio, alkylamino, a carboxyl group —(C=O)—OR', and alkylamido (preferably carbamoyl), the number of substituents on said alkyl portion being up to five for hydroxyl and up to three, more preferably up to two for any combination of said other substituents; as well as with optionally substituted aryl, optionally substituted heteroaryl, optionally substituted cycloheteroalkyl as defined herein. Cycloalkyl is preferably substituted with hydroxyl.

The alkyl group substituted with up to three independently selected aryl groups preferably refers to "aryl-($C_1$-$C_4$)-alkyl" or diaryl-($C_1$-$C_4$)-alkyl, wherein the aryl is phenyl, naphthyl, indanyl, indenyl, or 1,2,3,4-tetrahydro-naphthalen-1-yl, preferably aryl is phenyl or naphthyl, forming such groups as for example benzyl, diphenylmethyl, phenethyl, phenylpropyl, diphenylpropyl, phenylbutyl, naphthylmethyl or naphthylethyl. The alkyl chain may be further substituted as defined above; for example the alkyl chain may carry an additional hydroxyl group. Furthermore, the alkyl chain may be partially unsaturated, such as a vinyl group. The aryl moiety may optionally be substituted as defined herein; preferably the aryl moiety is substituted with substituents selected from the group consisting of halogen, hydroxyl, ($C_1$-$C_6$)-alkoxy, ($C_1$-$C_6$)-alkyl, halogenated ($C_1$-$C_4$)-alkyl, halogenated ($C_1$-$C_4$)- alkoxy, alkylamido, preferably carbamoyl, and sulfamoyl; the number of said substituents being up to five for halogen, and up to three for any combination of said other substituents. Furthermore, said aryl may be optionally substituted by two groups which are attached to adjacent carbon atoms and are combined into a saturated cyclic 5 or 6 membered ring system, optionally containing up to three heteroatoms, such as N or 0, the number of N atoms being 0-3 and the number of O atoms each being 0-2, as for example substituted with an [1,3]-dioxol group.

The alkyl group substituted with up to three independently selected heteroaryl group preferably refers to "heteroaryl-($C_1$-$C_4$)-alkyl", wherein the heteroaryl is pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, benzoimidazolyl, benzofuran, benzo[b]thiophene, preferably heteroaryl is furyl, indolyl, benzoimidazolyl, pyridinyl, thienyl or imidazolyl, forming such groups as for example benzoimidazolylmethyl, pyridinylmethyl, thienylmethyl, furylmethyl, indolylethyl, thienylethyl, pyridinylethyl, or imidazolylpropyl. The heteroaryl moiety may optionally be substituted as defined herein; preferably the heteroaryl moiety is substituted with substituents selected from the group consisting of ($C_1$-$C_4$)-alkoxy, preferably methoxy, ($C_1$-$C_4$)-alkyl, preferably methyl, or halogenated ($C_1$-$C_4$)-alkyl, the number of said substituents being up to two for any combination of said substituents.

The alkyl group substituted with up to three independently selected cycloheteroalkyl groups preferably refers to "cycloheteroalkyl-($C_1$-$C_4$)-alkyl", wherein the cycloheteroalkyl is pyrrolidinyl, tetrahydrofuryl, tetrahydrothiophenyl, piperidinyl, morpholinyl, thiomorpholinyl, piperazinyl, azepanyl, diazepanyl, oxazepanyl or thiazepanyl, preferably cycloheteroalkyl is piperidinyl, pyrrolidinyl, or morpholinyl, forming such groups as for example morpholinylethyl, morpholinylpropyl, piperidinylethyl or pyrrolidinylethyl.

The term "alkoxy" refers to a group —OR, where R may be alkyl (wherein the alkyl chain may be optionally further substituted as defined herein, preferably with up to three hydroxyl groups or up to five halogen residues), carbonyl, or acyl as defined herein. Preferably, the term "alkoxy" refers to —O—($C_1$-$C_6$)alkyl (or ($C_1$-$C_6$)alkoxy), with the ($C_1$-$C_6$) alkyl group as defined above and optionally substituted with up to three hydroxyl groups.

The term "aryloxy" refers to a group —OAr, where Ar represents aryl as defined herein, which is optionally substituted in the aryl group with up to five independently selected substituents, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents. Preferably, aryloxy refers to phenoxy, optionally substituted as defined above.

The term "arylalkyloxy" refers to a group —O—($C_1$-$C_4$) alkyl-Ar, where Ar represents aryl, which is optionally substituted in the aryl group with up to five independently selected substituents, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents. Preferably, arylalkyloxy refers to benzyloxy, optionally substituted as defined above.

The term "acyl" refers to a group —(C=O)—R, where R may be hydrogen, alkyl (optionally substituted in the alkyl chain with up to five independently selected substituents as defined herein, in particular hydroxyl, halogen or ($C_1$-$C_4$)-alkoxy), aryl or aryl-($C_1$-$C_4$)-alkyl (both optionally substituted in the aryl group with independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents), heteroaryl or heteroaryl-($C_1$-$C_4$)-alkyl (both optionally substituted in the heteroaryl group with up to three independently selected substituents as defined herein), as defined herein. Preferably, the term "acyl" refers to a group —(C=O)—R', where R' represents hydrogen, ($C_1$-$C_4$)alkyl, phenyl, or phenyl-($C_1$-$C_4$)alkyl, preferably benzyl, or heteroaryl-($C_1$-$C_4$)alkyl, preferably indolylmethyl; whereby the phenyl moiety may be optionally substituted with independently selected substituents, especially hydroxyl, halogen, ($C_1$-$C_4$)alkoxy, ($C_1$-$C_4$)-alkyl or halogenated ($C_1$-$C_4$)alkyl, the number of said substituents being up to five for halogen, and up to three for any combination of said other substituents.

The term "carbonyl" represents a preferred selection of the term "acyl" and refers to the group —CHO.

The term "alkylacyl" represents a preferred selection of the term "acyl" and refers to a group —(C=O)-alkyl, preferably —(C=O)—($C_1$-$C_4$)alkyl.

The term "carboxyl" refers to a group —(C=O)—OR, where R may be hydrogen, alkyl (optionally substituted in the alkyl chain with up to five independently selected substituents as defined herein, in particular hydroxyl, halogen or ($C_1$-$C_4$)-alkoxy), aryl or aryl-($C_1$-$C_4$)-alkyl (both optionally substituted in the aryl group with independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy, the number of said substituents being up to five for halogen, and up to three for any combination of said other substituents), heteroaryl or heteroaryl-($C_1$-$C_4$)-alkyl (both optionally substituted in the heteroaryl group with up to three independently selected substituents as defined herein), as defined herein. Preferably, the term "carboxyl" refers to a group —(C=O)—OR', where R' represents hydrogen, ($C_1$-$C_4$)alkyl, phenyl, or phenyl-($C_1$-$C_4$)alkyl, preferably benzyl; whereby the phenyl moiety may be optionally substituted with substituents independently selected from the group consisting of hydroxyl, halogen, ($C_1$-$C_4$) alkoxy, ($C_1$-$C_4$)-alkyl, halogenated ($C_1$-$C_4$)alkyl and halogenated ($C_1$-$C_4$)alkoxy, the number of said substituents being up to five for halogen, and up to three for any combination of said other substituents.

The terms "carboxyl-($C_1$-$C_6$)alkyl" and "carboxyl-($C_1$-$C_4$)alkyl" refer to groups —($C_1$-$C_6$)alkyl-(C=O)OR and —($C_1$-$C_4$)alkyl-(C=O)—OR, respectively, which refer to an alkyl group of 1 to 6 and 1 to 4 carbon atoms, respectively, as described above, substituted with a —(C=O)—OR group as described above. Preferably the carboxyl group refers to —(C=O)—OR', wherein R' represents hydrogen, ($C_1$-$C_4$) alkyl, phenyl, or ($C_1$-$C_4$)alkyl-phenyl, preferably benzyl. Preferred examples of such carboxyl-($C_1$-$C_6$)alkyl groups include acetic acid methyl ester, acetic acid ethyl ester, propionic acid benzyl ester, propionic acid ethyl ester, butyric acid methyl ester, and 3-methyl-butyric acid methyl ester.

The term "amino" refers to the group —NRR', where R and R' may independently be hydrogen, alkyl (optionally substituted in the alkyl chain with up to five independently selected substituents as defined herein, in particular hydroxyl, halogen or ($C_1$-$C_4$)-alkoxy), aryl or aryl-($C_1$-$C_4$)-alkyl (both optionally substituted in the aryl group with up to five independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy, the number of said substituents being up to five for halogen, and up to three for any combination of said other substituents), heteroaryl or heteroaryl-$(C_1$-$C_4)$-alkyl (both optionally substituted in the heteroaryl group with up to three independently selected substituents as defined herein), as defined herein.

The term "alkylamino" represents a preferred selection of the term "amino" and refers to the group —NRR', where R and R' may independently be hydrogen or $(C_1$-$C_4)$alkyl.

The term "alkylthio" or "alkylsulfanyl" refers to a group —SR, where R represents alkyl, optionally substituted in the alkyl chain with up to five substituents as defined herein, preferably hydroxyl, $(C_1$-$C_4)$-alkoxy or halogen; preferably R represents $(C_1$-$C_6)$alkyl, in particular $(C_1$-$C_4)$alkyl, as defined above.

The term "arylthio" or "arylsulfanyl" refers to a group —S—Ar, where Ar represents aryl, which is optionally substituted in the aryl group with independently selected substituents as defined herein, in particular hydroxyl, halogen, $(C_1$-$C_4)$-alkyl, $(C_1$-$C_4)$-alkoxy, halogenated $(C_1$-$C_4)$-alkyl, or halogenated $(C_1$-$C_4)$-alkoxy, the number of said substituents being up to five for halogen, and up to three for any combination of said other substituents. Preferably, arylthio refers to phenylsulfanyl, optionally substituted as defined above.

The term "arylalkylthio" or "arylalkylsulfanyl" refers to a group —S—$(C_1$-$C_4)$alkyl-Ar, where Ar represents aryl, which is optionally substituted in the aryl group with independently selected substituents as defined herein, in particular hydroxyl, halogen, $(C_1$-$C_4)$-alkyl, $(C_1$-$C_4)$-alkoxy, halogenated $(C_1$-$C_4)$-alkyl, or halogenated $(C_1$-$C_4)$-alkoxy, the number of said substituents being up to five for halogen, and up to three for any combination of said other substituents. Preferably, arylalkylthio refers to benzylsulfanyl, optionally substituted as defined above.

The term "alkylsulfonyl" refers to a group —$SO_2$—R, where R represents alkyl, optionally substituted in the alkyl chain with up to five substituents as defined herein, preferably hydroxyl, $(C_1$-$C_4)$-alkoxy or halogen; preferably R represents $(C_1$-$C_6)$alkyl, in particular $(C_1$-$C_4)$alkyl, as defined above.

The term "arylsulfonyl" refers to a group —$SO_2$—Ar, where Ar represents aryl, which is optionally substituted in the aryl group with independently selected substituents as defined herein, in particular hydroxyl, halogen, $(C_1$-$C_4)$-alkyl, $(C_1$-$C_4)$-alkoxy, halogenated $(C_1$-$C_4)$-alkyl, or halogenated $(C_1$-$C_4)$-alkoxy, the number of said substituents being up to five for halogen, and up to three for any combination of said other substituents. Preferably, arylsulfonyl refers to benzenesulfonyl, optionally substituted as defined above.

The term "arylalkylsulfonyl" refers to a group —$SO_2$—$(C_1$-$C_4)$alkyl-Ar, where Ar represents aryl, which is optionally substituted in the aryl group with independently selected substituents as defined herein, in particular hydroxyl, halogen, $(C_1$-$C_4)$-alkyl, $(C_1$-$C_4)$-alkoxy, halogenated $(C_1$-$C_4)$-alkyl, or halogenated $(C_1$-$C_4)$-alkoxy, the number of said substituents being up to five for halogen, and up to three for any combination of said other substituents. Preferably, arylalkylsulfonyl refers to benzylsulfonyl, optionally substituted as defined above.

The term "amido" refers to the group —(C=O)—NRR', where R and R' may independently be hydrogen, alkyl (optionally substituted in the alkyl chain with up to five independently selected substituents as defined herein, in particular hydroxyl, halogen or $(C_1$-$C_4)$-alkoxy), aryl or aryl-$(C_1$-$C_4)$-alkyl (both optionally substituted in the aryl group with independently selected substituents as defined herein, in particular hydroxyl, halogen, $(C_1$-$C_4)$-alkyl, $(C_1$-$C_4)$-alkoxy, halogenated $(C_1$-$C_4)$-alkyl, or halogenated $(C_1$-$C_4)$-alkoxy, the number of said substituents being up to five for halogen, and up to three for any combination of said other substituents), heteroaryl or heteroaryl-$(C_1$-$C_4)$-alkyl (both optionally substituted in the heteroaryl group with up to three independently selected substituents as defined herein), as defined herein.

The term "alkylamido" represents a preferred selection of the term "amido" and refers to the group —(C=O)—NRR', where R and R' may be independently selected from hydrogen or $(C_1$-$C_4)$alkyl.

The term "acylamino" refers to the group —NR—CO—R', where R and R' may independently be hydrogen, alkyl (optionally substituted in the alkyl chain with up to five independently selected substituents as defined herein, in particular hydroxyl, halogen or $(C_1$-$C_4)$-alkoxy), aryl or aryl-$(C_1$-$C_4)$-alkyl (both optionally substituted in the aryl group with independently selected substituents as defined herein, in particular hydroxyl, halogen, $(C_1$-$C_4)$-alkyl, $(C_1$-$C_4)$-alkoxy, halogenated $(C_1$-$C_4)$-alkyl, or halogenated $(C_1$-$C_4)$-alkoxy, the number of said substituents being up to five for halogen, and up to three for any combination of said other substituents), heteroaryl or heteroaryl-$(C_1$-$C_4)$-alkyl (both optionally substituted in the heteroaryl group with up to three independently selected substituents as defined herein), as defined herein. Preferably, acylamino refers to —NH—CO—$(C_1$-$C_4)$-alkyl.

The term "carbonylamino" represents a preferred selection of the term "acylamino" and refers to the group —NR—CO—$CH_2$—R', where R and R' may be independently selected from hydrogen or $(C_1$-$C_4)$alkyl.

The term "sulfonamide" refers to the group —$SO_2$—NRR', wherein R and R' may independently be selected from hydrogen or $(C_1$-$C_4)$alkyl.

Halogenated alkyl, halogenated alkoxy and halogenated alkylthio are substituents in which the alkyl moieties (preferably $(C_1$-$C_6)$alkyl, more preferred $(C_1$-$C_4)$alkyl, and most preferred methyl) are substituted either partially or in full with halogens, generally with chlorine and/or fluorine. Preferred examples of such substituents are trifluoromethyl, trifluoromethoxy, trifluoromethylthio, dichloromethyl, pentafluoroethyl, dichloropropyl, fluoromethyl and difluoromethyl.

The term "cycloheteroalkyl" refers to a four- to eight-membered heterocyclic ring containing at least one heteroatom, such as N, O or S, the number of N atoms being 0-3 and the number of O and S atoms each being 0-1, which system may be saturated, partly unsaturated or hydroaromatic, and which ring can be part of a multiple condensed ring-system in which some rings may be aromatic. Examples of such cycloheteroalkyls include pyrrolidinyl, tetrahydrofuryl, tetrahydrothiophenyl, tetrahydropyridinyl, azetidinyl, thiazolidinyl, oxazolidinyl, piperidinyl, morpholinyl, thiomorpholinyl, piperazinyl, azepanyl, diazepanyl, oxazepanyl, thiazepanyl, dihydro-1H-pyrrolyl, 3,6-dihydro-2H-pyridinyl, 1,3-dihydro-benzoimidazolyl and the like. Preferred examples of such cycloheteroalkyl groups are pyrrolidinyl, morpholinyl, tetrahydrofuryl, piperidinyl or azepanyl.

The cycloheteroalkyl group may optionally be substituted by up to three substituents, independently selected from the group consisting of oxo, alkyl, aryl or aryl-$(C_1$-$C_4)$-alkyl, hydroxyl, $(C_1$-$C_6)$alkoxy, halogenated $(C_1$-$C_6)$alkyl, halogenated $(C_1$-$C_6)$alkoxy, carboxyl-$(C_1$-$C_6)$alkyl, thiol, nitrile, sulfamoyl, sulfonamide, carboxyl, aryloxy or arylalkyloxy, $(C_1$-$C_6)$alkylthio, arylthio or arylalkylthio, amino, amido, acyl, and acylamino, as defined herein, whereby the aryl groups are optionally substituted with independently selected substituents as defined herein, in particular hydroxyl, halogen, $(C_1-C_4)$-alkyl, $(C_1-C_4)$-alkoxy, halogenated $(C_1-C_4)$-alkyl, or halogenated $(C_1-C_4)$-alkoxy, the number of said substituents being up to five for halogen, and up to three for any combination of said other substituents. The substituents of the cycloheteroalkyl groups may be attached to any carbon atom of the cycloheteroalkyl moiety. Substituted cycloheteroalkyl is preferably substituted with oxo, $(C_1-C_4)$alkyl, preferably methyl, phenyl and/or phenyl-$(C_1-C_4)$alkyl, in particular benzyl.

The terms "aryl" or "Ar" refer to an aromatic carbocyclic group comprising 6 to 14, more preferably 6 to 10, carbon atoms and having at least one aromatic ring or multiple condensed rings in which at least one ring is aromatic. Preferably, aryl is phenyl, naphthyl, indanyl, indenyl, or 1,2,3,4-tetrahydro-naphthalen-1-yl.

The term "heteroaryl" refers to an aromatic carbocyclic group of having a single 4 to 8 membered ring or multiple condensed rings comprising 6 to 14, more preferably 6 to 10, ring atoms and containing at least one heteroatom, such as N, O or S, within at least one ring, the number of N atoms being 0-3 and the number of O and S atoms each being 0-1; in which group at least one heterocyclic ring is aromatic. Examples of such groups include pyrrolyl, thienyl, furyl, imidazolyl, thiazolyl, isothiazolyl, oxazolyl, isoxazolyl, pyrazolyl, pyridinyl, pyrimidinyl, pyrazinyl, pyridazinyl, indolyl, quinolinyl, isoquinolinyl, benzothiazolyl, benzoimidazolyl, 1,3-dihydro-benzoimidazolyl, benzofuran, benzo[b]thiophene and the like. Preferably, heteroaryl is quinolinyl, furyl, benzoimidazolyl, pyridinyl, thienyl, indolyl, benzo[b]thiophene, pyridinyl, imidazolyl, pyrazolyl or thiazolyl.

The aryl and the heteroaryl group may optionally be substituted by substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, oxo, thiol, nitro, nitrile, sulfamoyl, sulfonamide, carboxyl, aryloxy or arylalkyloxy, $(C_1-C_6)$alkylthio, arylthio or arylalkylthio, alkylsulfonyl, arylsulfonyl, amino, amido, acyl, and acylamino, as defined herein, the number of said substituents being up to five for halogen, and up to three for any combination of said other substituents; whereby the aryloxy, arylalkyloxy, arylthio or arylalkylthio group may be further optionally substituted in the aryl moiety with independently selected substituents as defined herein, in particular hydroxyl, halogen, $(C_1-C_4)$-alkyl, $(C_1-C_4)$-alkoxy, halogenated $(C_1-C_4)$-alkyl, or halogenated $(C_1-C_4)$-alkoxy, the number of said substituents being up to five for halogen, and up to three for any combination of said other substituents. The heteroaryl group may further be optionally substituted with an aryl group, which may be optionally substituted in the aryl moiety with substituents, especially hydroxyl, halogen, $(C_1-C_6)$alkoxy, $(C_1-C_6)$alkyl, halogenated $(C_1-C_6)$alkyl or halogenated $(C_1-C_6)$alkoxy the number of said substituents being up to five for halogen, and up to three for any combination of said other substituents. The aryl group may further be optionally substituted with a heteroaryl group or a second aryl group.

Substituted aryl is preferably substituted by substituents selected from the group consisting of $(C_1-C_4)$alkyl, halogen, halogenated $(C_1-C_4)$alkyl, preferably halogenated methyl, $(C_1-C_6)$alkoxy, halogenated $(C_1-C_6)$alkoxy, hydroxyl, alkylacyl, carboxyl, nitro, nitrile, acylamino, $(C_1-C_4)$alkylsulfonyl, arylsulfonyl, and sulfamoyl, the number of said substituents being up to five for halogen, and up to three, preferably up to two, for any combination of said other substituents. Preferably substituted aryl is substituted phenyl.

The aryl may be further substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2. Preferably, the two groups which are attached to adjacent carbon atoms, are combined into a saturated cyclic 5 or 6 membered ring system, optionally containing up to three heteroatoms, such as N or O, the number of N atoms being 0-3 and the number of O atoms each being 0-2. This cyclic ring system may optionally be further substituted by an oxo group. Preferred examples of such a substituted aryl groups are benzo[1,3]dioxol and 1,3-dihydro-benzoimidazol-2-one.

Substituted heteroaryl is preferably substituted by up to three, preferably up to two substituents selected from the group consisting of halogen, $(C_1-C_4)$-alkoxy, $(C_1-C_4)$-alkyl, preferably methyl, halogenated $(C_1-C_4)$-alkyl, preferably halogenated methyl, halogenated $(C_1-C_4)$-alkoxy, phenoxy (optionally substituted with up to three, preferably one halogen), benzyloxy, benzenesulfonyl, phenyl or carboxyl-$(C_1-C_4)$-alkyl with a carboxyl group —(C=O)—OR', wherein R' represents hydrogen, $(C_1-C_4)$alkyl, preferably methyl, or $(C_1-C_4)$alkyl-phenyl, preferably benzyl.

The statement is made that when two side chains are found on a single N, they can be combined, including the N to which they are attached, into a heterocyclic ring of 4-, 5-, 6-, 7- or 8 atoms, which can be saturated, partly unsaturated or aromatic, which can optionally contain up to three additional heteroatoms selected from N, O or S, the number of N atoms being 0-3 and the number of O and S atoms each being 0-2; and which ring can be part of a multiple condensed ring-system, in which some rings may be aromatic. Preferred examples of such heterocyclic ring systems, including the N to which the respective side chains are attached, are:

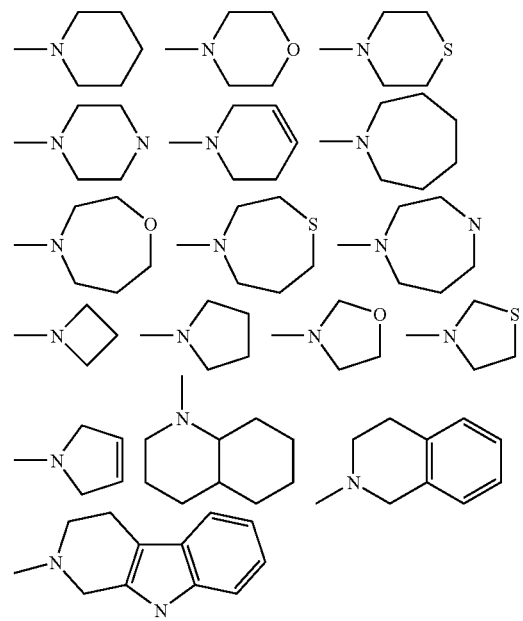

The aforementioned heterocyclic ring system can be optionally substituted by up to three substituents, which can be attached to any carbon or nitrogen atom of the heterocyclic ring system. Preferred examples of substituted heterocyclic ring systems are:

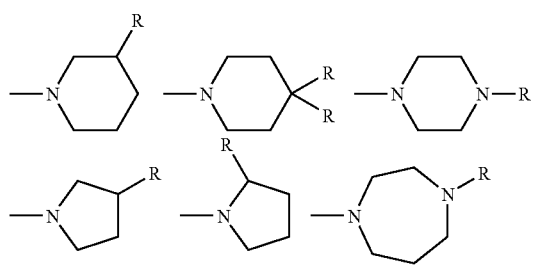

The optional up to three independently selected substituents for the heterocyclic ring system may be chosen among optionally substituted alkyl, halogen, hydroxyl, oxo, thiol, nitro, nitrile, ($C_1$-$C_6$)-alkoxy, aryl, heteroaryl, optionally substituted cycloheteroalkyl, aryloxy, arylalkyloxy, amino, amido, alkylthio, arylthio, arylalkylthio, sulfamoyl, sulfonamide, acyl, carboxyl, and acylamino, as defined herein, whereby all aryl or heteroaryl moieties may be optionally substituted with up to five, preferably up to three independently selected substituents as defined herein. Preferably, the heterocyclic ring system is optionally substituted with substituents independently selected from the group of hydroxyl, oxo, carboxyl, carboxyl-($C_1$-$C_6$)alkyl, amido; optionally substituted cycloheteroalkyl; aryl or aryl-($C_1$-$C_4$)-alkyl (both optionally substituted in the aryl group with substituents independently selected among hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy, the number of said substituents being up to five for halogen, and up to three for any combination of said other substituents, or wherein the aryl moiety may be optionally substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2), heteroaryl, and ($C_1$-$C_8$)-alkyl (optionally substituted with up to five substituents independently selected among hydroxyl, halogen, ($C_1$-$C_4$)-alkoxy, or halogenated ($C_1$-$C_4$)-alkoxy, whereby the alkyl-chain of the ($C_1$-$C_4$)-alkoxy moiety may optionally be further substituted with up to three hydroxyl), the number of said substituents being up to three, more preferably up to two for any combination of said substituents. Even more preferred, the heterocyclic ring system is optionally substituted with substituents independently selected from the group of hydroxyl, oxo, alkylamido, preferably carbamoyl; ($C_1$-$C_4$)-alkyl; cyclo($C_3$-$C_8$)alkyl; a carboxyl group —(C=O)—OR' where R' represents hydrogen or ($C_1$-$C_4$)alkyl; ($C_1$-$C_4$)-alkyl optionally substituted with up to two hydroxyl and/or ($C_1$-$C_4$)-alkoxy groups (whereby the alkyl-chain of the ($C_1$-$C_4$)-alkoxy moiety may optionally be further substituted with up to two, preferably one, hydroxyl groups); phenyl optionally substituted with halogen, ($C_1$-$C_4$)-alkyl, preferably methyl, ($C_1$-$C_4$)-alkoxy or halogenated ($C_1$-$C_4$)-alkyl, preferably halogenated methyl, the number of said substituents on the phenyl moiety being up to five for halogen, and up to three for any combination of said other substituents; phenyl-($C_1$-$C_4$)alkyl, preferably benzyl, optionally substituted in the phenyl group by substituents independently selected among halogen, ($C_1$-$C_4$)-alkyl, ($C_1$-$C_4$)-alkoxy or halogenated ($C_1$-$C_4$)-alkyl, preferably halogen, the number of said substituents being up to five for halogen, and up to three for any combination of said other substituents, or optionally substituted in the phenyl group by two groups which are attached to adjacent carbon atoms and are combined into a saturated or partly unsaturated cyclic 5 or 6-membered ring system, optionally containing up to two O atoms; heteroaryl, preferably pyridinyl, heteroaryl-($C_1$-$C_4$) alkyl or cycloheteroalkyl, preferably pyrrolidinyl or 1,3-dihydro-benzoimidazolyl, which cycloheteroalkyl group is optionally substituted with oxo.

Furthermore, the aforementioned heterocyclic ring system may be substituted by two groups which are attached to the same carbon atom and are combined into a saturated or partly unsaturated cyclic 4, 5, 6, 7, or 8 membered ring system, optionally containing up to three heteroatoms, such as N, O or S, the number of N atoms being 0-3 and the number of O and S atoms each being 0-2. This cyclic ring system may optionally be further substituted by up to three substituents independently selected from oxo, ($C_1$-$C_6$)-alkyl, aryl, preferably phenyl, and aryl-($C_1$-$C_4$)-alkyl, preferably benzyl. Preferred examples of such substituted heterocyclic ring systems are 1,4-dioxa-8-aza-spiro[4.5]decane, 1,3,8-triaza-spiro[4.5]decane, 1,3,8-triaza-spiro[4.5]decan-4-one, 1-Phenyl-1,3,8-triaza-spiro[4.5]decane, and 1-Phenyl-1,3,8-triaza-spiro[4.5]decan-4-one.

The term "pro-drug" as used herein, represents derivatives of the compounds of the invention that are drug precursors which, following administration to a patient, release the drug in vivo via a chemical or physiological process. In particular, pro-drugs are derivatives of the compounds of the invention in which functional groups carry additional substituents which may be cleaved under physiological conditions in vivo and thereby releasing the active principle of the compound (e. g., a pro-drug on being brought to a physiological pH or through an enzyme action is converted to the desired drug form).

The term "pharmaceutically acceptable salts" refers to salt forms that are pharmacologically acceptable and substantially non-toxic to the subject being administered the compounds of the invention. Pharmaceutically acceptable salts of compounds of formula I include conventional and stoichiometrical acid-addition salts or base-addition salts formed from suitable non-toxic organic or inorganic acids or inorganic bases. Acid addition salts, for example, from compounds of formula I with a basic nitrogen atom are formed preferably with organic or inorganic acids. Suitable inorganic acids are, for example, halogenic acids such as hydrochloric acid, sulfuric acid, or phosphoric acid. Suitable organic acids are, for example, carboxylic, phosphonic, or sulfonic acids, for example acetic acid, propionic acid, glycolic acid, lactic acid, hydroxybutyric acid, malic acid, malenic acid, malonic acid, salicylic acid, fumaric acid, succinic acid, adipic acid, tartaric acid, citric acid, glutaric acid, 2- or 3-glycerophosphoric acid and other mineral and carboxylic acids well known to those skilled in the art. The salts are prepared by contacting the free base forms with a sufficient amount of the desired acid to produce a salt in the conventional manner. Compounds containing acidic substituents may also form salts with inorganic or organic bases. Examples of suitable bases for salt formation include, but are not limited to, inorganic bases such as alkali or alkaline earth-metal (e.g., sodium, potassium, lithium, calcium, or magnesium) hydroxides, and those derived from ammonium hydroxides (e.g., a quaternary ammonium hydroxide such as tetramethylammonium hydroxide). Also contemplated are salts formed with pharmaceutical acceptable amines such as ammonia, alkyl amines, hydroxyalkylamines, N-methylglucamine, benzylamines, piperidines, and pyrrolidines and the like. Certain compounds will be acidic in nature, e. g. those compounds which possess a carboxyl or phenolic hydroxyl group. Salts of phenols can be made by heating acidic compounds with any of the above mentioned bases according to procedures well known to those skilled in the art.

As used herein, the term "composition" is intended to encompass a product comprising the specified ingredients in the specified amounts, as well as any product which results, directly or indirectly, from combination of the specified ingredients in the specified amounts.

The phrase "effective amount" as used herein, means an amount of a compound or composition which is sufficient enough to significantly and positively modify the symptoms and/or conditions to be treated (e. g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically acceptable excipient(s)/carrier(s) utilized, and like factors within the knowledge and expertise of the attending physician.

Administration Forms

The method of the invention is primarily intended for treatment in a mammal, preferably in humans and other primates, of steroid hormone dependent diseases or disorders, in particular estradiol dependent diseases or disorders, wherein the steroid hormone dependent disease or disorder preferably requires the inhibition of a 17β-HSD enzyme, preferably the 17β-HSD1 enzyme.

The compounds may be administered orally, dermally, parenterally, by injection, by pulmonal or nasal delivery, or sublingually, rectally or vaginally in dosage unit formulations. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical application or transdermal administration. One or more compounds may be present in association with one or more non-toxic pharmaceutically acceptable auxiliaries such as excipients, adjuvants (e.g. buffers), carriers, inert solid diluents, suspending agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated for example as immediate release, sustained release, pulsatile release, two or more step release, depot or other kind of release formulations.

The manufacture of the pharmaceutical compositions according to the invention may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc. Suitable auxiliaries and further ingredients may be such as recommended for pharmacy, cosmetics and related fields and which preferably are listed in the European Pharmacopoeia, FDA approved or cited in the "GRAS" list (FDA List of food additives that are 'generally recognized as safe' (GRAS)).

One mode of application of the compounds of general formula (I) or of pharmaceutical compositions comprising one or more of said compounds is oral administration, e. g., by tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the compounds suitable for the purposes of the present invention as defined above can be admixed with commonly known and used adjuvants and excipients such as for example, gum arabic, talcum, starch, sugars (such as, e. g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e. g., ethereal oils), solubility enhancers (e. g., benzyl benzoate or benzyl alcohol) or bio-availability enhancers (e.g. Gelucire™). In the pharmaceutical composition, the active ingredients may also be dispersed in a microparticle, e. g. a nanoparticulate, composition.

For parenteral administration, the active agents can be dissolved or suspended in a physiologically acceptable diluent, such as, e. g., water, buffer, oils with or without solubilizers, surface-active agents, dispersants or emulsifiers. Examples of suitable oils include without limitation olive oil, peanut oil, cottonseed oil, soybean oil, castor oil and sesame oil. More generally, for parenteral administration the active agent can be in the form of an aqueous, lipid, oily or other kind of solution or suspension or even administered in the form of liposomes or nano-suspensions.

Transdermal administration can be accomplished by suitable patches, as generally known in the art, specifically designed for the transdermal delivery of active agents, optionally in the presence of specific permeability enhancers. Furthermore, also emulsions, ointments, pastes, creams or gels may be used for transdermal delivery.

Another suitable mode of administration is via intravaginal devices (e. g. vaginal rings) or intrauterine systems (IUS) containing reservoirs for controlled release of active agents over extended periods of time. For rectal or vaginal administration of the drug the compounds may also be administered in the form of suppositories. These compositions can be prepared by mixing the drug with a suitable non-irritating excipient which is solid at ordinary temperatures but liquid at the rectal or vaginal temperature and will therefore melt in the rectum or vagina to release the drug.

Another mode of application is by implantation of a depot implant comprising an inert carrier material, such as biologically degradable polymers or synthetic silicones such as e. g. silicone rubber. Such implants are designed to release the active agent in a controlled manner over an extended period of time (e. g., 3 to 5 years).

It will be appreciated by those skilled in the art that the particular method of administration will depend on a variety of factors, all of which are considered routinely when administering therapeutics. It will also be understood, however, that the actual dosages of the agents of this invention for any given patient will depend upon a variety of factors, including, but not limited to the activity of the specific compound employed, the particular composition formulated, the mode of administration, time of administration, route of administration and the particular site, host, and disease being treated, and furthermore the age of the patient, the body weight of the patient, the general health of the patient, the gender of the patient, the diet of the patient, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests. Optimal dosages for a given set of conditions may be ascertained by those skilled in the art using conventional dosage-determination tests in view of the experimental data for a given compound. For oral administration, an exemplary daily dose generally employed will be from about 0.01 μg/kg to about 100 mg/kg of total body weight, whereby courses of treatment may be repeated at appropriate time intervals. Administration of pro-drugs may be dosed at weight levels that are chemically equivalent to the weight levels of the fully active compounds. The daily dosage for parenteral administration will generally be from about 0.01 μg/kg to about 100 mg/kg of total body weight. A daily rectal dosage regimen will generally be from about 0.01 μg/kg to about 200 mg/kg of total body weight. A daily vaginal dosage regimen will generally be from about 0.01 μg/kg to about 100 mg/kg of total body weight. The daily topical dosage regimen will generally be from about 0.1 μg to about 100 mg administered between one to four times daily. The transdermal concentration will generally be that required to maintain a daily dose of from 0.01 μg/kg to 100 mg/kg of total body weight.

Abbreviations and Acronyms

As employed herein, the following terms have the indicated meanings:

| | |
|---|---|
| ACN | acetonitrile |
| Bn | benzyl |
| BOC | tert-butoxycarbonyl |
| conc. | concentrated |
| EtOAc | ethyl acetate |
| d | day(s) |
| DCM | dichloromethane $CH_2Cl_2$ |
| DHP | 3,4-dihydro-[2H]-pyran |
| Dibal | Diisobutyl-aluminiumhydride |
| DMF | N,N-dimethylformamide |
| DMSO | dimethylsulfoxide |
| DIPEA | N,N-diisopropylethylamine |
| E1 | estron |
| E2 | estradiol |
| EDCl.HCl | 1-(3-dimethylaminopropyl)-3-ethylcarbodiimide hydrochloride |
| ER | estrogen receptor |
| h | hour(s) |
| HMPA | hexamethylphosphoramide |
| HOBT | 1-Hydroxybenzotriazole Hydrate |
| HSD | hydroxysteroid dehydrogenase |
| NAD(P)[H] | nicotinamide-adenine-dinucleotide (phosphate) [reduced NAD(P)] |
| NMR | nuclear magnetic resonance |
| MeOH | methanol |
| min | minute(s) |
| PG | protection group |
| pTosOH | para-toluene sulphonic acid |
| RT | room temperature |
| TBME | tert-butyl methyl ether |
| THF | tetrahydrofuran |
| THP | tetrahydropyran |
| TLC | thin-layer chromatography |
| TMSCl | trimethylsilylchloride |

General Preparative Methods

The compounds of the present invention may be prepared by use of known chemical reactions and procedures. Nevertheless, the following general preparative methods are presented to aid the reader in synthesizing the 17β-HSD1 inhibitors, with specific details provided below in the experimental section to illustrate working examples.

All variable groups of these methods are as described in the generic description if they are not specifically defined below. It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

Flow Diagrams

Certain formula I compounds, in which X represents a bond, A represents CO, Y represents NH or $NR^4$ and n represents an integer from 0 to 5, may be prepared by a reaction as shown in Flow Diagram Ia.

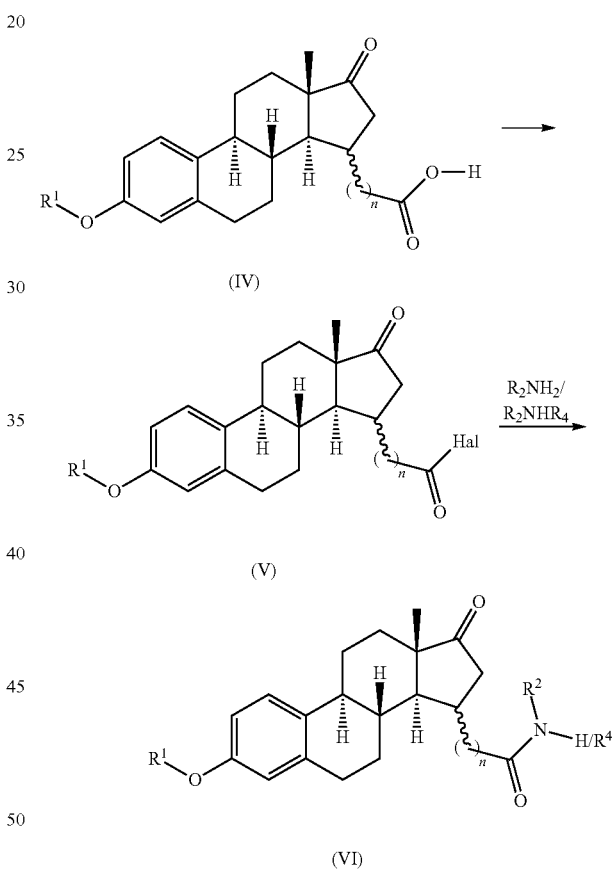

The free acid (IV) may be converted to the reactive acyl halide (V), in particular the acid chloride, by reaction with $SOCl_2$, $COCl_2$, $PCl_5$ or $PBr_3$ or the like. The amide derivatives (VI) may be prepared by a base catalyzed addition-elimination reaction, where the halogen residue is substituted with the appropriate amine $R^2NH_2$ or $R^2NHR^4$ in the presence of a base, for example DIPEA. Alternatively, especially suited for derivatives with n>2, the amide derivatives may be prepared directly from the free acids by nucleophilic substitution with the appropriate amine. Alternatively, the amide derivatives may be prepared directly from the free acids by nucleophilic substitution with the appropriate amine as shown in Flow Diagram Ib:

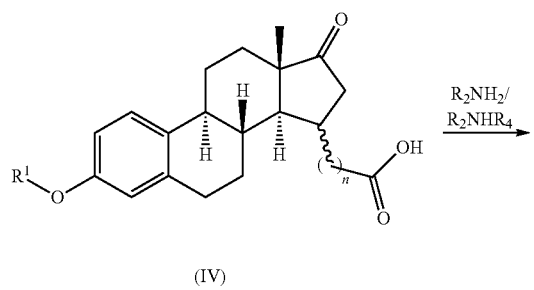

(IV)

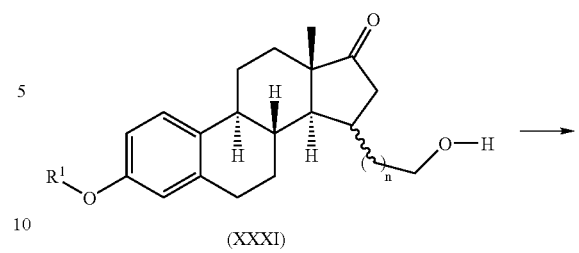

(XXXI)

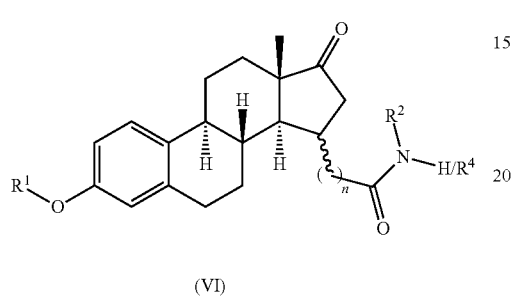

(VI)

Certain formula I compounds, in which X represents a bond, A represents CO, Y represents O, and n represents an integer from 0 to 5, may be prepared by a reaction as shown in Flow Diagram II:

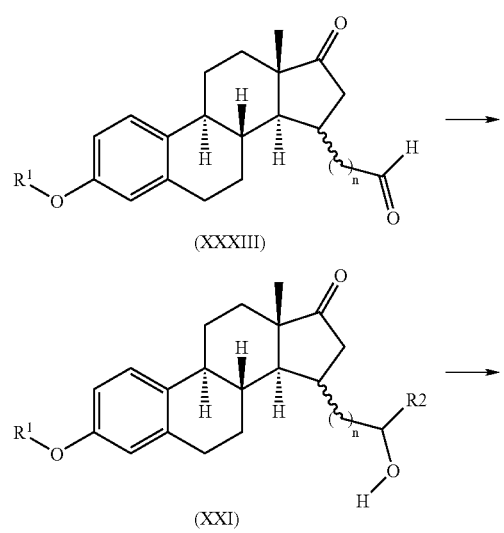

(XXXIII)

(XXI)

(VIII)

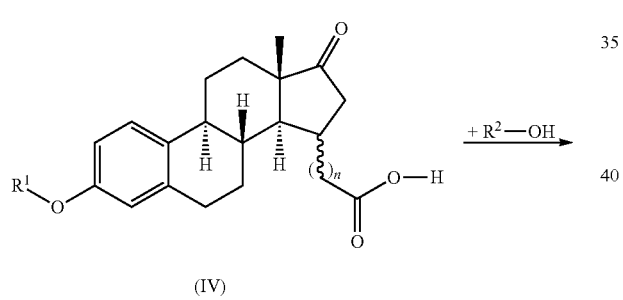

(IV)

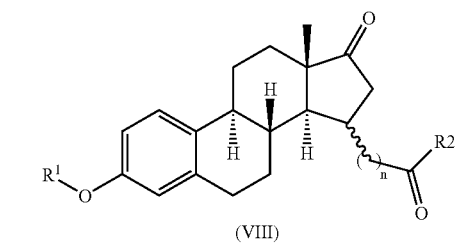

(VII)

The ester derivatives (VII) may be prepared from the free acid (IV) by esterification with the appropriate alcohol $R^2$—OH.

Certain formula I compounds, in which X represents a bond, A represents CO, Y represents a bond, and n represents an integer from 0 to 5, may be prepared by a reaction as shown in Flow Diagram III:

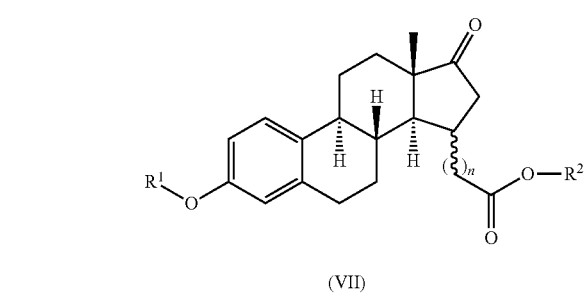

The alcohol (XXXI) may be converted to the corresponding aldehyde (XXXIII) via Dess-Martin Oxidation. Subsequently the aldehyde may be converted by a nucleophilic addition-elimination reaction with a Grignard or other organometallic reagent, substituted with the appropriate R2 residue to the corresponding secondary alcohol (XXI), which thereafter can be oxidized again to the desired ketone (VIII).

Certain formula I compounds, in which X represents a bond, A represents CO, Y represents NH—$NR^4$ or NH—NH, and n represents an integer from 0 to 5, may be prepared by a reaction as shown in Flow Diagram IVa.

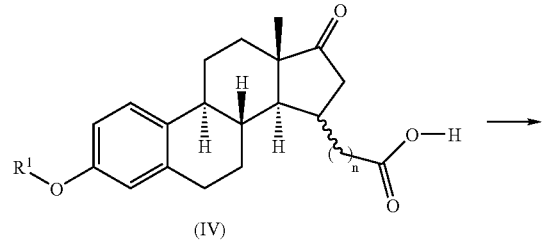

(IV)

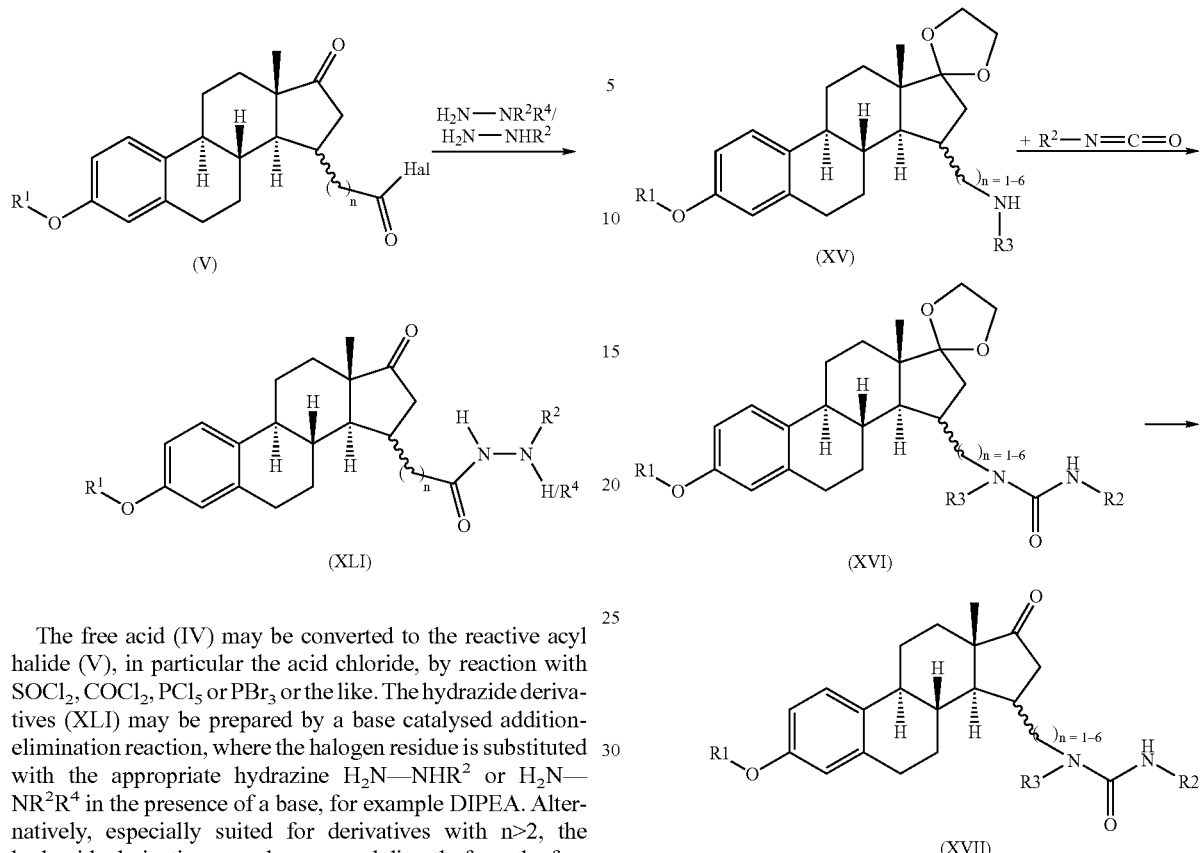

The free acid (IV) may be converted to the reactive acyl halide (V), in particular the acid chloride, by reaction with $SOCl_2$, $COCl_2$, $PCl_5$ or $PBr_3$ or the like. The hydrazide derivatives (XLI) may be prepared by a base catalysed addition-elimination reaction, where the halogen residue is substituted with the appropriate hydrazine $H_2N$—$NHR^2$ or $H_2N$—$NR^2R^4$ in the presence of a base, for example DIPEA. Alternatively, especially suited for derivatives with n>2, the hydrazide derivatives may be prepared directly from the free acids by nucleophilic substitution with the appropriate hydrazine using e.g. polymer bound carbodiimid, HOBT and DCM, as shown in Flow Diagram IVb:

The urea derivatives of the general formula (XVII) may be prepared by the reaction of the amine building block (XV) with an appropriately substituted Isocyanate ($R^2$—$N=C=O$). After the addition, the ketal function is converted into the keto function. Alternatively, the amine may be first reacted with carbodiimidazol or triphosghen to form a reactive carbamoyl compound, which than can react further with a suitable amine $R^2$ $R^4$—NH. A further synthesis variant may use the unprotected amine (XXIX) as starting material for the reaction with an appropriately substituted Isocyanate ($R^2$—$N=C=O$) as shown in Flow Diagram Vb

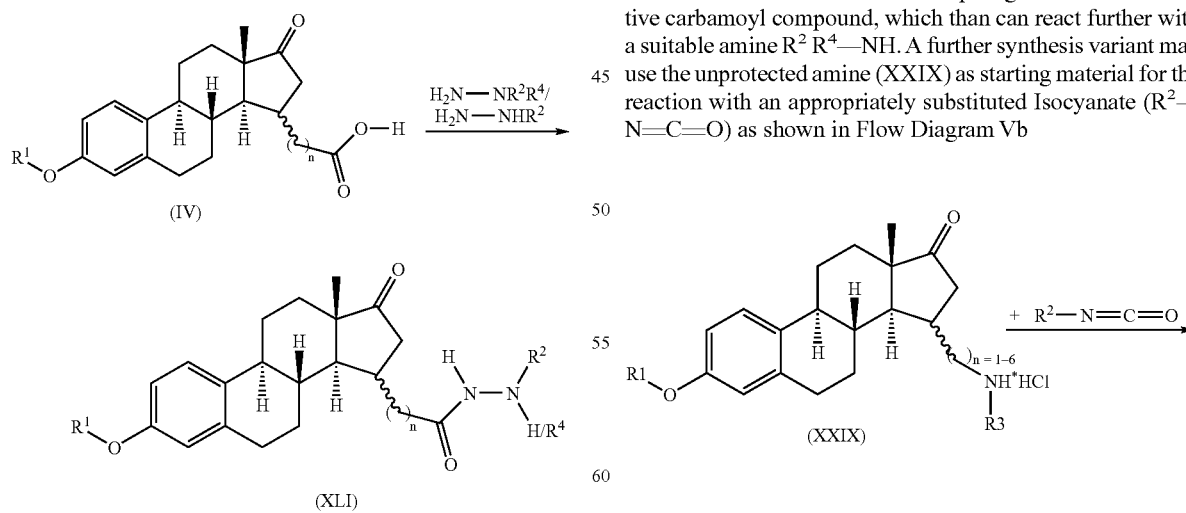

Certain formula I compounds, in which X represents a NH, A represents CO, Y represents NH, and n represents an integer from 1 to 6, may be prepared by a reaction as shown in Flow Diagram Va:

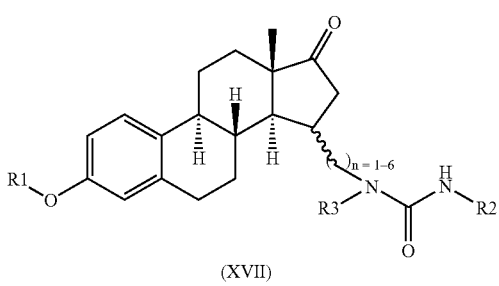

(XVII)

Certain formula I compounds, in which X represents a $NR^3$, A represents $SO_2$, Y represents NH, and n represents an integer from 1 to 6, may be prepared by a reaction as shown in Flow Diagram VI

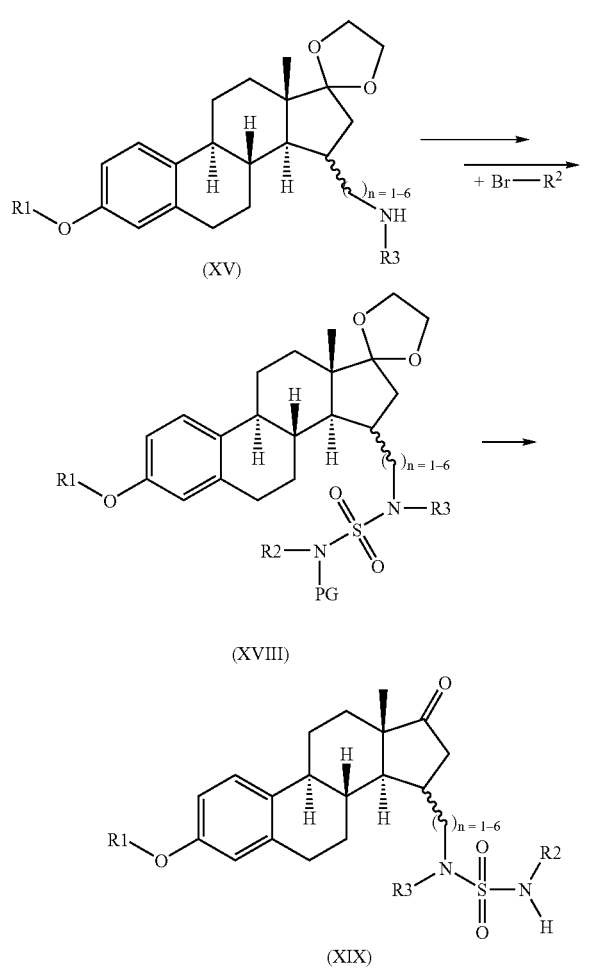

In a first step, the amine building block (XV) may be converted into a protected, for example Boc-protected, sulfamide compound by a reaction with the appropriately protected chlorosulfonyl isocyanate. In a second step, the protected sulfamide compound is allowed to react with the appropriate Bromo-reagent ($R^2$—Br) to provide the still protected, substituted sulfamide derivative of the formula (XVIII). After deprotection, the desired N-substituted sulfamide derivative of formula (XIX) is obtained.

Certain formula I compounds, in which X represents a $NR^3$, A represents CO, Y represents O, and n represents an integer from 1 to 6, may be prepared by a reaction as shown in Flow Diagram VII:

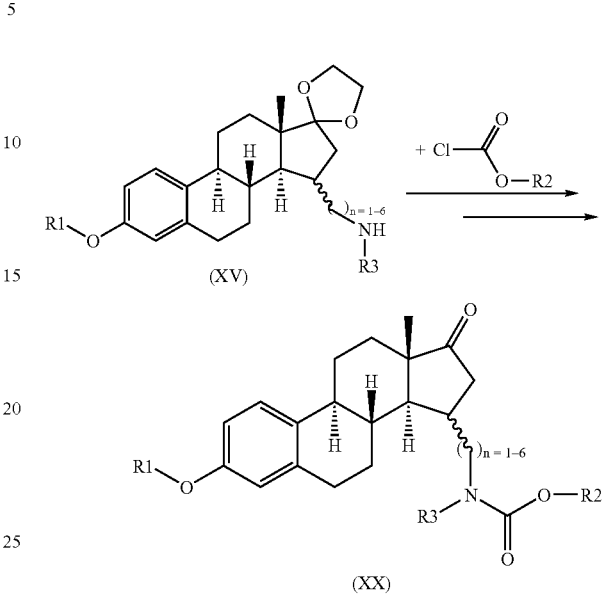

The carbamate derivatives of the general formula (XX) may be prepared by the reaction of the amine building block (XV) with an appropriate chloroformic acid ester ($R^2$—O—CO—Cl). After the addition-elimination reaction, in a second step the ketal function is converted into the keto function.

Certain formula I compounds, in which X represents a $NR^3$, A represents $SO_2$, Y represents O, and n represents an integer from 1 to 6, may be prepared by a reaction as shown in Flow Diagram VIII:

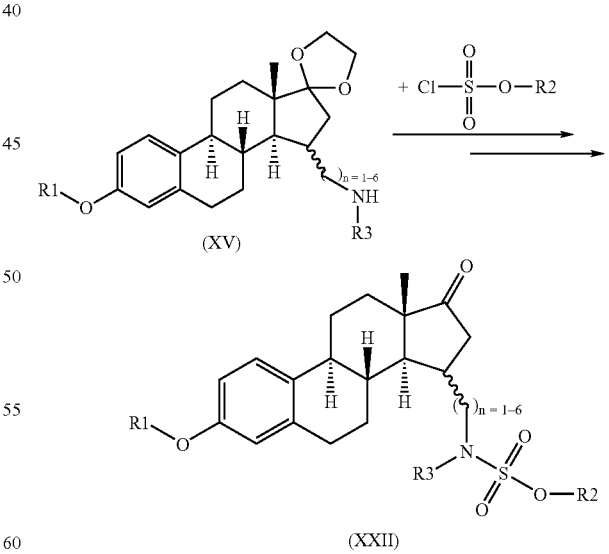

The sulfamate derivatives of the general formula (XXII) may be prepared by the reaction of the amine building block (XV) with an appropriate chlorosulfonic acid ester ($R^2$—O—$SO_2$—Cl). After the addition-elimination reaction, in a second step the ketal function is converted into the keto function.

Certain formula I compounds, in which X represents a NR³, A represents CO, Y represents a bond, and n represents an integer from 1 to 6, may be prepared by a reaction as shown in Flow Diagram IXa:

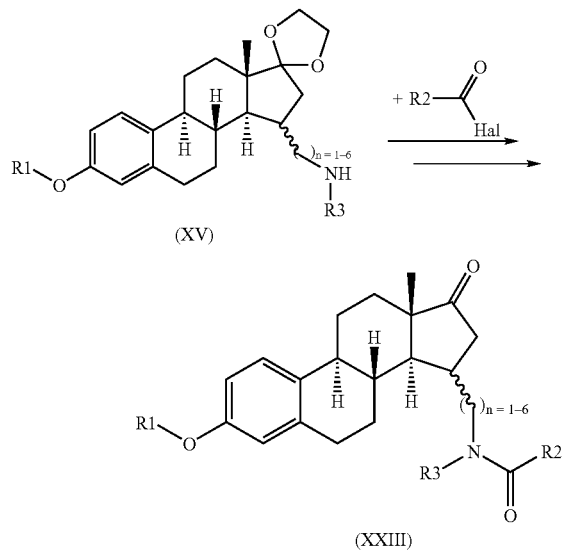

(XV)

(XXIII)

The "retro"-amide derivatives of the general formula (XXIII) may be prepared by the reaction of the amine building block (XV) with an appropriate acid halide, e.g. an acid chloride (R²—CO—Cl). After the addition-elimination reaction, in a second step the ketal function is converted into the keto function. Alternatively, the reaction with an appropriate acid halide, e.g. an acid chloride (R²—CO—Cl), can be performed using the amino-hydrochloride salt of the estrone (XXIX) as starting material as shown in the following Flow Diagram IXb:

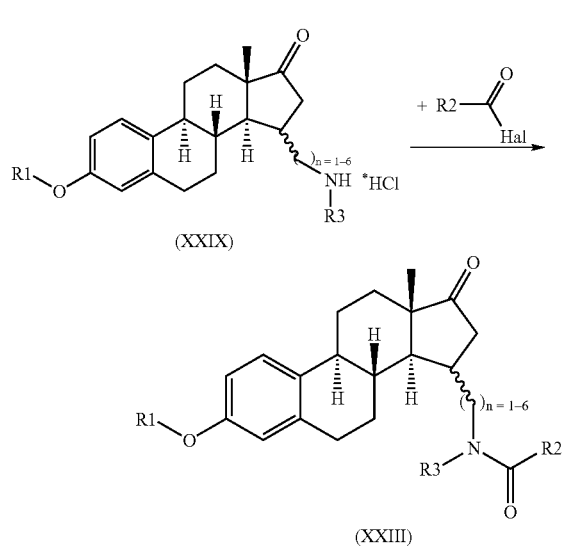

(XXIX)

(XXIII)

Certain formula I compounds, in which X represents a NR³, A represents SO₂, Y represents a bond, and n represents an integer from 1 to 6, may be prepared by a reaction as shown in Flow Diagram Xa:

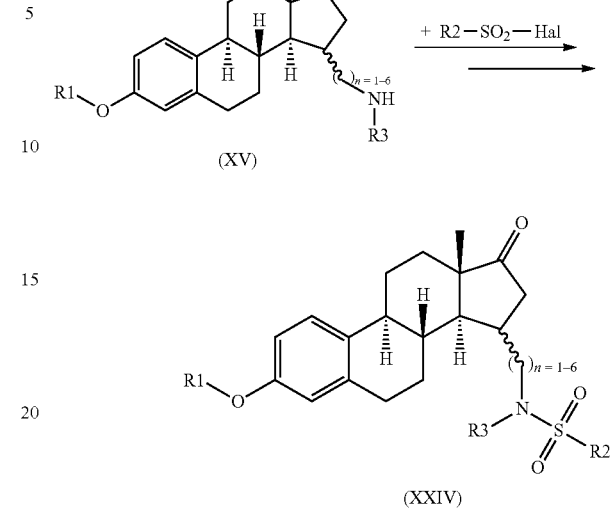

(XV)

(XXIV)

The sulfonamide derivatives of the general formula (XXIV) may be prepared by the reaction of the amine building block (XV) with an appropriate sulfonic acid halide, e.g. a sulfonic acid chloride (R2-SO₂—Cl). After the addition-elimination reaction, in a second step the ketal function is converted into the keto function. Alternatively, the reaction with an appropriate sulfonic acid halide, e.g. sulfonic acid chloride (R²—SO₂—Cl), can be performed using the amino-hydrochloride salt of the estrone (XXIX) as starting material as shown in the following Flow Diagram Xb:

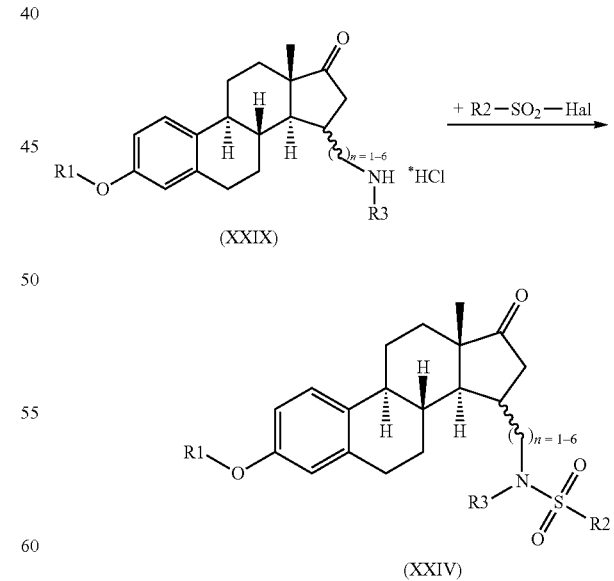

(XXIX)

(XXIV)

Certain formula I compounds, in which X represents a NR³, A represents CO, Y represents NH—SO₂, and n represents an integer from 1 to 6, may be prepared by a reaction as shown in Flow Diagram XI:

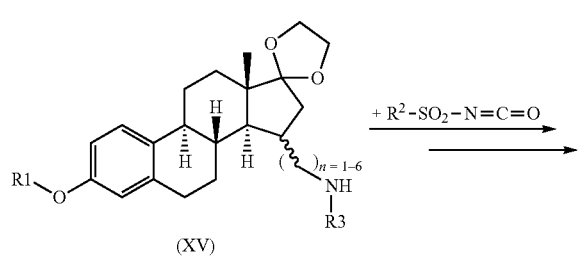

(XV)

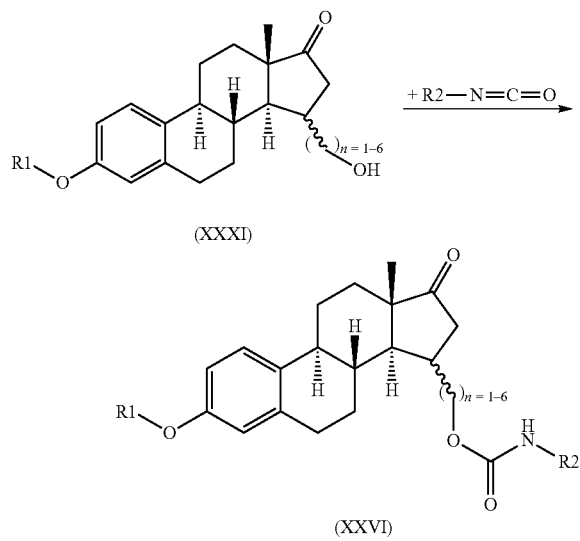

(XXV)

The sulfonyl urea derivatives of the general formula (XXV) may be prepared by the reaction of the amine building block (XV) with an appropriately substituted sulfonyl isocyanate ($R^2$—$SO_2$—N=C=O). After the addition, the ketal function is converted into the keto function.

Certain formula I compounds, in which X represents a O, A represents CO, Y represents $NR^4$, and n represents an integer from 1 to 6, may be prepared by a reaction as shown in Flow Diagram XII:

(XXXI)

(XXVI)

The "retro"-carbamate derivatives of the general formula (XXVI) may be prepared by the reaction of the estrone alcohol building block (XXXI) with an appropriately substituted isocyanate ($R^2$—N=C=O) and subsequent purification.

Certain formula I compounds, in which X represents a O, A represents CO, Y represents a bond, and n represents an integer from 1 to 6, may be prepared by a reaction as shown in Flow Diagram XIII:

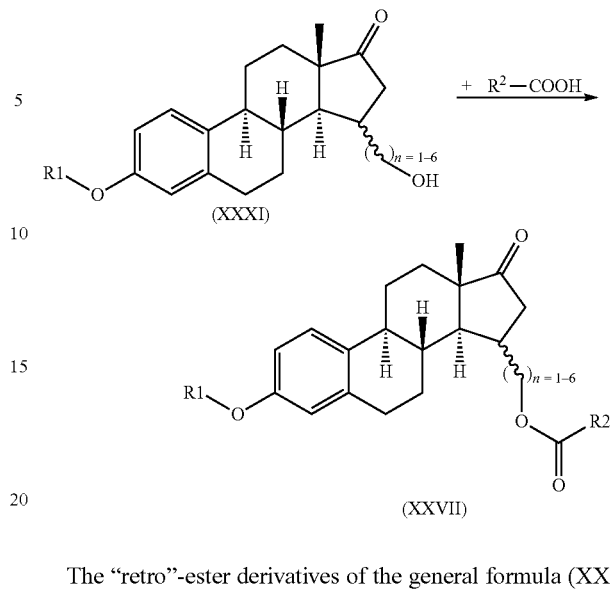

(XXXI)

(XXVII)

The "retro"-ester derivatives of the general formula (XXVII) may be prepared by the esterification of the estrone alcohol building block (XXXI) with the appropriate carboxylic acid $R^2$—COOH and subsequent purification.

Certain formula I compounds, in which X represents a O, A represents CO, Y represents NH—$SO_2$—$NR^4$, and n represents an integer from 1 to 6, may be prepared by a reaction as shown in Flow Diagram XIV:

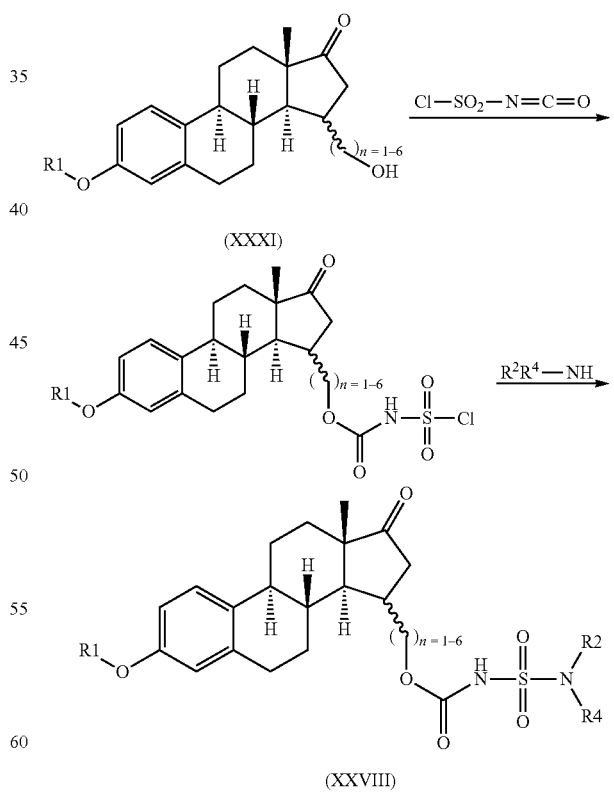

(XXXI)

(XXVIII)

The sulfonylcarbamate derivatives of the general formula (XXVIII) may be prepared by a two-step synthesis: In a first step, the estrone alcohol building block (XXXI) is converted to the chlorosulfonylcarbamate intermediate by reaction with chlorosulfonyl isocyanate. Subsequently, the intermediate is allowed to react with the appropriate primary or secondary amine HNR²R⁴ in order to give the desired sulfonylcarbamate derivative.

Certain formula I compounds, in which X-A-Y represents O, and R2 is different from H may be prepared by a reaction as shown in Flow Diagram XV:

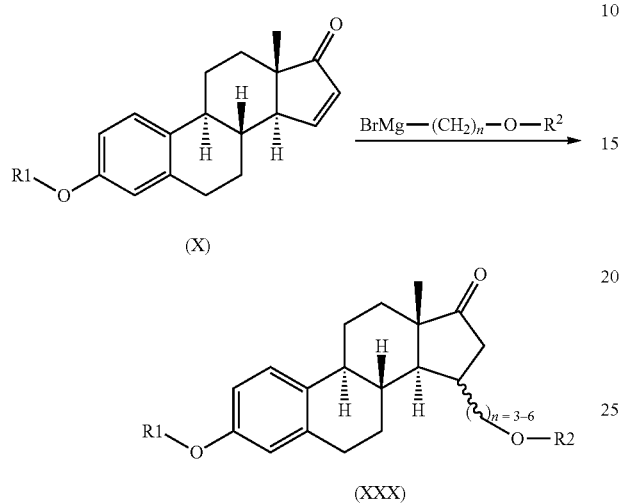

(X)

The ether derivatives of the general formula (XXX) may be prepared the reaction of an appropriate Grignard reagent BrMg—(CH$_2$)$_n$—O—R² (for n=3-6) with the 15,16-unsaturated estrone derivative of formula X. Alternatively, ether derivatives may be prepared by derivatisation of the corresponding alcohol of the general formula (XXXI).

The synthesis of certain formula I compounds, in which X-A-Y represents O, R2 represents H, and n represents an integer from 1 to 6, according to general formula (XXXI) is described within the section "Intermediates".

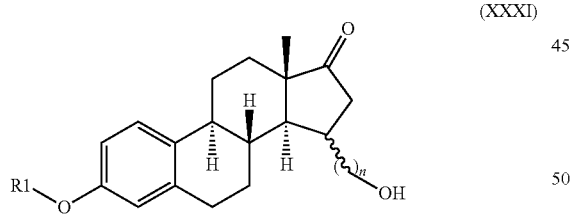

(XXXI)

Numbering of Compound Formulas and Intermediates

The general structure formulas are typically designated with a number in roman format, followed by α or β indicating the stereochemistry at the C15 atom of the estron core if necessary. If the number of methylene groups attached at the C15 position is specified (i.e. the value of "n"), the roman number is followed by a hyphen and a number indicating the amount of methylene groups. Finally, a letter a, b or c is attached after the number "n", indicating the nature of the substituent R1 at the O-atom in C3 position of the estron core (a=hydrogen, b=methyl, and c=benzyl).

For example, compound IV is the general acid building block:

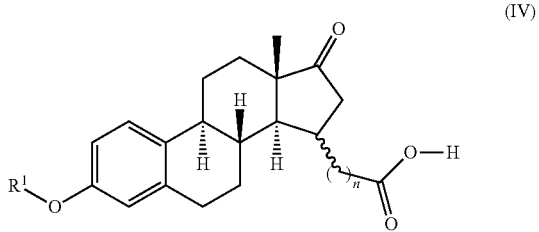

Therefore, a compound IVβ-3a would represent a derivative of IV with β stereochemistry at C15, three methylene groups and a hydroxy group in C3 position, i.e.:

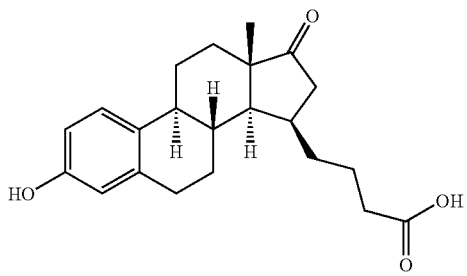

If particular structures of synthesized examples falling under a general formula are presented, then the designation of the general formula is followed by the particular number of this example, i.e. Example No. 652 of formula (XXXIIIα-1a)-652

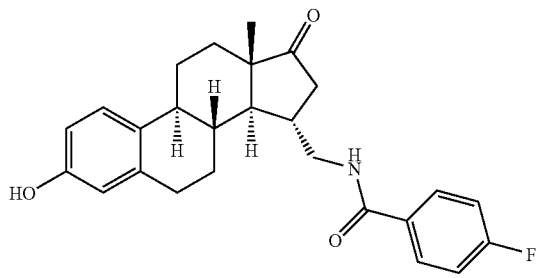

This example 652 is a particular compound of the general formula XXXIIIα-1a, wherein R2 is a 4-fluoro-phenyl residue.

Intermediates

I. The 15, 16-unsaturated Estrone of formula X

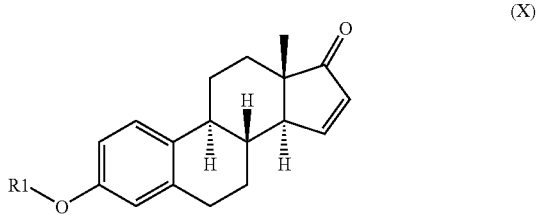

The enone intermediate of formula X with R¹=Benzyl as protecting group can be prepared according to a procedure described by Labaree and depicted within the following scheme 1 [Labaree et al. (2003) J. Med. Chem. 46:1886-1904].

II. The Ketal Derivative of the Estron-15α-yl-carbaldehyde of Formula XIII-0

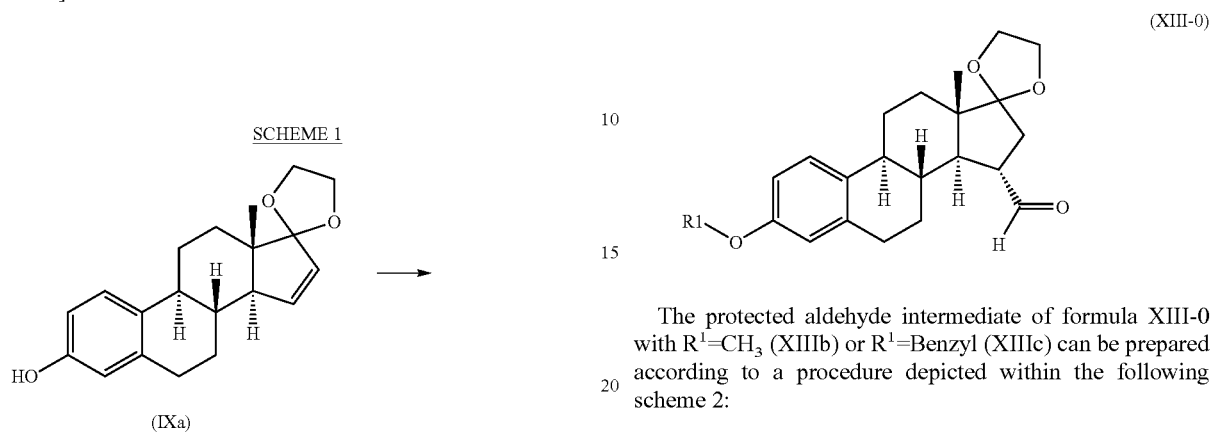

The protected aldehyde intermediate of formula XIII-0 with R¹=CH₃ (XIIIb) or R¹=Benzyl (XIIIc) can be prepared according to a procedure depicted within the following scheme 2:

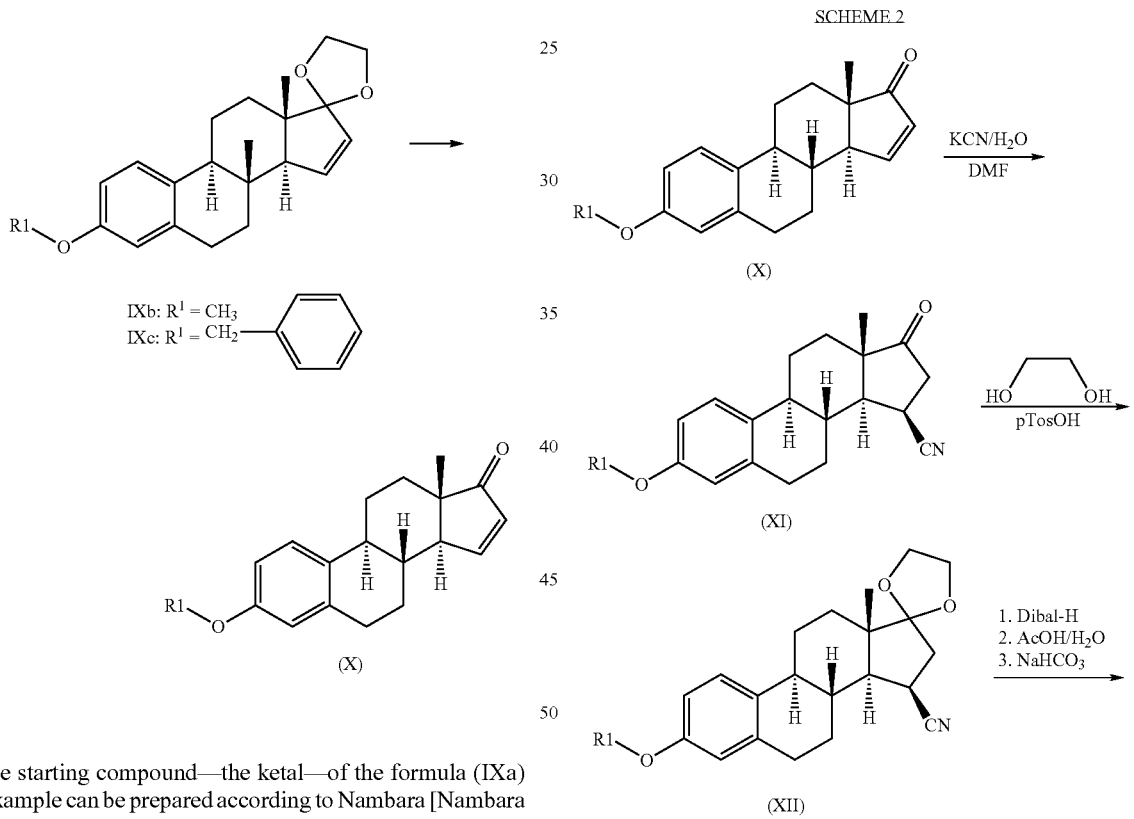

The starting compound—the ketal—of the formula (IXa) for example can be prepared according to Nambara [Nambara et al. (1976) Steroids 27:111-122]. The methyl derivative of formula (IXb, R1=CH₃) is prepared using MeJ and acetone, whereas the Benzyl-derivative of formula (IXc, R1=benzyl) is prepared using Benzylbromid, DIPEA and acetone. Enone intermediates with other substituents in R¹, in particular optionally substituted $C_1$-$C_4$-alkyl, can be prepared accordingly by using the appropriate optionally substituted $C_1$-$C_4$-alkyl-bromide or $C_1$-$C_4$-alkyl-iodide. Finally, the ketal derivative is hydrolysed to give the appropriate enone-derivative X (Xb for R1=CH₃ and Xc for R1=benzyl). Alternatively, the enone intermediate of formula X can be prepared according to a procedure described by Poirier et al. [Poirier et al. (1991) Tetrahedron, 47(37):7751-7766].

The 15,16-unsaturated estrone of formula (X) was converted into the corresponding cyano-estrone (XI) by a cyanide Michael addition at the D-ring. The nitrile was introduced in the beta configuration as was proven by 2D-NMR. Epimerization of this stereocenter had been accomplished in a following step. First the ketone functionality was protected as the acetal (XII), followed by conversion of the nitrile to the corresponding aldehyde (XIII-0) by the addition of Dibal-H to the nitrile and the consecutive hydrolysis of the imine product. At this stage the epimerization took place for about 90% (2D-NMR). Consecutive washing of the mixture with aqueous bicarbonate gave the α-isomer with a d.e≦98%.
Detailed Synthesis Cyanoestrone XIb: 3-Methoxy-17-oxo-estra-1,3,5(10)-triene-15β-carbonitrile Cyanoestrone XIc: 3-Benzyloxy-17-oxo-estra-1,3,5(10)-triene-15β-carbonitrile KCN (17.0 g, 261 mmol) (NaCN can also be used) was added to DMF (200 mL) at ambient temperature. H$_2$O (100-200 mL; minimum amount) was added until an almost clear solution was obtained. Unsaturated estrone Xb or Xc (25 mmol) was dissolved in DMF (400 mL) and added dropwise to the KCN solution as slow as possible during 8-10h and that a clear solution is maintained. After addition is complete the reaction mixture was stirred overnight. Water (1-2L) was slowly added to the stirring reaction mixture. The product was isolated by filtration and triturated two times with H$_2$O. The white solid was dissolved in DCM, the residual water was removed, and the organic layer was dried with Na$_2$SO$_4$. Evaporation to dryness gave cyano estrone XIb as a white foam in yields varying from 54%-90% (0.21 mol scale). Cyano estrone XIc needed additional purification by column chromatography (DCM/TBME, gradient 0-20%): yield 51% as a white foam when carried out on a 20 mmol scale.

Ketal XIIb: Ketal of 3-Methoxy-17-oxo-estra-1,3,5(10)-triene-15β-carbonitrile

Ketal XIIc: Ketal of 3-Benzyloxy-17-oxo-estra-1,3,5(10)-triene-15β-carbonitrile

A suspension of cyano estrone XIb or XIc (89.2 mmol), ethylene glycol (11.7 mL, 178 mmol), and p-TSA (0.5 g, cat.) in diglyme (500 mL) was stirred overnight. In most cases a clear solution was obtained. The reaction mixture was concentrated in vacuo on a water bath at 70° C. until precipitation started. After cooling to RT, the product was collected by filtration. The mother liquor was evaporated to dryness and the residue was recrystallized from diglyme. Yield of XIIb: 28.6 g (100%) as white flakes. On a 4.4 mmol scale, compound XIIc was also obtained in 100% yield.

Aldehyde XIII-0b: Ketal of 3-Methoxy-17-oxo-estra-1,3,5(10)-triene-15α-carbaldehyde Aldehyde XIII-0c: Ketal of 3-Benzyloxy-17-oxo-estra-1,3,5(10)-triene-15α-carbaldehyde A solution of ketal XIIb or XIIc (3.7 mmol) in dry THF (50 mL) was added dropwise to Dibal-H (20 mL, 25% in toluene, 30 mmol) in THF at −80° C. After addition is complete the reaction is stirred for 20 min and slowly warmed to RT overnight. The reaction is quenched at −10-0° C. by dropwise addition of 30% AcOH in H$_2$O (100-300 mL) until no gas evolves anymore and a clear solution is obtained. EtOAc (200 mL) was added and the layers were separated. The aqueous layer was extracted with EtOAc (3×200 mL). The combined organic layers were washed with NaHCO$_3$(aq) until no gas evolves and dried with Na$_2$SO$_4$. Column chromatography (DCM to remove impurities, TBME/DCM (1:1) to collect the product) gave XIII-0c (1.0 g) in 62% yield and XIII-0b in 85% yield (0.14 mol flash CH$_2$Cl$_2$).

III. Compounds of Formula IV (Acid Building Block): Estron-15-yl-C$_0$-C$_5$-alkyl-carboxylic acid Acid Building Block IV-0: (n=0)

IV-0b: (n=0 and R1=CH$_3$): 3-Methoxy-17-oxo-estra-1,3,5(10)-trien-15α-yl-carboxylic Acid IV-0c: (n=0 and R1=Bn): 3-benzyloxy-17-oxo-estra-1,3,5(10)-trien-15α-yl-carboxylic Acid

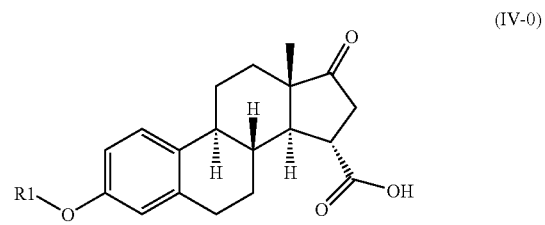

(IV-0)

The individual steps in the synthesis of acid building block of the formula IV-0b are depicted in the following scheme 3.

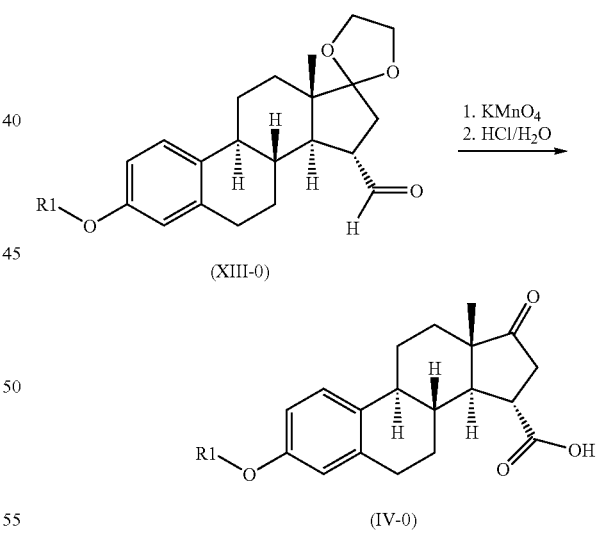

SCHEME 3

The ketal derivative of the 17-oxo-estra-1,3,5(10)-trien-15α-yl-carbaldehyde of formula XIII-0 is oxidized to the corresponding carboxylic acid and converted into the unprotected 15α-substituted estrone derivative of formula IV-0.
Detailed Synthesis IV-0b: (n=0 and R1=CH$_3$): 3-Methoxy-17-oxo-estra-1,3,5(10)-trien-15α-yl-carboxylic Acid KMnO$_4$ (7.5 g, 47.6 mmol) dissolved in H$_2$O (80 mL) was added dropwise to a solution of aldehyde XIII-0b (10.0 g, 28 mmol) in acetone (400 mL) at such a rate that 45° C.<T<55° C. After the addition is complete, the mixture was stirred at 50° C. for 1 h, cooled to RT, and treated (dropwise) with NaHSO$_3$(aq) until the purple color had gone. The reaction mixture was filtered through Celite and, consecutively, H$_2$O (400 mL) and AcOH (20 mL) were added. The emulsion obtained was evaporated until a sticky oil was obtained at the bottom of the flask. The clear supernatant was removed by decantation. Upon drying of the oil in vacuo, yellowish foam was obtained (10.0g, 100%). The foam was dissolved in CH$_2$Cl$_2$ (100-200 mL) and stirred with HCl (100 mL, 30% in H$_2$O) during a weekend. The aqueous layer was extracted with CH$_2$Cl$_2$ (2×200 mL). The combined organic layers were extracted with 4N NaOH (3×200 mL). The aqueous layer was acidified to pH~1 and extracted with CH$_2$Cl$_2$. The organic layer was dried with Na$_2$SO$_4$ and concentrated to ~20 mL and transferred onto a silica column (CH$_2$Cl$_2$). Elution with CH$_2$Cl$_2$/AcOH 99:1 gave compound IV-0b (4.6 g, 50%, 90% purity). Final purification was a recrystallization from CH$_2$Cl$_2$/heptane (3×) by evaporation of CH$_2$Cl$_2$ at ambient pressure and at reflux temperature until crystallization occurs.

Acid Building Block IV-1: (n=1)

IV-1b: (n=1 and R1=CH$_3$): 3-Methoxy-17-oxo-estra-1,3,5(10)-trien-15α-yl-acetic Acid IV-1c: (n=1 and R1=Bn): 3-Benzyloxy-17-oxo-estra-1,3,5(10)-trien-15α-yl-acetic Acid

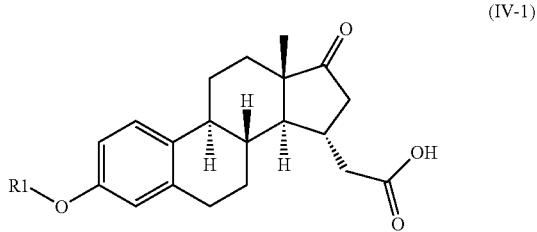

The acid building block IV-1 could be synthesized via two different routes. The individual steps of the first synthesis route of acid building block IV-1 are depicted in the following scheme 4. The same kind of procedure can be applied for n=2 and for other side chains within the R$^1$ position.

SCHEME 4

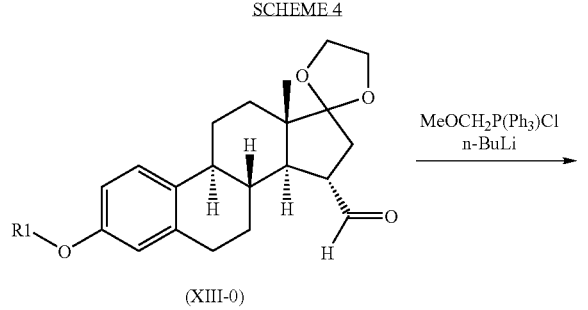

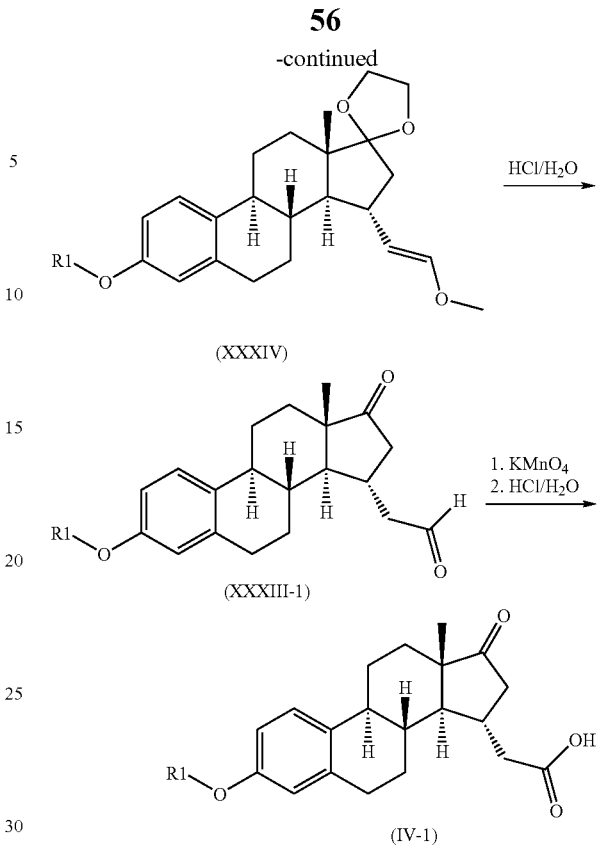

The ketal derivative of the 17-oxo-estra-1,3,5(10)-trien-15α-yl-carbaldehyde of formula XIII-0 is converted into the methyl enol ether of the formula XXXIV via a Wittig reaction with MeOCH$_2$LiP(Ph)$_3$. Hydrolysis with HCl$_{(aq)}$ delivered the unprotected acetaldehyde derivative XXXIII-1. The acetaldehyde derivative is then further oxidized to the corresponding carboxylic acid IV-1.

Detailed Synthesis

XXXIVb: 3-Methoxy-15α-(2-methoxy-vinyl)-estra-1,3,5(10)-trien-17-one n-BuLi (16.8 mL, 2.5M, in hexanes, 42 mmol) was added dropwise to a suspension of (methoxymethyl)triphenylphosphonium chloride (14.4 g, 42 mmol) in THF (120 mL) at −78° C. Upon slowly warming the reaction to RT, the orange suspension turned into an intense red clear solution. After 3 h, the reaction mixture was cooled to −78° C. and a solution of the aldehyde XIII-0b (10.0 g, 28 mmol) in THF (100 mL) was added. The reaction mixture was allowed to warm to RT overnight and was evaporated to dryness. The residue was suspended in NaOH (1N, 200 mL). Extraction with CH$_2$Cl$_2$ followed by flash column chromatography (CH$_2$Cl$_2$/heptane, 1:1) to remove the main impurities (OP(Ph)$_3$) gave a crude mixture of XXXIVb as a white foam (8.9 g).

XXXIII-1 b: 3-Methoxy-17-oxo-estra-1,3,5(10)-trien-15α-yl-acetaldehyde

HCl$_{(aq)}$ (6N, 200 mL) was added to a mixture containing XXXIVb (8.9 g) dissolved in CH$_2$Cl$_2$ (200 mL) and this reaction mixture was stirred overnight. Drying the organic layer (Na$_2$SO$_4$) and evaporation to dryness was followed by column chromatography (CH$_2$Cl$_2$/heptane, 1:1 gradually increasing the polarity to $CH_2Cl_2$/TBME, 8:3). Aldehyde XXXIII-1 b was isolated as the main product (2.89 g, 30%).

IV-1b: (n=1 and R1=$CH_3$): 3-Methoxy-17-oxo-estra-1,3,5(10)-trien-15α-yl-acetic Acid Oxidation of XXXIII-1b (2.3 g, 6.7 mmol), analogously to the procedure for IV-0b (see above), gave compound IV-1b (2.1 g, 91%, almost 95% pure). The product was further purified by column chromatography ($CH_2Cl_2$/AcOH, (95:5)) and by a consecutive crystallization from $CH_2Cl_2$/heptane (3×).

Alternative Synthesis Route for the Acid Building Block IV-1: (n=1)

IV-1b: (n=1 and R1=$CH_3$): 3-Methoxy-17-oxo-estra-1,3,5(10)-trien-15α-yl-acetic Acid Alternatively, compound IV-1b can be prepared directly from the enone derivative of formula X according to the following synthesis scheme 5:

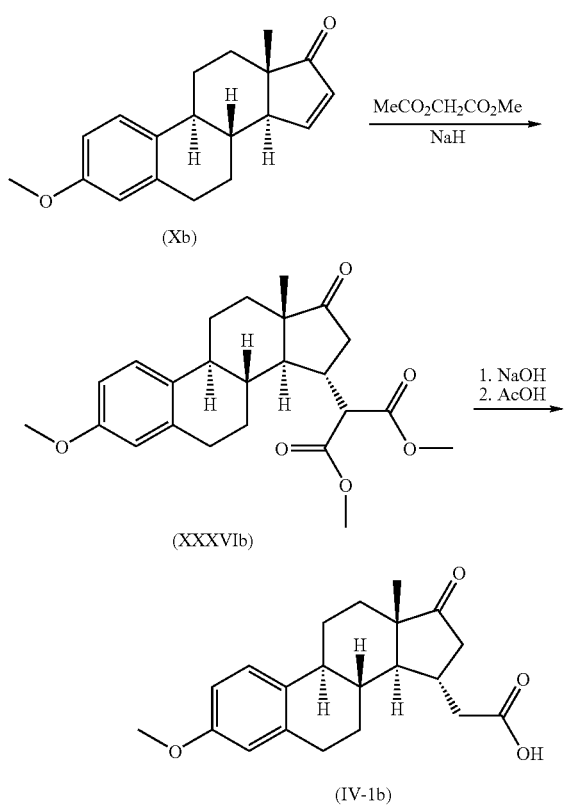

A Michael addition of the dimethylmalonate-anion to the enone derivative delivered the diester XXXVIb, which was converted into the acid building block of formula IV-b by alkaline ester hydrolysis and decarboxylation in refluxing acetic acid.

Detailed Synthesis

XXXVIb: Dimethylester of the Estrone-carbaldehyde

The dimethyl malonate anion was prepared by the dropwise addition of a dimethylmalonate (18.7 g, 142 mmol) solution in THF (200 mL) to a suspension of NaH (7.42 g, 170 mmol) in THF (200 mL) at 020 C. The reaction mixture was kept at 0° C. for 1 h. The reaction mixture became a grey solid mass which disappears upon reaction by the dropwise addition of enone Xb (10 g, 35.5 mmol, in 240 mL THF) and stirring at RT during a weekend. The reaction was quenched by the dropwise addition of $H_2O$. Consecutively, $H_2O$ (400 mL) was added and most of the THF was removed by evaporation in vacuo. The product was isolated by filtration and was triturated with heptane. The solid was dissolved in EtOAc (200-300 mL) and dried with $Na_2SO_4$. Evaporation to dryness gave XXXVIb (11.0 g, 84%) as colorless oil which solidifies upon standing.

IV-1b: (n=1 and R1=$CH_3$): 3-Methoxy-17-oxo-estra-1,3,5(10)-trien-15α-yl-acetic Acid Hydrolysis of diester XXXVIb (11.0 g, 29.8 mmol) by dissolving in THF and adding concentrated $NaOH_{(aq)}$ (50 mL) and stirring overnight. The organic solvent was removed by evaporation in vacuo, and the residue was acidified with HCl (30%) until pH~1. The product was extracted with $CH_2Cl_2$ (2×200 mL). The combined organic layers were dried with $Na_2SO_4$ and evaporated to dryness. The residue was a mixture of compounds (partly decarboxylated). Dissolving the residue in AcOH (200 mL) and refluxing overnight gave complete decarboxylation. Evaporation to dryness and column chromatography ($CH_2Cl_2$/AcOH, (95:5)) gave a white solid material IV-1b (4.92 g, 52%). The product was further purified by column chromatography ($CH_2Cl_2$/AcOH, (95:5)) and by a consecutive crystallization from $CH_2Cl_2$/heptane (3×).

Acid Building Blocks IVβ-2, IVβ-3, IVβ-4, IVβ-5, IVβ-6 (n=2, 3, 4, 5, 6)

IVβ-3b (n=3 and R1=$CH_3$): 4-(3-Methoxy-17-oxo-estra-1,3,5(10)-trien-15β-yl)-butyric Acid

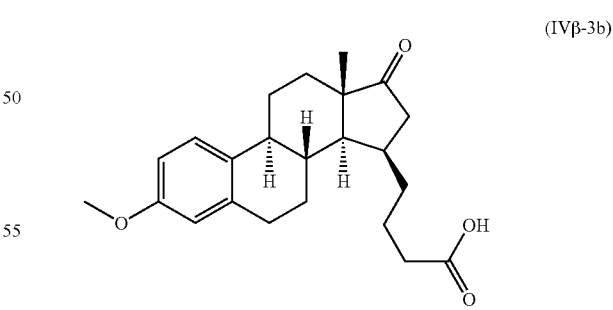

The individual steps in the synthesis of acid building block of the formula IVβ-3b are depicted in the following scheme 6. The same kind of procedure can be applied for n=4, 5, or 6 and for other alkyl side chains within the $R^1$ position using the appropriate BrMg—$C_5$-$C_7$-alkoxy-THP as Grignard Reagent. Furthermore, this reaction scheme also delivers the estrone-alcohol building block in form of the intermediate of formula XXXIβ-4b.

SCHEME 6

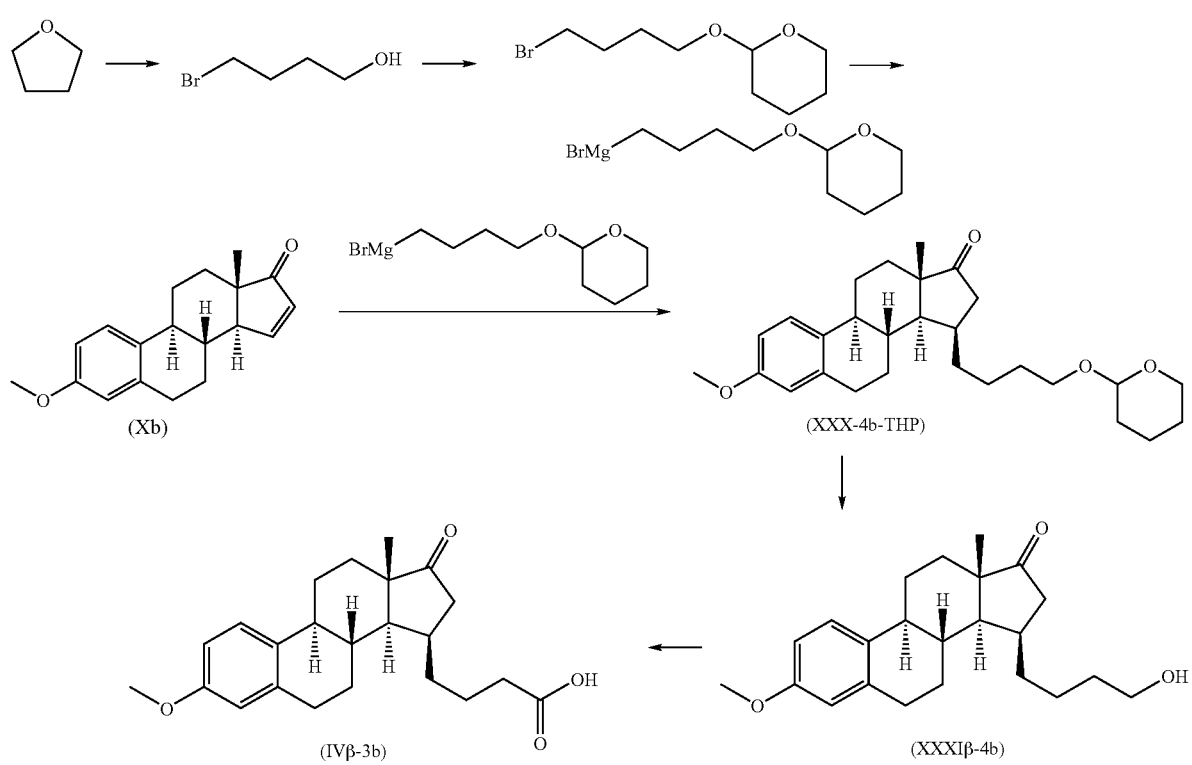

4-Bromo-butanol-THP ether was prepared by adding HBr solution to refluxing THF. The resulting bromide was dissolved in $CH_2Cl_2$, p-TosOH and DHP were added at 0° C. to give the protected alcohol. This was filtered over $SiO_2$ and further purified by column chromatography, yielding 9.3% over 2 steps. The protected alcohol was dissolved in THF and added to activated magnesium, and the resulting Grignard reagent added to $CuI_2$ in HMPA. The 15, 16-unsaturated Estrone derivative of formula Xb, dissolved in dry THF and TMSCl, was added at −40±5° C. Subsequently, after hydrolysis of the silyl ether, the resulting compound XXX-4b-THP was deprotected with p-TosOH/MeOH to give the alcohol derivative XXXI-4b, which was converted, without purification, into the free acid IV-3b by a Jones oxidation. The oil was purified by column chromatography, yielding the free acid of formula IV-3b in 30% yield over three steps.

Detailed Synthesis:

4-bromo-butanol

HBr solution (48% HBr in water, 1280 ml, 11.22 mol) was added dropwise to refluxing dry THF (810 ml, 9.99 mol) over a period of 2.25 hour. After complete addition, 1H-NMR analysis of a sample showed that the reaction was completed. The reaction mixture was cooled to RT, transferred to a 10 l reaction flask and, while stirred mechanically, carefully neutralized with $NaHCO_3$ solution. The layers were separated and the organic layer was washed with brine, dried over $Na_2SO_4$ and the solvent was removed on the rotary evaporator. The resulting yellow oil was used in the next step without further purification

2-(4-Bromo-butoxy)-tetrahydro-pyran

Crude product 4-bromo-butanol was dissolved in DCM (500 ml) and dried over $Na_2SO_4$ and p-TosOH (500 mg) was added. Dihydropyran (1181 ml) was added dropwise at 0° C. and during the addition the temperature was kept under 8° C. The reaction was allowed to reach RT overnight, washed with saturated $NaHCO_3$ solution (2×300 ml) and brine (9.3 l). The aqueous layers were washed with TBME (300 ml) and the combined organic layers were dried over anhydrous $K_2CO_3$. The mixture was filtered off and the solvent was removed on the rotary evaporator. This yielded 593 g (yield=25% over 2 steps). The obtained 4-bromo-butanol-THP ether was filtrated twice over $SiO_2$ (DCM with 1% MeOH). Finally, the compound was purified by column chromatography (20 l $SiO_2$, DCM with 1% MeOH). This yielded 220.6 g of 2-(4-Bromo-butoxy)-tetrahydro-pyran (yield=9.3% over 2 steps) as a TLC-pure light yellow oil.

3-Methoxy-15β-[4-(tetrahydro-pyran-2-yloxy)-butyl]-estra-1,3,5(10)-trien-17-one (XXX-4b-THP)

Magnesium (29.6 g, 2.0 mol) was stirred overnight with broken glass under $N_2$ in a flame dried 3 neck flask. The magnesium was extra activated by the addition of some iodine and by adding a few drops pure 2-(4-Bromo-butoxy)-tetrahydro-pyran. After the Grignard reaction had started, 2-(4-Bromo-butoxy)-tetrahydro-pyran (121 g, 510 mmol) in 500 ml dry THF was added dropwise, maintaining a gentle reflux. After complete addition of the reaction mixture, it was stirred for 0.5 hour. The solution was transferred to a flame dried 3-neck flask containing copper (I) iodide (9 g, 47 mmol) and HMPA (100 ml). The resulting reaction mixture was cooled to −40±50° C. after which a mixture of the 15, 16-unsaturated estron of the formula Xb (24 g, 85 mmol) and TMSCl (21 ml, 196 mmol), dissolved in dry THF (500 ml), was added dropwise. After complete addition, the mixture was allowed to reach RT over 3 days.

10% NH$_4$Cl (in water and ice, 1 l) was added to the reaction mixture. The layers were separated and the water layer was extracted with EtOAc (2×500 ml). The combined organic layers were washed with brine (500 ml), dried over Na$_2$SO$_4$ and the solvent was removed on the rotary evaporator. This yielded 103.6 g of yellow oil, containing HMPA. The oil was then stirred with K$_2$CO$_3$ (12.1 g, 87 mmol) in methanol (2.75 l) under N$_2$ to hydrolyze the silyl ether. The hydrolysis was followed by TLC (EtOAc/heptane: 1/9), which after 40 minutes showed that the reaction was complete. 0.75 l water was added and most of the methanol was removed on the rotary evaporator. 500 ml EtOAc was added, the layers were separated and the water layer was extracted with EtOAc (2×500 ml). The organic layers were combined, dried over Na$_2$SO$_4$ and the solvent was removed on the rotary evaporator. This yielded 82.5 g yellow oil which contains product XXX-4b-THP, HMPA and silyl residues.

15β-(4-Hydroxy-butyl)-3-methoxy-estra-1,3,5(10)-trien-17-one (XXXIβ-4b)

Crude compound XXX-4b-THP (82.5 g yellow oil) was dissolved in MeOH (2.5 L) and p-TosOH (6 g, 32 mmol) was added. The reaction was followed by TLC (toluene/acetone: 3/1) and 1H-NMR. After 1 hour the reaction was completed. Most of the MeOH was removed on the rotary evaporator and after this 1 l water was added. The resulting mixture was extracted with DCM (3×400 ml). The organic layers were combined, dried over Na$_2$SO$_4$ and the solvent was removed on the rotary evaporator. This yielded 46.8 g, which was purified by column chromatography (400 g SiO$_2$ toluene/acetone: 3/1) to yield 31.9 g of XXXIβ-4b as an impure yellow oil.

4-(3-Methoxy-17-oxo-estra-1,3,5(10)-trien-15β-yl)-butyric Acid (IVβ-3b)

To a cooled solution of alcohol XXXIβ-4b (31.9 g 89 mmol) at 0° C. in acetone (1 l) was added dropwise 140 ml of Jones reagent (prepared from 700 ml of water, 300 ml of H$_2$SO$_4$ and 100 g of CrO$_3$). Each drop leaves an orange color, which disappeared shortly after being formed. The color finally changes to green. After complete addition, the reaction was followed by TLC (EtOAc/heptane: 1/1) and was complete after 10 minutes. The reaction was stirred for 30 minutes more and then quenched with 500 ml of a cold saturated NaS$_2$O$_3$ solution and 500 ml of water. The resulting mixture was extracted with EtOAc (3×400 ml). The organic layers were combined, dried over Na$_2$SO$_4$ and the solvent was removed on the rotary evaporator. The resulting oil was purified by column chromatography (SiO$_2$; toluene/acetone: 3/1). This yielded 9.2 g (30% over 3 steps) of the compound of formula (IVβ-3b) as a yellow solid with a purity of 93%.

IVβ-2b (n=2 and R1=CH$_3$): 3-(3-Methoxy-17-oxo-estra-1,3,5(10)-trien-15β-yl)-propanoic Acid

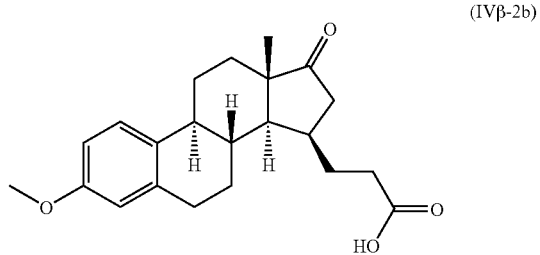

(IVβ-2b)

For n=2, the corresponding carboxylic acid IVβ-2b can be prepared by oxidation of the alcohol derivative of formula XXXIβ-3b according to the preparation of the carboxylic acid IVβ-3b (see section for the preparation of the alcohol derivatives below for synthesis of XXXIβ-3b).

LC-MS (ES−): rt 5.25 min, m/z (rel. Intens) 355 [(M−H)$^−$, 100%]

[α]$_D^{20}$=+79.6 (c=0.304, MeOH)

$^1$H NMR (400 MHz, CDCl$_3$) □ (ppm) 1.05 (s, 3H), 1.42-1.58 (m, 4H), 1.63-1.81 (m, 3H), 1.90-2.05 (m, 2H), 2.09-2.14 (m, 1H), 2.28-2.51 (m, 7H), 2.85-3.01 (m, 2H), 3.78 (s, 3H), 6.65 (d, 1H), 6.71 (dd, 1H), 7.19 (d, 1H).

$^{13}$C NMR (100.6 MHz, CDCl$_3$) δ (ppm) 17.8, 25.5, 26.0, 26.7, 29.5, 33.6, 33.9, 34.0, 36.0, 42.0, 44.6, 47.1, 52.7, 55.3, 111.5, 114.0, 126.0, 132.2, 137.7, 157.8, 178.5, 220.4.

Acid Building Block IVβ-3c: 4-(3-Benzyloxy-17-oxo-estra-1,3,5(10)-trien-15β-yl)-butyric Acid

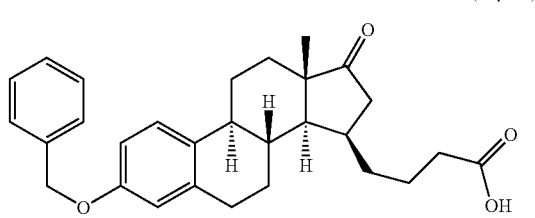

(IVβ-3c)

The individual steps in the synthesis of acid building block of the formula IVβ-3c are performed according to the procedure depicted in scheme 7. Furthermore, this reaction scheme also delivers the estrone-alcohol building block in form of the intermediate of formula XXXIβ-4c. The same kind of procedure can be applied for n=4, 5, or 6 and for other alkylaryl substituents within the R$^1$ position using the appropriate BrMg-C$_5$-C$_7$-alkoxy-THP as Grignard Reagent.

SCHEME 7

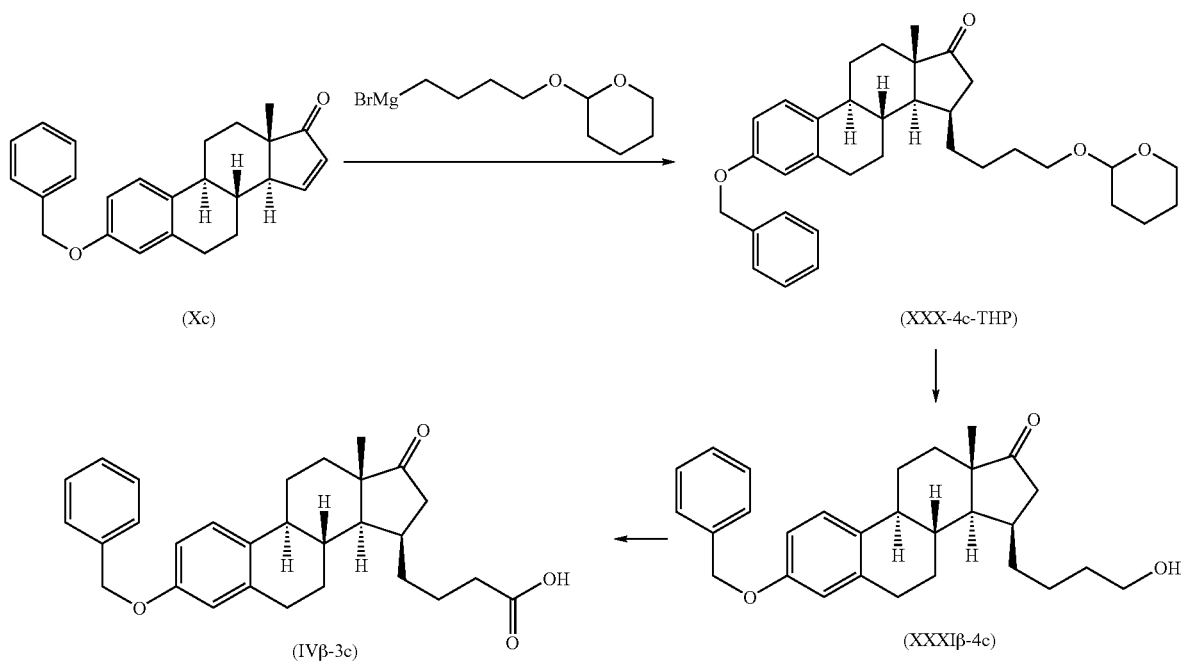

4-Bromo-butanol-THP ether was prepared by adding HBr solution to refluxing THF. The resulting bromide was dissolved in CH$_2$Cl$_2$, p-TosOH and DHP were added at 0° C. to give the protected alcohol. This was filtered over SiO$_2$ and further purified by column chromatography, yielding 9.3% over 2 steps. The protected alcohol was dissolved in THF and added to the activated magnesium, and the resulting Grignard reagent added to CuI$_2$ in HMPA. The 15, 16-unsaturated Estrone derivative of formula Xc, dissolved in dry THF and TMSCl, was added at −40±5° C. Subsequently, the resulting compound XXX-4c-THP was deprotected with p-TosOH/ MeOH to give XXXIβ-4c in 47% over 2 steps, which was converted, without purification, into the free acid IVβ-3c by a Jones oxidation in a yield of 96%.

Detailed Synthesis:

4-bromo-butanol and
2-(4-Bromo-butoxy)-tetrahydro-pyran: See Above

3-Benzyloxy-15β-[4-(tetrahydro-pyran-2-yloxy)-butyl]-estra-1,3,5(10)-trien-17-one (XXX-4c-THP)

Magnesium (10 g, 425 mmol) was stirred overnight with broken glass under N$_2$ in a flame dried 3 neck flask The magnesium was extra activated by the addition of some iodine and by adding a few drops pure 2-(4-Bromo-butoxy)-tetrahydro-pyran. After the Grignard reaction had started, 2-(4-Bromo-butoxy)-tetrahydro-pyran (25.2 g, 106 mmol) in 200 ml dry THF was added dropwise, maintaining a gentle reflux. After complete addition of the reaction mixture, it was stirred for 0.5 hour. The solution was transferred to a flame dried 3-neck flask containing copper (I) iodide (1.8 g, 9.5 mmol) and HMPA (20 ml). The resulting reaction mixture was cooled to −40±5° C. after which a mixture of the 15, 16-unsaturated estron derivative of formula Xc (6 g, 18 mmol) and TMSCl (4.5 ml, 35 mmol), dissolved in dry THF (100 ml), was added dropwise. After complete addition, the mixture was allowed to reach RT over 3 days.

10% NH$_4$Cl (in water and ice, 200 ml) was added to the reaction mixture. The layers were separated and the water layer was extracted with EtOAc (2×150 ml). The combined organic layers were washed with brine (150 ml), dried over Na$_2$SO$_4$ and the solvent was removed on the rotary evaporator. This yielded 22.7 g of yellow oil, containing HMPA. The oil was then stirred with K$_2$CO$_3$ (3 g, 22 mmol) in MeOH (650 ml) under N$_2$ to hydrolyze the silyl ether. The hydrolysis was followed by TLC (EtOAc /heptane: 1/9), which after 60 minutes showed that the reaction was complete. 200 ml water was added and most of the methanol was removed on the rotary evaporator. 150 ml EtOAc was added, the layers were separated and the water layer was extracted with EtOAc (2×150 ml). The organic layers were combined, dried over Na$_2$SO$_4$ and the solvent was removed on the rotary evaporator. This yielded 15.1 g yellow oil which contains product, HMPA and silyl residues.

3-Benzyloxy-15β-(4-Hydroxy-butyl)-estra-1,3,5 (10)-trien-17-one (XXXIβ-4c)

Crude compound (XXX-4c-THP) (15.1 g yellow oil) was dissolved in MeOH (500 ml) and p-TosOH (1.2 g, 6.3 mmol) was added. The reaction was followed by TLC (toluene /acetone: 3/1) and 1H-NMR. After 1.5 hour the reaction was completed. Most of the MeOH was removed on the rotary evaporator and after this 200 ml water was added. The resulting mixture was extracted with DCM (3×100 ml). The organic layers were combined, dried over Na$_2$SO$_4$ and the solvent was removed on the rotary evaporator. This yielded 8.2 g, which was purified by column chromatography (400 g SiO$_2$, toluene /acetone : 3/1) to yield 3.6 g (8.3 mmol, 47% over 2 steps) of XXXIβ-4c as a yellow oil.

4-(3-Benzyloxy-17-oxo-estra-1,3,5(10)-trien-15β-yl)-butyric Acid (IVβ-3c)

To a cooled solution of alcohol XXXIβ-4c (3.6 g 8.3 mmol) at 0° C. in acetone (100 ml) was added dropwise 13.3 ml of Jones reagent (prepared from 700 ml of water, 300 ml of $H_2SO_4$ and 100 g of $CrO_3$). Each drop leaves an orange color, which disappeared shortly after being formed. The color finally changes to green. After complete addition, the reaction was followed by TLC (EtOAc/heptane: 1/1) and was complete after 10 minutes. The reaction was then quenched with 100 ml of a cold saturated $NaS_2O_3$ solution, during which the temperature rose from 6 to 18° C., and 300 ml of water and 200 ml of EtOAc. The resulting mixture was stirred overnight and then the layers were separated and the aqueous layer was extracted with EtOAc (2×100 ml). The organic layers were combined, dried over $Na_2SO_4$ and the solvent was removed on the rotary evaporator. This yielded 3.6 g of IVβ-3c (8.0 mmol, y=97%) as a yellow solid.

Acid Building Block with α a Stereochemistry at C15

IVα-3a (n=3 and R1=H): 4-(3-Hydroxy-17-oxo-estra-1,3,5(10)-trien-15α-yl)-butyric Acid The individual steps in the synthesis of acid building block of the formula IVα-3a are performed according to the procedure depicted in scheme 8. Furthermore, this reaction scheme also delivers the still ketal-protected estrone-alcohol building block in form of the intermediate of formula XLIVα-1c. Debenzylation and deprotection delivers the estrone-alcohol XXXIα-1a.

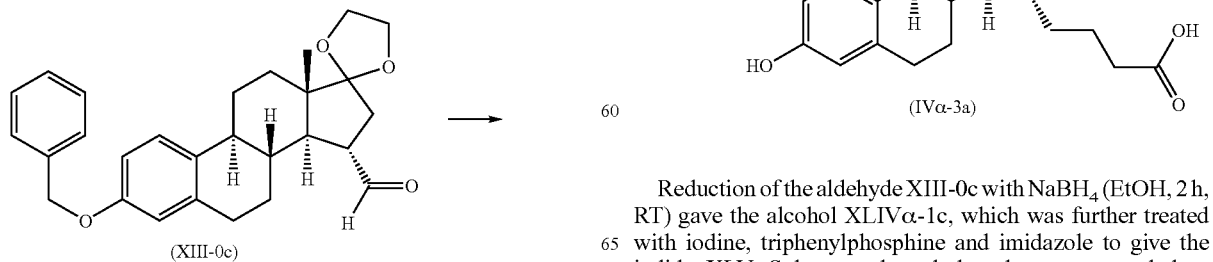

Reduction of the aldehyde XIII-0c with $NaBH_4$ (EtOH, 2 h, RT) gave the alcohol XLIVα-1c, which was further treated with iodine, triphenylphosphine and imidazole to give the iodide XLV. Subsequently, ethylacrylate was coupled to iodine XLV and gave compound XLVI after purification by column chromatography. Reduction of compound XLVI was performed under $H_2$ atmosphere to give compound XLVII, which was transformed into the protected carboxylic acid building block XLVIIIα-3a by saponification. The carboxylic acid IVα-3a was obtained by deprotection.

Detailed Synthesis

17-Ketal Derivative of 3-Benzyloxy-15-hydroxymethyl-estra-1,3,5(10)-trien-17-one (XLIVα-1c)

Aldehyde XIII-0c (1.23 g, 2.84 mmol) was dissolved in EtOH (13 mL) and cooled to 0° C. $NaBH_4$ (32.8 mg, 0.89 mmol) was added and the temperature was allowed to reach RT. After 2 h at RT acetic acid (0.313 mL) and $H_2O$ (33 mL) were added carefully. The reaction mixture was stirred at RT for 30 min. and was subsequently extracted with $CH_2Cl_2$ (2×25 mL). The organic layer was separated, dried over $Na_2SO_4$ and concentrated to yield 1.2 g of colorless oil. Purification was performed by column chromatography (eluent: heptane/ethylacetate 3:1, Rf=0.3) to give 1.09 g (88%) of alcohol XLIVα-1c as a white solid.

Ketal Derivative of 3-Benzyloxy-15-iodomethyl-estra-1,3,5(10)-trien-17-one (XLV)

Imidazole (749 mg, 11.0 mmol), $PPh_3$ (1.44 g, 5.5 mmol) and $I_2$ (1.33 g, 5.2. mmol) were stirred in $CH_2Cl_2$ (20 mL) for 30 min. The mixture was cooled to 0° C. Dropwise a solution of alcohol XLIVα-1c (1.09 g, 2.50 mmol) in $CH_2Cl_2$ (10 mL) was added over a period of 10 min. The reaction flask was covered with aluminium foil and the mixture was stirred for 90 min at RT. The solids were filtered off over celite and the filtrate was washed with 10% aq. $Na_2S_2O_4$. The organic layer was separated, dried over $Na_2SO_4$ and concentrated to yield an oil which was purified by column chromatography (eluent: heptane/ethylacetate 1:1, Rf=0.8) to give 0.944 g (69%) of iodide XLV as a white foam.

Ketal Derivative of 4-(3-Benzyloxy-17-oxo-estra-1,3,5(10)-trien-15-yl)-butyric Acid Ethyl Ester (XLVI)

$NiCl_2.6H_2O$ (409 mg, 1.72 mmol) was suspended in pyridine (7.3 mL). Subsequently activated zinc (566 mg, 8.66 mmol) and ethylacrylate (868 μL, 8.0 mmol) were added and the mixture was stirred at 56° C. for 20 min. A catalytic amount of iodine was added and the heating was switches off. When the temperature became 40° C., a solution of XLV (944 mg, 1.73 mmol) in pyridine (5.2 mL) was added dropwise and the stirring was continued for 90 min at RT. Solids were filtered off and the filtrate was concentrated. EtOAc (25 mL) was added and the organic layer was washed with brine (3×10 mL). The organic layer was separated, dried over $Na_2SO_4$ and concentrated to yield 1.18 g of an oil which was purified by column chromatography (eluent: heptane /ethylacetate 5:1, Rf=0.4) to give 0.449 g (50%) of ethylester XLVI as a colorless oil.

Ketal Derivative of 4-(3-Hydroxy-17-oxo-estra-1,3,5 (10)-trien-15-yl)-butyric Acid Ethyl Ester (XLVII)

Ethylester XLVI (0.449 g, 0.86 mmol) was dissolved in THF (15 mL). A suspension of a small spoon of Pd/C in THF (2 mL) was added and the reaction mixture was stirred for three days at RT with 1 bar $H_2$ pressure. The solids were filtered off over celite and washed with THF (10 mL). Concentration of the organic layer gave 0.375 mg of compound XLVII as yellow foam. Purification was performed by column chromatography (eluent: heptane/ethylacetate 5:1, Rf=0.2) to give 0.313 g (84%) of compound XLVII as a white solid.

Ketal Derivative of 4-(3-Hydroxy-17-oxo-estra-1,3,5 (10)-trien-15-yl)-butyric Acid (XLVIIIα-3a)

To a heated (60° C.) solution of Phenol XLVII (0.313 g, 0.73 mmol) in MeOH (12 mL) 2N aq. KOH (3.52 mL) was added. The mixture was stirred for 30 min. 60° C. The mixture was cooled by adding ice to the mixture. The pH was adjusted carefully to 3 a 4 using 5N aq. HCl. The carboxylic acid XLVIIIα-3a was extracted with TBME (50 mL), the organic layer was dried over $Na_2SO_4$ and concentrated to yield 0.266 g (91%) of carboxylic acid XLVIIIα-3a as a white solid. No purification was needed.

4-(3-Hydroxy-17-oxo-estra-1,3,5(10)-trien-15-yl)-butyric Acid (IVα-3a)

If necessary, the unprotected carboxylic acid may be obtained by treatment of the ketal derivative XLVIIIα-3a with an anorganic acid and subsequent purification.

IV. Compounds of Formula XXXI (Alcohol Derivatives): 15-Hydroxy-$C_1$-$C_6$-alkyl-Estron Alcohol XXXIα-1a: 15α-Hydroxymethyl-3-hydroxy-estra-1,3,5(10)-trien-17-one Alcohol XXXIα-1b: 15α-Hydroxymethyl-3-methoxy-estra-1,3,5(10)-trien-17-one Alcohol XXXIα-1c: 3-Benzyloxy-15α-hydroxymethyl-estra-1,3,5(10)-trien-17-one

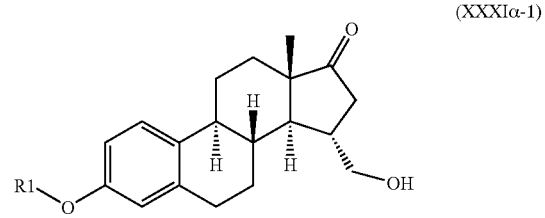

(XXXIα-1)

The synthesis of the alcohol derivatives XXXIα-1a ($R^1$=H), XXXIα-1b ($R^1$=$CH_3$), and XXXIα-1c ($R^1$=benzyl) is depicted in the following scheme 9:

SCHEME 9

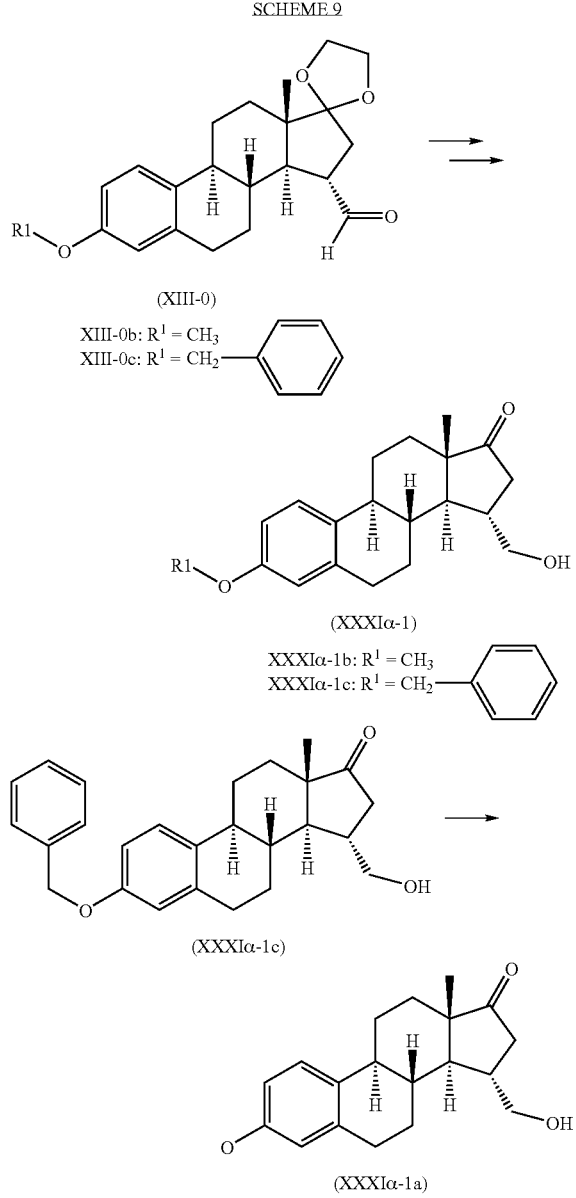

Reduction of the aldehydes XIII-0b or XIII-0c using NaBH₄ followed by ketal hydrolysis gave the corresponding alcohols XXXIα-1b and XXXIα-1c. The alcohol XXXIα-1c was debenzylated to give XXXIα-1a using Pd/C and a 5 bar hydrogen atmosphere.

Detailed Synthesis

Alcohol XXXIα-1b: 15α-Hydroxymethyl-3-methoxy-estra-1,3,5(10)-trien-17-one

Alcohol XXXIα-1c: 3-Benzyloxy-15α-hydroxymethyl-estra-1,3,5(10)-trien-17-one

NaBH₄ (500 mg, 13.2 mmol) was added in aliquots of 100 mg per 10 min to a solution of aldehyde XIII-0b or XIII-0c (2.3 mmol) in THF (20 mL) and reaction was continued overnight. The reaction was quenched upon the addition of MeOH (20 mL). The reaction mixture was evaporated to dryness (high vacuum). The residue was dissolved in CH₂Cl₂ (50 mL) and stirred with HCl (15%, 50 mL) during 72 h. CH₂Cl₂ (50 mL) was added and the organic layer was dried with Na₂SO₄ and evaporated to dryness. A yield of 95-98% was obtained for both products (HPLC-MS: 90% pure). A sample of XXXI-1b (230 mg) with a 95%+ purity was obtained by crystallization from CH₂Cl₂/MeOH upon standing to air. Compound XXXIα-1c was used in the next step without further purification.

Alcohol XXXIα-1a: 15α-Hydroxymethyl-3-hydroxy-estra-1,3,5(10)-trien-17-one

A suspension of estrone XXXIα-1c (0.81 g, 90% pure), Pd/C (50-100 mg, cat) in MeOH (100 mL) was stirred in a 5 bar H₂-atmosphere for 30 min. Pd/C was removed by filtration through Celite. Evaporation to dryness (0.52 g, 90% pure) and recrystallization of the residue from MeOH gave XXXIα-1a as an off-white solid (308 mg).

Alcohol Building Blocks XXXI-3 (n=3)

15β-(3-Hydroxypropyl)-3-methoxyestra-1,3,5(10)-trien-17-one (XXXI-3b)

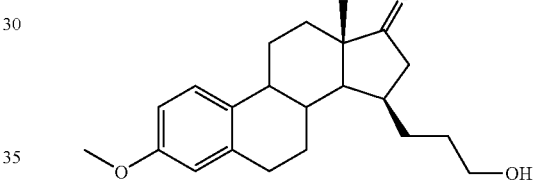

Detailed Synthesis:

To a solution of 2-(3-bromopropyloxy)-tetrahydro-2H-pyran (4.45 g, 19.95 mmol) in dry THF (50 mL) at −78° C. under nitrogen atmosphere was added t-BuLi (1.5 M solution in pentane, 25 mL, 37.5 mmol). After 30 min stirring CuCN (0.89 g, 9.94 mmol) was added. The mixture was stirred for additional 30 min while the reaction mixture is allowed to reach −40° C. After cooling to −78° C. a solution of the 15,16-unsaturated estron derivative of formula Xb (1.50 g, 5.24 mmol) and TMSCl (1.3 mL, 10 mmol) in 50 mL THF was added dropwise over a period of 15 min. The mixture was allowed to reach 0° C. (over a period of 4 h). Then saturated NH₄Cl-solution was added, the layers were separated and the aqueous phase was extracted with ethyl acetate. The crude product was dissolved in methanol (250 mL) and K₂CO₃ (0.80 g, 5.97 mmol) was added. After 2 h stirring at RT water (50 mL) was added and most of the methanol was evaporated. The mixture was diluted with EtOAc, the layers were separated and the water layer was extracted with EtOAc. The combined organic layers were dried over Na₂SO₄ and the solvent was evaporated. The crude product was dissolved in methanol (250 mL) and p-TosOH (0.80 g, 4.21 mmol) was added. The reaction mixture was stirred for 90 min. Most of the methanol was removed on the rotary evaporator. Water was added and the aqueous phase was extracted with DCM (3×). The combined organic layers were dried over Na₂SO₄ and the solvent was removed. The crude product was purified by column chromatography (SiO₂, cyclohexane/ethyl acetate 1:1) to yield compound XXXI-3b (0.81 g, 45%) as a colorless oil.

LC-MS (ES+): rt 5.75 min, m/z (rel. Intens) 343 [(M+H)+, 40%], 360 [(M+NH$_4$)+, 100%] $^1$H NMR (400 MHz, CDCl$_3$) δ (ppm) 1.03 (s, 3H), 1.44-1.76 (m, 9H), 1.88-1.92 (m, 1H), 2.03-2.07 (m, 1H), 2.27-2.48 (m, 5H), 2.91-2.95 (m, 2H), 3.65-3.69 (m, 2H), 3.78 (s, 3H), 6.65 (d, 1H), 6.71 (dd, 1H), 7.19 (d, 1H).

$^{13}$C NMR (100.6 MHz, CDCl$_3$) δ (ppm) 17.8, 25.5, 26.8, 27.2, 29.5, 32.8, 34.0, 34.2, 36.1, 42.7, 44.6, 47.1, 52.9, 55.2, 62.6, 76.7, 77.0, 77.4, 111.5, 113.9, 126.0, 132.4, 137.7, 157.7, 221.0. [α]$_D^{20}$=+79.6 (c=0.314, MeOH)

Alcohol Building Blocks XXXI-3c and XXXI-3a
(n=3, R$^1$=benzyl, n=3, R$^1$=H)

3-Benzyloxy-15β-(3-hydroxypropyl)-estra-1,3,5(10)-trien-17-one (XXXI-3c)

3-Hydroxy-15β-(3-hydroxypropyl)-estra-1,3,5(10)-trien-17-one (XXXI-3a)

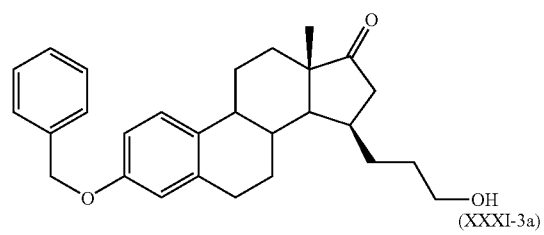
(XXXI-3c)

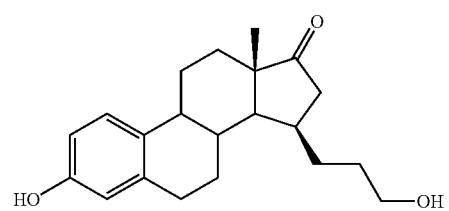
(XXXI-3a)

The synthesis of the alcohol building blocks of formula XXXI-3c and XXXI-3a is depicted in the following scheme 10.

SCHEME 10

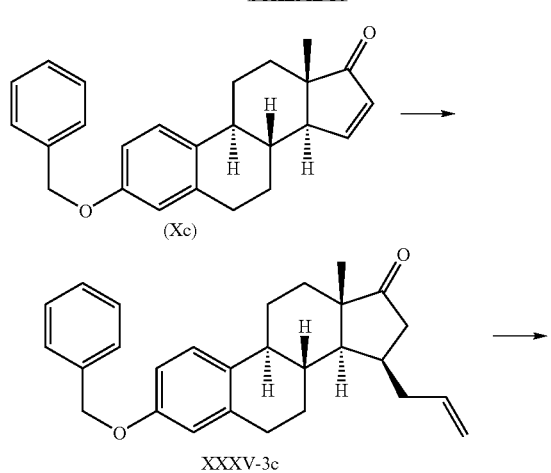

-continued

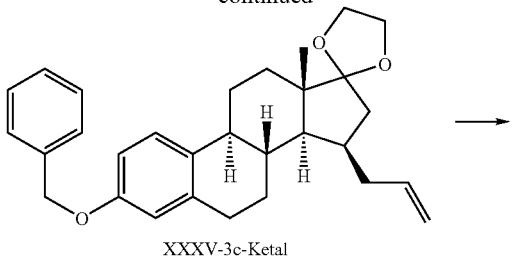
XXXV-3c-Ketal

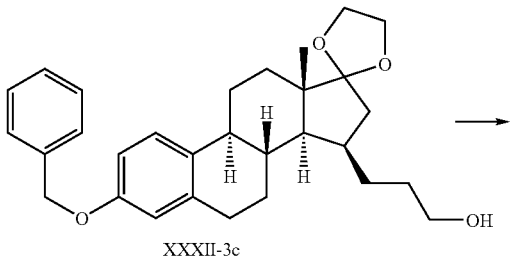
XXXII-3c

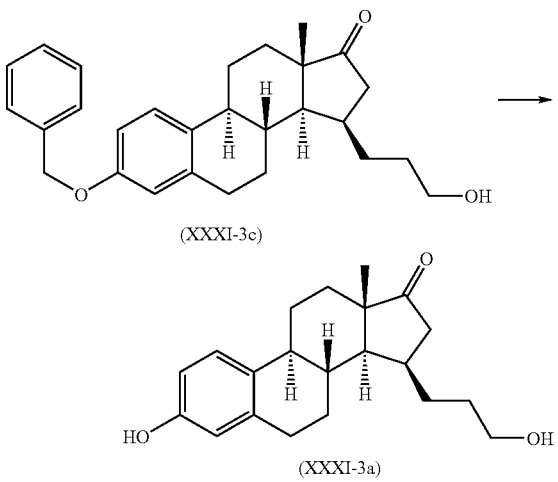
(XXXI-3c)

(XXXI-3a)

Detailed Synthesis

3-Benzyloxy-15β-(prop-2-enyl)-estra-1,3,5(10)-trien-17-one (XXXV-3c)

A 3-neck flask was charged with CuI (18.76 g; 98.5 mol) and lithium chloride (4.17 g; 98.4 mol) and evacuated and purged with N$_2$ (2×). THF (dry, 150 mL) was added and the mixture was stirred at RT during 20 minutes. The resulting clear green solution was cooled to −78° C. Allylmagnesiumbromide (1.0 M solution in diethyl ether; 100 mL; 100 mmol) was added dropwise at −78° C. After complete addition trimethyl silylchloride (9.1 mL; 71.2 mol) was added, immediately followed by the dropwise addition of a solution of the 15,16-unsaturated estron Xc (10.08 g; 28.1 mol) in THF (dry, 120 mL). After the complete addition the suspension was stirred during 1 hour at −78° C. The mixture was warmed up to RT and stirred for 3 d. Saturated NH$_4$Cl solution (500 mL) was added and the layers were separated. The aqueous layer was extracted with EtOAc (2×300 mL). The combined organic layers were washed with HCl (1M, 2×300 mL) and aqueous ammonia (25%, 3×300 mL). The organic layer was dried over Na$_2$SO$_4$ and the solvent was evaporated. The resulting brown oil was crystallized from EtOAc to yield XXXV-3c (5.81 g; 51%).

3-Benzyloxy-15β-(prop-2-enyl)-estra-1,3,5(10)-trien-17-dioxolane (XXXV-3c-ketal)

Triethyl orthoformate (25 mL; 150 mmol) and ethylene glycol (11 mL; 197 mmol) were added to XXXV-3c (10 g; 25.0 mmol). p-TosOH (0.40 g; 2.10 mmol) was added to the slurry which was heated to 35° C. overnight. Then the reaction mixture was poured into ice (100 mL) and pyridine (3 mL) was added. This mixture was stirred for 5 h. The mixture was diluted with ethyl acetate, the layers were separated and the aqueous layer was extracted with ethyl acetate (100 mL). The organic layers were washed with water (2×100 mL), dried over $Na_2SO_4$ and evaporated. The crude product was purified by column chromatography (heptane /EtOAc 9:1) to yield XXXV-3c-ketal (9.94 g; 90%).

3-Benzyloxy-15β-(3-hydroxypropyl)-estra-1,3,5(10)-trien-17-dioxolane XXXII-3c Compound XXXV-3c-ketal (9.94 g; 22.36 mmol) was dissolved in THF (500 mL). Borane dimethylsulfide (2M in diethylether; 72 mL; 144 mmol) was added and the solution was heated at reflux for 2 hours. The solution was then cooled in ice bath and NaOH (3M; 99 mL) was added dropwise. Then $H_2O_2$ (35%; 50 mL) was added and the resulting biphasic system was stirred overnight at 40° C. The excess of peroxide was destroyed by addition of dimethylsulfide. After work-up XXXII-3c (8.22 g) was obtained which contains ~40% of a side product. The crude product was used in the next step without further purification.

3-Benzyloxy-15β-(3-hydroxypropyl)-estra-1,3,5(10)-trien-17-one XXX-3c

Crude compound XXXII-3c (8.82 g) was dissolved in acetone (88 mL) and water (22 mL) and p-TosOH (0.36 g; 1.89 mmol) was added. The solution was stirred for 3 d at RT. After work-up the crude product was purified by column chromatography (heptane /EtOAc 1:1, $R_f$ 0.3) to yield compound XXX-3c (2.90 g; 31% over 2 steps).

3-Hydroxy-15β-(3-Hydroxypropyl)-estra-1,3,5(10)-trien-17-one XXX-3a

Compound XXX-3c (2.90 g; 6.93 mmol) was dissolved in MeOH (250 mL) and Pd/C was added as a slurry in MeOH. The mixture was stirred overnight at RT under a $H_2$ atmosphere. The reaction mixture was filtered over Celite. The filtrate was evaporated and the product was dissolved in EtOAc (50 mL) and crystallized as needles, which were filtered off and washed with pentane to yield compound XXX-3a (1.63 g; 72%). (LC-MS (ES−): rt 5.75 min, m/z (rel Intens) 327 [(M−H)+, 100%]).

Alcohol Building Blocks XXXI-4b. XXXI-5b. XXXI-6b (n=4, 5, 6)

15β-(4-Hydroxy-$C_4$-$C_6$-alkyl)-3-methoxy-estra-1,3,5(10)-trien-17-one

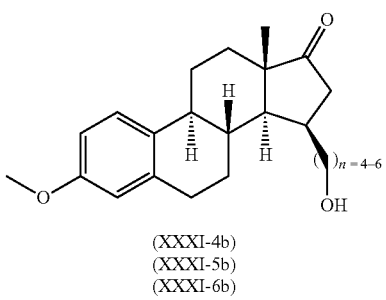

(XXXI-4b)
(XXXI-5b)
(XXXI-6b)

The general synthesis of the alcohol building block of formula XXXI-4/5/6b is depicted in the following scheme 11.

SCHEME 11

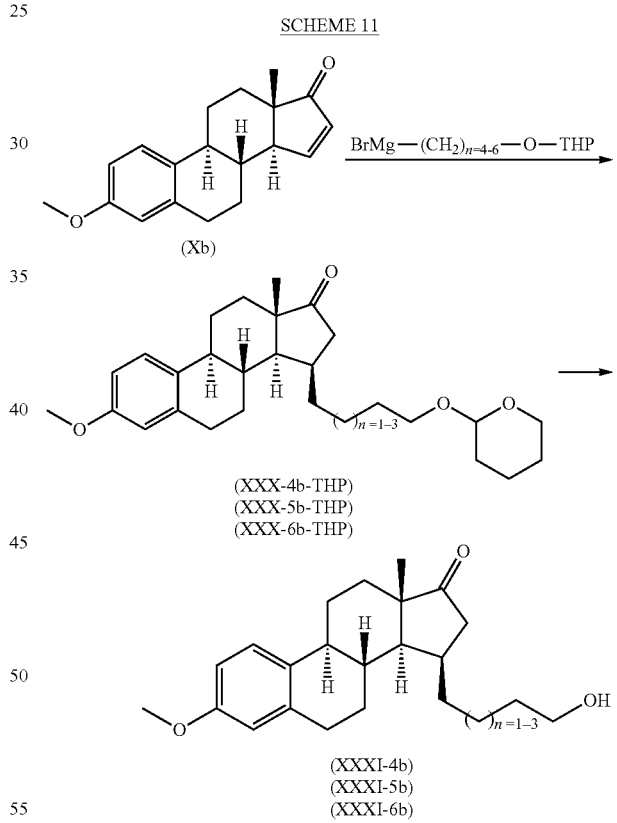

General Procedure

Magnesium (3-10 eq) is added in a dry three-neck flask under $N_2$ atmosphere and activated by iodine. The bromo compound (2-6.5 eq) dissolved in dry THF is added dropwise to the magnesium. The reaction mixture is allowed to react for 1-2 h at RT or reflux. The solution is transferred to dry three-neck flask containing CuI (0.06-0.7 eq) and DMPU or HMPA (2-7 eq) in dry THF cooled to −40° C. The resulting mixture is stirred for 30 min at −40° C. after which a mixture of 15,16-unsaturated estron derivative of formula X (1 eq) and TMSCl (2-2.5 eq) dissolved in THF is added dropwise. After complete addition the mixture is allowed to reach RT. Then NH$_4$Cl-solution is added, the layers are separated and the aqueous phase is extracted with ethyl acetate (3×). The combined organic phases are dried over Na$_2$SO$_4$ and the solvent is evaporated. The crude product is dissolved in methanol and K$_2$CO$_3$ (1 eq) is added to hydrolyse the silyl ether. After complete hydrolysis water is added and most of the methanol is evaporated. The mixture is diluted with EtOAc, the layers are separated and the water layer is extracted with EtOAc. The combined organic layers are dried over Na$_2$SO$_4$ and the solvent is evaporated. The resulting product of general formula XXX is then further worked-up to give the alcohol of general formula XXXI.
Detailed Synthesis XXXI-4b (n=4 and R1=CH$_3$): 15β-(4-Hydroxybutyl)-3-methoxy-estra-1,3,5(10)-trien-17-one The detailed synthesis of this compound is already displayed within the section for the synthesis of acid building block of the formula IV-3b above.

XXXI-5b (n=5 and R1=CH$_3$): 15β-(5-Hydroxypentyl)-3-methoxy-estra-1,3,5(10)-trien-17-one According to the general procedure displayed in SCHEME 11, the copper reagent was prepared from magnesium (3.80 g, 156 mmol), 2-(5-bromopentyloxy)-THP (23.6 g, 94.00 mmol), CuI (0.54 g, 2.83 mmol) and DMPU (12 mL, 100 mmol) in THF. A mixture of estron derivative of formula Xb (13.68 g, 48.5 mmol) and TMSCl (13 mL, 100 mmol) in THF was added dropwise. The reaction mixture was allowed to reach RT and was stirred for two days. After work-up and hydrolysis of the silyl ether the crude product was dissolved in methanol (50 mL) and p-TosOH (11.4 g, 60 mmol) was added. The reaction mixture was stirred overnight. Most of the methanol was removed on the rotary evaporator. Water was added and aqueous phase was extracted with DCM (3×). The combined organic layers were dried over Na$_2$SO$_4$ and the solvent was removed. The crude product was purified by column chromatography (SiO$_2$, cyclohexane/ethyl acetate gradient from 10:1 to 2:1) to yield XXXI-5b (14.21 g, 79%).
LC-MS (ES+): rt 6.31 min, m/z (rel. Intens) 388 [(M+NH$_4$)$^+$, 100%] [α]$_D^{20}$=+85.7 (c=0.105, CH$_2$Cl$_2$)

XXXI-6b (n=6 and R1=CH$_3$): 15β-(6-Hydroxyhexyl)-3-methoxy-estra-1,3,5(10)-trien-17-one According to the general procedure displayed in SCHEME 11, the copper reagent was prepared from magnesium (2.19 g, 91.00 mmol), 2-(6-bromohexyloxy)-THP (20.67 g, 78.00 mmol), CuI (1.98 g, 10.40 mmol) and DMPU (9.4 mL, 78 mmol) in THF. A mixture of estron derivative of formula Xb (7.33 g, 26.00 mmol) and TMSCl (5.56 g, 52.00 mmol) in THF was added dropwise. The reaction mixture was allowed to reach RT and was stirred for two days. After work-up and hydrolysis of the silyl ether the crude product was dissolved in methanol (200 mL) and p-TosOH (0.95 g, 5.00 mmol) was added. The reaction mixture was stirred for 1 h. Most of the methanol was removed on the rotary evaporator. Water was added and aqueous phase was extracted with DCM (3×). The combined organic layers were dried over Na$_2$SO$_4$ and the solvent was removed. The crude product was purified by column chromatography (SiO$_2$, cyclohexane/ethyl acetate gradient from 10:1 to 2:1) to yield XXXI-6b (7.50 g, 75%).

LC-MS (ES−): rt 6.63 min, m/z (rel. Intens) 443 [(M+OAc)$^-$, 100%]

Alcohol Building Block XXXI-4c (n=4. R$^1$=benzyl) and XXXI-4a (n=4. R$^1$=H)

3-Benzyloxy-15β-(4-hydroxybutyl)-estra-1,3,5(10)-trien-17-one (XXXI-4c)

3-Hydroxy-15β-(4-hydroxybutyl)-estra-1,3,5(10)-trien-17-one (XXXI-4a)

The detailed synthesis of this compound is already displayed within the section for the synthesis of acid building block of the formula IV-3c above. The 3-Hydroxy-Derivative can be obtained by hydrolysis of the XXXI-4c compound.

Alcohol building blocks XXXI-5c and XXXI-5a (n=5, R$^1$=benzyl, n=3. R$^1$=H)

3-Benzyloxy-15β-(5-hydroxypentyl)-estra-1,3,5(10)-trien-17-one (XXXI-5c)

3-Hydroxy-15β-(5-Hydroxypentyl)-estra-1,3,5(10)-trien-17-one (XXXI-5a)

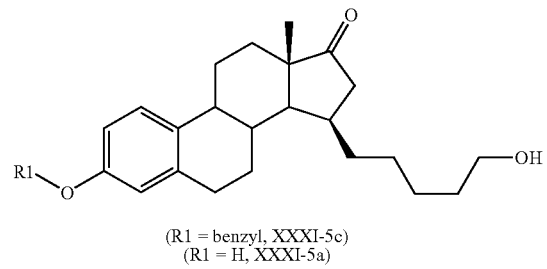

(R1 = benzyl, XXXI-5c)
(R1 = H, XXXI-5a)

The synthesis of the alcohol building block of formula XXXI-5c and XXXI-5a is depicted in the following scheme 12.

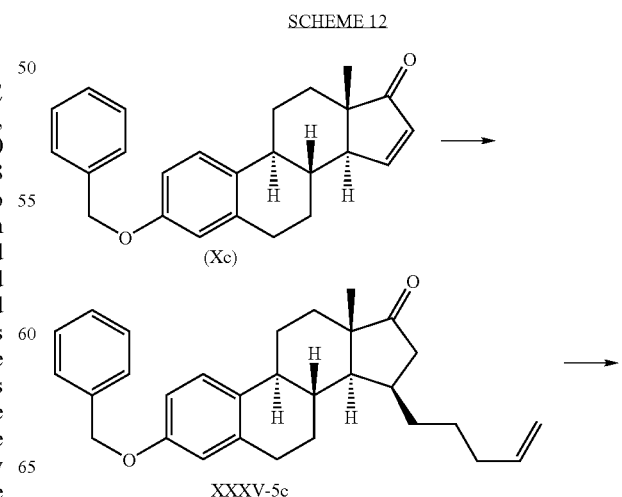

SCHEME 12

(Xc)

XXXV-5c

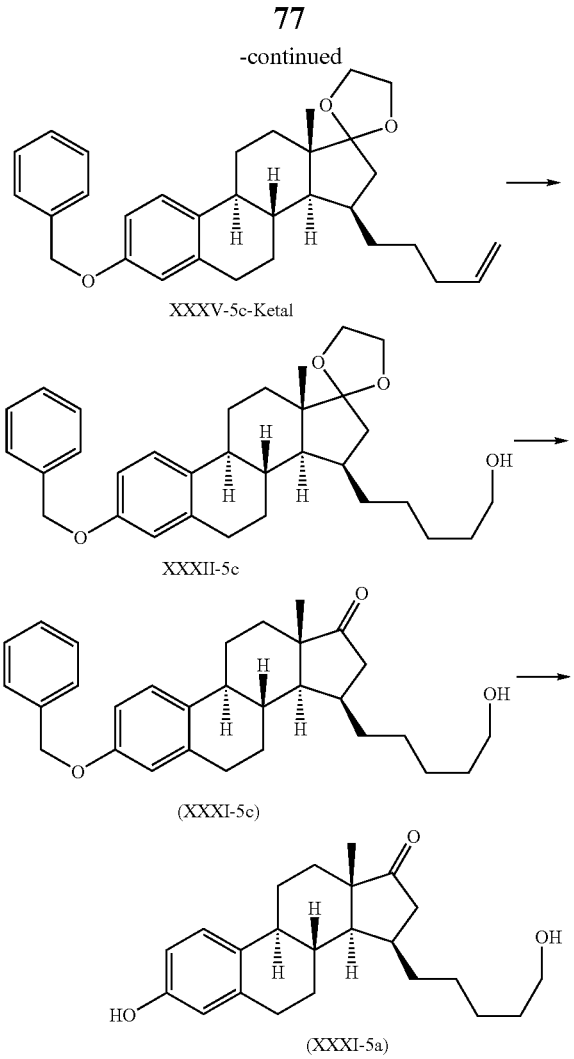

Detailed Synthesis

3-Benzyloxy-15β-(pent-4-enyl)-estra-1,3,5(10)-trien-17-one (XXXV-5c)

Magnesium turnings (4.43 g; 0.182 mol) were activated by addition of a I$_2$ crystal and a drop of pure bromide. A solution of 5-bromo-1-pentene (19.5 mL; 0.164 mol) in THF (dry, 160 mL) was added drop wise, while maintaining reflux. After complete addition the mixture was stirred at RT for 1 hour. A 3-neck flask was charged with CuI (30.47 g; 0.159 mol) and lithium chloride (6.78 g; 0.159 mol) and evacuated and purged with N$_2$ (2×). THF (dry, 240 mL) was added and the mixture was stirred at RT during 20 minutes. The resulting clear green solution was cooled to −78° C. The Grignard reagent was added drop wise between −78° C. and −70° C. After complete addition trimethyl silylchloride (20.4 mL; 0.159 mol) was added to the brown reaction mixture at −78° C., immediately followed by the drop wise addition of a solution of 15, 16-unsaturated estron Xc (22.94 g; 0.064 mol) in THF (dry, 280 mL). After the complete addition the suspension was stirred during 1 hour at −78° C. The mixture was warmed up to RT and stirred for 3 d. Saturated NH$_4$Cl solution (500 mL) was added and the layers were separated. The aqueous layer was extracted with EtOAc (2×300 mL). The combined organic layers were washed with HCl (1M, 2×300 mL) and aqueous ammonia (25%, 3×300 mL). The organic layer was dried over Na$_2$SO$_4$ and the solvent was evaporated. The resulting brown oil was crystallized from EtOAc to yield XXXV-5c (18 g; 66%).

3-Benzyloxy-15β-(Pent-4-enyl)-estra-1,3,5(10)-trien-17-dioxolane (XXXV-5c-ketal)

Triethyl orthoformate (42 mL; 252 mmol) and ethylene glycol (19 mL; 340 mmol) were added to compound XXXV-5c (18 g; 42.0 mmol). pTosOH (0.67 g; 3.52 mmol) was added to the slurry which was heated to 35° C. overnight. Then the reaction mixture was poured into ice (100 mL) and pyridine (3 mL) was added. This mixture was stirred for 5 h. The mixture was diluted with ethyl acetate, the layers were separated and the aqueous layer was extracted with ethyl acetate (100 mL). The organic layers were washed with water (2×100 mL), dried over Na$_2$SO$_4$ and evaporated. The crude product was purified by column chromatography (heptane/EtOAc 9:1) to yield XXXV-5c-ketal (18.85 g; 95%).

3-Benzyloxy-15β-(5-hydroxypentyl)-estra-1,3,5(10)-trien-17-dioxolane (XXXII-5c)

Compound XXXV-5c (18.85 g; 39.88 mmol) was dissolved in THF (850 mL). Borane dimethylsulfide (2M in diethylether; 128 mL; 256 mmol) was added and the solution was heated at reflux for 2 hours. The solution was then cooled in ice bath and NaOH (3M; 176 mL) was added dropwise. Then H$_2$O$_2$ (35%; 89 mL) was added and the resulting biphasic system was stirred overnight at 40° C. The excess of peroxide was destroyed by addition of dimethylsulfide (380 mL). The solvent was evaporated and water (500 mL) and ethyl acetate (500 mL) was added. The layers were separated and the aqueous layer was extracted with ethyl acetate (500 mL). The organic layer was dried over Na$_2$SO$_4$ and the solvent was evaporated to yield XXXII-5c (15.36 g). The crude product was used in the next step without further purification.

3-Benzyloxy-15β-(5-hydroxypentyl)-estra-1,3,5(10)-trien-17-one (XXXI-5c)

Crude compound XXXII-5c (15.36 g) was dissolved in acetone (135 mL) and water (35 mL) and p-TosOH (0.62 g; 3.26 mmol) was added. The solution was stirred for 3 d at RT. Saturated NaHCO$_3$ solution (50 mL) was added and the solvent was evaporated. More sat. NaHCO$_3$ solution (20 mL) was added and the mixture was extracted with CH$_2$Cl$_2$ (2×100 mL). The organic layer was dried over Na$_2$SO$_4$ and the solvent was evaporated. The crude product was purified by column chromatography (heptane/EtOAc 1:1, R$_f$ 0.3) to yield XXXI-5c (8.65 g; 49% over 2 steps).

3-Hydroxy-15β-(5-Hydroxypentyl)-estra-1,3,5(10)-trien-17-one (XXXI-5a)

Compound XXXI-5c (8.65 g; 19.37 mmol) was dissolved in MeOH (95 mL) and Pd/C (2.3 g) was added as a slurry in some MeOH. Ammonium formate (9.77 g; 154.9 mmol) was added and the solution was stirred at RT. After 1 hour 45 minutes NMR (in CD$_3$OD) showed complete conversion. The reaction mixture was filtered over Celite and washed with MeOH (300 mL). The filtrate was evaporated, remaining a sticky material which was stirred in water (100 mL) at RT. The compound became a solid and the water was decanted after 5 hours. EtOH (100 mL) was added and evaporated to remove the water. The oil was evaporated twice from EtOAc (100 mL), yielding 6 g of an white foam, which contained 10% of the secondary alcohol as an impurity. The side product was removed by transformation to the acetic acid ester (with pyridine and acetic anhydride) and separation by column chromatography (heptane/EtOAc from 2:1 to 1:2). The ester was cleaved by heating with potassium carbonate in MeOH. After work-up the product XXXI-5a (2.21 g; 32%) was obtained as a colorless foam.

LC-MS (ES−): rt 5.23 min, m/z (rel Intens) 355 [(M−H)+, 100%]

Alcohol Building Blocks XXXI-6c and XXXI-6a (n=6, $R^1$=benzyl, n=3, $R^1$=H)

3-Benzyloxy-15β-(6-hydroxyhexyl)-estra-1,3,5(10)-trien-17-one (XXXI-6c)

3-Hydroxy-15β-(6-hydroxyhexyl)-estra-1,3,5(10)-trien-17-one (XXXI-6a)

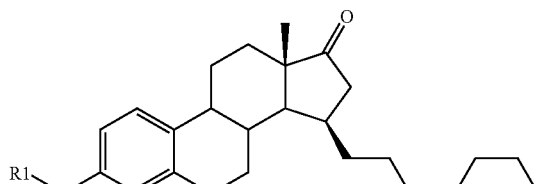

(XXXI-6)

3-Benzyloxy-15β-(6-hydroxyhexyl)-estra-1,3,5(10)-trien-17-one (XXXI-6c)

According to the general procedure displayed in SCHEME 11, the copper reagent was prepared from magnesium (6.56 g, 270 mmol), 2-(6-bromohexyloxy)tetrahydro-2H-pyran (47.2 g, 180 mmol), CuI (3.18 g, 17 mmol) and HMPA (33 mL, 190 mmol) in THF. A mixture of the 15,16 unsaturated estron derivative Xc (10.1 g, 28.00 mmol) and TMSCl (8 ml, 63 mmol) in THF was added dropwise. The reaction mixture was allowed to reach RT and was stirred overnight. After work-up and hydrolysis of the silyl ether the crude product was dissolved in methanol (890 mL) and p-TosOH (3.30 g, 17.35 mmol) was added. The reaction mixture was stirred overnight. Most of the methanol was removed on the rotary evaporator. Water was added and aqueous phase was extracted with DCM (3×). The combined organic layers were dried over $Na_2SO_4$ and the solvent was removed. The crude product was purified by column chromatography ($SiO_2$, heptane/ethyl acetate 2:1) to yield XXXI-6c (7.99 g, 62%).

3-Hydroxy-15β-(6-hydroxyhexyl)-3-estra-1,3,5(10)-trien-17-one (XXXI-6a)

Compound XXXI-6c (7.99 g; 17.35 mmol) was dissolved in MeOH. Pd/C (in water; 2.3 g) was added, followed by ammonium formate (8.58 g; 136 mmol). The mixture was stirred at RT for 1.5 hour after which the mixture was filtered over Celite. The filtrate was evaporated and dissolved in EtOAc (200 mL) and water (150 mL). The layers were separated, the organic layer was dried over $Na_2SO_4$ and the solvent was evaporated. Purification by column chromatography ($SiO_2$, heptane/EtOAc 1:1) yielded # (2.69 g; 42%).

LC-MS (ES−): rt 5.49 min, m/z (rel Intens) 369 [(M−H)+, 100%]

V. Compounds of Formula XV (Protected Amine Building Block) (n=1-6): $R^3$ preferably=H

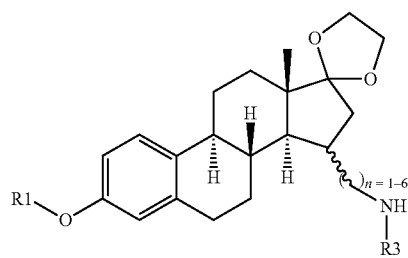

(XV)

XV-1: (n=1)

XV-1b: Ketal Derivative of the 15α-aminomethyl-3-methoxy-estra-1,3,5(10)-trien-17-one XV-1c: Ketal Derivative of the 15β-aminomethyl-3-benzyloxy-estra-1,3,5(10)-trien-17-one

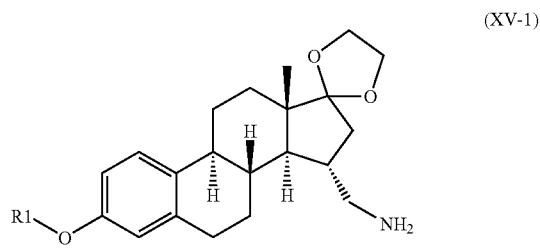

(XV-1)

The individual steps in the synthesis of amine building block of the formula XV-1 are depicted in the following scheme 13.

SCHEME 13

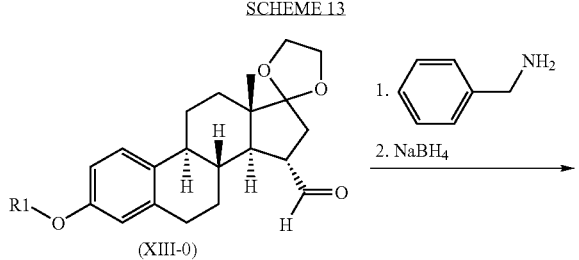

(XIII-0)

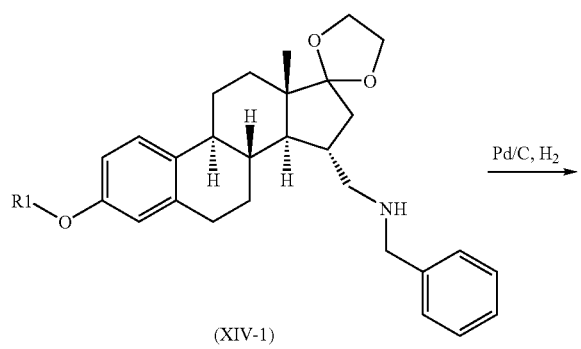

(XIV-1)

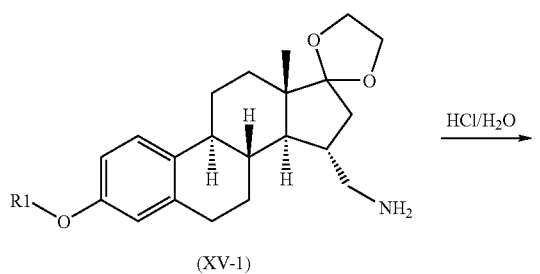

(XV-1)

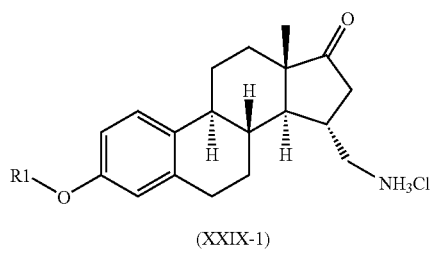

(XXIX-1)

Dissolving aldehydes XIII-0b (R$^1$=CH$_3$) or XIII-0c (R$^1$=benzyl) in benzylamine and reduction of the residual imine in THF gave benzylamine XIV-1b (R$^1$=CH$_3$) and XIV-1c (R$^1$=benzyl), which were debenzylated to XV-1b (R$^1$=CH$_3$) and XV-1a (R$^1$=H), using Pd/C and H$_2$ at 5 bar, and dissolved in dilute HCl to give the respective ammonium chlorides XXIX-1b (R$^1$=CH$_3$) and XXIX-1a (R$^1$=H). Standard purification methods failed due to what seems to be instability of these ammonium salts. For these amines it was known that these should be treated as HCl salts since the free amine is not stable (ene-amines), but even the salts seem to be at least heat-sensitive. The crude reaction mixture has a purity of ~90% (HPLC-MS).

Detailed Synthesis

XIV-1b: Ketal of 15α-(Benzylamino-methyl)-3-methoxy-estra-1,3,5(10)-trien-17-one XIV-1c: Ketal of 15α-(Benzylamino-methyl)-3-benzyloxy-estra-1,3,5(10)-trien-17-one The aldehyde XIIIb or XIIIc (0.93 mmol) was dissolved in benzylamine (0.4 mL, 3.9 mmol) and MeOH (10 mL) upon heating and the mixture was stirred for 30 min and evaporated to dryness. The residue was dissolved in dry THF and aliquots of 50 mg of NaBH$_4$ were added each hour until 300 mg (4.0 mmol) was added. The mixture was stirred overnight: only a baseline spot was observed on TLC (TBME). The mixture was evaporated to dryness and the residue was stirred with NaHCO$_3$(aq) (200 mL) until no gas evolved anymore. The suspension was extracted with CH$_2$Cl$_2$ (2×200mL) and upon drying the organic layer with Na$_2$SO$_4$ and evaporation to dryness, compounds XIVb and XIVc were obtained as colorless oils: yield 92-100%.

XV-1b: Ketal Derivative of the 15α-Aminomethyl-3-methoxy-estra-1,3,5(10)-trien-17-one XV-1a: Ketal Derivative of the 15α-Aminomethyl-3-hydroxy-estra-1,3,5(10)-trien-17-one A suspension of benzylamines XIVb or XIVc (22 mmol) and Pd/C (10%, 1.0 g, cat) in MeOH (500 mL) was stirred in a 5 bar H$_2$-atmosphere for 48 h. Filtration through Celite and evaporation to dryness gave crude amines XV-1a and XV-1b. Amine XV-1a was purified by column chromatography (CHCl$_2$/MeOH (7N NH$_3$); 925:75) giving XV-1a as a colorless oil (5.0 g, 63% for three steps starting from aldehyde XIIIc). Amine XV-1b decomposed in many products upon standing overnight. Therefore in a second attempt it was used instantly without purification in the next step.

XXIX-1b: 15α-Aminomethyl-3-methoxy-estra-1,3,5(10)-trien-17-one/HCl

XXIX-1a: 15α-Aminomethyl-3-benzyloxy-estra-1,3,5(10)-trien-17-one/HCl

A solution of amine XV-1b (1.1 mmol) in MeOH (10 mL) was added to HCl (5 mL, 30% in H$_2$O). The reaction mixture was stirred overnight and concentrated until crystallization starts. Filtration gave the product XXIX-1b (130 mg, 33%).

A pure sample (95%+) of XXIX-1a was obtained by dissolving XV-1a in 1N HCl (20 mL) and isolating XXIX-1a via preparative HPLC (20 runs of 1 mL injections of reaction mixture). Evaporation of the eluent in vacuo at 40-45° C. introduced the degradation product for 3-4%.

The compound XIV-1 is an example for a secondary amine which can be used as building block for the further synthesis of the compounds according to the invention, in which the R$^3$ residue is other than hydrogen. Further secondary amines according to formula XIV-1 which can be used as building blocks may be synthesized by the addition of the appropriate primary amines in the first step of the above indicated synthesis SCHEME 13.

A further example for a secondary amine which may be used as a building block is 15α-(methylamino-methyl )-3-methoxy-estra-1,3,5(10)-trien-17-one:

XXXVIII-1a: Ketal of 15α-(Methylamino-methyl)-3-hydroxy-estra-1,3,5(10)-trien-17-one XXXVIII-1b: Ketal of 15α-(Methylamino-methyl)-3-methoxy-estra-1,3,5(10)-trien-17-one XXXVIII-1c: Ketal of 15α-(Methylamino-methyl)-3-benzyloxy-estra-1,3,5(10)-trien-17-one

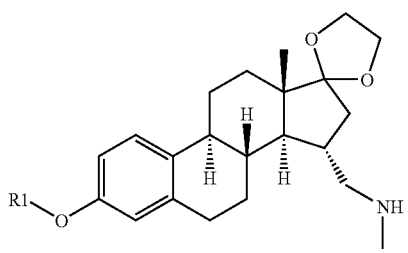
(XXXVIII-1)

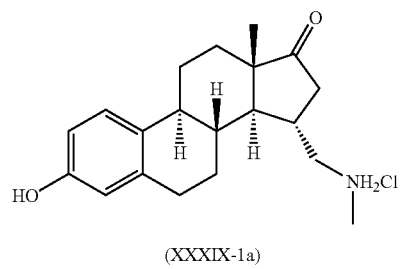
(XXXIX-1a)

Conversion of the aldehyde XIIIc to the methylimine using Ti(i-OPr)$_4$ and the consecutive imine-reduction gave methylamine XXXVIII-1c. Debenzylation of XXXVIII-1c gave XXXVIII-1a. Dissolving XXXVIII-1a in dilute HCl and crystallization from MeOH/H$_2$O gave XXXIX-1a.

The individual steps in the synthesis of secondary amine building block of the formulas XXXVIII-1b and XXXVIII-1c are depicted in the following scheme 15.

The individual steps in the synthesis of secondary amine building block of the formula XXXVIII-1a are depicted in the following scheme 14.

SCHEME 14

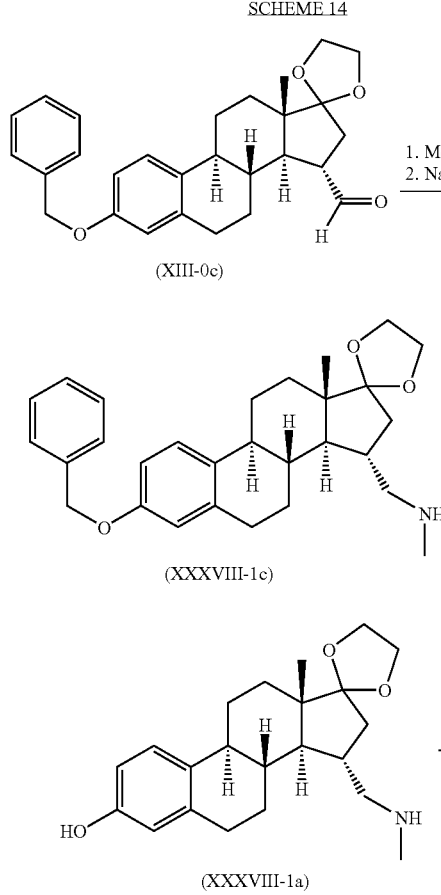

SCHEME 15

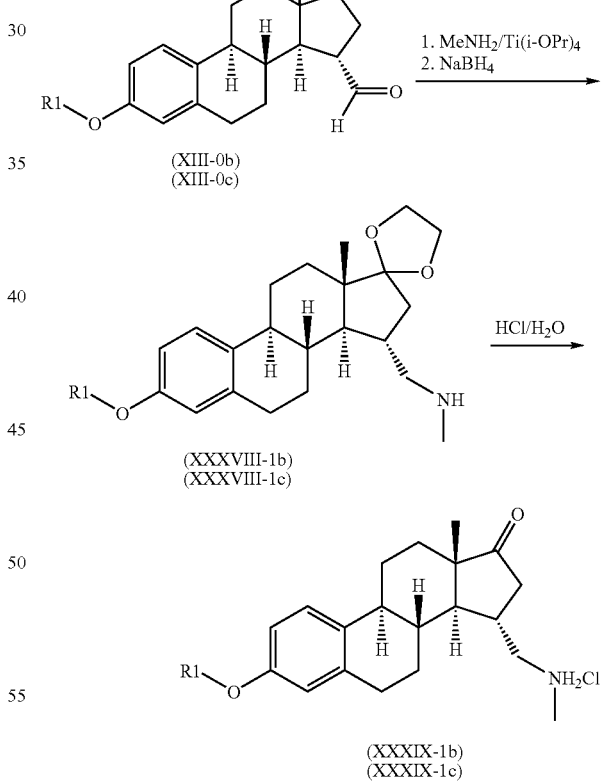

Conversion of the aldehydes XIIIb (R$^1$=CH$_3$) and XIIIc (R$^1$=benzyl) to the methylimine using Ti(i-OPr)$_4$ and the consecutive imine-reduction gave respective methylamines XXXVIII-1c and XXXVIII-1b. Dissolving XXXVIII-1c or XXXVIII-1b in dilute HCl and crystallization from MeOH/H$_2$O gave XXXIX-1b (R$^1$=CH$_3$) and XXXIX-1c (R$^1$=benzyl).

Detailed Synthesis

XXXVIII-1 b: Ketal of 15α-(Methylamino-methyl)-3-methoxy-estra-1,3,5(10)-trien-17-one XXXVIII-1c: Ketal of 15α-(Methylamino-methyl)-3-benzyloxy-estra-1,3,5(10)-trien-17-one NH$_2$Me (9.26 mL, 2.0M in MeOH, 18.52 mmol) was added to a suspension of aldehyde XIIIb or XIIIc (1.85 mmol) in Ti(i-OPr)$_4$ (0.84 mL, 2.78 mmol). The suspension became a clear solution upon stirring for 2.5 h. This reaction has to be followed by TLC (TBME/CH$_2$Cl$_2$,1:1). When reaction was complete, NaBH$_4$ was added (500 mg, 13.2 mmol) and reaction was continued overnight. NaHCO$_3$(aq) (200 mL) was added and the mixture was evaporated to dryness. The residue was extracted with CHCl$_3$ (100 mL) using ultrasound. This extraction was repeated until at least 75% yield was obtained.

XXXVIII-1a: Ketal of 15α-(Methylamino-methyl)-3-hydroxy-estra-1,3,5(10)-trien-17-one Debenzylation of XXXVIII-1c with Pd/C (10%, 1.0 g, cat) in MeOH (500 mL) in a 5 bar H$_2$-atmosphere for 48 h gave the crude amine XXXVIII-a.

XXXVIII-1a: 15α-(Methylamino-methyl)-3-hydroxy-estra-1,3,5(10)-trien-17-one

XXXVIII-1b: 15α-(Methylamino-methyl)-3-methoxy-estra-1,3,5(10)-trien-17-one

A solution of amine XXXVIII-1b or XXXVIII-1a (1.1 mmol) in MeOH (10 mL) was added to HCl (5 mL, 30% in H$_2$O). The reaction mixture was stirred overnight and evaporated to dryness. In case of XXXIX-1a fractioned recrystallization of the residue (~90% pure) from MeOH gave a sample of pure material (110 mg). In case of XXXIX-1b a sample (100 mg) was isolated by column chromatography (CH$_3$Cl/NEt$_3$/MeOH, 17:2:1).

Amine Building Block XVα-3: (n=3)

XVα-3a: Ketal Derivative of the 15α-Aminopropyl-3-hydroxy-estra-1,3,5(10)-trien-17-one XVα-3b: Ketal Derivative of the 15α-Aminopropyl-3-methoxy-estra-1,3,5(10)-trien-17-one (XVα-3)

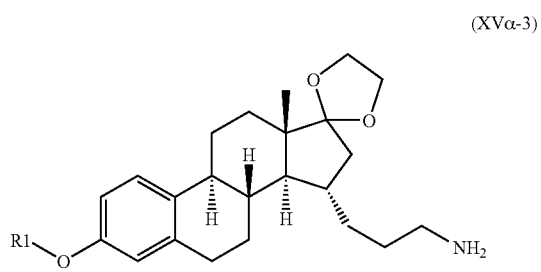

The individual steps in the synthesis of amine building block of the formula XVα-3 are depicted in the following scheme 16.

SCHEME 16:

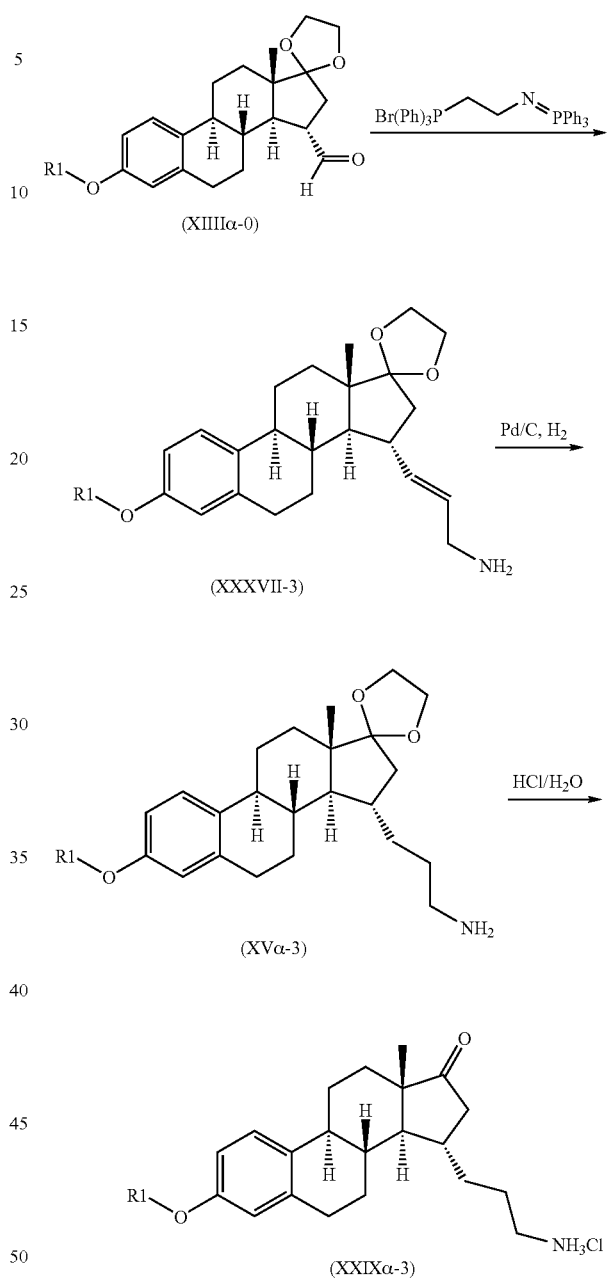

The protected aldehyde derivative of formula (XIIIα-0) is converted into the corresponding aminopropenyl by a Wittig reaction (see also SCHEME 4). The aminopropenyl (XXXVII-3) is subsequently reduced to the 15-aminopropyl derivative of formula XVα-3. The protecting ketal group is converted into the 17-oxo group via acid hydrolysis.

The same kind of procedure can be applied using different Wittig reagents of the general formula Hal(Ph)$_3$P-(CH$_2$)$_{n=3-5}$-R* in order to obtain amine building blocks with longer side chains (i.e. n=4, 5, or 6), wherein R* for example represents —N=P(Ph)$_3$, —N$_3$, or —NH—CO—O—CH$_3$.

87

Amine Building Block XVα-4: (n=4)

XVα-4a: Ketal Derivative of the 15α-Aminobutyl-3-hydroxy-estra-1,3,5(10)-trien-17-one XVα-4b: Ketal Derivative of the 15α-Aminobutyl-3-methoxy-estra-1,3,5(10)-trien-17-one (XVα-4)

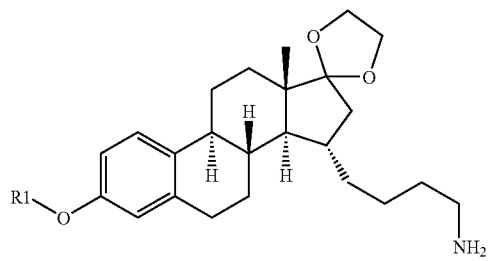

Furthermore, the amine building block XVα-4b was synthesized corresponding to SCHEME 16 using HalPh$_3$P—CH$_2$—CH$_2$—CH$_2$—N$_3$ as Wittig reagent. (LC-MS (ES+): rt 4.57 min, m/z (rel. Intens) 386 [(M+H)+, 100%])

XVβ-4: (n=4)

XVβ-1b: Ketal Derivative of the 15β-Aminobutyl-3-methoxy-estra-1,3,5(10)-trien-17-one XVβ-1c: Ketal Derivative of the 15β-Aminobutyl-3-benzyloxy-estra-1,3,5(10)-trien-17-one (XV-4)

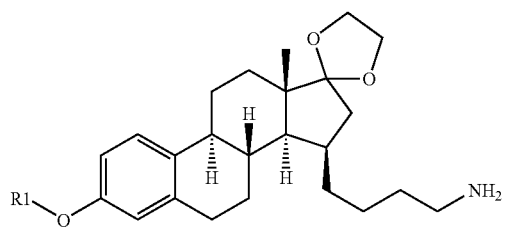

The individual steps in the synthesis of amine building block of the formula XVβ-4 with β configuration at the C 15 atom of the steroidal core are depicted in the following scheme 17.

SCHEME 17

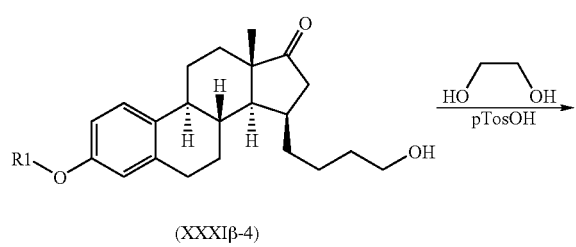

(XXXIβ-4)

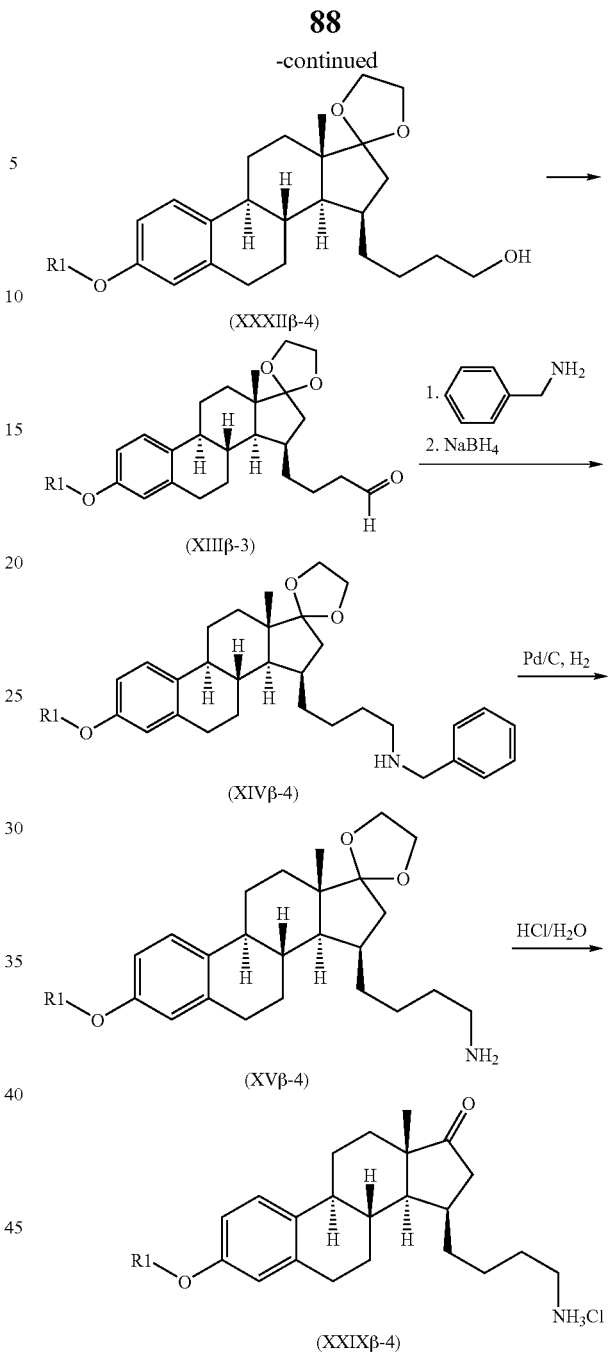

In a first step, the 17 oxo function of the butanol derivative of the formula XXXIβ-4 (for synthesis of XXXIβ-4 see above) is converted into the ketal group (compound of formula XXXIIβ-4). Then, the alcohol function is selectively reduced to the aldehyde giving compound of the formula XIIIβ-3. The protected aldehyde derivative of the formula XIIIβ-3 is converted into a secondary amine by addition of Benzylamine and subsequent reduction (reductive amination). Further reduction of the secondary amine delivers the desired, still protected amine building block of the XVβ-4. The protecting ketal group can be converted into the 17-oxo group via acid hydrolysis.

The same kind of procedure can be applied for n=5 of 6 and for other substituents within the R$^1$ position.

Furthermore, the compound XIVβ-4 is an example for a secondary amine which can be used as building block for the further synthesis of the compounds according to the invention, in which the R3 residue is other than hydrogen. Further secondary amines which can be used as building blocks may be synthesized by the addition of the appropriate primary amines in the first step of the above indicated synthesis scheme 17.

Amine Building Block (n=1-6): $R^3$ preferably=H of general formula XXIX

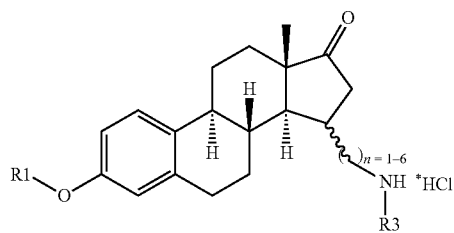

(XXIX)

Alternatively, the synthesis of the amine building blocks of general formula XXIX can also be performed starting with an activated alcohol function and a subsequence substitution reaction, and does not need any protection of the Estron-C17 keto function according to the following general scheme 18.

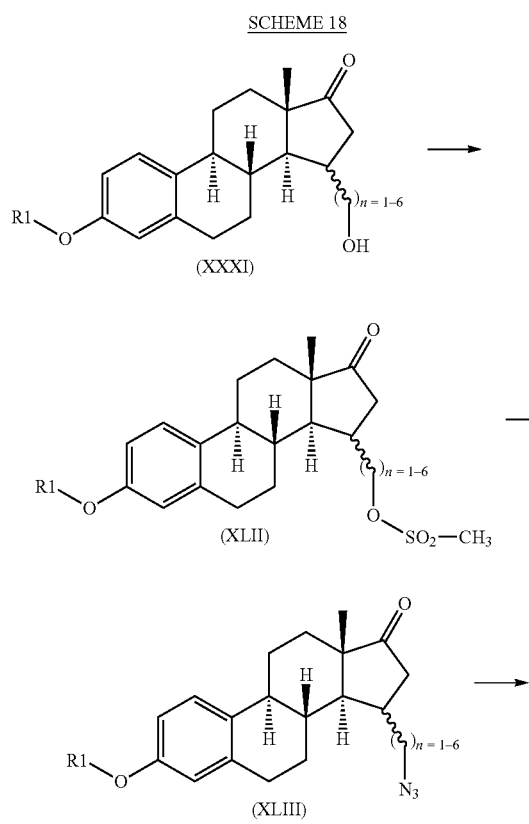

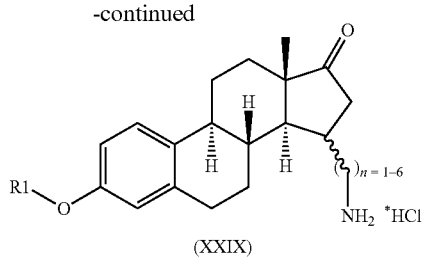

Example: XXIXβ-4b: 15β-Aminobutyl-3-methoxy-estra-1,3,5(10)-trien-17-one (XXIXβ-4)

Detailed Synthesis

XLIIβ-4b: Methanesulfonic Acid 4-(3-methoxy-17-oxo-estra-1,3,5(10)-trien-15-yl)-butyl Ester (XLII with n=4 and $R^1$=$CH_3$ and β configuration at C15)

4 g (11,22 mMol) alcohol (XXXIβ-4b) dissolved in 50 ml THF were cooled down to 0° C. under dry conditions before adding 1 eq TEA and 1 eq methansulfonic acid chloride dropwise. After stirring 3 hours at 0° C. another 0.25 eq TEA and methansulfonic acid chloride were added; this procedure was repeated after 2 hours to drive the reaction to completeness. For work up, the reaction mixture was pured on ice/water at the next morning. The water was extracted twice with EE, which thereafter was combined and washed with 1 molare $NaHCO_3$ solution. After evaporation 5.19 g oil containing compound XLIIβ-4b (LC MS: MH+ 435, rt 6.50 min, still containing some solvent residues) were obtained, which were used further without any purification.

XLIIIβ-4b: 15-(4-Azido-butyl)-3-methoxy-13-methyl-estra-1,3,5(10)-trien-17-one (XLIII with n=4 and $R^1$=$CH_3$ and β configuration at C15)

5.19 of XLIIβ-4b obtained in the previous step (approx. 11 mmol) and 0.91 g $NaN_3$ were dissolved in 150 ml ethanol and kept under reflux for 10 h. Next morning most of the ethanol was distilled off under reduced pressure. Subsequently, the residue was partitioned between water and EE. The water layer was extracted twice with EE. The organic layers were combined, dried with $NaSO_4$ and evaporated yielding 4.4 g oil XLIIIβ-4b (LC-MS: MH+=382, rt 7.32 min, still containing some solvent residues), which can be used without further purification.

XXIXβ-4b: 15β-Aminobutyl-3-methoxy-estra-1,3,5(10)-trien-17-one 3,3 g azide (XLIIIβ-4b) were dissolved in 300 ml ethanol. 20 ml 18% $HCl_{aq}$ and 50 mg Pd/C 5% were added. The suspension was put in a shaker unit which was pressurized with 3 bar hydrogen for 6 hours. After filtration the filtrate was evaporated and the remaining solid dried for 4 hours at 60° C. in a vacuum drying oven yielding 3.2 g of the amine hydrochloride salt XXIXβ-4b.

(LC-MS: MH+: 356; rt: 4.84 min)

Experimental

Examples of preparations of compounds of the invention are provided in the following detailed synthetic procedures. In the tables of compounds to follow, the synthesis of each compound is referenced back to these exemplary preparative steps.

In single compound synthesis as well as in combinatorial synthesis all reactions were stirred magnetically or shaken with an orbital shaker unless otherwise indicated. Sensitive liquids and solutions were transferred via syringe or cannula, and introduced into reaction vessels through rubber septa, in these cases the reaction were carried out under a positive pressure of dry argon or dry nitrogen. Commercial grade reagents and solvents were used without further purification.

Unless otherwise stated, the term "concentration under reduced pressure" refers to use of a Buchi or Heidolph rotary evaporator ("Rotavapor") or vacuum centrifuges ("Gene-Vac") at approximately 15 mm of Hg. All temperatures are reported uncorrected in degrees Celsius (° C.). Unless otherwise indicated, all parts and percentages are by volume.

Thin-layer chromatography (TLC) was performed on Merck® pre-coated glass-backed silica gel or aluminium sheets 60A F-254 250 μm plates. Visualization of plates was effected by one or more of the following techniques: (a) ultraviolet illumination (254 nm or 266 nm), (b) exposure to iodine vapor, (c) spraying of the plate with Schlittler's reagent solution followed by heating, (d) spraying of the plate with anisaldehyde solution followed by heating, and/or (e) spraying of the plate with Rauxz reagent solution followed by heating. Column chromatography (flash chromatography) was performed using 230-630 mesh ICN, SiliTech 60A silica gel.

Melting points (mp) were determined using a Reichert Thermovar melting point apparatus or a Mettler DSC822 automated melting point apparatus and are uncorrected.

Fourier transform infrared spectra were obtained using a Perkin Elmer spectrophotometer.

Proton (1H) nuclear magnetic resonance (NMR) spectra were measured with a Bruker ARX (400 MHz) or Bruker ADVANCE (500 MHz) spectrometer with either Me$_4$Si (δ 0.00) or residual protonated solvent (CHCl$_3$ δ 7.26; CHD$_2$OD δ 3.30; DMSO-d$_5$ δ 2.50) as standard. Carbon ($^{13}$C) NMR spectra were measured with a Bruker ARX (100 MHz) spectrometer with either Me$_4$Si (δ 0.00) or solvent (CDCl$_3$ δ 77.05; CD$_3$OD δ 49.0; DMSO-d$_6$ δ 39.45) as standard.

HPLC electrospray mass spectra (HPLC ES-MS) were obtained using the following method and equipment: Samples were separated by reversed phase high pressure liquid chromatography (RP-HPLC) coupled to a quadrupol MS. HPLC was performed at a flow of 1000 μl/min using XterraMS C18 columns (i.d. 4.6 mm, length 50 mm, particle size 2.5 μm) or Phenomenex Luna C18(2) 30*4.6 mm columns. For most samples, a gradient from 0% eluent B to 95% B was run in 10 min, with eluent A consisting of water, 10 mM ammonium-acetate at pH 5+5% acetonitrile and eluent B consisting of acetonitrile. Two different setups were used: 1. Waters Alliance 2795 coupled to a Waters ZQ MS, a Waters 2996 diode array detector (DAD) and an evaporative light scattering detector (ELSD, EL-ELS1000, PolymerLabs).

Ionization: electrospray positive and negative mode ES +/−. Or 2. LC200 pump (PE) coupled to an API100 MS (Applied Biosystems Sciex), a variable wavelength detector Waters 2487 set to 225 nm, and an ELSD (Sedex 75), ES+. In both setup versions spectra were scanned with a scan range of m/z 100 to 800 or 100 to 900.

Gas chromatography—mass spectra (GC-MS) analyses were performed with an Agilent 6890 gas chromatograph equipped with an DB-5MS column (0.25 i.d., length 30 m) and an Agilent 5973 MSD quadrupol detector (ionization with electron impact (EI) at 70 eV; source temperature 230° C.).

Elemental analyses were conducted by a VarioEL elemental analyzer (Elementar Analysensysteme) for determination of C, H, and N. Acetanilide was used for conditioning and calibration.

NMR spectra, LRMS, elemental analyses and HRMS of the compounds were consistent with the assigned structures.

EXAMPLES

In order to more fully illustrate the nature of the invention and the manner of practicing the same, the following examples are presented, but they should not be taken as limiting.

Examples 1, 2, 3A, 3B and 4B

No. 1. 3-Hydroxy-15β-(4-morpholin-4-yl-4-oxo-butyl)-estra-1,3,5(10)-trien-17-one (VIβ-3a)-1

No. 2. 3-Methoxy-15β-(4-morpholin-4-yl-4-oxo-butyl)-estra-1,3,5(10)-trien-17-one (VIβ-3b)-2

No. 3.A. N-Benzyl-4-(3-hydroxy-17-oxo-estra-1,3,5(10)-trien-15β-yl)-butyramide (VIβ-3a)-3A No. 3.B. N-Benzyl-4-(3-methoxy-17-oxo-estra-1,3,5(10)-trien-15β-yl)-butyramide (VIβ-3b)-3B No. 4.B. 4-(3-Methoxy-17-oxo-estra-1,3,5(10)-trien-15β-yl)-N-methyl-butyramide (VIβ-3b)-4B The individual steps in the synthesis of the examples 1, 2, 3.A., 3.B. and 4.B. are depicted in the following scheme 19.

SCHEME 19

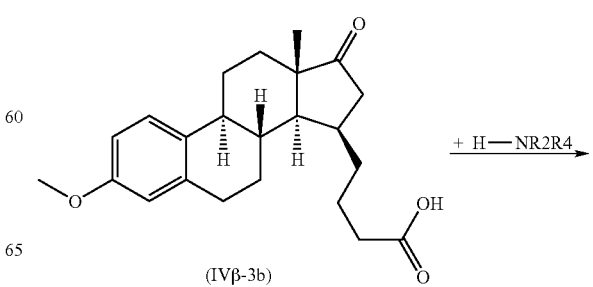

(IVβ-3b)

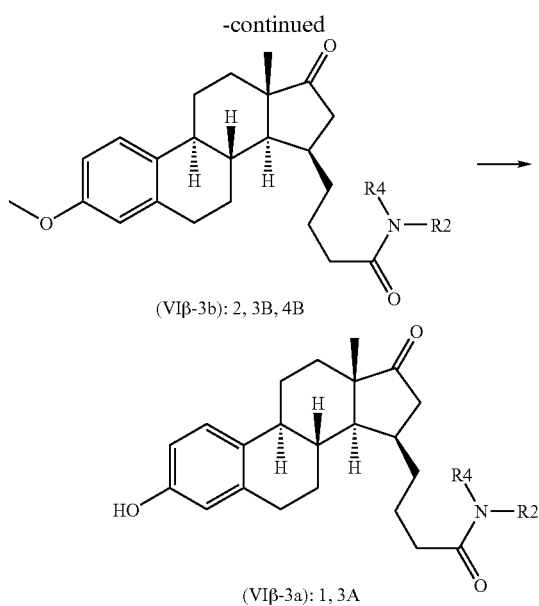

(VIβ-3b): 2, 3B, 4B (VIβ-3a): 1, 3A

Starting with the free acid building block of formula IVβ-3b, the corresponding acid chloride was prepared using oxalylchloride. The acid chloride was reacted with an amine of general structure $R^2R^4NH$, which represents morpholine for the synthesis of compounds No. 1 and 2, benzylamine for compounds No. 3A and 3B, and methylamine for compound No. 4B, delivering after the first synthesis step the amides of general formula (VIβ-3b): compound No. 2 (with —$NR^2R^4$=morpholine), 3B (with —$NR^2R^4$=—NH-benzyl) and 4B (with —$NR^2R^4$=—NH—$CH_3$). Compound 3B was purified by column chromatography followed by trituration with $Et_2O$ and isolated in 8% yield. Compound 4B was purified by trituration with $Et_2O$ and some MeOH and isolated in a yield of 48%. Compound 2 was purified by column chromatography and obtained in a yield of 33%.

Demethylation of the 3-hydroxyfunction was successful for compound No. 2 and No. 3B with $BBr_3$, resulting in the amide of general formula (VIβ-3a) representing compounds No. 1 and No. 3A in respectively 21 and 48% yield. Compound No. 1 was obtained, after column chromatography, as a mixture of α and β isomer. Purification of the compound No. 3A was accomplished by column chromatography.

Detailed Synthesis

Example No. 2

3-Methoxy-15β-(4-morpholin-4-yl-4-oxo-butyl)-estra-1,3,5(10)-trien-17-one of Formula (VIβ-3b)-2

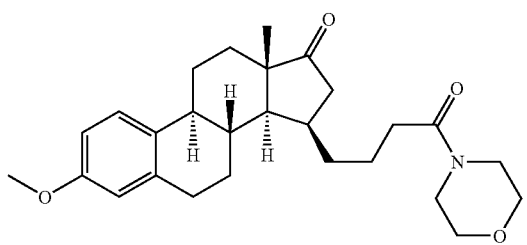

The acid building block IVβ-3b (1.1 g, 2.7 mmol) was dissolved in DCM (20 ml) and 1 drop DMF was added. The reaction mixture was cooled to 0° C. and oxalylchloride (0.25 ml, 2.7 mmol) was added dropwise. After stirring the mixture for 1 hour at 0° C., the solvent was removed on the rotary evaporator. The acid chloride was dissolved in DCM (20 ml) and morpholine (0.31 ml, 3.51 mmol) was added dropwise. The reaction mixture was stirred overnight. Water (20 ml) and DCM (30 ml) were added. After separating the layers, the water layer was extracted with DCM (2×25 ml). The combined organic layers were washed with water (20 ml) and brine (60 ml). The organic layer was dried over $Na_2SO_4$ and the solvent was removed on the rotary evaporator. This yielded 1.3 g of yellow oil, which was dissolved in TBME and $Et_2O$/EtOH, some brown solid precipitated. The liquid phase was decanted and the solvent was removed on the rotary evaporator. This yielded 865 mg yellow/white solid. HPLC analysis showed that the compound was ca. 80% pure. The solid was purified by column chromatography (50 g $SiO_2$, EtOAc/heptane: 1/2). This yielded 670 mg with a purity of 86% according to HPLC. A second purification by column chromatography (25 g $SiO_2$, EtOAc/heptane: 2/1) finally gave 414 mg (0.94 mmol, 33%) of the desired compound No. 2 as a white solid with a purity of 96% according to HPLC [MS m/z 439.1].

Example No. 1

3-Hydroxy-15β-(4-morpholin-4-yl-4-oxo-butyl)-estra-1,3,5(10)-trien-17-one of Formula (VIβ-3a)-1

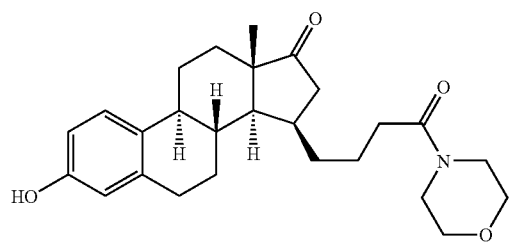

Methoxy compound (VIβ-3b)-2 (898 mg, 2.0 mmol) was dissolved in DCM (20 ml) and cooled to 0° C. $BBr_3$ solution (12.3 ml, 1 M in $CH_2Cl_2$) was added dropwise while the temperature was maintained at 0° C. The color changed from colorless to yellow/orange to orange/red to pink. The reaction was followed by TLC ($SiO_2$, EtOAc) and after 1 ¾ hour the reaction was completed. 40 ml of water was added followed by 30 ml of a saturated $NaHCO_3$ solution and further 200 ml of water. The layers were separated and the water layer was extracted with DCM. The combined organic layers were dried over $Na_2SO_4$ and the solvent was removed on the rotary evaporator. This yielded 915 mg yellow oily solid. The product was purified by column chromatography (50 g $SiO_2$, toluene/acetone: 3/1) to afford 183 mg (0.43 mmol, 21%) of the desired compound No. 1 as a yellow solid, with a purity of 95% [MS m/z 425.2]

Example No. 3B

N-Benzyl-4-(3-methoxy-17-oxo-estra-1,3,5(10)-trien-15β-yl)-butyramide of Formula (VIβ-3b)-3B

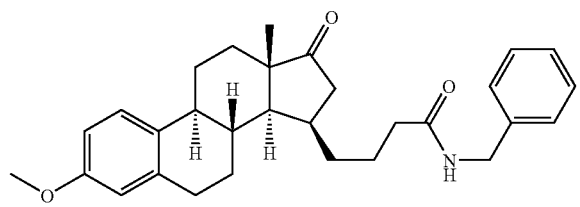

The acid building block IVβ-3b (1.2 g, 3.3 mmol) was dissolved in DCM (20 ml) and 1 drop DMF was added. The reaction mixture was cooled to 0° C. and oxalylchloride (0.28 ml, 3.3 mmol) was added dropwise. The mixture was stirred for 1 hour at 0° C. and the solvent was removed on the rotary evaporator. The acid chloride was dissolved in 20 ml DCM and benzylamine (0.48 ml, 4.34 mmol) was added dropwise. The yellow/orange solution turned turbid yellow/white. Stirring was continued for 0.5 hour at RT followed by the addition of 20 ml water and 25 ml DCM. The water layer was extracted with DCM (2×20 ml) and the combined organic layers were washed with water (20 ml) and brine (20 ml). The organic layer was dried over $Na_2SO_4$ and the solvent was removed on the rotary evaporator. This yielded 1.3 g of yellow oil (56% pure according to HPLC analysis), which was then purified by column chromatography (53 g $SiO_2$, TBME /heptane: 2/1). This purification yielded 668 mg of a white solid (44%, 87% pure according to HPLC analysis). 400 mg was used for demethylation to prepare (VIβ-3a)-3A; 268 mg was triturated with $Et_2O$ to yield 124 mg white solid (0.27 mmol, 8%) with a purity of 94% according to HPLC [MS m/z 459.1].

Example: No. 3A

N-Benzyl-4-(3-hydroxy-17-oxo-estra-1,3,5(10)-trien-15β-yl)-butyramide of Formula (VIβ-3a)-3A

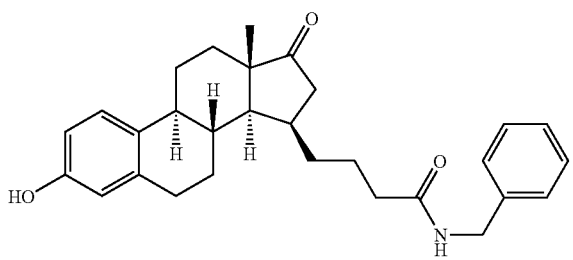

To a solution of the methoxy compound (VIβ-3a)-3B (400 mg, 0.87 mmol) in DCM (100 ml) at 0° C., 5.2 ml of an 1 M solution of $BBr_3$ in DCM was added dropwise at such a rate that the temperature was maintained at 0° C. The color changes from colorless to orange. After complete addition, the reaction was monitored by TLC (EtOAc/heptane: 2/1). The reaction was complete after 1.5 h. Then, water (40 ml), saturated $NaHCO_3$ solution and more water (150 ml) were added. The layers were separated and the aqueous layer was extracted with DCM (2×100 ml). The organic layers were combined, dried over $Na_2SO_4$ and the solvent was removed on the rotary evaporator. This yielded 310 mg red/purple product, which was purified by column chromatography (15 g $SiO_2$, toluene/acetone: 3/1) to afford 173 mg yellow foam with a purity of 82%. The product was again purified by column chromatography (11 g $SiO_2$, toluene/acetone: 3/1). This purification yielded 160 mg yellow solid (0.36 mmol, 41%) with a purity of 93% according to HPLC [MS m/z 445.1].

Example No. 4B 4-(3-Methoxy-17-oxo-estra-1,3,5(10)-trien-15β-yl)-N-methyl-butyramide of Formula (VIβ-3b)-4B

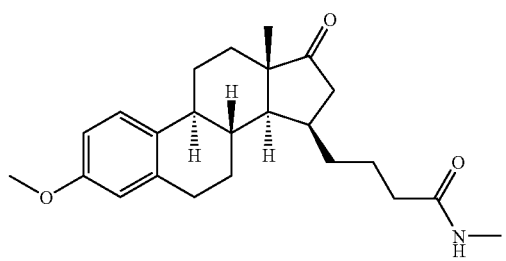

The acid building block IVβ-3b (846 mg, 2.3 mmol) was dissolved in DCM (20 ml) and 1 drop DMF was added. The reaction mixture was cooled to 0° C. and oxalylchloride (0.20 ml, 2.3 mmol) was added dropwise. After stirring for 1 hour at 0° C., the solvent was removed on the rotary evaporator. The acid chloride was dissolved in DCM (20 ml) and 5.7 ml of a 2 M solution of methylamine in THF was added dropwise. The reaction mixture was stirred for 0.5 hour. Water (20 ml) and DCM (25 ml) were added. After separating the layers, the water layer was extracted with DCM (2×25 ml). The combined organic layers were washed with water (20 ml) and brine (20 ml). The organic layer was dried over $Na_2SO_4$ and the solvent was removed on the rotary evaporator. This yielded 593 mg solid, which was stirred in $Et_2O$ and some MeOH. The white solid was isolated, filtered and dried. This yielded 424 mg (1.1 mmol, 48%) with a purity of 95% according to HPLC [MS m/z 383.2].

Examples 4A and 4C

No. 4.A. 4-(3-Hydroxy-17-oxo-estra-1,3,5(10)-trien-15β-yl)-N-methyl-butyramide (VIβ-3a)

No. 4.C. 4-(3-Benzyloxy-17-oxo-estra-1,3,5(10)-trien-15β-yl)-N-methyl-butyramide (VIβ-3a)

The individual steps in the synthesis of the examples No. 4A (compound (VIβ-3a)-4A) and No. 4C (compound (VIβ-3c)-4C) are depicted in the following scheme 20 (according to general flow diagram Ib).

SCHEME 20

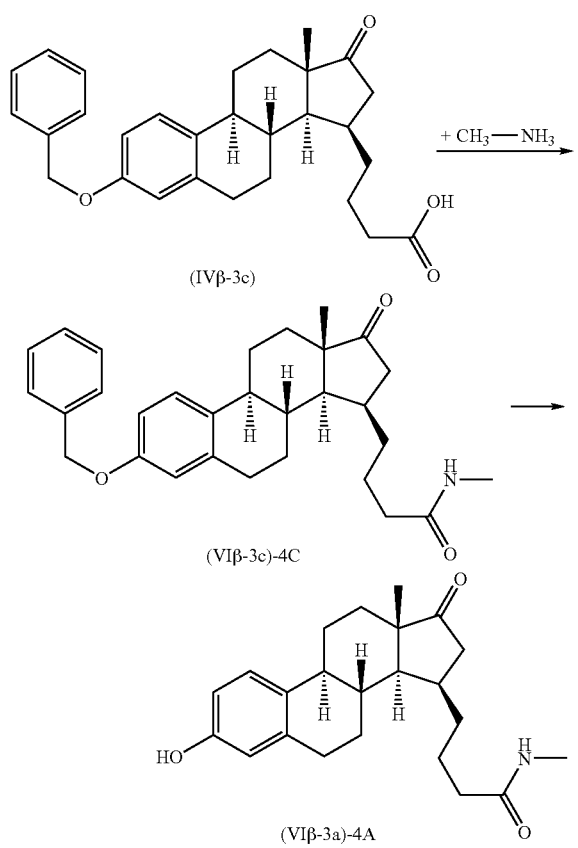

Starting with the free acid building block of formula IVβ-3c, the corresponding acid chloride was prepared using oxalylchloride and this was converted into the amide (VIβ3c)-4C (y=26%). Finally this amide was debenzylated to yield compound (VIβ-3a)-4A (y=13%) as a white solid with a purity of 83% (mixture of α and β isomer).

Detailed Synthesis

No. 4C: 4-(3-Benzyloxy-17-oxo-estra-1,3,5(10)-trien-15β-yl)-N-methyl-butyramide (VIβ-3-3c)-4C

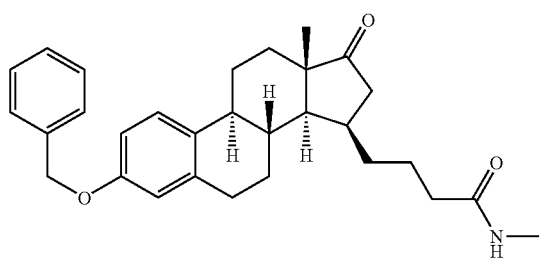

The acid building block IVβ-3c (1.9 g, 4.4 mmol) was dissolved in DCM (40 ml) and 1 drop DMF was added. The reaction mixture was cooled to 0° C. and oxalylchloride (0.38 ml, 4.4 mmol) was added dropwise. After stirring for 1 h at 0° C., the solvent was removed on the rotary evaporator. The acid chloride was dissolved in DCM (20 ml) and 13.1 ml of a 2 M solution of methylamine in THF was added dropwise. The reaction mixture was stirred overnight. To the light yellow mixture was added water (40 ml) and DCM (50 ml) were added. After separating the layers, the water layer was extracted with DCM (2×40 ml). The combined organic layers were washed with water (40 ml) and brine (40 ml). The organic layer was dried over Na$_2$SO$_4$ and the solvent was removed on the rotary evaporator. This yielded 1.4 g solid, which was purified by column chromatography (42 g SiO$_2$, toluene/acetone: 3/1). This yielded 509 mg (11.2 mmol, 26%) of the compound (VIβ-3c)-4C as a yellow/white solid with a purity of 91% according to HPLC.

No. 4A: 4-(3-Hydroxy-17-oxo-estra-1,3,5(10)-trien-15β-yl)-N-methyl-butyramide (VIβ-3a)-4A

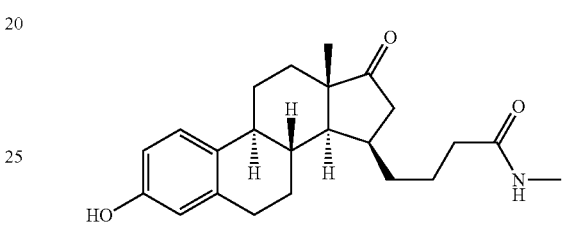

The compound (VIβ-3c)-4C (509 mg, 11.2 mmol) was dissolved MeOH (75 ml) and N$_2$ was bubbled through for a few minutes. Pd/C (500 mg) was added and a H$_2$ balloon was placed on the flask. The mixture was stirred overnight. The mixture was then filtered over Celite and the MeOH was removed on the rotary evaporator until crystallization started. The white precipitate was filtered off and dried. This purification yielded 54 mg (0.146 mmole) of the compound (VIβ-3a)-4A (13%) as a mixture of α and β isomer, with a purity of 83% according to HPLC [MS m/z 369.1].

Examples 5 to 35

A variety of formula I compounds (examples 5 to 35), in which X represents a bond, A represents CO, Y represents NR$^4$, n is 3, R$^1$ represents CH$_3$, and C15 is substituted in the β position, was prepared by parallel chemistry using a reaction as shown in the following scheme 21 (according to general flow diagram Ib):

SCHEME 21

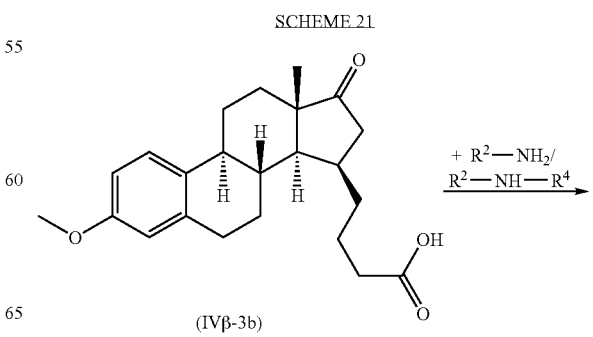

-continued

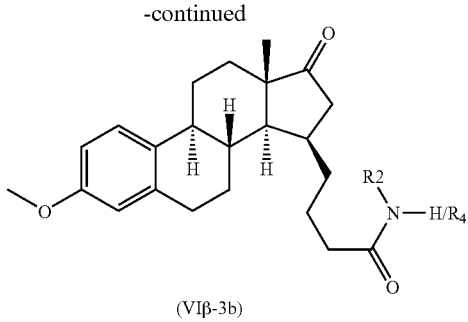

(VIβ-3b)

A mixture of 0.13 mmol of the acid building block of formula (IVβ-3b), 0.19 mmol of the respective amine ($R^2$—$NH_2$ or $R^2$—NH—$R^4$), 0.19 mmol hydroxybenzotriazole, 0.19 mmol N-methylmorpholine and 0.19 mmol EDCI were dissolved in DCM and stirred for 24 h at RT. DCM was evaporated and replaced by EtOAc. The organic layer was washed twice with water. If necessary the material was purified by flash chromatography. The material thereafter was analyzed by LC-MS.

The following group of compounds was prepared by this method (table 1):

TABLE 1

Compounds of the formula VIβ-3b, wherein $R^4$ is H and $R^2$ is varied, and with the general name
N—"$R^2$"-4-(3-methoxy-17-oxo-estra-1,3,5(10)-trien-15-yl)-butyramide:

| No. | $R^2$ | MS m/z | Rt min. |
|---|---|---|---|
| 5 | Cyclopropyl | 409.3 | 5.89 |
| 6 | Cyclohexyl | 451.3 | 6.10 |
| 7 | Furan-2-yl | 449.3 | 5.74 |
| 8 | Benzo[1,3]dioxol-5-yl-methyl | 503.3 | 5.81 |
| 9 | 2-Morpholin-4-yl-ethyl | 482.2 | 5.05 |
| 10 | 3-Morpholin-4-yl-propyl | 496.3 | 4.87 |
| 11 | Pyridin-3-yl-methyl | 460.3 | 5.26 |
| 12 | 1-Benzyl-piperidin-4-yl | 542.3 | 5.24 |
| 13 | Quinolin-3-yl | 496.3 | 5.98 |
| 14 | 2-Methoxy-benzyl | 489.3 | 6.01 |
| 15 | 3,4-Dichloro-benzyl | 527.2 | 6.35 |
| 16 | 3,4-Dimethoxy-benzyl | 519.3 | 5.66 |
| 17 | 2-Hydroxy-2-phenyl-ethyl | 489.3 | 5.60 |
| 18 | 2-Dimethylamino-ethyl | 440.3 | 4.71 |
| 19 | 2-(2-Hydroxy-ethoxy)-ethyl | 457.3 | 5.04 |
| 20 | 2-Hydroxy-ethyl | 413.3 | 5.01 |
| 21 | 2-(3,4-Dimethoxy-phenyl)-ethyl | 533.3 | 5.79 |
| 22 | 2-(4-Hydroxy-phenyl)-ethyl | 489.3 | 5.50 |
| 23 | 3-Imidazol-1-yl-propyl | 477.3 | 4.95 |
| 24 | 1H-Benzoimidazol-2-yl-methyl | 499.3 | 5.39 |
| 25 | 4-Hydroxy-3-methoxy-benzyl | 505.3 | 5.49 |
| 26 | Carbamoyl-methyl | 426.2 | 6.30 |
| 27 | Cyclopropyl-methyl | 423.3 | 5.72 |
| 28 | 2-(4-Sulfamoyl-phenyl)-ethyl | 552.3 | 5.37 |
| 29 | 2-Thiophen-2-yl-ethyl | 479.3 | 5.97 |
| 30 | 4-Trifluoromethoxy-benzyl | 543.3 | 6.35 |
| 31 | 2-(7-Methyl-1H-indol-3-yl)-ethyl | 526.3 | 6.07 |
| 32 | 4-Fluoro-3-trifluoromethyl-benzyl | 545.3 | 6.30 |
| 33 | 2-Oxo-tetrahydro-furan-3-yl | 453.2 | 5.32 |
| 34 | 2-Oxo-azepan-3-yl | 480.3 | 5.33 |
| 35 | 4-Hydroxy-cyclohexyl | 467.3 | 5.18 |

Examples 36 to 38

Furthermore, the following compounds No. 36-38 of general formula (VIβ-3a) were prepared by debenzylation of the acid building block (IVβ 3c) by the method described for the synthesis of Example No. 4A but using THF as solvent and subsequent reaction of the obtained acid building block (IVβ 3a) with the correspondent amine according to the method described in SCHEME 21.

No. 36: 4-(3-Hydroxy-17-oxo-estra-1,3,5(10)-trien-15β-yl)-N-[2-(7-methyl-1H-indol-3-yl)-ethyl]-butyramide (VIβ-3a)-36

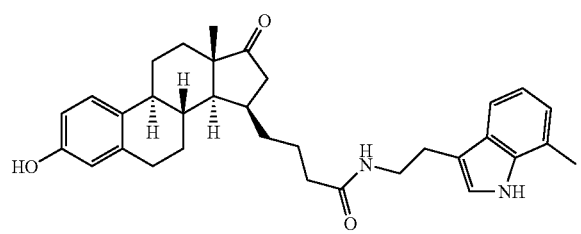

$C^{13}$ NMR: (solvent dDMSO): 16.6, 17.15, 25.33, 26.09, 28.84, 29.63, 33.47, 33.54, 35.15, 35.6, 39.24, 39.45, 41.97, 43.85, 46.28, 51.76, 112.22, 112.58, 114.83, 115.71, 118.28, 120.27, 121.26, 122.09, 125.58, 126.8, 130.15, 135.64, 136.99, 154.94, 171.76, 219.82 ppm.

No. 37: N-(2,4-Difluoro-benzyl)-4-(3-hydroxy-17-oxo-estra-1,3,5(10)-trien-15β-yl)-butyramide (VIβ-3a)-37

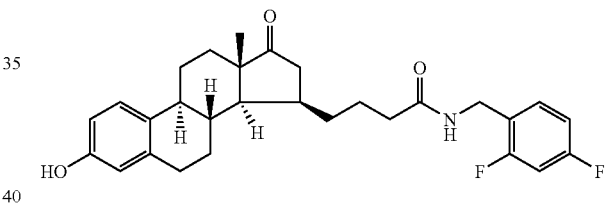

LC-MS: MH+ 482; rt 5.50 min; fragments: M-17: 464; M-17: 464; M-287: 194; M-324: 157; M-354: 127

No. 38: N-Benzyl-4-(3-hydroxy-17-oxo-estra-1,3,5(10)-trien-15β-yl)-N-methyl-butyramide (VIβ-3a)-38

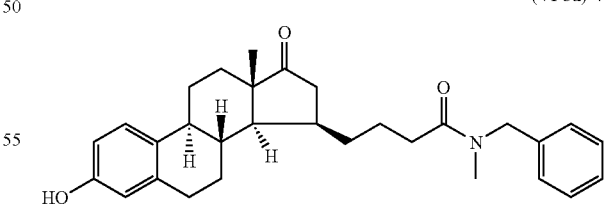

(VI-3a)-40

Mp: 160-162° C.
LC-MS: MH+ 560, Rt 5.77 min
$C^{13}$-NMR: 221.23, 173.42/172.95 (amide rotamer), 154.13, 137.92, 137.28/136.53 (amide rotamer), 131.88, 128.99, 128.62, 128.02, 127.72/127.43 (amide rotamer), 126.20, 126.00, 115.34, 112.80, 53.48/50.97 (amide rotamer), 52.84, 47.15, 44.51, 42.76/42.72 (amide rotamer), 35.99, 34.89/34.38 (amide rotamer), 34.33/34.27 (amide rotamer), 33.89, 33.36/332.83 (amide rotamer), 30.85, 29.29, 26.70, 25.53, 25.41/25.17 (amide rotamer), 17.72/17.68 (amide rotamer)

Example 39

N-Benzyl-4-(3-hydroxy-17-oxo-estra-1,3,5(10)-trien-15α-yl)-butyramide (VIα-3a)-39

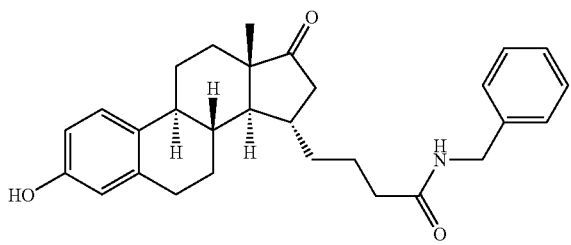

Compound (VIα-3a)-39 was prepared in a two step synthesis starting from the ketal protected acid building block XLVIIIα-3a as depicted in the following scheme 22. In the first step, the acid building block XLVIIIα-3a is reacted with benzylamine using EDCi, HOBt as coupling reagent and subsequent purification. Deprotection of the ketone gave the desired compound (VIα-3a).

SCHEME 22

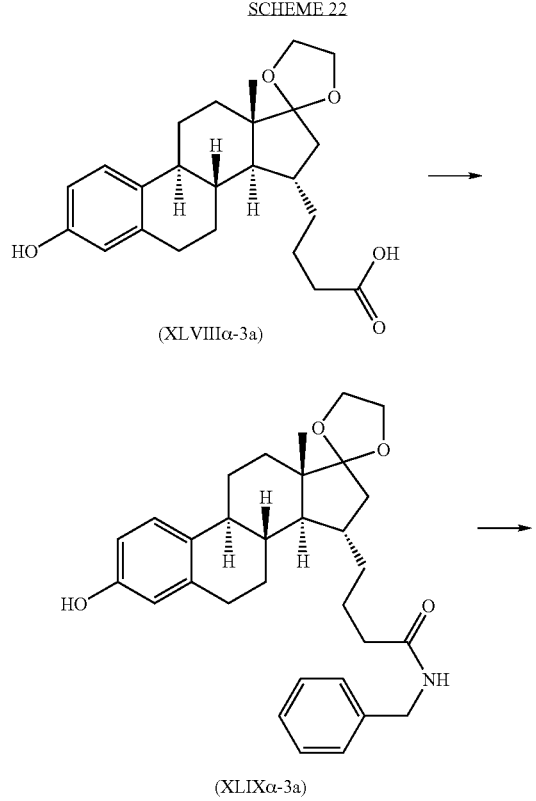

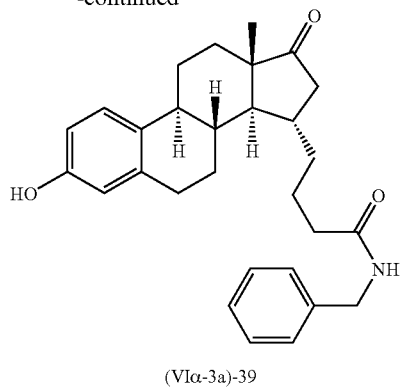

(VIα-3a)-39

Detailed Synthesis

Ketal of N-Benzyl-4-(3-hydroxy-17-oxo-estra-1,3,5 (10)-trien-15α-yl)-butyramide (XLIXα-3a)

To a solution of carboxylic acid XLVIIIα-3a (0.266 g, 0.664 mmol) in THF (12.4 mL) were added benzylamine (85 mg, 796 mmol), N-methylmorpholine (218 µL, 1.98 mmol), HOBt (107 mg, 793 mmol) and EDCi (152 mg, 796 mmol). The reaction mixture was stirred for 32 h at RT, concentrated and taken up in $CH_2Cl_2$ (50 mL) and washed with 1 N aq. HCl. The organic layer was dried over $Na_2SO_4$ and concentrated to yield 0.353 g of crude benzylamide XLIXα-3a Purification was performed by column chromatography (eluent: heptane/ethylacetate 1:1, Rf=0.4) to give 0.220 g (67%) of benzylamide XLIXα-3a as a nearly white oil.

N-Benzyl-4-(3-hydroxy-17-oxo-estra-1,3,5(10)-trien-15α-yl)-butyramide (VIα-3a)-39

To a solution of benzylamide XLIXα-3a (0.220 g, 0.44 mmol) in THF (11 mL) was added 4N aq. HCl (2.8 mL). After 1 h at RT $CH_2Cl_2$ (25 mL) and $H_2O$ (25 mL) were added. The organic layer was dried over $Na_2SO_4$ and concentrated to yield 0.178 g white foam. Purification was performed by column chromatography (eluent: ethylacetate, Rf=0.8) to give 0.170 g white solid. The solid was further purified by stirring in $Et_2O$ (50 mL) for 30 min. The solid was filtered off, washed with $Et_2O$ (20 mL) and dried to give 120 mg (60%) pure (VIα-3a)-39 as a white solid (purity 95+% based on LC-MS).

$C^{13}$ NMR: (solvent $CDCl_3$): 219.6; 172.5; 153.7; 138.2; 137.6; 131.8; 128.8(*2); 127.9(*2); 127.7; 127.0; 115.0; 113.1; 54.8; 50.4; 44.2; 43.8; 43.1; 39.7; 36.8; 36.3; 36.1; 31.6; 29.8; 27.8; 26.5; 24.4; 15.7 ppm

Example 40

3-Hydroxy-15α-(4-morpholin-4-yl-4-oxo-butyl)-estra-1,3,5(10)-trien-17-one (VIIα-3a)-40

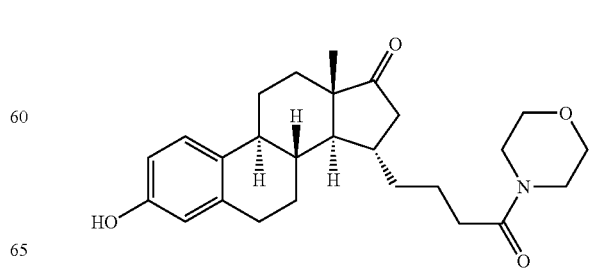

Furthermore, the following compound No. 40 of general formula (VIα-3a) representing the α stereoisomer of compound No. 1 was prepared according to the method displayed in SCHEME 22 starting with the acid building block of formula (XLVIIIα-3a) and the appropriate amine (morpholine), and subsequent ketal cleavage according to the procedures described for the synthesis of compounds No. 39.

$C^{13}$ NMR: (solvent $CDCl_3$): 219.7; 171.7; 154.2; 137.5; 131.3; 126.82; 115.1; 113.14; 66.9; 66.8; 54.7; 50.4; 46.1; 44.1; 43.1; 42.1; 39.6; 36.3; 36.1; 33.2; 31.6; 29.8; 27.75; 26.5; 23.8; 15.7 ppm Examples 41 to 309

Amides

A variety of formula I compounds (examples 41 to 309), in which X represents a bond, A represents CO, Y represents $NR^4$, $R^1$ represents $CH_3$, n is 0 (Scheme 23) or 1 (Scheme 24), and C15 is substituted in the α position were prepared by parallel chemistry using a reaction as shown in the following reaction schemes 23 and 24 (according to general flow diagram Ia):

SCHEME 23

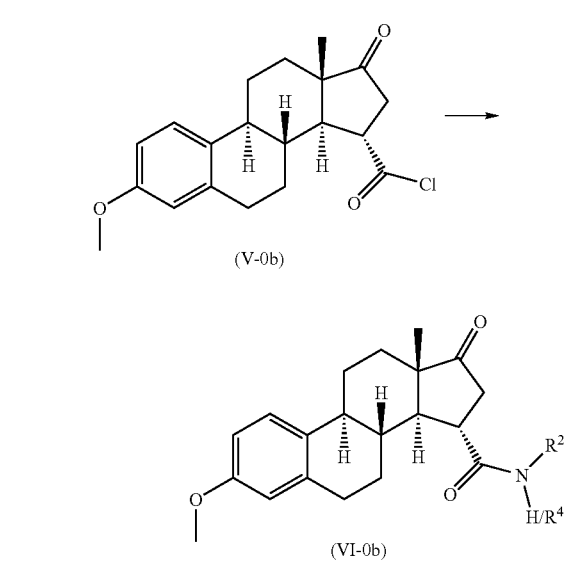

SCHEME 24

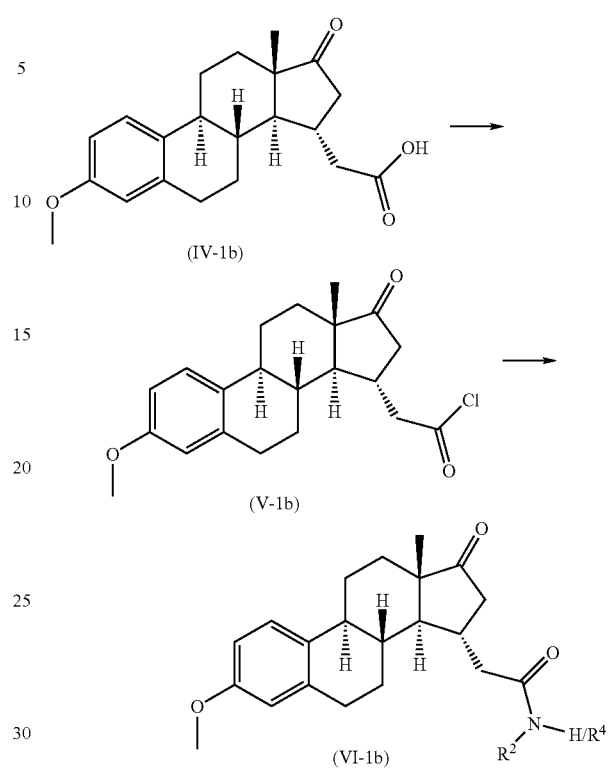

Preparation of the Acid Chlorides V-0b and V-1b:

1.714 g of compound IV-0b (5.219 mmol) were dissolved in 85 ml toluene, 55.2 ml of a 0.189 M $SOCl_2$ solution (10.438 mmol $SOCl_2$), which was prepared by dissolving 5.613 9 $SOCl_2$ in toluene till 25 ml solution was obtained, were added and stirred for 17 h at RT. Since the reaction was still not completed, again 55.2 ml of a 0.189 M $SOCl_2$ solution (10.438 mmol $SOCl_2$) were added and stirred for further 24 h at RT. The analysis by LC-MS shows a conversion of 96% of the educt to the acid chloride V-0b (detection with pyrolidine).

1.670 g of compound IV-1b (4.877 mmol) were dissolved in 85 ml toluene, 51.6 ml of a 0.189 M $SOCl_2$ solution (9.754 mmol $SOCl_2$), which was prepared by dissolving 5.613 g $SOCl_2$ in toluene till 25 ml solution was obtained, were added and stirred for 17 h at RT. The analysis by LC_MS shows a conversion of 99% of the educt to the acid chloride V-1b (detection with pyrolidine.

Both solutions were evaporated at 40° C. using the rotavapor. The oily residues were dissolved in THF at a concentration of 0.25 M.

Preparation of the Amides VI-0b and VI-1 b:

DIPEA was dissolved in THF to yield a 0.25 M solution. Stock solutions (B) of different amines $R^2NH_2$ and $R^2NHR_4$ are prepared in THF at a concentration of 0.25 M. The reactions were carried out in a 24 well format. In each well 100 μl of the respective acid chloride V-0b or V-1b were mixed with 100 μl of a amine solution (B) and with 100 μl of the DIPEA solution. The reaction mixtures in the 24 well plates were allowed to react for 17 h at 30° C. with shaking and for additional 48 h at 15° C. with shaking. The solutions were evaporated at 40° C. for 180 min with final pressure of 5 mbar using the GeneVac. To each oily residue were added 1000 μl of a 5% NaHCO$_3$ solution. The solution was extracted two times with 1.5 ml of EtOAc, and the obtained extracts were washed two times with 500 μl of water. The washed EtOAc-solutions were transferred into collection vials and then evaporated in the GeneVac under the same conditions as above. The obtained products were analyzed by ESI-MS.

The following groups of compounds were prepared by this method (tables 2 to 4 for n=0, and tables 5 to 7 for n=1):

TABLE 2

Compounds of the formula VI-0b, wherein $R^4$ is H and $R^2$ is varied, of the general name 3-Methoxy-17-oxo-estra-1,3,5(10)-trien-15-carboxylic acid "$R^2$"-amide:

| No. | $R^2$ | MS m/z | HPLC Rt [min] |
|---|---|---|---|
| 41 | Cyclohexyl | 409.3 | 1.98 |
| 42 | 2-(1H-Indol-3-yl)-ethyl | 470.3 | 1.92 |
| 43 | Benzo[1,3]dioxol-5-yl-methyl | 461.2 | 1.86 |
| 44 | 1-Benzyl-pyrrolidin-3-yl | 486.3 | 1.48 |
| 45 | Cyclopropyl | 367.2 | 1.72 |
| 46 | Pyridin-3-ylmethyl | 418.2 | 1.49 |
| 47 | Phenethyl | 431.2 | 1.95 |
| 48 | Butyl | 383.2 | 1.88 |
| 49 | Cyclopropylmethyl | 381.2 | 1.83 |
| 50 | Cyclohexylmethyl | 423.3 | 2.06 |
| 51 | 2,2-Diphenyl-ethyl | 507.3 | 2.12 |
| 52 | 2-thiophen-2-yl-ethyl | 437.2 | 1.91 |
| 53 | 2-piperidin-1-yl-ethyl | 438.3 | 1.42 |
| 54 | 3,3-diphenyl-propyl | 521.3 | 2.14 |
| 55 | furan-2-ylmethyl | 407.2 | 1.82 |
| 56 | 2-pyridin-2-yl-ethyl | 432.2 | 1.46 |
| 57 | 1-benzyl-piperidin-4-yl | 500.3 | 1.45 |
| 58 | 1H-benzoimidazol-2-yl-methyl | 457.2 | 1.51 |
| 59 | Cyclopentyl | 395.2 | 1.88 |
| 60 | 4-methoxy-benzyl | 447.2 | 1.89 |
| 61 | 3-phenyl-propyl | 445.3 | 2.01 |
| 62 | 3-imidazol-1-yl-propyl | 435.2 | 1.37 |
| 63 | sec-butyl | 383.2 | 1.87 |
| 64 | 2-methoxy-benzyl | 447.2 | 1.93 |
| 65 | 1-ethyl-propyl | 397.3 | 1.95 |
| 66 | bicyclo[2.2.1]hept-2-yl | 421.3 | 2.02 |
| 67 | 2-methoxy-ethyl | 385.2 | 1.68 |
| 68 | 2-pyrrolidin-1-yl-ethyl | 424.3 | 1.37 |
| 69 | 2-(5-methoxy-1H-indol-3-yl)-ethyl | 500.3 | 1.85 |
| 70 | pyridin-4-yl-methyl | 418.2 | 1.42 |

TABLE 2-continued

Compounds of the formula VI-0b, wherein $R^4$ is H and $R^2$ is varied, of the general name 3-Methoxy-17-oxo-estra-1,3,5(10)-trien-15-carboxylic acid "$R^2$"-amide:

| No. | $R^2$ | MS m/z | HPLC Rt [min] |
|---|---|---|---|
| 71 | indan-2-yl | 443.2 | 1.97 |
| 72 | 1-phenyl-ethyl | 431.2 | 1.97 |
| 73 | 2-hydroxy-ethyl | 371.2 | 1.55 |
| 74 | 3,5-dimethoxy-benzyl | 477.3 | 1.90 |
| 75 | 3,4-dimethoxy-benzyl | 477.3 | 1.80 |
| 76 | 1-naphthalen-1-yl-ethyl | 481.3 | 2.07 |
| 77 | 3-morpholin-4-yl-propyl | 454.3 | 1.37 |
| 78 | 2-(2-hydroxy-ethoxy)-ethyl | 415.2 | 1.56 |
| 79 | 4-phenyl-butyl | 459.3 | 2.08 |
| 80 | —(CH$_2$)$_3$—CO—O—CH$_3$/ (butyric acid methyl ester)-4-yl | 427.2 | 1.74 |
| 81 | 1-oxo-1-benzoxy-propan-2-yl/ (propionic acid benzyl ester)-2-yl | 489.3 | 1.99 |
| 82 | 3-fluoro-benzyl | 435.2 | 1.93 |
| 83 | 1,2,3,4-tetrahydro-naphthalen-1-yl | 457.3 | 2.08 |
| 84 | 2-fluoro-benzyl | 435.2 | 1.92 |
| 85 | 3-hydroxy-propyl | 385.2 | 1.58 |
| 86 | 2,4-difluoro-benzyl | 453.2 | 1.95 |
| 87 | 2-hydroxy-2-phenyl-ethyl | 447.2 | 1.79 |
| 88 | isobutyl- | 383.2 | 1.90 |
| 89 | 2-phenyl-propyl | 445.3 | 2.02 |
| 90 | 2-cyclohex-1-enyl-ethyl | 435.3 | 2.11 |
| 91 | 2-hydroxy-1-methyl-ethyl | 385.2 | 1.61 |
| 92 | 2-methylsulfanyl-ethyl | 401.2 | 1.81 |
| 93 | 3,4,5-trimethoxy-benzyl | 507.3 | 1.83 |
| 94 | Cyclooctyl | 437.3 | 2.13 |
| 95 | 2-hydroxy-cyclohexyl | 425.3 | 1.72 |
| 96 | 2-thiazol-4-yl-acetic acid ethyl ester/ 4-(acetic acid ethyl ester)-thiazol-2-yl | 496.2 | 1.97 |
| 97 | thiophen-2-yl-methyl | 423.2 | 1.91 |
| 98 | 2-dimethylamino-ethyl | 398.3 | 1.37 |
| 99 | 3-diethylamino-propyl | 440.3 | 1.40 |
| 100 | Hexyl | 411.3 | 2.08 |
| 101 | 3,4-difluoro-benzyl | 453.2 | 1.96 |
| 102 | 2-trifluoromethyl-benzyl | 485.2 | 2.05 |
| 103 | 1-hydroxymethyl-cyclopentyl | 425.3 | 1.81 |
| 104 | [(3-methyl)-butyric acid methyl ester]-2-yl/ 2-(3-methyl)-butyric acid methyl ester | 441.3 | 1.94 |
| 105 | 5-methyl-thiazol-2-yl | 424.2 | 1.95 |
| 106 | Cyclobutyl | 381.2 | 1.86 |

TABLE 3

Compounds of the formula VI-0b, wherein $R^2$ and $R^4$ together with the nitrogen atom, where they are attached, are forming a variable ring or ringsystem, and with the general name 15-["(—NR$^2$R$^4$)"-carbonyl]-3-methoxy-estra-1,3,5(10)-trien-17-one:

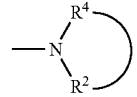

| No. | | MS m/z | HPLC Rt |
|---|---|---|---|
| 107 | 4-Benzyl-piperidin-1-yl | 485.3 | 2.22 |
| 108 | 4-Benzo[1,3]dioxol-5-ylmethyl-piperazin-1-yl | 530.3 | 1.53 |
| 109 | 3,4-Dihydro-1H-isoquinolin-2-yl | 443.2 | 2.05 |
| 110 | 4-phenyl-piperazin-1-yl | 472.3 | 2.06 |
| 111 | 4-pyridin-2-yl-piperazin-1-yl | 473.3 | 1.63 |
| 112 | pyrrolidin-1-yl | 381.2 | 1.84 |
| 113 | 4-(4-Fluoro-phenyl)-piperazin-1-yl | 490.3 | 2.05 |
| 114 | 4-(2-methoxy-phenyl)-piperazin-1-yl | 502.3 | 2.04 |
| 115 | 4-(4-Chloro-phenyl)-4-hydroxy-piperidin-1-yl | 521.2 | 2.00 |
| 116 | 4-(4-trifluaromethyl-phenyl)-piperazin-1-yl | 540.3 | 2.18 |
| 117 | 4-(4-Chloro-benzyl)-piperazin-1-yl | 520.2 | 1.67 |
| 118 | 4-(3-Chloro-phenyl)-piperazin-1-yl | 506.2 | 2.16 |
| 119 | 4-methyl-[1,4]diazepan-1-yl | 424.3 | 1.41 |
| 120 | 4-[2-(2-Hydroxy-ethoxy)-ethyl]-piperazin-1-yl | 484.3 | 1.39 |
| 121 | 4-(4-Chloro-phenyl)-piperazin-1-yl | 506.2 | 2.16 |
| 122 | 1,4-Dioxa-8-aza-spiro[4.5]decan-8-yl | 453.3 | 1.85 |

TABLE 3-continued

Compounds of the formula VI-0b, wherein $R^2$ and $R^4$ together with the nitrogen atom, where they are attached, are forming a variable ring or ringsystem, and with the general name 15-["(—$NR^2R^4$)"-carbonyl]-3-methoxy-estra-1,3,5(10)-trien-17-one:

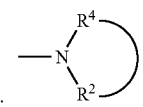

| No. | | MS m/z | HPLC Rt |
|---|---|---|---|
| 123 | 1-piperidine-4-carboxylic acid ethyl ester/4-(carboxylic acid ethyl ester)-piperidin-1-yl | 467.3 | 1.96 |
| 124 | 1,3,4,9-tetrahydro-beta-carbolin-2-yl | 482.3 | 2.04 |
| 125 | 4-Hydroxy-4-phenyl-piperidin-1-yl | 487.3 | 1.90 |
| 126 | 4-(2-Chloro-phenyl)-piperazin-1-yl | 506.2 | 2.20 |
| 127 | 4-(4-methoxy-phenyl)-piperazin-1-yl | 502.3 | 2.01 |
| 128 | 1-piperidine-3-carboxylic acid amide/3-(carboxylic acid amide)-piperidin-1-yl | 438.3 | 1.63 |
| 129 | Azepan-1-yl | 409.3 | 2.03 |
| 130 | 4-methyl-piperazin-1-yl | 410.3 | 1.40 |
| 131 | 3-Hydroxy-pyrrolidin-1-yl | 397.2 | 1.61 |
| 132 | 2-methoxymethyl-pyrrolidin-1-yl | 425.3 | 1.93 |
| 133 | 4-(2-Fluoro-phenyl)-piperazin-1-yl | 490.3 | 2.10 |
| 134 | 4-pyridin-4-yl-piperazin-1-yl | 473.3 | 1.45 |
| 135 | 4-Hydroxy-piperidin-1-yl | 411.2 | 1.64 |
| 136 | 3-Hydroxy-piperidin-1-yl | 411.2 | 1.67 |
| 137 | thiomorpholin-4-yl | 413.2 | 1.92 |
| 138 | 3,6-Dihydro-2H-pyridin-1-yl | 393.2 | 1.92 |
| 139 | 1-pyrrolidine-2-carboxylic acid methyl ester/2-(carboxylic acid methyl ester)-pyrrolidin-1-yl | 439.2 | 1.86 |
| 140 | 1-pyrrolidine-2-carboxylic acid amide/2-(carboxylic acid amide)-pyrrolidin-1-yl | 424.2 | 1.60 |
| 141 | 2-Hydroxymethyl-pyrrolidin-1-yl | 411.2 | 1.73 |
| 142 | 4-o-tolyl-piperazin-1-yl | 486.3 | 2.21 |
| 143 | 4-(2-Ethoxy-phenyl)-piperazin-1-yl | 516.3 | 2.15 |
| 144 | 4-Cyclohexyl-piperazin-1-yl | 478.3 | 1.51 |
| 145 | 4-pyrrolidin-1-yl-piperidin-1-yl | 464.3 | 1.43 |
| 146 | thiazolidin-3-yl | 399.2 | 1.86 |
| 147 | Azetidin-1-yl | 367.2 | 1.74 |

TABLE 4

Compounds of the formula VI-0b, wherein $R^2$ and $R^4$ are individually varied, with the general name 3-Methoxy-17-oxo-estra-1,3,5(10)-trien-15-carboxylic acid "$R^2$"—"$R^4$"-amide:

| No. | $R^2$ | $R^4$ | MS m/z | HPLC Rt |
|---|---|---|---|---|
| 148 | methyl | 2-pyridin-2-yl-ethyl | 446.3 | 1.58 |
| 149 | methyl | benzyl | 431.2 | 2.04 |
| 150 | propyl | cyclopropylmethyl | 423.3 | 2.13 |
| 151 | 2-cyano-ethyl | pyridin-3-ylmethyl | 471.3 | 1.67 |
| 152 | methyl | naphthalen-1-yl-methyl | 481.3 | 2.17 |
| 153 | methyl | cyclohexyl | 423.3 | 2.13 |
| 154 | benzyl | 2-dimethylamino-ethyl | 488.3 | 1.56 |
| 155 | benzyl | ethyl | 445.3 | 2.13 |
| 156 | 2-methoxy-ethyl | 2-methoxy-ethyl | 443.3 | 1.90 |
| 157 | methyl | 1-methyl-piperidin-4-yl | 438.3 | 1.43 |
| 158 | ethyl | 2-hydroxy-ethyl | 399.2 | 1.71 |
| 159 | benzyl | 2-cyano-ethyl | 470.3 | 2.02 |
| 160 | propyl | methyl | 383.2 | 1.96 |
| 161 | propyl | propyl | 411.3 | 2.11 |
| 162 | methyl | 2-dimethylamino-ethyl | 412.3 | 1.42 |
| 163 | methyl | phenethyl | 445.3 | 2.08 |
| 164 | methyl | allyl | 381.2 | 1.92 |
| 165 | ethyl | pyridin-4-yl-methyl | 446.3 | 1.61 |
| 166 | methyl | methyl | 355.2 | 1.78 |

TABLE 5

Compounds of the formula VI-1b, wherein $R^4$ is H and $R^2$ is varied, with the general name 2-(3-Methoxy-17-oxo-estra-1,3,5(10)-trien-15-yl)-N—($R^2$)-acetamide:

| No. | $R^2$ | MS m/z | HPLC Rt |
|---|---|---|---|
| 167 | Benzyl | 431.6 | |
| 168 | Diphenyl-methyl | 507.3 | 2.14 |
| 169 | Cyclohexyl | 423.3 | 2.03 |
| 170 | 2-morpholin-4-yl-ethyl | 454.3 | 1.44 |
| 171 | naphthalen-1-ylmethyl | 481.3 | 2.10 |
| 172 | 2-(1H-Indol-3-yl)-ethyl | 484.3 | 1.94 |
| 173 | Benzo[1,3]dioxol-5-yl-methyl | 475.2 | 1.93 |
| 174 | 1-Benzyl-pyrrolidin-3-yl | 500.3 | 1.54 |
| 175 | Cyclopropyl | 381.2 | 1.79 |
| 176 | pyridin-3-yl-methyl | 432.2 | 1.57 |
| 177 | Phenethyl | 445.3 | 1.99 |
| 178 | Butyl | 397.3 | 1.94 |
| 179 | Cyclopropylmethyl | 395.2 | 1.88 |
| 180 | Cyclohexylmethyl | 437.3 | 2.10 |
| 181 | 2,2-Diphenyl-ethyl | 521.3 | 2.15 |
| 182 | 2-thiophen-2-yl-ethyl | 451.2 | 1.96 |
| 183 | 2-piperidin-1-yl-ethyl | 452.3 | 1.47 |
| 184 | 3,3-Diphenyl-propyl | 535.3 | 2.19 |
| 185 | Furan-2-ylmethyl | 421.2 | 1.89 |
| 186 | 2-pyridin-2-yl-ethyl | 446.3 | 1.54 |
| 187 | 1-Benzyl-piperidin-4-yl | 514.3 | 1.52 |
| 188 | 1H-Benzoimidazol-2-ylmethyl | 471.3 | 1.58 |
| 189 | Cyclopentyl | 409.3 | 1.95 |
| 190 | 4-Methoxy-benzyl | 461.3 | 1.95 |
| 191 | 3-phenyl-propyl | 459.3 | 2.05 |
| 192 | 3-Imidazol-1-yl-propyl | 449.3 | 1.44 |
| 193 | sec-Butyl | 397.3 | 1.92 |
| 194 | 2-Methoxy-benzyl | 461.3 | 1.98 |
| 195 | 1-Ethyl-propyl | 411.3 | 1.99 |
| 196 | Bicyclo[2.2.1]hept-2-yl | 435.3 | 2.04 |

TABLE 5-continued

Compounds of the formula VI-1b, wherein $R^4$ is H and $R^2$ is varied, with the general name 2-(3-Methoxy-17-oxo-estra-1,3,5(10)-trien-15-yl)-N—($R^2$)-acetamide:

| No. | $R^2$ | MS m/z | HPLC Rt |
|---|---|---|---|
| 197 | 2-Methoxy-ethyl | 399.2 | 1.74 |
| 198 | 2-pyrrolidin-1-yl-ethyl | 438.3 | 1.46 |
| 199 | 2-(5-Methoxy-1H-indol-3-yl)-ethyl | 514.3 | 1.91 |
| 200 | Pyridin-4-ylmethyl | 432.2 | 1.51 |
| 201 | Indan-2-yl | 457.3 | 2.05 |
| 202 | 4-Chloro-benzyl | 465.2 | 2.03 |
| 203 | 1-phenyl-ethyl | 445.3 | 2.02 |
| 204 | 1,2-Diphenyl-ethyl | 521.3 | 2.17 |
| 205 | 2-Hydroxy-ethyl | 385.2 | 1.62 |
| 206 | 2,6-Dimethoxy-benzyl | 491.3 | 2.00 |
| 207 | 4-Fluoro-benzyl | 449.2 | 1.98 |
| 208 | 3,5-Dimethoxy-benzyl | 491.3 | 1.95 |
| 209 | 2-phenoxy-ethyl | 461.3 | 1.99 |
| 210 | 3,4-Dimethoxy-benzyl | 491.3 | 1.87 |
| 211 | 1-naphthalen-1-yl-ethyl | 495.3 | 2.13 |
| 212 | 3-morpholin-4-yl-propyl | 468.3 | 1.44 |
| 213 | 2-(2-Hydroxy-ethoxy)-ethyl | 429.3 | 1.63 |
| 214 | 4-phenyl-butyl | 473.3 | 2.13 |
| 215 | 2-(propionic acid benzyl ester) | 503.3 | 2.04 |
| 216 | 3-Fluoro-benzyl | 449.2 | 1.99 |
| 217 | 2-Fluoro-benzyl | 449.2 | 1.99 |
| 218 | 3-Hydroxy-propyl | 399.2 | 1.63 |
| 219 | 2,4-Difluoro-benzyl | 467.2 | 2.00 |
| 220 | 4-Hydroxy-cyclohexyl | 439.3 | 1.69 |
| 221 | 2-Hydroxy-2-phenyl-ethyl | 461.3 | 2.06 |
| 222 | Isobutyl | 397.3 | 1.94 |
| 223 | 2-phenyl-propyl | 459.3 | 2.06 |
| 224 | 2-Cyclohex-1-enyl-ethyl | 449.3 | 2.18 |
| 225 | 2-Hydroxy-1-methyl-ethyl | 399.2 | 1.65 |
| 226 | 2-methylsulfanyl-ethyl | 415.2 | 1.85 |
| 227 | 3,4,5-trimethoxy-benzyl | 521.3 | 1.90 |
| 228 | Cyclooctyl | 451.3 | 2.17 |
| 229 | 2-Hydroxy-cyclohexyl | 439.3 | 1.76 |
| 230 | 2-thiazol-4-yl-acetic acid ethyl ester/4-(acetic acid ethyl ester)-thiazol-2-yl | 510.2 | 2.03 |
| 231 | thiophen-2-ylmethyl | 437.2 | 1.94 |
| 232 | 2-Dimethylamino-ethyl | 412.3 | 1.44 |
| 233 | 3-Diethylamino-propyl | 454.3 | 1.49 |
| 234 | Hexyl | 425.3 | 2.11 |
| 235 | 3,4-Difluoro-benzyl | 467.2 | 1.99 |
| 236 | 2-trifluoromethyl-benzyl | 499.2 | 2.05 |
| 237 | 1-Hydroxymethyl-cyclopentyl | 439.3 | 1.79 |
| 238 | (3-methyl-butyric acid methyl ester)-2-yl/ 2-(3-methyl)-butyric acid methyl ester | 455.3 | 1.92 |
| 239 | 5-methyl-thiazol-2-yl | 438.2 | 1.95 |
| 240 | Cyclobutyl | 395.2 | 1.85 |

TABLE 6

Compounds of the formula VI-1b, wherein $R^2$ and $R^4$ together with the nitrogen atom, where they are attached, are forming a variable ring or ringsystem, with the general name 15-[2-("—$NR^2R^4$")-2-oxo-ethyl]-3-methoxy-estra-1,3,5(10)-trien-17-one:

| No. | | MS m/z | HPLC Rt |
|---|---|---|---|
| 241 | 4-Benzyl-piperazin-1-yl | 500.3 | 1.56 |
| 242 | 4-Benzyl-piperidin-1-yl | 499.3 | 2.30 |
| 243 | 4-Benzo[1,3]dioxal-5-ylmethyl-piperazin-1-yl | 544.3 | 1.54 |
| 244 | 4-(2-oxo-1,3-dihydro-benzoimidazol-1-yl)-piperidin-1-yl | 541.3 | 1.83 |
| 245 | 3,4-Dihydro-1H-isoquinolin-2-yl | 457.3 | 2.12 |
| 246 | 2,5-Dihydro-pyrrol-1-yl | 393.2 | 1.89 |
| 247 | 4-phenyl-piperazin-1-yl | 486.3 | 2.11 |
| 248 | 4-pyridin-2-yl-piperazin-1-yl | 487.3 | 1.67 |
| 249 | pyrrolidin-1-yl | 395.2 | 1.89 |
| 250 | 4-(4-Fluoro-phenyl)-piperazin-1-yl | 504.3 | 2.10 |
| 251 | 4-(2-methoxy-phenyl)-piperazin-1-yl | 516.3 | 2.08 |
| 252 | 4-(4-Chloro-phenyl)-4-hydroxy-piperidin-1-yl | 535.2 | 2.04 |
| 253 | 4-(4-trifluoromethyl-phenyl)-piperazin-1-yl | 554.3 | 2.23 |
| 254 | 4-(4-Chloro-benzyl)-piperazin-1-yl | 534.3 | 1.66 |
| 255 | 4-(3-Chloro-phenyl)-piperazin-1-yl | 520.2 | 2.20 |
| 256 | 4-methyl-[1,4]diazepan-1-yl | 438.3 | 1.43 |
| 257 | 4-[2-(2-Hydroxy-ethoxy)-ethyl]-piperazin-1-yl | 498.3 | 1.40 |
| 258 | 4-(4-Chloro-phenyl)-piperazin-1-yl | 520.2 | 2.20 |
| 259 | 1,4-Dioxa-8-aza-spiro[4.5]decan-8-yl | 467.3 | 1.89 |
| 260 | 1-piperidine-4-carboxylic acid ethyl ester/4-(carboxylic acid ethyl ester)-piperidin-1-yl | 481.3 | 1.98 |
| 261 | 1,3,4,9-tetrahydro-beta-carbolin-2-yl | 496.3 | 2.10 |
| 262 | 4-Hydroxy-4-phenyl-piperidin-1-yl | 501.3 | 1.94 |
| 263 | 4-(2-Chloro-phenyl)-piperazin-1-yl | 520.2 | 2.25 |
| 264 | 4-(4-methoxy-phenyl)-piperazin-1-yl | 516.3 | 2.04 |
| 265 | 1-piperidine-3-carbaxylic acid amide/3-(carboxylic acid amide)-piperidin-1-yl | 452.3 | 1.65 |
| 266 | Azepan-1-yl | 423.3 | 2.08 |
| 267 | 4-methyl-piperazin-1-yl | 424.3 | 1.40 |
| 268 | 4-(3-trifluoromethyl-phenyl)-piperazin-1-yl | 554.3 | 2.23 |
| 269 | 3-Hydroxy-pyrralidin-1-yl | 411.2 | 1.62 |
| 270 | 2-methoxymethyl-pyrralidin-1-yl | 439.3 | 1.93 |
| 271 | 4-Oxo-1-phenyl-1,3,8-triaza-spiro[4.5]decan-8-yl | 555.3 | 1.87 |
| 272 | 4-(2-Fluora-phenyl)-piperazin-1-yl | 504.3 | 2.14 |
| 273 | 4-pyridin-4-yl-piperazin-1-yl | 487.3 | 1.46 |
| 274 | 4-Hydroxy-piperidin-1-yl | 425.3 | 1.64 |

TABLE 6-continued

Compounds of the formula VI-1b, wherein $R^2$ and $R^4$ together with the nitrogen atom, where they are attached, are forming a variable ring or ringsystem, with the general name 15-[2-("—$NR^2R^4$")-2-oxo-ethyl]-3-methoxy-estra-1,3,5(10)-trien-17-one:

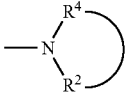

| No. | | MS m/z | HPLC Rt |
|---|---|---|---|
| 275 | octahydro-quinolin-1-yl | 463.3 | 2.29 |
| 276 | 3-Hydroxy-piperidin-1-yl | 425.3 | 1.70 |
| 277 | thiomorpholin-4-yl | 427.2 | 1.93 |
| 278 | 3,6-Dihydro-2H-pyridin-1-yl | 407.2 | 1.95 |
| 279 | 1-pyrrolidine-2-carboxylic acid methyl ester/2-(carboxylic acid methyl ester)-pyrrolidin-1-yl | 453.3 | 1.86 |
| 280 | 1-pyrrolidine-2-carboxylic acid amide/2-(carboxylic acid amide)-pyrrolidin-1-yl | 438.3 | 1.62 |
| 281 | 2-Hydroxymethyl-pyrrolidin-1-yl | 425.3 | 1.73 |
| 282 | 4-o-tolyl-piperazin-1-yl | 500.3 | 2.23 |
| 283 | 4-(2-Ethoxy-phenyl)-piperazin-1-yl | 530.3 | 2.14 |
| 284 | 4-Cyclohexyl-piperazin-1-yl | 492.3 | 1.48 |
| 285 | 4-pyrrolidin-1-yl-piperidin-1-yl | 478.3 | 1.42 |
| 286 | thiazolidin-3-yl | 413.2 | 1.89 |
| 287 | Azetidin-1-yl | 381.2 | 1.76 |

TABLE 7

Compounds of the formula VI-1b, wherein $R^2$ and $R^4$ are individually varied, with the general name 2-(3-Methoxy-17-oxo-estra-1,3,5(10)-trien-15-yl)-N—"$R^2$"—N—"$R^4$"-acetamide:

| No. | $R^2$ | $R^4$ | MS m/z | HPLC Rt |
|---|---|---|---|---|
| 288 | methyl | 2-pyridin-2-yl-ethyl | 460.3 | 1.66 |
| 289 | Methyl | 2,3,4,5,6-pentahydroxy-hexyl | 519.3 | 1.49 |
| 290 | methyl | Benzyl | 445.3 | 2.08 |
| 291 | propyl | Cyclopropylmethyl | 437.3 | 2.17 |
| 292 | 2-Cyano-ethyl | pyridin-3-ylmethyl | 485.3 | 1.69 |
| 293 | methyl | naphthalen-1-ylmethyl | 495.3 | 2.20 |
| 294 | methyl | Cyclohexyl | 437.3 | 2.16 |
| 295 | benzyl | 2-dimethylamino-ethyl | 502.3 | 1.60 |
| 296 | benzyl | ethyl | 459.3 | 2.15 |
| 297 | benzyl | phenethyl | 535.3 | 2.31 |
| 298 | 2-methoxy-ethyl | 2-methoxy-ethyl | 457.3 | 1.90 |
| 299 | methyl | Butyl | 411.3 | 2.06 |
| 300 | methyl | 1-methyl-piperidin-4-yl | 452.3 | 1.40 |
| 301 | ethyl | 2-hydroxy-ethyl | 413.3 | 1.72 |
| 302 | Benzyl | 2-cyano-ethyl | 484.3 | 2.01 |
| 303 | propyl | methyl | 397.3 | 1.97 |
| 304 | propyl | propyl | 425.3 | 2.13 |
| 305 | methyl | 2-Dimethylamino-ethyl | 426.3 | 1.40 |
| 306 | phenethyl | methyl | 459.3 | 2.08 |
| 307 | Methyl | Allyl | 395.2 | 1.93 |
| 308 | ethyl | pyridin-4-ylmethyl | 460.3 | 1.61 |
| 309 | methyl | methyl | 369.2 | 1.79 |

Examples 310 to 368

Amides

Further formula I compounds (examples 310 to 368), in which X represents a bond, A represents CO, Y represents $NR^4$, $R^1$ represents $CH_3$, and C15 is substituted in the β position with side chains of different length (n=2, n=4 and n=5) were prepared by parallel chemistry using a reaction as shown in SCHEME 21 with the following building blocks (IV-2b, IV-4b and IV-5b) as starting material.

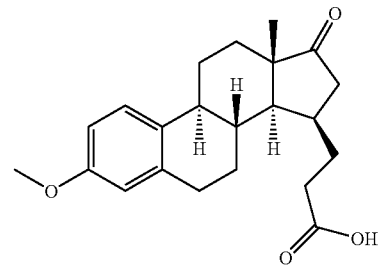
(IV-2b)

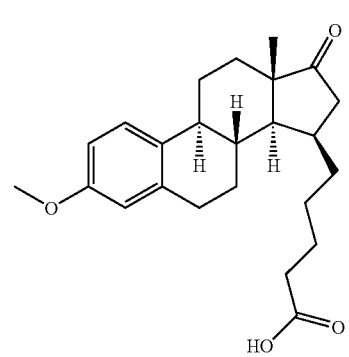
(IV-4b)

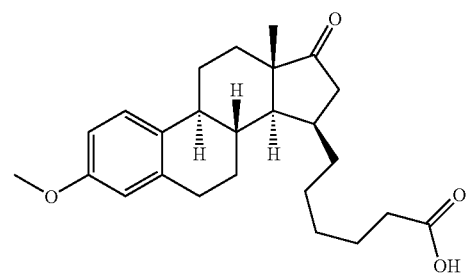
(IV-5b)

The following groups of compounds were prepared by this method (tables 8, 9, and 10).

TABLE 8

Compounds of the formula VI-2b:

(VI-2b)

| No. | R2 | R4 | MS m/z | HPLC Rt [min] |
|---|---|---|---|---|
| 310 | Cyclohexyl | H | 437.29 | 6.37 |
| 311 | Cyclooctyl | H | 465.32 | 6.86 |
| 312 | Furan-2-ylmethyl | H | 435.24 | 5.93 |
| 313 | Methyl | Cyclohexyl | 451.31 | 6.86 |
| 314 | 2-thiazol-4-yl-acetic acid ethyl ester/4-(acetic acid ethyl ester)-thiozol-2-yl | H | 524 | |
| 315 | Benzo[1,3]dioxol-5-ylmethyl | H | 489.25 | 6.06 |
| 316 | morpholin-4-yl | | 425.57 | |
| 317 | thiomorpholin-4-yl | | 441.23 | 6.15 |
| 318 | pyridin-3-ylmethyl | H | 446.26 | 5.33 |
| 319 | pyridin-4-ylmethyl | H | 446.26 | 5.3 |
| 320 | benzyl | H | | |
| 321 | 2-Methoxy-benzyl | H | 475.27 | 6.25 |
| 322 | 3-Fluoro-benzyl | H | 463.25 | 6.24 |
| 323 | 4-Chloro-benzyl | H | 479.22 | 6.45 |
| 324 | 2-(4-Hydroxy-phenyl)-ethyl | H | 475.27 | 5.58 |
| 325 | Methyl | Benzyl | 459.28 | 6.59 |
| 326 | Butyl | H | 411.28 | 6.1 |
| 327 | 2-thiophen-2-yl-ethyl | H | 465.23 | 6.18 |
| 328 | 2-(7-methyl-1H-indol-3-yl)-ethyl | H | 512.3 | 6.25 |
| 329 | 5-methyl-thiazol-2-yl | H | 452.21 | 6.26 |

TABLE 9

Compounds of the formula VI-4b:

(VI-4b)

| No. | R2 | R4 | MS m/z | HPLC Rt [min] |
|---|---|---|---|---|
| 330 | cyclopropyl | H | 423.28 | 4.14 |
| 331 | Cyclohexyl | H | 465.32 | 4.69 |
| 332 | cyclooctyl | H | 493.36 | 5.05 |
| 333 | Furan-2-ylmethyl | H | 463.27 | 4.34 |
| 334 | 2-thiazol-4-yl-acetic acid ethyl ester/4-(acetic acid ethyl ester)-thiazol-2-yl | H | 552.27 | 4.6 |
| 335 | Benzo[1,3]dioxol-5-ylmethyl | H | 517.28 | 4.41 |
| 336 | morpholin-4-yl | | 453.29 | 4.2 |
| 337 | thiomorpholin-4-yl | | 469.27 | 4.57 |

TABLE 9-continued

Compounds of the formula VI-4b:

(VI-4b)

| No. | R2 | R4 | MS m/z | HPLC Rt [min] |
|---|---|---|---|---|
| 338 | pyridin-3-ylmethyl | H | 474.29 | 3.96 |
| 339 | pyridin-4-ylmethyl | H | 474.29 | 3.93 |
| 340 | benzyl | H | 473.29 | 4.52 |
| 341 | 2-Methoxy-benzyl | H | 503.3 | 4.56 |
| 342 | 3-Fluoro-benzyl | H | 491.28 | 4.54 |
| 343 | 4-Chloro-benzyl | H | 507.25 | 4.7 |
| 344 | methyl | benzyl | 487.31 | 4.88 |
| 345 | butyl | H | 439.31 | 4.49 |
| 346 | 2-thiophen-2-yl-ethyl | H | 493.27 | 4.54 |
| 347 | 2-(7-methyl-1H-indol-3-yl)-ethyl | H | 540.34 | 4.58 |

TABLE 10

Compounds of the formula VI-5b:

(VI-5b)

| No. | R2 | R4 | MS m/z | HPLC Rt [min] |
|---|---|---|---|---|
| 348 | Cyclohexyl | H | 479.34 | 7 |
| 349 | Cyclooctyl | H | 507.37 | 7.42 |
| 350 | Furan-2-ylmethyl | H | 477.29 | 6.54 |
| 351 | Methyl | Cyclohexyl | 493.36 | 7.58 |
| 352 | 2-thiazol-4-yl-acetic acid ethyl ester/4-(acetic acid ethyl ester)-thiazol-2-yl | H | 566 | |
| 353 | Benzo[1,3]dioxal-5-ylmethyl | H | 531.3 | 6.65 |
| 354 | morpholin-4-yl | | 467.65 | |
| 355 | thiomorpholin-4-yl | | 483.28 | 6.86 |
| 356 | pyridin-3-ylmethyl | H | 488.3 | 5.98 |
| 357 | pyridin-4-ylmethyl | H | 488.3 | 5.94 |
| 358 | phenyl | H | 473.29 | 7.00 |
| 359 | benzyl | H | 487.31 | 6.78 |
| 360 | 2-Methoxy-benzyl | H | 517.32 | 6.83 |
| 361 | 3-Fluoro-benzyl | H | 505.3 | 6.82 |
| 362 | 4-Chlaro-benzyl | H | 521.27 | 7.00 |
| 363 | 2-(4-Hydroxy-phenyl)-ethyl | H | 517.32 | 6.22 |
| 364 | methyl | benzyl | 501.32 | 7.25 |
| 365 | butyl | H | 453.32 | 6.74 |
| 366 | 2-thiophen-2-yl-ethyl | H | 507.28 | 6.81 |
| 367 | 2-(7-methyl-1H-indol-3-yl)-ethyl | H | 554.35 | 6.88 |
| 368 | 5-methyl-thiazol-2-yl | H | 494.26 | 6.87 |

Example 329A 3-(3-Hydroxy-17-oxo-estra-1,3,5(10)-trien-15-yl)-N-(5-methyl-thiazol-2-yl)-propionamide

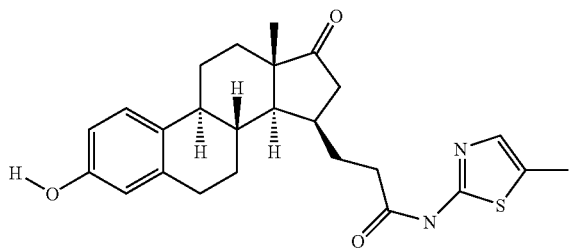

Example 329A of formula (VI-2a)-329A was synthesized according to the method displayed in SCHEME 20 using the acid building block IVβ-2c as starting material and the appropriate amine, and subsequent debenzylation according to the procedures described for the synthesis of compounds No. 4C and 4A.

$^{13}$C NMR (ppm) 219.76, 170.78, 156.18, 155.05, 137.17, 134.61, 130.19, 125.90, 125.75, 114.96, 112.67, 51.73, 46.38, 44.09, 41.47, 35.62, 34.73, 33.75, 33.40, 28.98, 26.13, 25.92, 25.15, 17.34, 11.05.

Example 363A 6-(3-Hydroxy-17-oxo-estra-1,3,5(10)-trien-15-yl)-hexanoic Acid [2-(4-hydroxy-phenyl)-ethyl]-amide

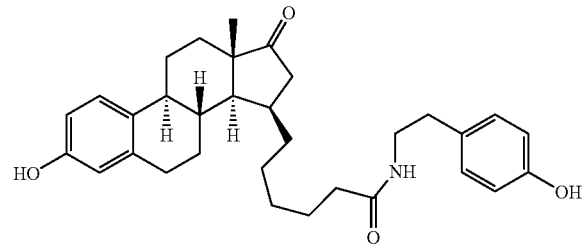

Example 363A of formula (VI-5a)-363A was synthesized according to the method displayed in SCHEME 20 using the acid building block IVβ-5c as starting material and the appropriate amine, and subsequent debenzylation according to the procedures described for the synthesis of compounds No. 4C and 4A.

$^{13}$C NMR (ppm) 214.67, 166.64, 147.42, 146.66, 129.27, 122.90, 121.75, 121.20 (*2), 117.39, 106.73, 106.63(*2), 104.28, 44.58, 38.96, 36.38, 34.28, 32.65, 28.05, 27.55, 26.21, 26.17, 25.65, 22.56, 21.03, 20.89, 20.67, 18.51, 17.49, 17.24, 8.74

Example 369

6-(3-Methoxy-17-oxo-estra-1,3,5(10)-trien-15-yl)-hexanoic Acid Isopropyl Ester

One compound of formula I, in which X represents a bond, A represents CO, Y represents O, n is 5, and C15 is substituted in the β position (VII-5b-369), was prepared by a reaction as shown in the following scheme 25 (according to general flow diagram II):

SCHEME 25

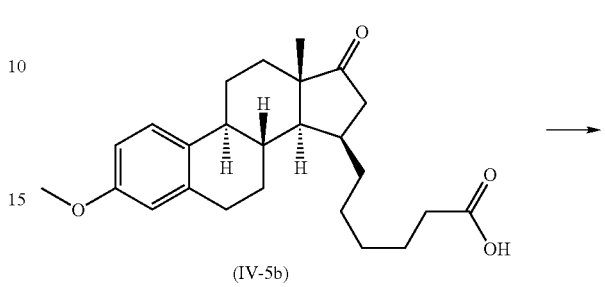

(IV-5b)

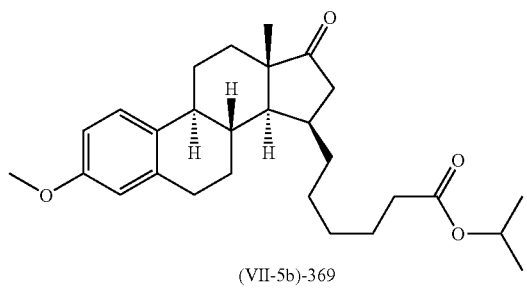

(VII-5b)-369

6-(3-Methoxy-17-oxo-estra-1,3,5(10)-trien-15-yl)-hexanoic Acid Isopropyl Ester (VII-5b)-369

A mixture of 0.13 mmol of the free acid of formula (IV-5b), 0.26 mmol isopropanol, 0.26 mmol Hydroxy-benzotriazole, 0.26 mmol N-methylmorpholine and 0.26 mmol EDCI.HCl were dissolved in DCM and stirred for 4 h at RT. After filtration the organic layer was washed twice with 1 M KHSO$_4$ solution. The material was purified by flash chromatography after evaporation (cyclohexane/EE 5:1→4:1) yielding to 29 mg of white foam (VII-5b)-369 (LC-MS: MH+ 441; rt 7.81 min).

C$^{13}$ NMR: (Solvent CDCl3): 17.74, 21.89, 21.89, 25.58, 26.81, 29.53, 31.00, 33.95, 34.39, 34.61, 36.08, 42.88, 44.55, 47.17, 52.95, 55.25, 67.44, 111.47, 113.96, 125.99, 132.47, 137.77, 157.73, 173.24, 221.22

Example 370

3-Methoxy-15-(3-oxo-pentyl)-estra-1,3,5(10)-trien-17-one

One compound of formula I, in which X represents a bond, A represents CO, Y represents a bond, n is 2, and C15 is substituted in the β position (VIII-2b-370), was prepared by a reaction as shown in the following scheme 26 (according to general flow diagram III):

SCHEME 26

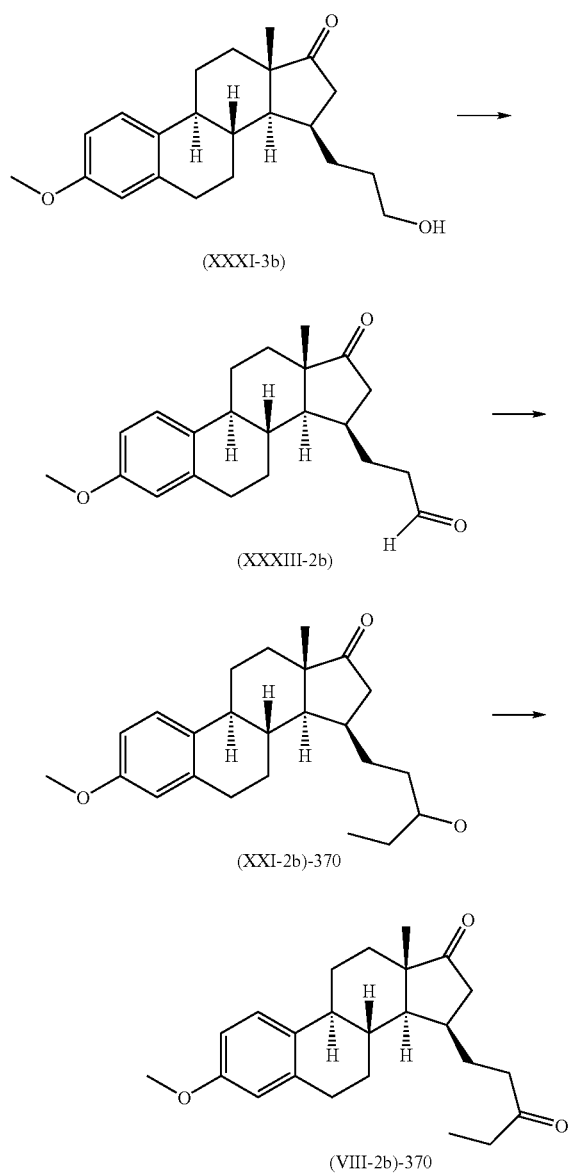

Detailed Synthesis

3-(3-Methoxy-17-oxo-estra-1,3,5(10)-trien-15-yl)-propionaldehyde (XXXIII-2b):

505 mg of the alcohol (XXX1-3b) (1.47 mmol) were dissolved in 50 ml DCM, and cooled down to 0° C. Than 4.5 ml (2.2 mmol) Dess Martin reagent were added at 0° C. and the reaction mixture is stirred for an additional hour. The organic layer was thereafter washed with sat. NaHCO$_3$, twice with 1 M Na$_2$S$_2$O$_3$ solution, dried over Na$_2$SO$_4$ an evaporated. After purifying the material by flash chromatography (solvent Cyclohexane/EE 3:1) 420 mg of solid material XXXIII-2b were obtained.

15-(3-Hydroxy-pentyl)-3-methoxy-estra-1,3,5(10)-trien-17-one (XXI-2b)-370

The aldehyde of formula XXXIII-2b was dissolved in 20 ml dry THF and cooled down to 0° C. At this temperature ethyl magnesia bromide and tetramethyldiaminoethan both dissolved separately were added slowly. After additional 2 hours stirring the reaction mixture was left over night at room temperature. Thereafter 5 ml saturated NH$_4$Cl solution were added and the mixture extracted several times with 50 ml EE. After drying the combined organic layers over Na$_2$SO$_4$ and evaporating the solvent 160 mg solid material of (XXI-2b)-370 were obtained which were used in the next step without further purification (LCMS: MH+: 371; rt 6.35 min).

3-Methoxy-15-(3-oxo-pentyl)-estra-1,3,5(10)-trien-17-one (VIII-2b)-370

The previously obtained alcohol (XXI-2b)-370 was dissolved in 10 ml acetone and cooled down to 0° C. At that temperature Jones reagent was added, till the reaction mixture stayed green in color. The reaction was stirred for 1 hour at RT before the excess of Jones reagents was destroyed by adding 2 ml isopropanol. The reaction mixture was afterwards diluted with 200 ml EE and 100 ml saturated NaCl solution. After separation the organic layer was washed with saturated NaCl solution twice before it was dried over Na$_2$SO$_4$ and evaporated under reduced pressure to dryness. The obtained material was purified by flash chromatography (cyclohexane/EE 3:1) yielding 33 mg of solid material (VIII-2b)-370.

C$^{13}$-NMR (Solvent CDCl$_3$): 220.4; 210.8; 157.6; 137.7; 132.2; 125.9; 113.8; 111.4; 55.2; 52.7; 47.0; 44.6; 42.0; 41.54; 36.1; 36.0; 33.9; 33.8; 29.5; 26.7; 25.4; 24.7; 17.8; 7.8 μm Examples 371 to 418

Hydrazides

A variety of compounds of formula I, in which X represents a bond, A represents CO, Y represents NH—NR$^4$ or NH—NH, and C15 is substituted in the β position with side chains of different length (n=2, 3, 4 or 5) were prepared by parallel chemistry using a reaction as shown in the following scheme 27 (according to general flow diagram IVb):

SCHEME 27

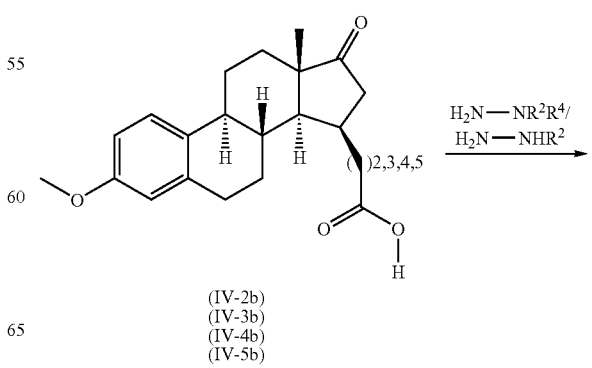

(IV-2b)
(IV-3b)
(IV-4b)
(IV-5b)

-continued

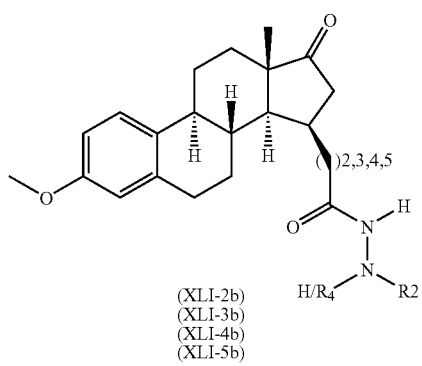

(XLI-2b)
(XLI-3b)
(XLI-4b)
(XLI-5b)

The acids of general formula IV (0.057 mmol per reaction) were used as stock solutions in DCM and were added to a mixture of the respective hydrazine $H_2N—NR^2R^4$ (0.8 eq), polymer bound carbodiimid (3 eq), HOBT (1.7 eq), and 5 ml DCM. After stirring for 24 hours at RT approximately 40 mg polymer bound trisaminomethyl was added to scavange excess of acid. After another 24 hours reaction time, the suspension was filtered and the filtrate evaporated under reduced pressure. The obtained products of general formula XLI were analyzed by LC-MS.

Four groups of compounds according to formula XLI-2b, XLI-3b, XLI-4b, XLI-5b were prepared by this method as depicted in the following tables 11, 12, 13 and 14.

TABLE 11

Compounds of the formula XLI-2b:

(XLI-2b)

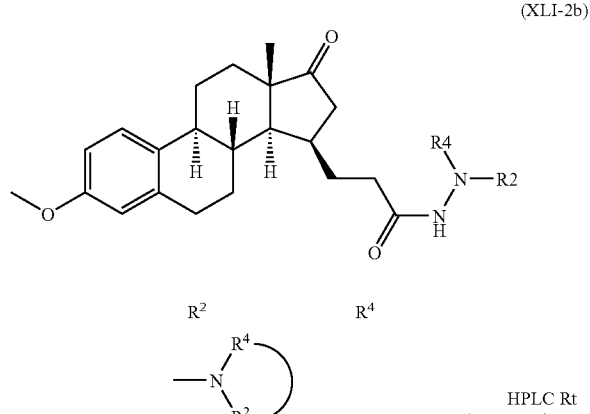

| No. | $R^2$ / $-N(R^4)(R^2)$ | $R^4$ | MS m/z | HPLC Rt [min] |
|---|---|---|---|---|
| 371 | morpholin-4-yl | | 440.27 | 3.62 |
| 372 | 7-chloro-quinolin-4-yl | H | 531.23 | 3.9 |
| 373 | —CO-phenyl | H | 474.25 | 3.82 |
| 374 | —CO—CH₃/acetyl | H | 412.24 | 3.43 |
| 375 | methyl | methyl | 398.26 | 3.66 |
| 376 | —CH₂—CO—O—CH₂—CH₃ | H | 456.26 | 3.82 |
| 377 | 2-fluoro-phenyl | H | 464.25 | 4.21 |
| 378 | —CO-(3,4,5-trimethoxy)phenyl | H | 564.28 | 3.83 |
| 379 | benzothiazol-2-yl | H | 503.22 | 4.86 |
| 380 | 4-methyl-piperazin-1-yl | | 453.3 | 3.25 |

TABLE 12

Compounds of the formula XLI-3b (XLI-3b)

| No. | $R^2$ / $-N(R^4)(R^2)$ | $R^4$ | MS m/z | HPLC Rt [min] |
|---|---|---|---|---|
| 381 | Azepan-1-yl | | 466.32 | 4.45 |
| 382 | 2-(1H-indol-3-1)-acetyl | H | 541.29 | 3.93 |
| 383 | morpholin-4-yl | | 454.28 | 3.72 |
| 384 | piperidin-1-yl- | | 452.3 | 4.19 |
| 385 | 7-chloro-guinolin-4-yl | H | 545.24 | 4.01 |
| 386 | —CO-phenyl | H | 488.27 | 3.93 |
| 387 | —CO-(3-Methoxy-)phenyl | H | 518.28 | 3.99 |
| 388 | methyl | phenyl | 474.29 | 4.37 |
| 389 | —CH₂—CO—O—CH₂—CH₃ | H | 470.28 | 3.92 |
| 390 | 3,5-dichloro-phenyl | H | 528.19 | 4.66 |
| 391 | —CO-(3,4,5-trimethoxy)-phenyl | H | 578.3 | 3.92 |
| 392 | benzothiozal-2-yl | H | 517.24 | 5 |
| 393 | 3-methoxy-phenyl | H | 490.28 | 4.19 |
| 394 | 6-chloro-pyridazin-3-yl | H | 496.22 | 4.47 |
| 395 | 2-methoxymethyl-pyrralidin-1-yl | | 482.31 | 4.03 |

TABLE 13

Compounds of the formula XLI-4b (XLI-4b)

| No. | $R^2$ / $-N(R^4)(R^2)$ | $R^4$ | MS m/z | HPLC Rt [min] |
|---|---|---|---|---|
| 396 | azepan-1-yl | | 480.34 | 4.68 |
| 397 | 2-1H-indol-3-1-acetyl | H | 555.31 | 4.05 |
| 398 | morpholin-4-yl | | 468.3 | 3.88 |
| 399 | piperidin-1-yl | | 466.32 | 4.38 |
| 400 | 7-chloro-quinolin-4-yl | H | 559.26 | 4.16 |
| 401 | methyl | Methyl | 426.29 | 3.94 |
| 402 | benzyl | H | 488.3 | 4.6 |
| 403 | —CH₂—CO—O—CH₂—CH₃ | H | 484.29 | 4.09 |
| 404 | —CO-(3,4,5-trimethoxy)-phenyl | H | 592.31 | 4.06 |
| 405 | benzothiazol-2-yl | H | 531.26 | 5.19 |
| 406 | 4-methyl-piperazin-1-yl | | 481.33 | 3.46 |

TABLE 14

Compounds of the formula (XLI-5b)

(XLI-5b)

| No. | R² | R⁴ | MS m/z | HPLC Rt [min] |
|-----|----|----|--------|---------------|
| 407 | azepan-1-yl | | 494.35 | 4.89 |
| 408 | piperidin-1-yl | | 480.34 | 4.58 |
| 409 | 4-methanesulfonyl-phenyl | H | 566.28 | 4.15 |
| 410 | —CO-(3-Methoxy-)phenyl | H | 546.31 | 4.26 |
| 411 | acetyl | H | 454.28 | 3.8 |
| 412 | methyl | Methyl | 440.3 | 4.11 |
| 413 | benzyl | H | 502.32 | 4.78 |
| 414 | —CH₂—CO—O—CH₂—CH₃ | H | 498.31 | 4.25 |
| 415 | 2-fluoro-phenyl | H | 506.29 | 4.63 |
| 416 | 3,4-dichloro-phenyl | H | 556.23 | 4.9 |
| 417 | 3,5-dichloro-phenyl | H | 556.23 | 5.0 |
| 418 | 4-methyl-piperazin-1-yl | | 495.35 | 3.59 |

Examples 419 to 440

Urea Derivatives

A variety of compounds of formula I, in which X represents NH or NCH₃, A represents CO, Y represents NH and n represents 1 and C15 is substituted in the α position, were prepared by parallel chemistry using a reaction as shown in the following scheme 28A and 28B, respectively (according to general flow diagram Va):

SCHEME 28A

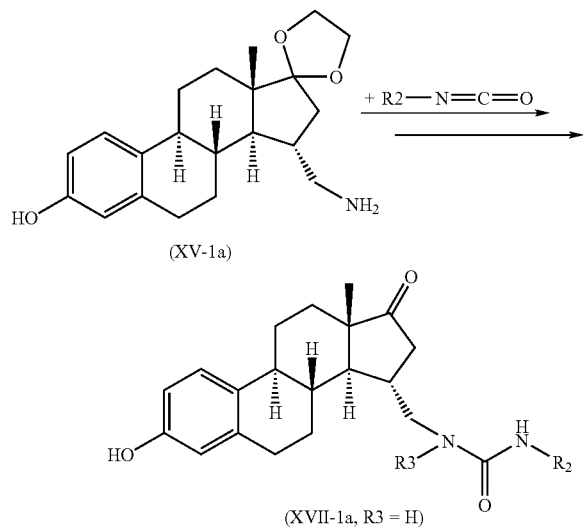

SCHEME 28B

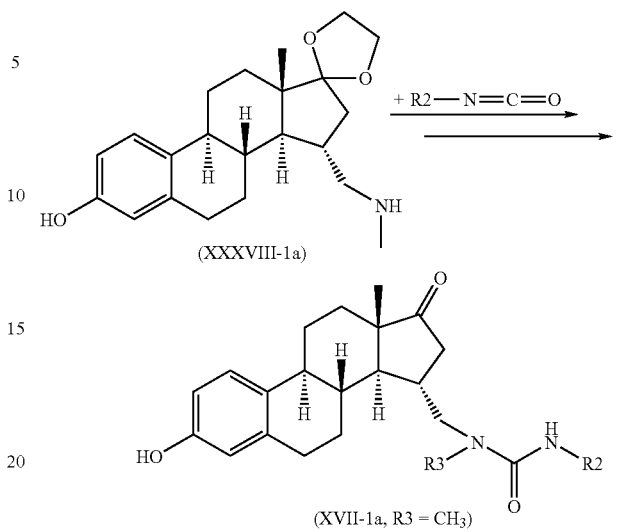

Detailed Syntheses

Step 1: 0.11 mmol Isocyanate (R²—N═C═O) were dissolved in 2 ml ACN. To this solution, 2 ml of the amine building block of formula XV-1a or XXXVIII-1a (0.09 mmol) dissolved in ACN were added. The reaction mixture was stirred at RT for 24 h. In order to remove unreacted isocyanate or amine, polymer bound isocyante and trisamine were added. Again the reaction mixture was stirred for 24 h at RT. The solid material was removed by filtration. The solvent was evaporated in a vacuum centrifuge. Without further purification this material was used in the next step.

Step 2: The material obtained in step 1 was dissolved in 2 ml acetone. 2 mg of p-TsOH were added. The reaction mixture was kept in a microwave oven in a sealed tube at 150° C. for 3 minutes. Thereafter, the solvent was removed in a vacuum centrifuge. The obtained material was separated between EtOAc and NaHCO₃ solution. The organic layer was collected and evaporated again. The material thereafter was analyzed by LC-MS.

Two groups of compounds according to formula XVII-1b were prepared by this method as depicted in the following tables 15 and 16.

TABLE 15

Compounds of the formula XVII-1b, with R³ = H:

| No. | R² | MS m/z | HPLC Rt [min] |
|-----|----|--------|---------------|
| 419 | 2,4-Dichloro-phenyl | 486.15 | 4.14 |
| 420 | 3-nitro-phenyl | 436.22 | 3.74 |
| 421 | 3,4-Dichloro-benzyl | 486.21 | 3.98 |
| 422 | 3-Fluoro-phenyl | 448.24 | 3.56 |

TABLE 15-continued

Compounds of the formula XVII-1b, with R³ = H:

![Structure]

| No. | R² | MS m/z | HPLC Rt [min] |
|---|---|---|---|
| 423 | Benzyl | 490.25 | 3.8 |
| 424 | 3,4-Dimethoxy-phenyl | 486.21 | 3.98 |
| 425 | 3-trifluoromethyl-phenyl | 384.24 | 3.34 |
| 426 | 2-benzoic acid methyl ester/ 2-(carbaxylic acid methyl ester)-phenyl | 468.24 | 3.79 |
| 427 | 4-methoxy-phenyl | 463.21 | 3.76 |
| 428 | 3-Cyano-phenyl | 432.24 | 3.56 |
| 429 | 4-benzoic acid ethyl ester/ 4-(carboxylic acid ethyl ester)-phenyl | 476.23 | 3.94 |
| 430 | 4-trifluoromethoxy-phenyl | 443.22 | 3.64 |
| 431 | 4-trifluoromethyl-phenyl | 502.21 | 3.99 |
| 432 | Biphenyl-2-yl | 494.26 | 3.99 |
| 433 | Isopropyl | 454.32 | 4.17 |
| 434 | Octyl | 442.25 | 3.34 |
| 435 | naphthalen-1-yl | 500.16 | 3.84 |
| 436 | 3-propionic acid ethyl ester/ 1-ethoxy-1-oxo-propan-3-yl | 478.25 | 3.44 |

TABLE 16

UZ,5/28 Compounds of the formula XVII-1b, with R³ = —CH₃

| No. | R² | MS m/z | HPLC Rt |
|---|---|---|---|
| 437 | Octyl | 468.34 | 4.39 |
| 438 | 2-benzoic acid methyl ester/ 2-(carboxylic acid methyl ester)-phenyl | 490.25 | 4.2 |
| 439 | Cyclohexyl | 438.29 | 3.84 |
| 440 | Isopropyl | 398.26 | 3.49 |

Examples 441 to 489

Urea Derivatives

Further compounds of formula I, in which X represents NH, A represents CO, Y represents NH and n represents 3 or 4 and C15 is substituted in the β position, were prepared by parallel chemistry using a reaction as shown in the following schemes 29A and 29B (according to general flow diagram Vb):

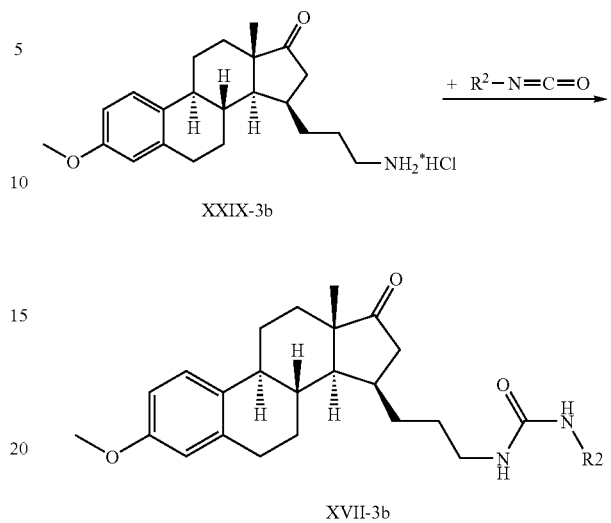

SCHEME 29A

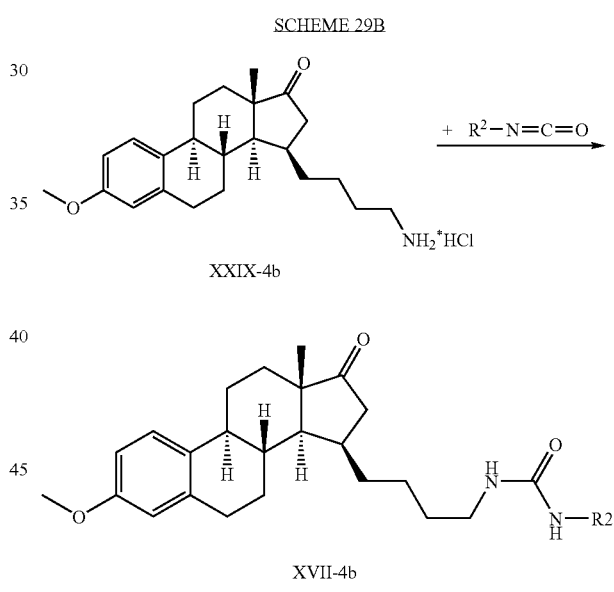

SCHEME 29B

Detailed Synthesis 0.11 mmol Isocyanate (R²—N=C=O) were dissolved in 2 ml ACN. To this solution, 2 ml of the amine building block of formula XXIX-3b or XXIX-4b (0.09 mmol) dissolved in ACN and approximately 40 mg polymere bound diisopropylethylamine were added. The reaction mixture was stirred at RT for 24 h. In order to remove unreacted isocyanate or amine, polymer bound isocyante and trisamine were added. Again the reaction mixture was stirred for 24 h at RT. The solid material was removed by filtration. The solvent was evaporated in a vacuum centrifuge. The obtained material was analyzed by LC-MS.

Two groups of compounds according to formula XVII-3b and XVII-4b were prepared by this method as depicted in the following tables 17 and 18.

TABLE 17

Compounds of the formula XVII-3b

XVII-3b

| No. | R² | MS m/z | HPLC Rt [min] |
|---|---|---|---|
| 441 | 2,4-Dichloro-phenyl | 528.19 | 4.97 |
| 442 | 3-Fluoro-phenyl | 478.26 | 4.45 |
| 443 | 3-Methoxy-phenyl | 490.28 | 4.33 |
| 444 | 3-trifluoromethyl-phenyl | 528.26 | 4.69 |
| 445 | 4-Fluoro-phenyl | 478.26 | 4.36 |
| 446 | 4-methoxy-phenyl | 490.28 | 4.24 |
| 447 | 4-benzoic acid ethyl ester/ 4-(carboxylic acid ethyl ester)-phenyl | 532.29 | 4.52 |
| 448 | 4-trifluoromethyl-phenyl | 528.26 | 4.7 |
| 449 | Isopropyl | 426.29 | 4.04 |
| 450 | Cyclohexyl | 466.32 | 4.36 |
| 451 | naphthalen-1-yl | 510.29 | 4.5 |
| 452 | aenzyl | 474.29 | 4.23 |
| 453 | 2-benzoic acid methyl ester/ 2-(carboxylic acid methyl ester)-phenyl | 518.28 | 4.76 |
| 454 | 3-Cyano-phenyl | 485.27 | 4.33 |
| 455 | 3-Acetyl-phenyl | 502.28 | 4.23 |
| 456 | 4-Acetyl-phenyl | 502.28 | 4.19 |
| 457 | 4-trifluoromethoxy-phenyl | 544.25 | 4.72 |
| 458 | Biphenyl-2-yl | 536.3 | 4.79 |
| 459 | Octyl | 496.37 | 4.98 |
| 460 | naphthalen-2-yl | 510.29 | 4.63 |
| 461 | 3-propionic acid ethyl ester/ 1-ethoxy-1-oxo-propan-3-yl | 484.29 | 4.02 |
| 462 | 4-(6-methyl-benzothiazol-2-yl)-phenyl | | |
| 463 | 3,4-bichloro-benzyl | 542.21 | 4.57 |
| 464 | 3,4-Dimethoxy-phenyl | 520.29 | 4.1 |
| 465 | Benzo[1,3]dioxol-5-yl | 504.26 | 4.23 |

TABLE 18

Compounds of the formula XVII-4b

XVII-4b

| No. | R² | MS m/z | HPLC Rt [min] |
|---|---|---|---|
| 466 | 2,4-Dichloro-phenyl | 542.21 | 5.19 |
| 467 | 3-Fluoro-phenyl | 492.28 | 4.63 |
| 468 | 3-methoxy-phenyl | 504.3 | 4.5 |
| 469 | 3-trifluoromethyl-phenyl | 542.28 | 4.88 |
| 470 | 4-Fluoro-phenyl | 492.28 | 4.54 |
| 471 | 4-methoxy-phenyl | 504.3 | 4.42 |
| 472 | 4-benzoic acid ethyl ester/ 4-(carboxylic acid ethyl ester)-phenyl | 546.31 | 4.7 |
| 473 | 4-trifluoromethyl-phenyl | 542.28 | 4.88 |

TABLE 18-continued

Compounds of the formula XVII-4b

XVII-4b

| No. | R² | MS m/z | HPLC Rt [min] |
|---|---|---|---|
| 474 | Isopropyl | 440.3 | 4.21 |
| 475 | Cyclohexyl | 480.34 | 4.56 |
| 476 | naphthalen-1-yl | 524.3 | 4.7 |
| 477 | Benzyl | 488.3 | 4.41 |
| 478 | 2-benzoic acid methyl ester/ 2-(carboxylic acid methyl ester)-phenyl | 532.29 | 4.96 |
| 479 | 3-Cyano-phenyl | 499.28 | 4.51 |
| 480 | 3-Acetyl-phenyl | 516.3 | 4.4 |
| 481 | 4-Acetyl-phenyl | 516.3 | 4.37 |
| 482 | 4-trifluoromethoxy-phenyl | 558.27 | 4.89 |
| 483 | Biphenyl-2-yl | 550.32 | 4.97 |
| 484 | Octyl | 510.38 | 5.18 |
| 485 | naphthalen-2-yl | 524.3 | 4.82 |
| 486 | 3-propionic acid ethyl ester/ 1-ethoxy-1-oxo-propan-3-yl | 498.31 | 4.18 |
| 487 | 3,4-Dichloro-benzyl | 556.23 | 4.76 |
| 488 | 3,4-Dimethoxy-phenyl | 534.31 | 4.28 |
| 489 | Benzo[1,3]dioxol-5-yl | 518.28 | 4.42 |

Examples 490 to 492

Urea Derivatives

Further three compounds of formula I, in which X represents NH, A represents CO, Y represents NH, n represents 4, and C15 is substituted in the α position, were prepared by individual synthesis using a reaction as shown in scheme 28C and described above for scheme 28A (according to general flow diagram Va). The individual compounds of formula XVIIα-4a are depicted in Table 19.

SCHEME 28C

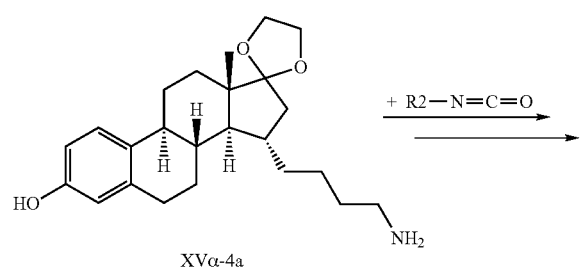

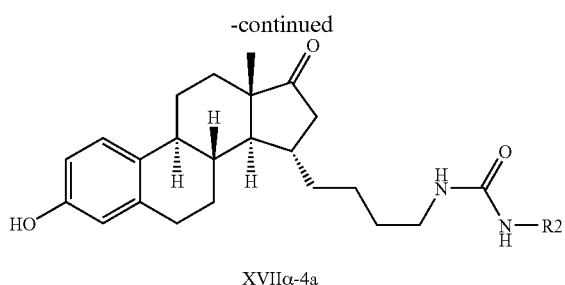

XVIIα-4a

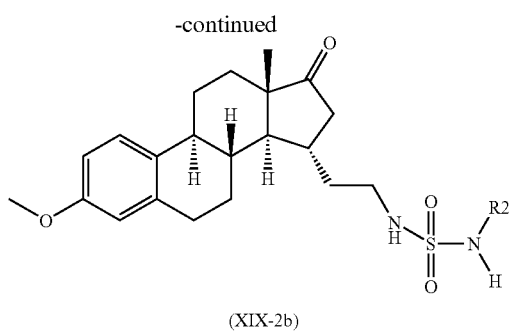

(XIX-2b)

TABLE 19

Compounds of the formula XVIIα-4a

| No. | $R^2$ | MS m/z | HPLC Rt [min] |
|---|---|---|---|
| 490 | 4-benzoic acid ethyl ester/ 4-(carboxylic acid ethyl ester)-phenyl | 532 | 5.91 |
| 491 | Cyclohexylmethyl | 480 | 6.42 |
| 492 | Phenyl | 460 | 5.65 |

Examples 493 to 537

Sulfamides

A variety of compounds of formula I, in which X represents NH, A represents $SO_2$, Y represents NH and n represents 2, and C15 is substituted in the α position, may be prepared by parallel chemistry using a reaction as shown in the following scheme 30 (according to general flow diagram VI):

SCHEME 30

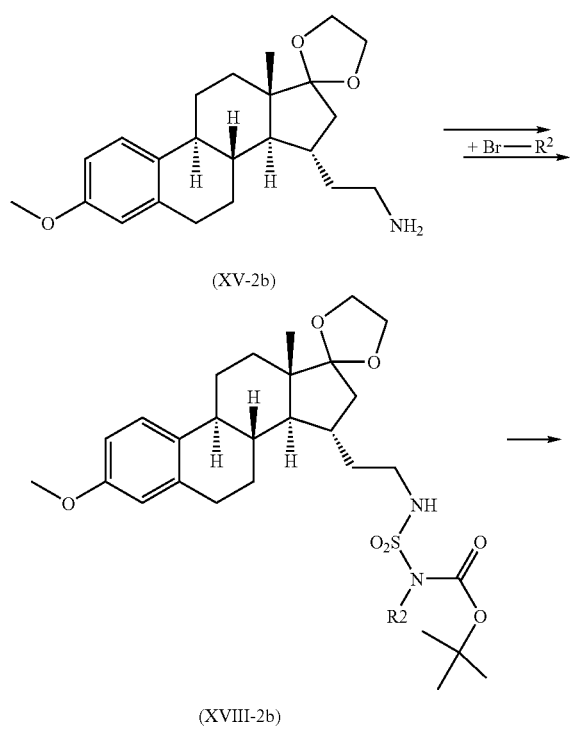

Detailed Synthesis

Step 1: Tert. butyl alcohol (6.5 ml=5.13 g=69.3 mmol) in 30 ml DCM is added dropwise to a cold solution of 6.0 ml (9.76 g=68.9 mmol.) chlorosulfonyl isocyanate in 40 ml DCM. After 30 min the mixture is diluted with DCM up to 100 ml to get a 0.854 molar stock solution. (18.29 g/100 ml; density 1.318 g/ml; LC-MS found the mass M+H 216). 2 ml of this solution are added to the amine building block of formula XV-1b (0.5 mMol) and (1 mMol) triethylamine dissolved in DCM at 0° C. The mixture is stirred overnight at RT. The reaction mixture is worked up by liquid/liquid extraction with DCM/water. The crude product is purified on silica gel with DCM as eluent.

Step 2: 0.1 mMol of the Boc-protected sulfamide obtained in step 1 are dissolved in acetone. 0.3 mMol $K_2CO_3$ and 0.1 mMol bromo-alkane (or correspondent bromoreagent) are added. The reaction is kept at 60° C. for 24 h. After filtration and concentration the crude mixture is purified by column chromatography on silica gel.

Step 3: The material obtained in step 2 is dissolved in 2 ml acetone. 2 mg of p-TosOH were added. The reaction mixture is kept in a microwave oven in a sealed tube at 150° C. for 3 minutes. Thereafter the solvent is removed in a vacuum centrifuge. The obtained material is separated between EtOAc and $NaHCO_3$ solution. The organic layer is collected and evaporated again. Thereafter the material is analyzed by LC-MS.

A group of compounds according to formula XIX-2b may be prepared by this method; the compounds listed in Table 12 represent reaction products of a compound of formula XV-2b with a bromo-reagent ($R^2$—Br).

TABLE 12

Compounds of the formula XIX-2b, which are prepared by reaction with variable $R^2$—Br compounds:

| No. | Reactant $R^2$—Br |
|---|---|
| 493 | (2-BROMOETHYL)BENZENE |
| 494 | 1-(2-BROMOETHYL)NAPHTHALENE |
| 495 | 1-BROMO-3,3-DIPHENYLPROPANE |
| 496 | 1-BROMO-3-METHYLBUTANE |
| 497 | 1-BROMOMETHYL-2-(PHENYLSULFONYL)METHYL)BENZENE |
| 498 | 2-(BROMOMETHYL)NAPHTHALENE |
| 499 | 2-(DIFLUOROMETHOXY)BENZYL BROMIDE |
| 500 | 2-(N-(2-BROMOETHYL)ANILINO)-ETHANOL |
| 501 | 2,5-BIS(TRIFLUOROMETHYL)BENZYL BROMIDE |
| 502 | 2-BROMOETHYL ACETATE |
| 503 | 2-BROMOETHYL N-(1-NAPHTHYL)CARBAMATE |
| 504 | 2-BROMOETHYL N-(2,3-DICHLOROPHENYL)CARBAMATE |
| 505 | 2-BROMOMETHYL-1,4-BENZODIOXANE |
| 506 | 2-BROMOMETHYL-5-FLUOROCOUMARAN |
| 507 | 2-PHENYLBENZYL BROMIDE |
| 508 | 3-(2-BROMOETHYL)INDOLE |
| 509 | 3-(BROMOMETHYL)BENZOIC ACID METHYL ESTER |

TABLE 12-continued

Compounds of the formula XIX-2b, which are prepared by reaction with variable R²—Br compounds:

| No. | Reactant R²—Br |
|---|---|
| 510 | 3,4-DICHLOROBENZYL BROMIDE |
| 511 | 3,5-BIS(TRIFLUOROMETHYL)BENZYL BROMIDE |
| 512 | 3-BENZOYLBENZYLBROMIDE |
| 513 | 3-BROMO-1,2-PROPANEDIOL |
| 514 | 3-BROMOMETHYL-2-(4-CHLOROBENZOYL)BENZOFURAN |
| 515 | 3-BROMOPROPIONIC ACID ETYHL ESTER |
| 516 | 3-PHENOXYPROPYL BROMIDE |
| 517 | 4-(2-BROMOETHYL)-ACETOPHENONE |
| 518 | 4-(4-BROMOMETHYLPHENYL)-1,2,3-THIADIAZOLE |
| 519 | 4-(BROMOMETHYL)BENZOIC ACID METHYL ESTER |
| 520 | 4-(BROMOMETHYL)PHENYLACETIC ACID PHENACYL ESTER |
| 521 | 4-(TERT-BUTYL)BENZYL BROMIDE |
| 522 | 4-BROMOBUTYRIC ACID ETHYL ESTER |
| 523 | 4-BROMOMETHYL-7-METHOXYCOUMARIN |
| 524 | 4-BROMOMETHYLBENZYL |
| 525 | 4-METHYLSULFONYLBENZYL BROMIDE |
| 526 | 4-PHENOXYBUTYL BROMIDE |
| 527 | 5-(BROMOMETHYL)BENZOFURAZAN |
| 528 | 6-AMINO-9-(2-BROMOETHYL)-9H-PURINE |
| 529 | ALPHA-BROMO-M-TOLUNITRILE |
| 530 | ALPHA-BROMO-O-TOLUNITRILE |
| 531 | ALPHA-BROMO-P-TOLUNITRILE |
| 532 | BENZOIC ACID 2-BROMOETHYL ESTER |
| 533 | BENZYL BROMIDE |
| 534 | CYCLOPROPYLMETHYL BROMIDE |
| 535 | DELTA-BROMOBUTYLHYDANTOIN |
| 536 | N-(4-BROMOBUTYL)PHTHALIMIDE |
| 537 | PHENACYL 4-BROMOCROTONATE |

Examples 538 and 539

Carbamates

Two compounds of formula I, in which X represents NH, A represents CO, Y represents O, n represents 1, and C15 is substituted in the α position, were prepared using a reaction as shown in the following scheme 31 (according to general flow diagram VII):

SCHEME 31

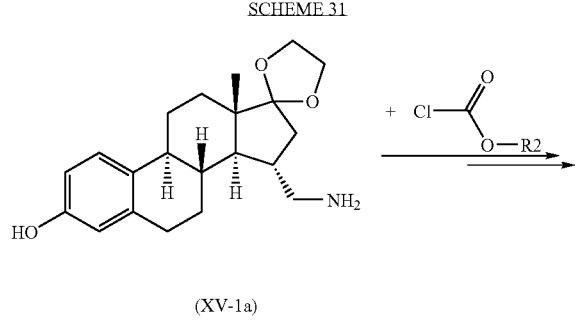

(XV-1a)

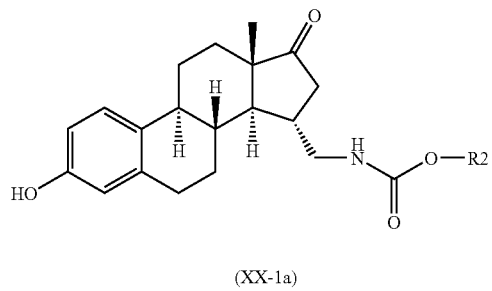

(XX-1a)

Detailed Synthesis

Step 1: 0.132 mMol Chloroformic acid ester (R²—O—CO—Cl) were dissolved in 2 ml DCM. To this solution 2 ml of the amine building block of formula XV-1a (0.112 mMol) dissolved in DCM were added. The reaction mixture was stirred at RT for 24 h. To remove unreacted Chloroformic acid ester or amine polymer bound isocyanate and trisamine were added. Again the reaction mixture was stirred for 24 h at RT. The solid material was removed by filtration. The solvent was evaporated in a vacuum centrifuge. Without further purification this material was used in the next step.

Step 2: The material obtained in step 1 was dissolved in 2 ml acetone. 2 mg of p-toluene sulfonic acid were added. The reaction mixture was kept in a microwave oven in a sealed tube at 150° C. for 3 minutes. Thereafter the solvent was removed in a vacuum centrifuge. The obtained material was separated between EtOAc and NaHCO₃ solution. The organic layer was collected and evaporated again. The material thereafter was analyzed by LC-MS.

Two compounds according to general formula XX-1a were prepared by this method as depicted in Table 21.

TABLE 21

Compounds of the formula XX-1a:

| No. | R² | MS m/z | HPLC Rt [min] |
|---|---|---|---|
| 538 | Isobutyl | 400 | 5.58 |
| 539 | 4-Nitro-benzyl | 478 | 5.62 |

Examples 540 to 543

Sulfamates

A variety of compounds of formula I, in which X represents NH, A represents SO₂, Y represents O, and n represents for example 1, and C15 is substituted in the α position, may be prepared by parallel chemistry using a reaction as shown in the following scheme 32 (according to general flow diagram VIII):

SCHEME 32

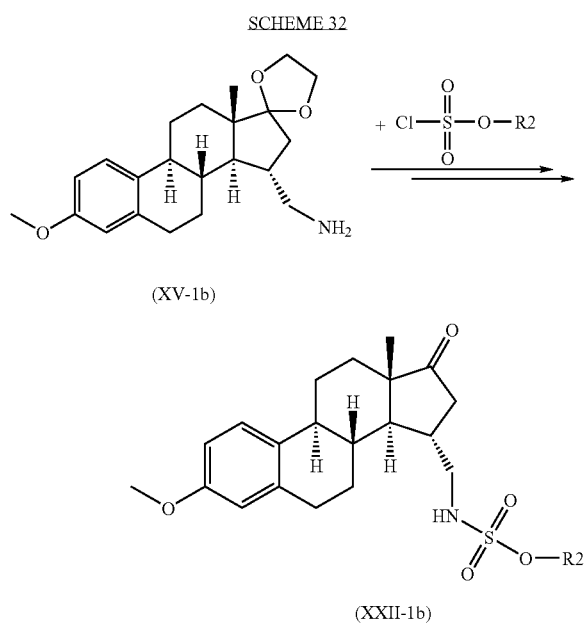

(XV-1b)

(XXII-1b)

Detailed Synthesis

Step 1: To a solution of 0.132 mmol chlorosulfonic acid ester ($R^2$—O—$SO_2$—Cl) in 2 ml DCM 0.112 mmol of the amine building block XV-1b, dissolved in 2 ml DCM, and an excess of polymer bound morpholine are added subsequently at −40° C. After an hour the reaction mixture is heated to 20° C. and left over night. To remove unreacted chlorosulfonic acid ester and amine polymere bound isocyanate and trisamine are added. Again the reaction mixture is stirred for 24 h at RT. The solid material is removed by filtration. The solvent is evaporated in a vacuum centrifuge. Without further purification this material is used in the next step.

Step 2: The material obtained in step 1 is dissolved in 2 ml acetone. 2 mg of p-TosOH are added. The reaction mixture is kept in a microwave oven in a sealed tube at 150° C. for 3 minutes. Thereafter the solvent is removed in a vacuum centrifuge. The obtained material is separated between EtOAc and $NaHCO_3$ solution. The organic layer is collected and evaporated again. The material thereafter is analyzed by LC-MS.

A group of compounds according to formula XXII-1b may be prepared by this method; the compounds represent reaction products of a compound of formula XV-1b with a chlorosulfuric acid ester ($R^2$—O—$SO_2$—Cl). Table 14 shows the number of the reaction products together with the corresponding chlorosulfuric acid ester ($R^2$—O—$SO_2$—Cl).

TABLE 14

Compounds of the formula XXII-1b, prepared by reaction with ($R^2$—O—$SO_2$—Cl):

| No. | Reactant $R^2$—O—$SO_2$—Cl |
|---|---|
| 537 | Chloro sulfonic acid ethyl ester |
| 538 | Chloro sulfonic acid butyl ester |
| 539 | Chloro sulfonic acid benzyl ester |
| 540 | Chloro sulfonic acid phenyl ester |

Examples 544 to 570

"Retro"-Amides

A variety of formula I compounds, in which X represents —NH, A represents CO, Y represents a bond, n represents 1, $R^1$ represents $CH_3$, and $R^2$ is varied, and C15 is substituted in the α position, were prepared by parallel chemistry using a reaction as shown in the following scheme 33 (according to general flow diagram IXa). The group of compounds prepared by this method is listed in table 23.

SCHEME 33

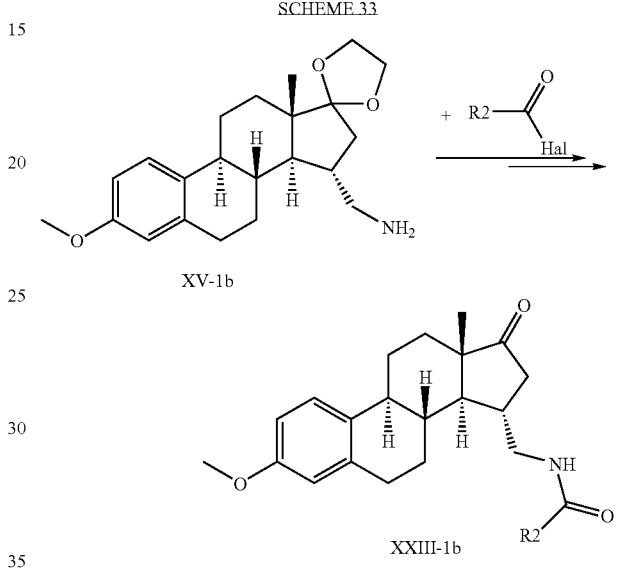

XV-1b

XXIII-1b

Detailed Synthesis

Step 1: 0.132 mMol of the appropriate acid chloride $R^2$—CO—Cl were dissolved in 2 ml DCM. To this solution 2 ml of the amine building block of the formula XV-1b (0.112 mMol) dissolved in DCM and 160 mg morpholine polymer bound were added. The reaction mixture was stirred at RT for 48 h. To remove unreacted acid chloride or amine polymer bound isocyanate and trisamine had been added. Again the reaction mixture was stirred for 24 h at RT. The solid material was removed by filtration. The solvent was evaporated in a vacuum centrifuge. Without further purification this material was used in the next step.

Step 2: The material obtained in step 1 was dissolved in 2 ml acetone. 2 mg of p-toluene sulfonic acid were added. The reaction mixture was kept in a microwave oven in a sealed tube at 150° C. for 3 minutes. Thereafter the solvent was removed in a vacuum centrifuge. The obtained material was separated between EtOAc and $NaHCO_3$ solution. The organic layer was collected and evaporated again. The material thereafter was analyzed by LC-MS.

TABLE 23

Compounds of the formula XXIII-1b, wherein R2 is varied:

| No. | $R^2$ | MS m/z | HPLC Rt [min] |
|---|---|---|---|
| 544 | 3,5-Bis-trifluoromethyl-phenyl | 553.21 | 4.73 |
| 545 | 2,4-Dichloro-phenyl | 485.15 | 4.54 |
| 546 | 2-Methoxy-phenyl | 447.24 | 4.36 |
| 547 | 3,4-Dichloro-phenyl | | |

TABLE 23-continued

Compounds of the formula XXIII-1b, wherein R2 is varied:

| No. | R² | MS m/z | HPLC Rt [min] |
|---|---|---|---|
| 548 | 3-Methoxy-phenyl | 447.24 | 4.27 |
| 549 | 4-Fluoro-phenyl | 435.22 | 4.3 |
| 550 | 4-Methoxy-phenyl | 447.24 | 4.21 |
| 551 | 4-Hexyloxy-phenyl | 517.32 | 5.25 |
| 552 | 4-Trifluoromethyl-phenyl | 485.22 | 4.59 |
| 553 | Tert. Butyl | 397.26 | 4.21 |
| 554 | Phenoxy-methyl | 447.24 | 4.31 |
| 555 | Methoxy-methyl | 385.23 | 3.79 |
| 556 | Benzyl | 431.25 | 4.19 |
| 557 | Ethyl | 369.23 | 3.81 |
| 558 | Phenethyl | 445.26 | 4.26 |
| 559 | 2-Cyclopentyl-ethyl | 437.29 | 4.56 |
| 560 | Cyclohexyl | 423.28 | 4.35 |
| 561 | Furan-2-yl | 407.21 | 4.03 |
| 562 | Thiophen-2-yl-methyl | 437.2 | 4.15 |
| 563 | Benzyloxy-methyl | 461.26 | 4.35 |
| 564 | Diphenyl-methyl | | |
| 565 | Acetic acid methyl ester/—$CH_2$—CO—O—$CH_3$ | 413.22 | 3.79 |
| 566 | Benzo[b]thiophen-2-yl | 473.2 | 4.64 |
| 567 | 2,4,5-Trifluorophenyl | 471.2 | 4.51 |
| 568 | 2-(4-Chloro-phenoxy)-pyridin-3-yl | | |
| 569 | 1-Phenyl-5-trifluoromethyl-1H-pyrazol-4-yl | 551.24 | 4.53 |
| 570 | Adamantan-1-yl | 475.31 | 4.89 |

Examples 571 to 593

"Retro"-Amides

A variety of formula I compounds, in which X represents —NH, A represents CO, Y represents a bond, n represents 4, $R^1$ represents H, $R^2$ is varied, and C15 is substituted in the α position, were prepared by parallel chemistry using a reaction as shown in the following scheme 34 and described above for scheme 33 (according to general flow diagram IXa). The compounds are listed in table 24.

TABLE 24

Compounds of the formula XXIIIα-4a, wherein R2 is varied:

| No. | R² | MS m/z | HPLC Rt [min] |
|---|---|---|---|
| 571 | Phenyl | 445.26 | 5.59 |
| 572 | 2-bromo-phenyl | 523.17 | 5.71 |
| 573 | 2,4-Dichloro-phenyl | 513.18 | 6.03 |
| 574 | 2-methoxy-phenyl | 475.27 | 5.77 |
| 575 | 3-Chloro-phenyl | 479.22 | 5.98 |
| 576 | 3-methoxy-phenyl | 475.27 | 5.64 |
| 577 | 4-Chloro-phenyl | 479.22 | 5.95 |
| 578 | 4-methoxy-phenyl | 475.27 | 5.58 |
| 579 | Methyl | 383.25 | 4.81 |
| 580 | Methoxymethyl | 413.26 | 5.01 |
| 581 | Benzyl | 459.28 | 5.57 |
| 582 | 2,2-dimethyl-propyl | 439.31 | 5.68 |
| 583 | Phenethyl | 473.29 | 5.7 |
| 584 | 1-ethoxy-1-oxo-propan-3-yl | 469.28 | 5.25 |
| 585 | Cyclohexyl | 451.31 | 5.79 |
| 586 | 4-Cyano-phenyl | 470.26 | 5.56 |
| 587 | naphthalen-1-yl | 495.28 | 5.94 |
| 588 | naphthalen-2-yl | 495.28 | 6.04 |
| 589 | 3,5-Dichloro-phenyl | 513.18 | 6.3 |
| 590 | 3,4-Difluoro-phenyl | 481.24 | 5.86 |
| 591 | Benzyloxy-methyl | 489.29 | 5.8 |
| 592 | 3-Cyano-phenyl | 470.26 | 5.58 |
| 593 | Benzo[b]thiophene-2-yl | 501.23 | 6.09 |

Examples 594 to 651

"Retro"-Amides

A variety of formula I compounds, in which X represents —NH, A represents CO, Y represents a bond, n represents 3 or 4, $R^1$ represents H or $CH_3$, $R^2$ is varied, and C15 is substituted in the α or β position, were prepared by parallel chemistry using a reaction as shown in the following schemes 35A, 35B and 35C (according to general flow diagram IXb).

SCHEME 34

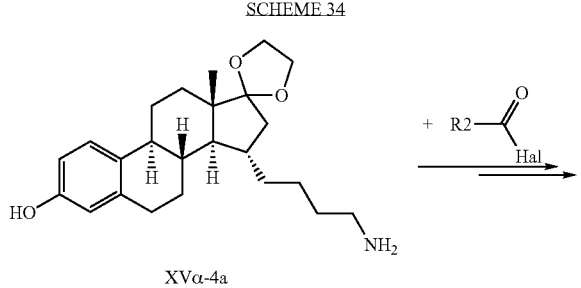

XVα-4a

XXIIIα-4a

SCHEME 35A

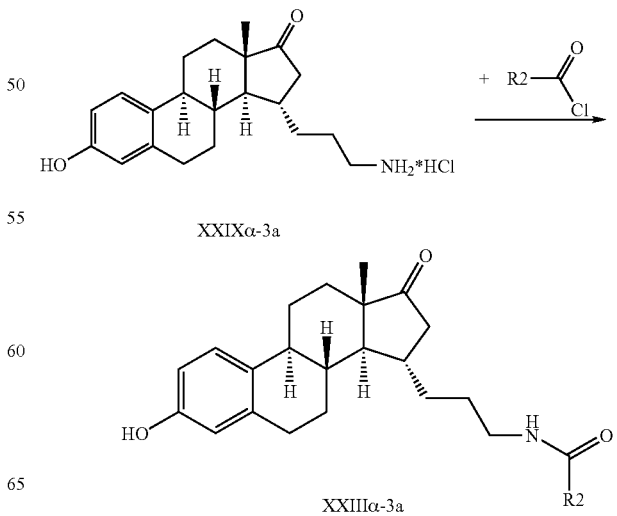

XXIXα-3a

XXIIIα-3a

SCHEME 35B

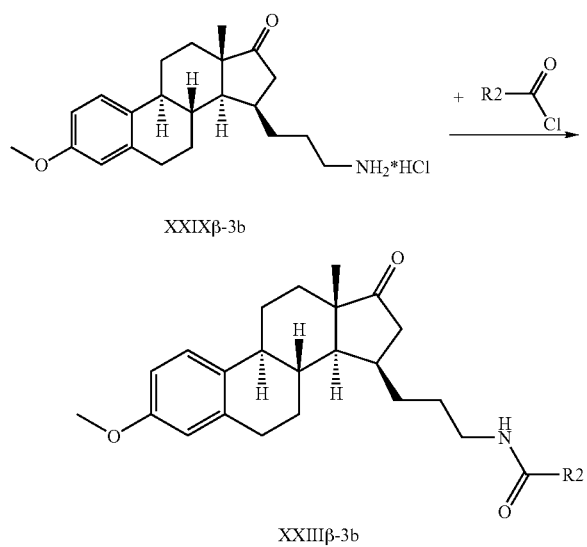

SCHEME 35C

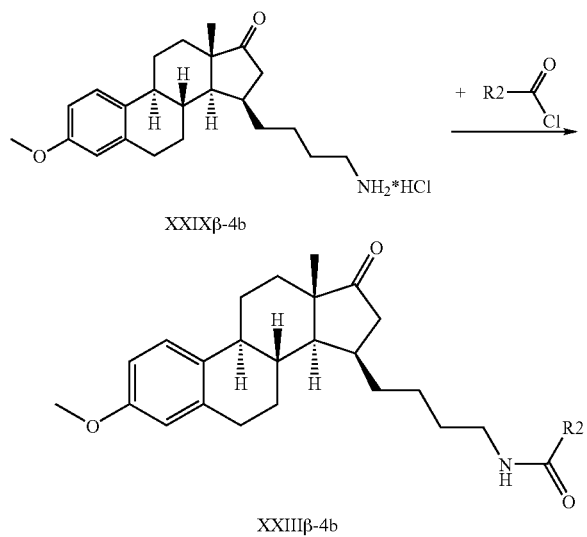

Detailed Synthesis:

0.132 mMol of the appropriate acid chloride $R^2$—CO—Cl were dissolved in 2 ml DCM. To this solution 2 mL of the amine building block of the formula XXIXα-3a, XXIXβ-3b, or XXIXβ-4b (0.112 mMol) dissolved in DCM and 160 mg morpholine polymer bound were added. The reaction mixture was stirred at room temperature for 48 hours. To remove unreacted acid chloride or amine polymer bound isocyanate and trisamine was added. Again the reaction mixture was stirred for 24 h at RT. The solid material was removed by filtration. The solvent was evaporated in a vacuum centrifuge. The material thereafter was analyzed by LC-MS.

Three groups of compounds according to general formulas XXIIIα-3a, XXIIIβ-3b and XXIIIβ-4b were prepared by this method as depicted in the following tables 25, 26 and 27, respectively.

TABLE 25

Compounds of the formula XXIIIα-3a, wherein R2 is varied

XXIIIα-3a

| No. | $R^2$ | MS m/z | HPLC Rt [min] |
|---|---|---|---|
| 594 | Phenyl | 431.57 | 5.36 |
| 595 | 3-Chloro-phenyl | 465.21 | 3.94 |
| 596 | 3-methoxy-phenyl | 461.26 | 3.75 |
| 597 | 4-Chloro-benzyl | 465.21 | 3.93 |
| 598 | 4-methoxy-phenyl | 461.26 | 3.7 |
| 599 | Methyl | 369.23 | 3.29 |
| 600 | methoxy-methyl | 399.24 | 3.39 |
| 601 | Benzyl | 445.26 | 3.69 |
| 602 | Phenethyl | 459.28 | 3.78 |
| 603 | Cyclohexyl | 437.29 | 3.82 |
| 604 | 3,4-Difluoro-phenyl | 467.23 | 3.88 |
| 605 | Benzyloxy-methyl | 475.27 | 3.84 |
| 606 | 3-Cyano-phenyl | 456.24 | 3.72 |

TABLE 26

Compounds of the formula XXIIIβ-3b, wherein R2 is varied:

| No. | $R^2$ | MS m/z | XXIIIβ-3b HPLC Rt [min] |
|---|---|---|---|
| 607 | Phenyl | 445.26 | 6.28 |
| 608 | 2-bromo-phenyl | 523.17 | 6.42 |
| 609 | 2,4-Dichloro-phenyl | 513.18 | 6.74 |
| 610 | 3-Chloro-phenyl | 479.22 | 6.68 |
| 611 | 3,4-Dichloro-phenyl | 513.18 | 7.02 |
| 612 | 3-methoxy-phenyl | 475.27 | 6.33 |
| 613 | 4-Chloro-phenyl | 479.22 | 6.64 |
| 614 | 4-methoxy-phenyl | 475.27 | 6.27 |
| 615 | Methyl | 383.25 | 5.5 |
| 616 | Methoxymethyl | 413.26 | 5.72 |
| 617 | Benzyl | 459.28 | 6.28 |
| 618 | 2,2-dimethyl-propyl | 439.31 | 6.43 |
| 619 | Phenethyl | 473.29 | 6.43 |
| 620 | 1-ethoxy-1-oxo-propan-3-yl | 469.28 | 5.98 |
| 621 | Cyclohexyl | 451.31 | 6.51 |
| 622 | 4-Cyano-phenyl | 470.26 | 6.24 |
| 623 | naphtholen-1-yl | 495.28 | 6.63 |
| 624 | naphthalen-2-yl | 495.28 | 6.73 |
| 625 | 3,5-Dichloro-phenyl | 513.18 | 7.16 |
| 626 | 3,4-Difluoro-phenyl | 481.24 | 6.56 |
| 627 | Benzyloxy-methyl | 489.29 | 6.53 |
| 628 | 2-(3-trifluoromethyl-phenyl)-vinyl | | |

TABLE 27

Compounds of the formula XXIIIβ-4b, wherein R2 is varied:

XXIIIβ3-4b

| No. | R² | MS m/z | HPLC Rt [min] |
|---|---|---|---|
| 629 | 3,4-Difluoro-phenyl | 495.26 | 6.84 |
| 630 | Benzyloxy-methyl | 503.3 | 6.79 |
| 631 | Benzo[b]thiophene-2- | 515.25 | 7.06 |
| 632 | 2-(3-trifluoromethyl-phenyl)-vinyl | 553.28 | 7.09 |
| 633 | 3,5-Dichloro-phenyl | 527.2 | 7.43 |
| 634 | Phenyl | 459.28 | 6.58 |
| 635 | 2-bromo-phenyl | 537.19 | 6.7 |
| 636 | 2,4-Dichloro-phenyl | 527.2 | 7.01 |
| 637 | 3-Chloro-phenyl | 493.24 | 6.97 |
| 638 | 3,4-Dichloro-phenyl | 527.2 | 7.3 |
| 639 | 3-methoxy-phenyl | 489.29 | 6.63 |
| 640 | 4-Chloro-phenyl | 493.24 | 6.93 |
| 641 | 4-methoxy-phenyl | 489.29 | 6.54 |
| 642 | Methyl | 397.26 | 5.77 |
| 643 | Methoxymethyl | 427.27 | 6.01 |
| 644 | Benzyl | 473.29 | 6.54 |
| 645 | 2,2-dimethyl-propyl | 453.32 | 6.72 |
| 646 | Phenethyl | 487.31 | 6.68 |
| 647 | 1-ethoxy-1-oxo-propan-3-yl | 483.3 | 6.23 |
| 648 | Cyclohexyl | 465.32 | 6.82 |
| 649 | 4-Cyono-phenyl | 484.27 | 6.53 |
| 650 | naphthalen-1-yl | 509.29 | 6.93 |
| 651 | naphthalen-2-yl | 509.29 | 7.01 |

Examples 652 to 660

"Retro"-Amides

Alternatively, particular compounds of formula I compounds, in which X represents —NH, A represents CO, Y represents a bond, and R² is varied, were prepared individually using a reaction as shown in the following scheme 36 (according to general flow diagram IXb), but using the appropriate free acid R2-COOH instead of the acid chloride R2-CO—Cl.

SCHEME 36

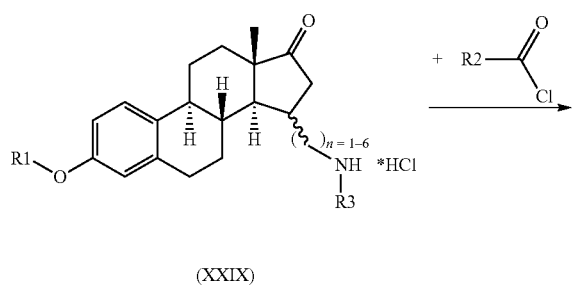

(XXIX)

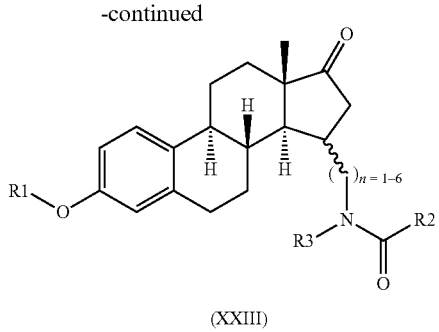

(XXIII)

Detailed Synthesis:

0.132 mmol of the appropriate acid (R2-COOH) were dissolved in 2 ml DCM. To this solution 2 ml of the amine building blocks stock solution in DCM of the general formula XXIX (each vial 0.112 mmol), approximate 120 mg polymer bound morpholine, 120 mg polymer bound carbodiimide and 125 mg polymer bound HOBT were added. The reaction mixture was stirred at RT for 2 days. To remove unreacted acid and amine approx, 40 mg polymer bound isocyanat and trisamine were added. After stirring the reaction mixture for another 24 hours the solid material was removed by filtration. After solvent removal under reduced pressure the samples were analyzed by LC-MS.

Example 652

4-Fluoro-N-(3-hydroxy-17-oxo-estra-1,3,5(10)-trien-15-ylmethyl)-benzamide

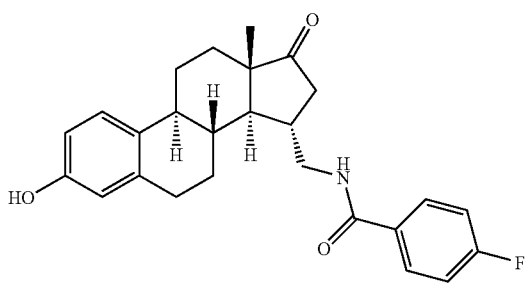

Example 652 of formula (XXXIIα-1a)-652 was synthesized according to SCHEME 36 using XXIXα-1a as starting material (MH+ 422, Rt 5.34 min).

Example 653

3,4-Dichloro-N-[3-(3-hydroxy-17-oxo-estra-1,3,5(10)-trien-15-yl)-propyl]-benzamide

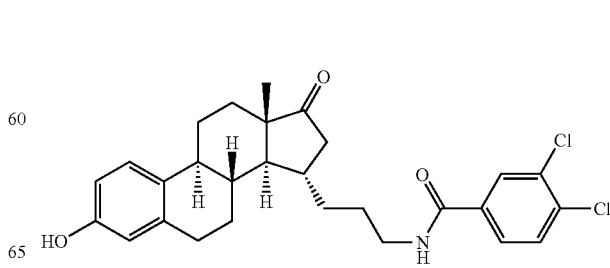

Example 653 of formula (XXXIIIα-3a)-653 was synthesized according to SCHEME 36 using XXIXα-3a as starting material (MH+ 500; Rt 4.17 min).

Example 654

3,4-Dichloro-N-[4-(3-hydroxy-17-oxo-estra-1,3,5(10)-trien-15-yl)-butyl]-benzamide

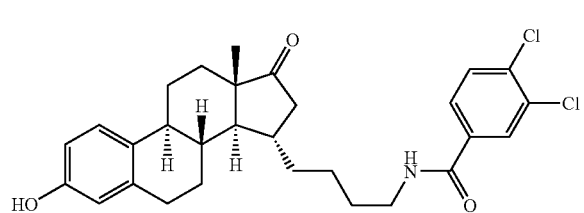

Example 654 of formula (XXXIIIα-4a)-654 was synthesized according to SCHEME 36 using XXIXα-4a as starting material (MH+ 514; Rt 6.31 min).

Example 655

2-(4-Fluoro-Phenyl)-N-[4-(3-hydroxy-17-oxo-estra-1,3,5(10)-trien-15-yl)-butyl]-acetamide

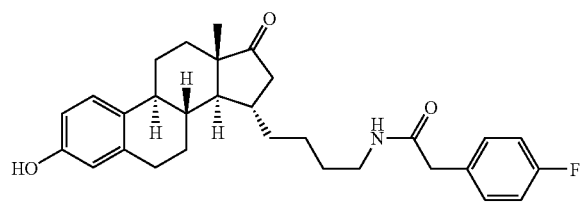

Example 655 of formula (XXXIIIα-4a)-655 was synthesized according to SCHEME 36 using XXIXα-4a as starting material (MH+ 478; Rt 5.72 min).

Example 656

4-Fluoro-N-[4-(3-hydroxy-17-oxo-estra-1,3,5(10)-trien-15-yl)-butyl]-benzamide

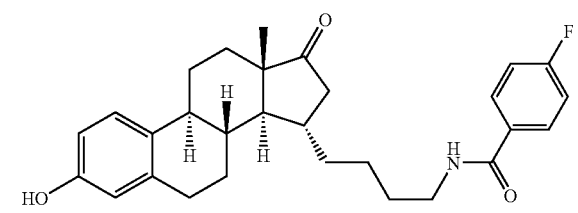

Example 656 of formula (XXXIIIα-4a)-656 was synthesized according to SCHEME 36 using XXIXα-4a as starting material (MH+ 464; Rt 5.70 min).

Example 657

2,4-Difluoro-N-[4-(3-hydroxy-17-oxo-estra-1,3,5(10)-trien-15-yl)-butyl]-benzamide

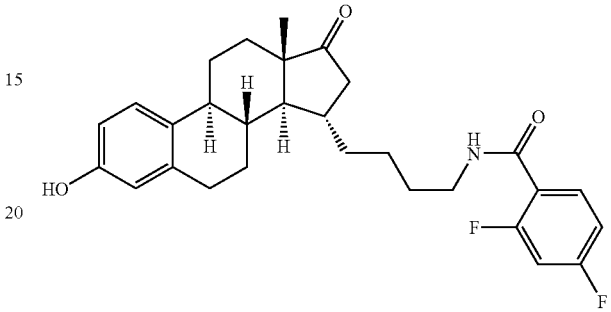

Example 657 of formula (XXXIIIα-4a)-657 was synthesized according to SCHEME 36 using XXIXα-4a as starting material (MH+ 482; Rt 5.86 min).

Example 658

N-[5-(3-Methoxy-17-oxo-estra-1,3,5(10)-trien-15-yl)-pentyl]-benzamide

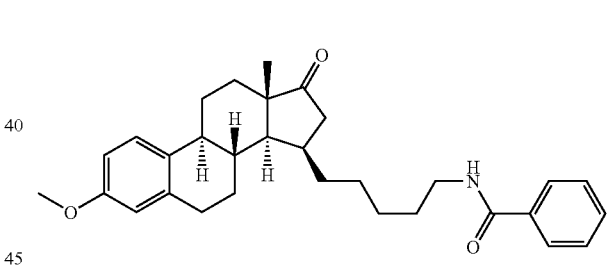

Example 658 of formula (XXXIIIβ-5b)-658 was synthesized according to SCHEME 36 using XXIXβ-5b as starting material (MH+ 474; Rt 6.80 min).

Example 659

N-[5-(3-Methoxy-17-oxo-estra-1,3,5(10)-trien-15-yl)-pentyl]-acetamide

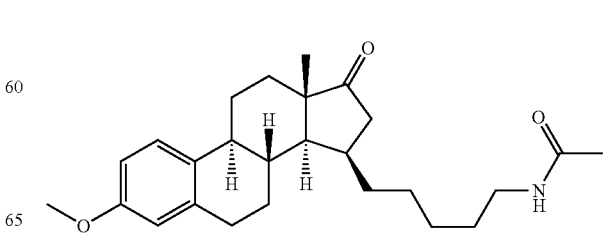

Example 659 of formula (XXXIIIβ-5b)-659 was synthesized according to SCHEME 36 using XXIXβ-5b as starting material (MH+ 412; Rt 6.90 min).

Example 660

4-Fluoro N-[5-(3-Methoxy-17-oxo-estra-1,3,5(10)-trien-15-yl)-pentyl]-benzamide

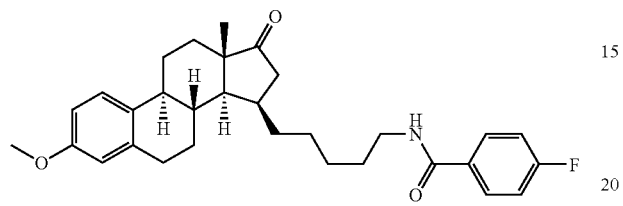

Example 660 of formula (XXXIIIβ-5b)-660 was synthesized according to SCHEME 36 using XXIXβ-5b as starting material (MH+ 492; Rt 6.68 min).

Examples 661 to 697

"Retro"-Sulfonamides

A variety of compounds of formula I, in which X represents NH or NCH$_3$, A represents SO$_2$, Y represents a bond, n represents 1, and C15 is substituted in the α position, were prepared by parallel chemistry using a reaction as shown in the following scheme 37 (according to general flow diagram Xa). Two groups of compounds according to formula XXIV-1a and XXIV-1a* were prepared by this method and are listed in tables 28 and 29 below.

SCHEME 37

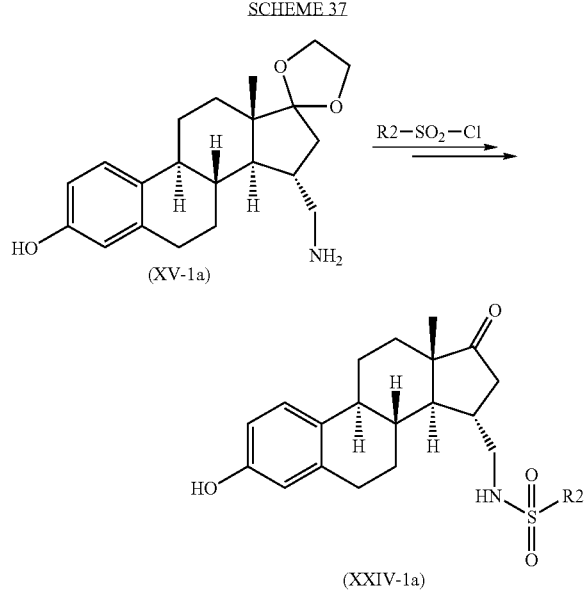

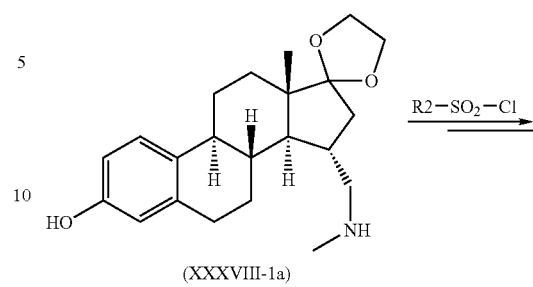

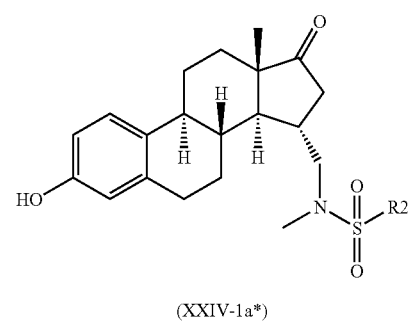

Detailed Synthesis:

Step 1: 0.062 mMol of the respective sulfonic acid chloride R2-SO$_2$—Cl were dissolved in 2 ml DCM. To this solution 2 ml of the amine building block of the formula XV1-a or XXXVIII-1a (0.056 mMol) dissolved in DCM and 100 mg morpholine polymer bound were added. The reaction mixture was stirred at RT for 24 h. To remove unreacted sulfonic acid chloride polymer bound trisamine was added. Again the reaction mixture was stirred for 24 h at RT. The solid material was removed by filtration. The solvent was evaporated in a vacuum centrifuge. Without further purification this material was used in the next step.

Step 2: The material obtained in step 1 was dissolved in 2 ml acetone acetone/methanol/water (1:10:0.1). 2 mg of p-TosOH were added. The reaction mixture was kept in a microwave oven in a sealed tube at 150° C. for 3 minutes. Thereafter the solvent was removed in a vacuum centrifuge. The obtained material was separated between EtOAc and NaHCO$_3$ solution. The organic layer was collected and evaporated again. The material thereafter was analyzed by LC-MS.

Two groups of compounds according to formula XXIV-1a and XXIV-1a* were prepared by this method (Tables 28 and 29).

TABLE 28

Compounds of the formula XXIV-1a:

(XXIV-1a)

| No. | R² | MS m/z | HPLC Rt [min] |
|---|---|---|---|
| 661 | Naphthalene-2-yl | 489.2 | 5.75 |
| 662 | Thiophene-2-yl | 445.14 | 5.28 |
| 663 | Quinolune-8-yl | 490.19 | 5.41 |
| 664 | Phenyl | 439.57 | |
| 665 | 4-Fluoro-phenyl | 457.17 | 5.45 |
| 666 | 4-(N-acetyl)-amino-phenyl | 496.2 | 4.83 |
| 667 | 4-nitro-phenyl | 484.17 | 5.5 |
| 668 | 4-methoxy-phenyl | 469.19 | 5.35 |
| 669 | Propyl | 405.2 | 5.04 |
| 670 | 3-trifluoromethyl-phenyl | 507.17 | 5.79 |
| 671 | 3,5-Bis-trifluoromethyl-phenyl | 575.16 | 6.21 |
| 672 | 2,5-dimethoxy-phenyl | 499.2 | 5.38 |
| 673 | 3,4-bichloro-phenyl | 507.1 | 5.98 |
| 674 | 4-trifluoromethoxy-phenyl | 523.16 | 5.89 |
| 675 | 2.5-Dichloro-thiophene-3-yl | 513.06 | 5.93 |
| 676 | 3-Chloro-phenyl | 473.14 | 5.67 |
| 677 | 3-methyl-phenyl | 453.2 | 5.52 |
| 678 | 3,4-dimethoxy-phenyl | 499.2 | 5.18 |
| 679 | 4-Benzenesulfonyl-thiophene-2-yl | 585.13 | 5.6 |
| 680 | 2,4-Dichloro-phenyl | 507.1 | 5.88 |

TABLE 29

Compounds of the formula XXIV-1a*:

(XXIV-1a*)

| No. | R² | MS m/z | HPLC Rt [min] |
|---|---|---|---|
| 681 | Naphthalene-2-yl | 503.21 | 6.15 |
| 682 | Thiophene-2-yl | 459.15 | 5.67 |
| 683 | Quinoline-8-yl | 504.21 | 5.63 |
| 684 | Phenyl | 453.2 | 5.7 |
| 685 | 4-Fluoro-phenyl | 471.19 | 5.8 |
| 686 | 4-(N-acetyl)-amino-phenyl | 510.22 | 5.17 |
| 687 | 4-nitro-phenyl | 498.18 | 5.84 |
| 688 | 4-methoxy-phenyl | 483.21 | 5.74 |
| 689 | 3-trifluoromethyl-phenyl | 521.18 | 6.13 |
| 690 | 2,5-dimethgoxy-phenyl | 513.22 | 5.67 |
| 691 | 4-trifluoromethoxy-phenyl | 537.18 | 6.23 |
| 692 | 2,5-Dichloro-thiophene-3-yl | 527.08 | 6.38 |
| 693 | 3-Chloro-phenyl | 487.16 | 6.06 |
| 694 | 3-methyl-phenyl | 467.21 | 5.92 |
| 695 | 3,4-dimethoxy-phenyl | 513.22 | 5.55 |

TABLE 29-continued

Compounds of the formula XXIV-1a*:

(XXIV-1a*)

| No. | R² | MS m/z | HPLC Rt [min] |
|---|---|---|---|
| 696 | 4-Benzenesulfonyl-thiophene-2-yl | 599.15 | 5.94 |
| 697 | 2,4-Dichloro-phenyl | 521.12 | 6.29 |

Examples 698 to 737

"Retro"-Sulfonamides

Further compounds of formula I, in which X represents NH, A represents SO₂, Y represents a bond, n represents 3 or 4, and C15 is substituted in the β position, were prepared by parallel chemistry using a reaction as shown in the following schemes 38A and 38B (according to general flow diagram Xb):

SCHEME 38A

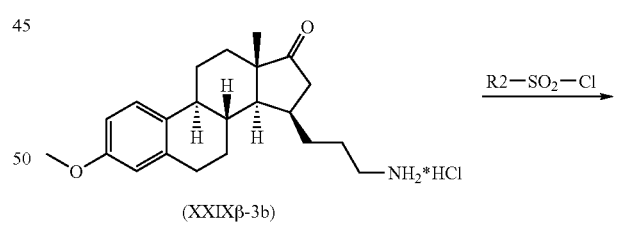

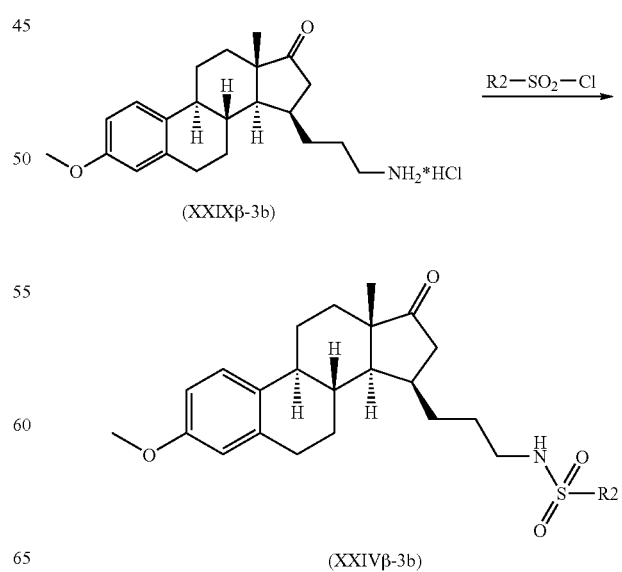

(XXIVβ-3b)

SCHEME 38B

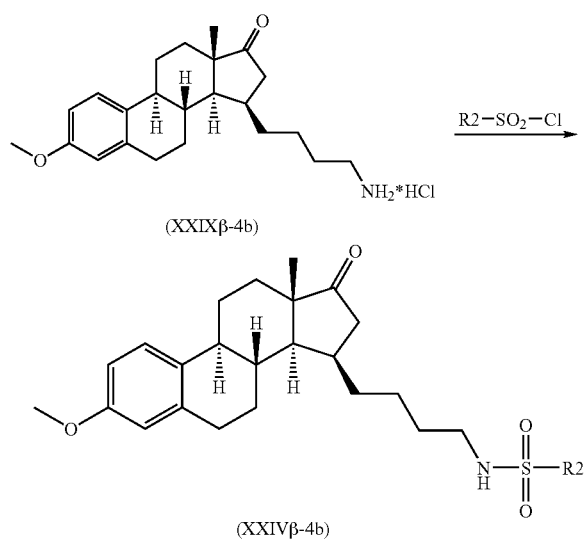

Detailed Synthesis 0.062 mMole of the respective sulfonic acid chloride R2-SO$_2$—Cl were dissolved in 2 ml DCM. To this solution 2 ml of the amine building block of the formula XXIXβ-3b or XXIXβ-4b (0.056 mMol) dissolved in DCM and 100 mg morpholine polymer bound were added. The reaction mixture was stirred at RT for 24 h. To remove unreacted sulfonic acid chloride polymer bound trisamine was added. Again the reaction mixture was stirred for 24 h at RT. The solid material was removed by filtration. After solvent removal under reduced pressure the samples were analyzed by LC-MS.

Two groups of compounds according to formula XXIVβ-3b and XXIVβ-4b were prepared by this method (Tables 30 and 31).

TABLE 30

Compounds of the formula XXIVβ-3b:

(XXIVβ-3b)

| No. | R² | MS m/z | HPLC Rt [min] |
|---|---|---|---|
| 698 | Naphthalene-2-yl | 531.24 | 4.81 |
| 699 | Thiophene-2-yl | 487.19 | 4.47 |
| 700 | Quinoline-8-yl | 532.24 | 4.6 |
| 701 | Phenyl | 481.23 | 4.53 |
| 702 | 4-Fluoro-phenyl | 499.22 | 4.56 |
| 703 | 4-(N-acetyl)-amino-phenyl | 538.25 | 4.07 |
| 704 | 4-nitro-phenyl | 526.21 | 4.54 |
| 705 | 4-methoxy-phenyl | 511.24 | 4.51 |
| 706 | Benzyl | 495.24 | 4.51 |
| 707 | Propyl | 447.24 | 4.34 |
| 708 | 3-trifluoromethyl-phenyl | 549.22 | 4.81 |
| 709 | 3,5-Bis-trifluoromethyl-phenyl | 617.2 | 5.08 |
| 710 | 2,5-dimethoxy-phenyl | 541.25 | 4.57 |
| 711 | 3,4-Dichloro-phenyl | 549.15 | 4.99 |
| 712 | 4-trifluoromethoxy-phenyl | 565.21 | 4.86 |
| 713 | 2,5-Dichloro-thiophene-3-yl | 555.11 | 5.04 |
| 714 | 3-Chloro-phenyl | 515.19 | 4.77 |
| 715 | 3-methyl-phenyl | 495.24 | 4.67 |
| 716 | 3,4-dimethoxy-phenyl | 541.25 | 4.37 |
| 717 | 4-Benzenesulfonyl-thiophene-2-yl | 627.18 | 4.59 |
| 718 | 2,4-Dichloro-phenyl | 549.15 | 4.94 |

TABLE 31

Compounds of the formula XXIVβ-4b:

(XXIVβ-4b)

| No. | R² | MS m/z | HPLC Rt [min] |
|---|---|---|---|
| 719 | Naphthalene-2-yl | 545.26 | 4.98 |
| 720 | Thiophene-2-yl | 501.2 | 4.65 |
| 721 | Quinoline-8-yl | 546.26 | 4.78 |
| 722 | Phenyl | 495.24 | 4.7 |
| 723 | 4-Fluoro-phenyl | 513.23 | 4.74 |
| 724 | 4-(N-ocetyl)-amino-phenyl | 552.27 | 4.24 |
| 725 | 4-nitro-phenyl | 540.23 | 4.71 |
| 726 | 4-methoxy-phenyl | 525.25 | 4.69 |
| 727 | 3-trifluoromethyl-phenyl | 563.23 | 4.97 |
| 728 | 3,5-Bis-trifluoromethyl-phenyl | 631.22 | 5.23 |
| 729 | 2,5-dimethoxy-phenyl | 555.27 | 4.72 |
| 730 | 3,4-Dichloro-phenyl | 563.17 | 5.19 |
| 731 | 4-trifluoromethoxy-phenyl | 579.23 | 5.03 |
| 732 | 2,5-Dichloro-thiophene-3-yl | 569.12 | 5.23 |
| 733 | 3-Chloro-phenyl | 529.21 | 4.95 |
| 734 | 3-methyl-phenyl | 509.26 | 4.85 |
| 735 | 3,4-dimethoxy-phenyl | 555.27 | 4.54 |
| 736 | 4-Benzenesulfonyl-thiophene-2-yl | 641.19 | 4.74 |
| 737 | 2,4-Dichloro-phenyl | 563.17 | 5.14 |

Examples 738 and 739

"Retro"-Sulfonamides

Further two compounds of formula I, in which X represents NH or NCH$_3$, A represents SO$_2$, Y represents a bond, n represents 3 or 5, and C15 is substituted in the β position, were individually synthesized according to the reaction as shown in schemes 38A and 38B (according to general flow diagram Xb), using the respective amine building blocks as starting material.

Example 738

N-[3-(3-Methoxy-17-oxo-estra-1,3,5(10)-trien-15-yl)-propyl]-4-methyl-benzenesulfonamide

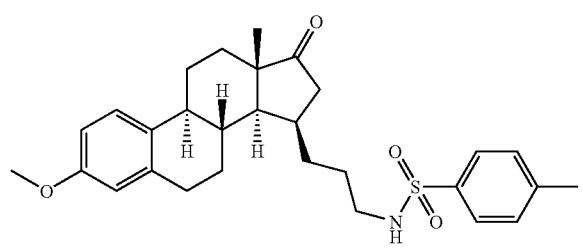

Example 738 of formula (XXIVβ-3b)-738 was synthesized according to SCHEME 38A using XXIXβ-3b as starting material (MH+ 496; Rt 6.85 min).

Example 739

N-[3-(3-Methoxy-17-oxo-estra-1,3,5(10)-trien-15-yl)-pentyl]-4-methyl-benzenesulfonamide

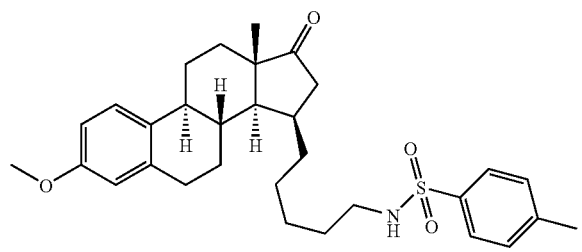

Example 739 of formula (XXIVβ-5b)-739 was synthesized according to SCHEME 38B using XXIXβ-5b as starting material (MH+ 524; Rt 6.91 min).

Examples 740 to 743

Sulfonylurea Derivatives

A variety of compounds of formula I, in which X represents NH, A represents CO, Y represents NH—SO$_2$— and n represents, for example, 2, and C15 is substituted in the α position, may be prepared by parallel chemistry using a reaction as shown in the following scheme 39 (according to general flow diagram XI):

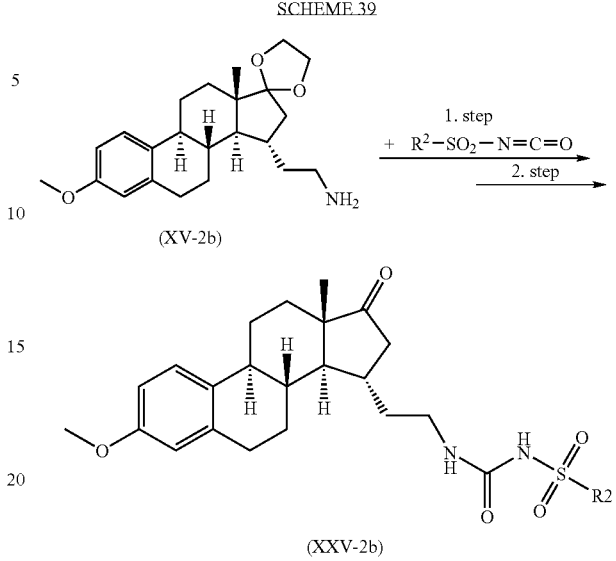

SCHEME 39

Detailed Synthesis

Step 1: 0.224 mMol of the appropriate sulfonylisocyanate are dissolved in 2 ml THF. To this solution 2 ml of the amine building block of the formula XV-b (0.112 mMol) dissolved in THF are added. The reaction mixture was stirred at 60° C. for 5 h. To remove unreacted sulfonylisocyanate polymer bound trisamine is added. The reaction mixture is stirred further for 24 h at RT. The solid material is removed by filtration. The solvent is evaporated in a vacuum centrifuge. Without further purification this material is used in the next step.

Step 2: The material obtained in step 1 is dissolved in 2 ml acetone. 2 mg of p-tosOH are added. The reaction mixture is kept in a microwave oven in a sealed tube at 150° C. for 3 minutes. Thereafter the solvent is removed in a vacuum centrifuge. The obtained material is separated between EtOAc and NaHCO$_3$ solution. The organic layer is collected and evaporated again. The material thereafter is analyzed by LC-MS.

A group of compounds according to formula XXV-2b may be prepared by this method; the compounds represent reaction products of a compound of formula XV-2b with a sulfonylisocyanate (R$^2$—SO$_2$—N=C=O). Table 17 shows the number of the reaction products together with the corresponding sulfonylisocyanate (R$^2$—SO$_2$—N=C=O).

TABLE 32

Compounds of the formula XXV-2b, which may be prepared by reaction with variable sulfonylisocyanate (R$^2$—SO$_2$—N=C=O) compounds:

| No. | Reactant R$^2$—SO$_2$—N=C=O |
|-----|------------------------------|
| 740 | BENZOLSULFONYLISOCYANATE |
| 741 | 4-CHLORBENZOLSULFONYL ISOCYANATE |
| 742 | 4-TOLUOLSULFONYLISOCYANATE |
| 743 | O-TOLUOLSULFONYLISOCYANATE |

Examples 744 to 773

"Retro"-Carbamate

A variety of formula I compounds, in which X represents O, A represents CO, Y represents NH, R¹ represents CH₃, n is 3, 4, 5 or 6, and C15 is substituted in the β position, were prepared by parallel chemistry using a reaction as shown in the following schemes 40 (according to general flow diagram XII):

SCHEME 40

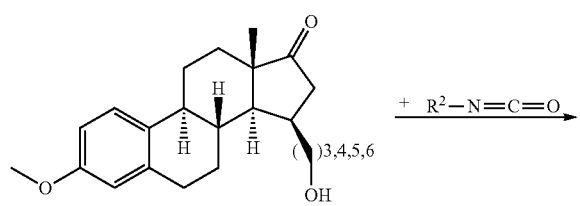

(XXXIβ-3b)
(XXXIβ-4b)
(XXXIβ-5b)
(XXXIβ-6b)

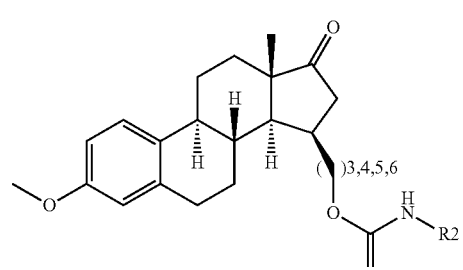

(XXVIβ-3b)
(XXVIβ-4b)
(XXVIβ-5b)
(XXVIβ-6b)

Detailed Synthesis

0/06 mmol of the estrone-alcohol XXXI were dissolved in 5 ml acetonitrile. To this solution 0.072 mmol of the respective isocyanate were added. The whole reaction mixture was stirred for 24 h at RT. The excess of isocyanate was scavenged thereafter by adding polymer bound trisaminoethylamine (approx. 20 mg) and stirring for additional 4 h. The suspension was filtered. The solid residue washed twice with 0.5 ml acetonitrile. The filtrated was evaporated under reduced pressure in a vacuum centrifuge. Control with LC-MS showed that further purification was needed, therefore, polymer bound isocyanate was added to scavenge remaining estron-alcohol in the same way as mentioned above. In case further purification was necessary either flash chromatography was used or preparative HPLC.

The following groups of compounds were prepared by this method (table 33 for n=3, table 34 for n=4, table 35 for n=5 and table 36 for n=3):

TABLE 33

Compounds of the formula XXVIβ-3b:

(XXVIβ-3b)

| No. | R² | MS m/z | HPLC Rt [min] |
|---|---|---|---|
| 744 | 2,4-Dichloro-phenyl | 529 | 5.52 |
| 745 | 4-Trifluoromethyl-phenyl | 529 | 5.18 |
| 746 | 2-benzoic acid methyl ester | 519 | 5.48 |
| 747 | 3-Cyano-phenyl | 486 | 4.74 |
| 748 | Benzo[1,3]dioxol-5-yl- | 505 | 4.68 |
| 749 | 3,4-Dichloro-phenyl | 529 | 5.4 |

TABLE 34

Compounds of the formula XXV1β-4b:

(XXVIβ-4b)

| No. | R² | MS m/z | HPLC Rt [min] |
|---|---|---|---|
| 750 | 2,4-Dichloro-phenyl | 543 | 5.76 |
| 751 | 3-Fluoro-phenyl | 493 | 5.1 |
| 752 | 4-benzoic acid ethyl ester | 547 | 5.19 |
| 753 | 4-Trifluoromethyl-phenyl | 543 | 5.34 |
| 754 | 3-Nitro-phenyl | 520 | 5.02 |
| 755 | 2-benzoic acid methyl ester | 533 | 5.67 |
| 756 | 3-Cyano-phenyl | 500 | 4.91 |
| 757 | 3,4-Dichloro-benzyl | 557 | 5.29 |
| 758 | 3,4-Dichloro-phenyl | 543 | 5.58 |

TABLE 35

Compounds of the formula XXVIβ3-5b:

(XXVIβ-5b)

| No. | R² | MS m/z | HPLC Rt [min] |
|---|---|---|---|
| 759 | 2,4-Dichloro-phenyl | 557 | 5.99 |
| 760 | Naphthalen-1-yl | 539 | 5.35 |

TABLE 35-continued

Compounds of the formula XXVIβ3-5b:

(XXVIβ-5b)

| No. | R² | MS m/z | HPLC Rt [min] |
|---|---|---|---|
| 761 | 3-Nitro-phenyl | 534 | 5.21 |
| 762 | 2-benzoic acid methyl ester | 547 | 5.91 |
| 763 | 3-Cyano-phenyl | 514 | 5.1 |
| 764 | 3,4-Dichloro-benzyl | 571 | 5.48 |
| 765 | 3,4-Dichloro-phenyl | 557 | 5.76 |

TABLE 36

Compounds of the formula XXVIβ-6b:

(XXVIβ-6b)

| No. | R² | MS m/z | HPLC Rt [min] |
|---|---|---|---|
| 766 | 2,4-Dichloro-phenyl | 571 | 5.7 |
| 767 | 4-benzoic acid ethyl ester | 553 | 5.56 |
| 768 | 4-Trifluoromethyl-phenyl | 548 | 5.39 |
| 769 | Naphthalen-1-yl | 561 | 6.12 |
| 770 | 3-Nitro-phenyl | 528 | 5.29 |
| 771 | 2-benzoic acid methyl ester | 571 | 5.96 |
| 772 | 3-Cyano-phenyl | 571 | 5.7 |
| 773 | 3,4-Dichloro-phenyl | 553 | 5.56 |

Examples 774 and 775

"Retro"-Ester

Two formula I compounds, in which X represents O, A represents CO, Y represents a bond, R¹ represents CH₃, n is 4 or 5, and C15 is substituted in the β position, were individually prepared by a reaction as shown in the following scheme 41 (according to general flow diagram XIII):

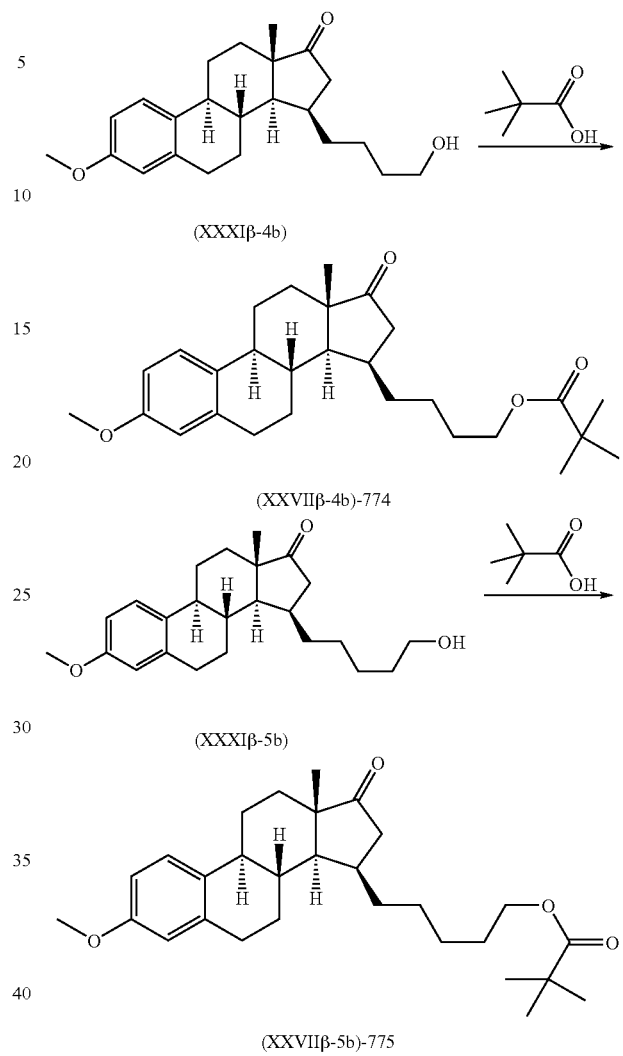

SCHEME 41

(XXXIβ-4b)

(XXVIIβ-4b)-774

(XXXIβ-5b)

(XXVIIβ-5b)-775

Detailed Synthesis

No. 774: 2,2-Dimethyl-propionic Acid 4-(3-methoxy-17-oxo-estra-1,3,5(10)-trien-15-yl)-butyl Ester 124.6 mg (0.35 mmol) Estron-alcohol XXXIβ-4b, 71.4 (0.4 mmol) pivalic acid, 0.7 mmol 4-dimethylaminopyridin (DMAP), and 0.7 mmol EDCI were dissolved in 50 ml dry dichloromethane and stirred for 20 h at RT. TLC control showed complete conversion. For workup, the mixture was extracted twice with 20 ml 1 M KHSO₄ solution and 20 ml 1 M NaHCO₃ solution. After evaporation the residue was further purified by flash chromatography on silica gel 60 with cyclohexane/ethylacetate (ratio 99/1 to 90/10). 184 mg oil was obtained which crystallized over night in ether; the crystals were filtered and dried yielding 87 mg pure material (XXVIIβ-4b)-774.

Mp: 75-84° C.
LC-MS: MH+ 441, Rt 7.85 min

No. 775: 2,2-Dimethyl-propionic Acid 5-(3-methoxy-17-oxo-estra-1,3,5(10)-trien-15-yl)-pentyl Ester Compound (XXVIIβ-5b)-775 was prepared accordingly, using estron-alcohol XXXIβ-5b as starting material.
LC-MS: MH+ 455, Rt 8.07 min

Examples 776 to 819

Sulfonylcarbamate

A variety of formula I compounds, in which X represents O, A represents CO, Y represents NH—SO$_2$—NR$^4$, R$^1$ represents CH$_3$, n is 3, 4, 5 or 6, and C15 is substituted in the β position, were prepared by parallel chemistry using a reaction as shown in the following scheme 42 (according to general flow diagram XIV):

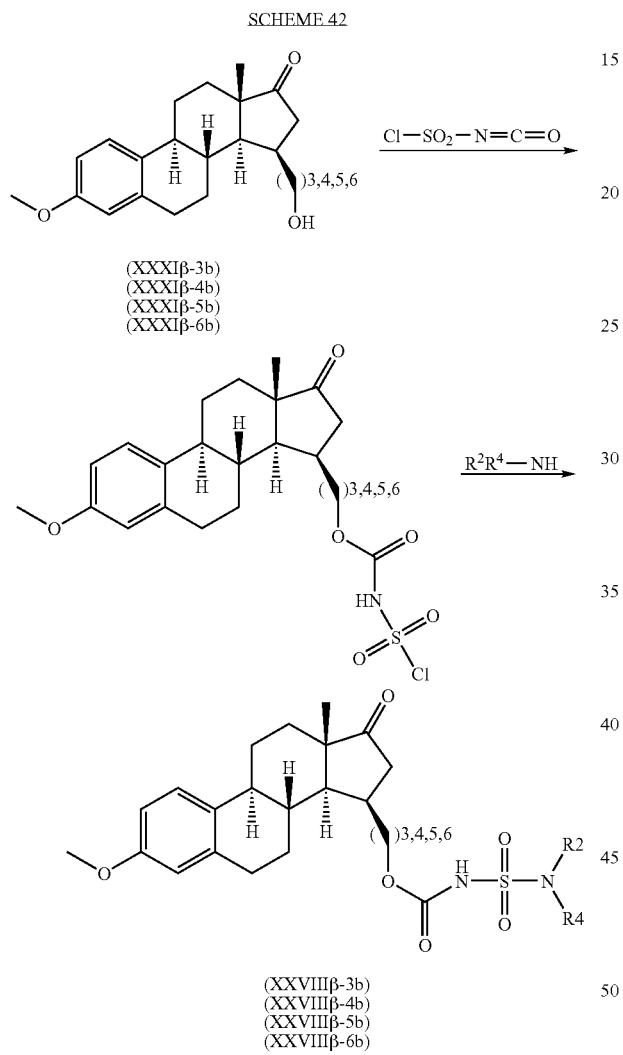

(XXXIβ-3b)
(XXXIβ-4b)
(XXXIβ-5b)
(XXXIβ-6b)

(XXVIIIβ-3b)
(XXVIIIβ-4b)
(XXVIIIβ-5b)
(XXVIIIβ-6b)

Detailed Synthesis

The estrone-alcohol XXXI (0.055 mmol) dissolved in 1 ml DCM was added drop wise to a cold solution of 1.1 eq. chlorosulfonyl isocyanate (CSI) in 0.5 ml DCM. The mixture was left for 30 min at RT. Then 1.2 eq. of DIPEA and 1.1 eq amine were added and the solution was stirred over night. If desired a TLC (silica gel 60; eluent: 80 toluene/20 ethanol/1 ammonia) can be used to control the reaction. Work up of the reaction mixture was done by extraction with 1 M citric acid. After evaporation a solid material was obtained, which was subject for further purification by flash chromatography. This procedure was used for single compound synthesis as well as for library production.

The following groups of compounds were prepared by this method (table 37 for n=5 (single compound synthesis), table 38 for n=3, table 39 for n=4, table 40 for n=5 and table 41 for n=6, all library production):

TABLE 37

Compounds of the formula XXVIIIβ-5b, which were prepared individually:

(XXVIIIβ-5b)

| No. | R$^2$ / R$^4$ | | MS m/z | HPLC Rt [min] |
|---|---|---|---|---|
| 776 | benzyl | H | 583 | 4.79 |
| 777 | phenyl | H | 569 | 4.43 |
| 778 | morpholine-4-yl | | 563 | 4.45 |
| 779 | butyl | H | 549 | 4.87 |
| 780 | methyl | butyl | 563 | 5.2 |
| 781 | methyl | benzyl | 597 | 5.08 |
| 782 | 2-(1H-Indol-3-yl)-ethyl | H | 636 | 4.78 |
| 783 | 4-methyl-piperazine-1-yl | | 576 | 3.82 |
| 784 | cyclohexyl | H | 575 | 5.01 |

Besides the products, two by-products could be isolated by flash chromatography showing the following structures, most likely obtained due to water contamination of the reaction mixtures.

Example 785

Carbamic Acid 5-(3-methoxy-17-oxo-estra-1,3,5 (10)-trien-15-yl)-pentyl Ester (XXVIβ-5b)-785

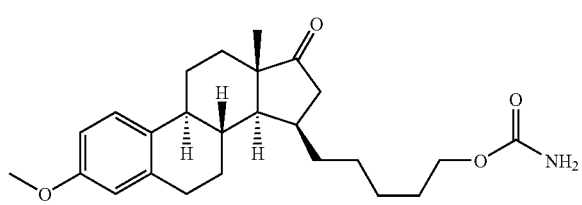

(XXVIβ-5b)-785

LC-MS rt: 4.53 min, MH+ 414

Example 786

Sulfamic Acid 5-(3-methoxy-17-oxo-estra-1,3,5(10)-trien-15-yl)-pentyl Ester (786)

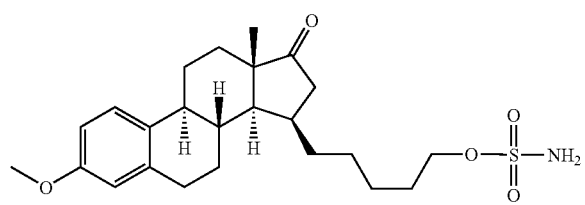

No. 786

LC-MS rt: 4.37 min, MH+ 450

TABLE 38

Compounds of the formula XXVIIIβ-3b, which were prepared by library synthesis:

(XXVIIIβ-3b)

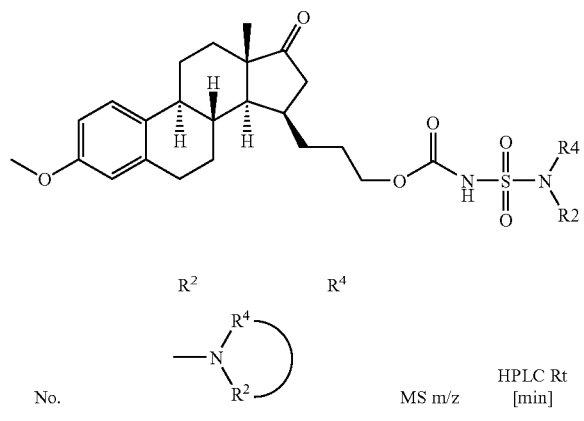

| No. | R² | R⁴ | MS m/z | HPLC Rt [min] |
|---|---|---|---|---|
| 787 | pheneyl | H | 540 | 4.07 |
| 788 | 4-methyl-piperazine-1-yl | | 547 | 3.44 |
| 789 | benzyl | H | 554 | 4.34 |
| 790 | 2-(1H-indol-3-yl)-ethyl | H | 607 | 4.36 |
| 791 | butyl | H | 520 | 4.41 |
| 792 | cyclohexyl | H | 546 | 4.59 |
| 793 | methyl | butyl | 534 | 4.76 |
| 794 | methyl | benzyl | 568 | 4.67 |
| 795 | morphaline-4-yl | | 534 | 3.96 |

TABLE 39

Compounds of the formula XXVIIIβ-4b, which were prepared by library synthesis:

(XXVIIIβ-4b)

| No. | R² | R⁴ | MS m/z | HPLC Rt [min] |
|---|---|---|---|---|
| 796 | pheneyl | H | 554 | 4.2 |
| 797 | 4-methyl-piperazine-1-yl | | 561 | 3.57 |
| 798 | benzyl | H | 568 | 4.5 |
| 799 | 2-(1H-indol-3-yl)-ethyl | H | 621 | 4.5 |
| 800 | butyl | H | 534 | 4.57 |
| 801 | cyclohexyl | H | 560 | 4.75 |
| 802 | methyl | benzyl | 582 | 4.84 |
| 803 | methyl | butyl | 548 | 4.94 |
| 804 | morpholine-4-yl | | 548 | 4.12 |

TABLE 40

Compounds of the formula XXVIIIβ-5b, which were prepared by library synthesis:

(XXVIIIβ-5b)

| No. | R² | R⁴ | MS m/z | HPLC Rt [min] |
|---|---|---|---|---|
| 805 | benzyl | H | 582 | 4.64 |
| 806 | 2-(1H-indol-3-1)-ethyl | H | 635 | 4.63 |
| 807 | 4-methyl-piperazine-1-yl | | 575 | 3.72 |
| 808 | butyl | H | 548 | 4.74 |
| 809 | cyclohexyl | H | 574 | 4.89 |
| 810 | phenyl | H | 568 | 4.31 |
| 811 | methyl | butyl | 562 | 5.09 |
| 812 | morpholine-4-yl | | 562 | 4.26 |

TABLE 41

Compounds of the formula XXVIIIβ-6b, which were prepared by library synthesis:

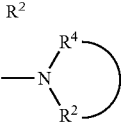

(XXVIIIβ-6b)

| No. | R² | R⁴ | MS m/z | HPLC Rt [min] |
|---|---|---|---|---|
| 813 | benzyl | H | 596 | 4.81 |
| 814 | 4-methyl-piperazine-1-yl |  | 589 | 3.88 |
| 815 | cyclohexyl | H | 588 | 5.09 |
| 816 | methyl | benzyl | 610 | 5.17 |
| 817 | butyl | H | 562 | 4.9 |
| 818 | phenyl | H | 582 | 4.46 |
| 819 | 2-(1H-indol-3-yl)-ethyl | H | 649 | 4.8 |

Examples 820 to 834

Alcohols

The synthesis of the following estrone-alcohol derivatives of general formula XXXI, which also show 17β-HSD1 inhibitory properties, is described in the section "Intermediates, Chapter IV".

Example 820

15α-Hydroxymethyl-3-hydroxy-estra-1,3,5(10)-trien-17-one (XXXIα-1a)

Example 821

15α-Hydroxymethyl-3-methoxy-estra-1,3,5(10)-trien-17-one (XXXIα-1b)

Example 822

3-Benzyloxy-15α-hydroxymethyl-estra-1,3,5(10)-trien-17-one (XXXIα-1c)

Example 823

3-Hydroxy-15β-(3-Hydroxypropyl)-estra-1,3,5(10)-trien-17-one (XXXIβ-3a)

Example 824

15β-(3-Hydroxypropyl)-3-methoxyestra-1,3,5(10)-trien-17-one (XXXIβ-3b)

Example 825

3-Benzyloxy-15β-(3-hydroxypropyl)-estra-1,3,5(10)-trien-17-one (XXXIβ-3c)

Example 826

3-Hydroxy-15β-(4-hydroxybutyl)-estra-1,3,5(10)-trien-17-one (XXXIβ-4a)

Example 827

15β-(4-Hydroxybutyl)-3-methoxy-estra-1,3,5(10)-trien-17-one (XXXIβ-4b)

Example 828

3-Benzyloxy-15β-(4-hydroxybutyl)-estra-1,3,5(10)-trien-17-one (XXXIβ-4c)

Example 829

3-Hydroxy-15β-(5-Hydroxypentyl)-estra-1,3,5(10)-trien-17-one (XXXIβ-5a)

Example 830

15β-(5-Hydroxypentyl)-3-methoxy-estra-1,3,5(10)-trien-17-one (XXXIβ-5b)

Example 831

3-Benzyloxy-15β-(5-hydroxypentyl)-estra-1,3,5(10)-trien-17-one (XXXIβ-5c)

Example 832

3-Hydroxy-15β-(6-hydroxyhexyl)-3-estra-1,3,5(10)-trien-17-one (XXXIβ-6a)

Example 833

15β-(6-Hydroxyhexyl)-3-methoxy-estra-1,3,5(10)-trien-17-one (XXXIβ-6b)

Example 834

3-Benzyloxy-15β-(6-hydroxyhexyl)-estra-1,3,5(10)-trien-17-one (XXXIβ-6c)

Examples 835 and 836

Ether Derivatives

Two compounds of formula I, in which X-A-Y represents O, $R^1$ represents $CH_3$, n is 3 or 4, and C15 is substituted in the β position, were individually prepared according to general flow diagram XV.

Example 835

3-Methoxy-15β-(3-methoxypropyl)-estra-1,3,5(10)-trien-17-one (XXXβ-3b)-835

Compound (XXXβ-3b)-835 was prepared as depicted in the following scheme 43

SCHEME 43

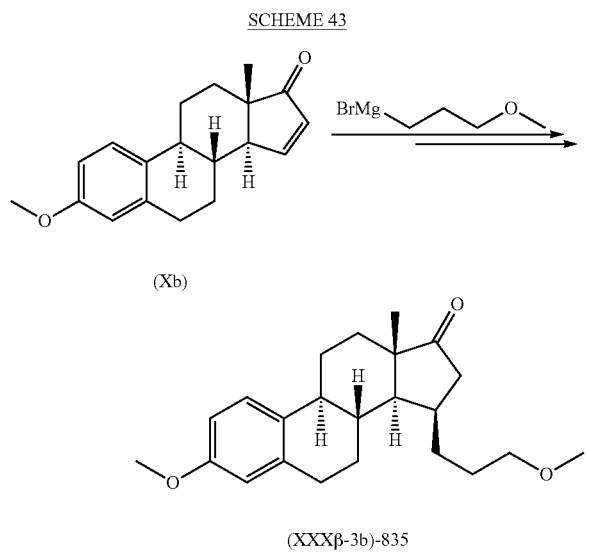

(Xb)

(XXXβ-3b)-835

Detailed Synthesis

According to the general procedure described for SCHEME 11, the copper reagent was prepared from magnesium (0.252 g, 10.50 mmol), 1-bromo-3methoxypropane (0.813 g, 5.31 mmol), CuI (0.200 mg, 1.05 mmol) and DMPU (0.53 mL, 4.40 mmol) in THF. A mixture of the 15,16-unsaturated estron Xb (0.500 mg, 1.77 mmol) and TMSCl (0.56 mL, 4.38 mmol) in THF was added dropwise. The reaction mixture was allowed to reach RT and was stirred over night. After work-up and hydrolysis, compound (XXXβ-3 b)-835 (0.605 g, 96%) was obtained (purity by HPLC>99%).

LC-MS (ES+): rt 6.8 min, m/z (rel. Intens) 374 [(M+NH$_4$)$^+$, 100%]

Example 836

3-Methoxy-15β-(4-phenoxybutyl)-estra-1,3,5(10)-trien-17-one (XXXβ-4b)-836

Compound (XXXβ-4b)-836 was prepared as depicted in the following scheme 44

SCHEME 44

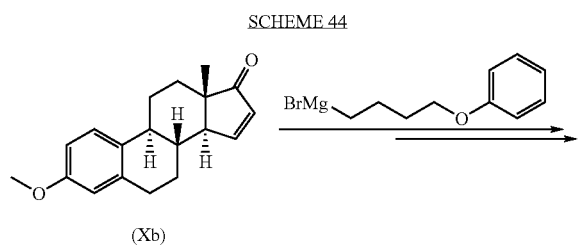

(Xb)

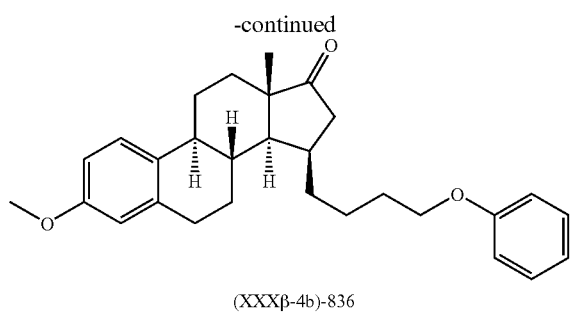

(XXXβ-4b)-836

Detailed Synthesis

According to the general procedure described for SCHEME 11, the copper reagent was prepared from magnesium (0.212 g, 8.72 mmol), 3-phenoxybutylbromid (0.917 g, 4.00 mmol), CuI (0.133 mg, 0.70 mmol) and DMPU (0.45 mL, 3.73 mmol) in THF. A mixture of the 15,16-unsaturated estron Xb (0.282 mg, 1.00 mmol) and TMSCl (0.32 mL, 2.5 mmol) in THF was added dropwise. The reaction mixture was allowed to reach RT and was stirred over night. After work-up and hydrolysis of the silyl ether the crude product was purified by column chromatography (SiO$_2$, cyclohexane/ethyl acetate 10:1) to yield (XXXβ-4b)-836 (0.240 g, 55%).

LC-MS (ES+): rt 7.77 min, m/z (rel Intens) 450 [(M+NH$_4$)$^+$, 100%]

Biological Testing Materials and Methods

1. Inhibition of the 17β-hydroxysteroid Dehydrogenase Type 1 Enzyme

17β-HSD1 Purification: Recombinant baculovirus was generated by the "Bac to Bac Expression System" (Invitrogen). Recombinant bacmid was transfected to Sf9 insect cells using "Cellfectin Reagent" (Invitrogen). 60 h later cells were harvested; the microsomal fraction was isolated as described by Puranen et al. 1994. Aliquots were stored frozen until determination of enzymatic activity.

Assay—Inhibition of Recombinant Human 17β-hydroxysteroid Dehydrogenase Type 1:

Recombinant protein (0.1 µg/ml) was incubated in 20 mM KH$_2$PO$_4$ pH 7.4 with 30 nM 3H-estrone and 1 mM NADPH for 30 min at RT, in the presence of potential inhibitors at concentrations of 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min of acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(cpm \text{ estradiol in sample with inhibitor})/[(cpm \text{ estrone in sample with inhibitor}) + (cpm \text{ estradiol in sample with inhibitor})]\}}{\{(cpm \text{ estradiol in sample without inhibitor})/[(cpm \text{ estrone in sample without inhibitor}) + (cpm \text{ estradiol in sample without inhibitor})]\}}.$$

Percent inhibition was calculated as follows: % inhibition=100−% conversion

The values "% inhibition" were determined for exemplified compounds, and the results are summarized in Table 42.

TABLE 42

| | Inhibition of 17β-HSD enzyme type I | | |
|---|---|---|---|
| Compound | | Inhibition of rec. 17β-HSD1 | |
| No. | Compound Structure | 100 nM | 1 μm |
| 1 | | 49.9 | 80.2 |
| 3A | | 51.6 | 84.1 |
| 3B | | 77.4 | 82.1 |
| 4A | | 47.1 | 66.0 |
| 4B | | 30.5 | 60.8 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 7 | 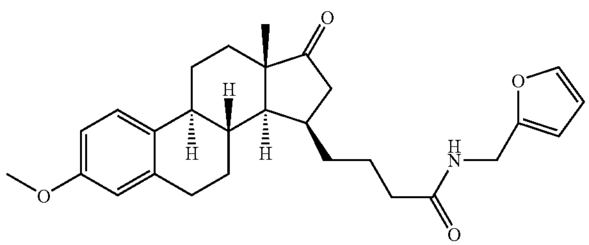 | 28.7 | 63.4 |
| 22 | 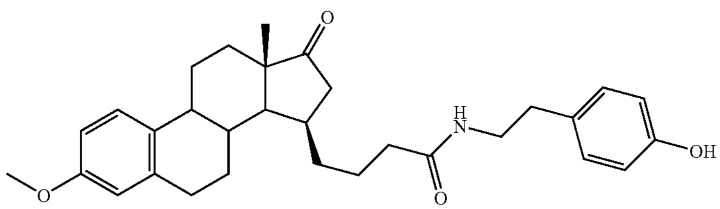 | 27.3 | 57.8 |
| 29 | 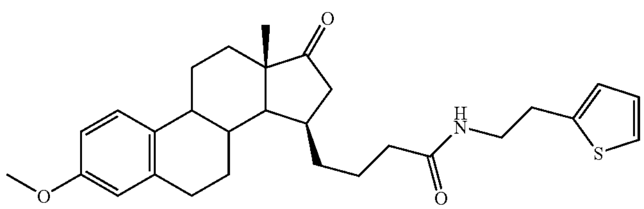 | 29.6 | 69.3 |
| 31 | 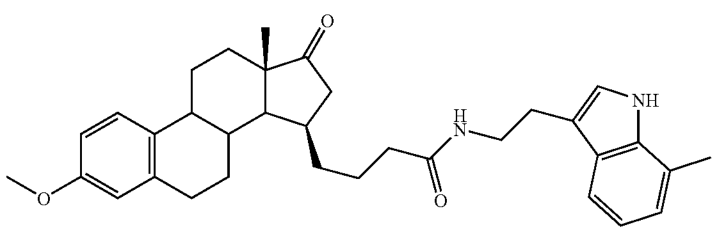 | 52.8 | 77.9 |
| 36 | 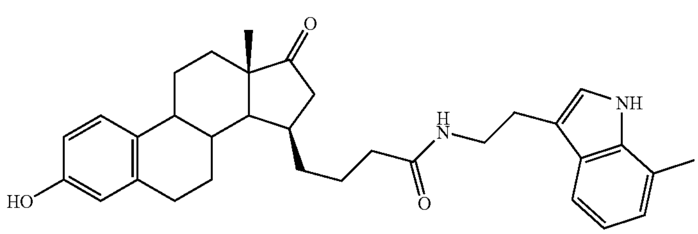 | 72.9 | 94.3 |
| 37 | 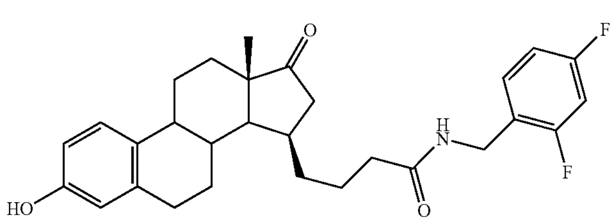 | 47.4 | 87.2 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 38 | 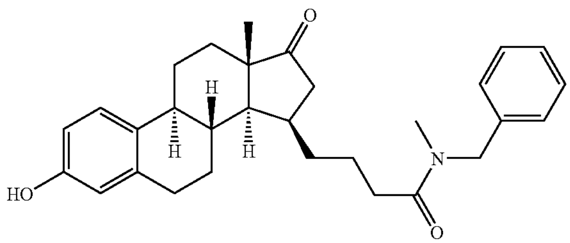 | 60.5 | 89.5 |
| 39 | 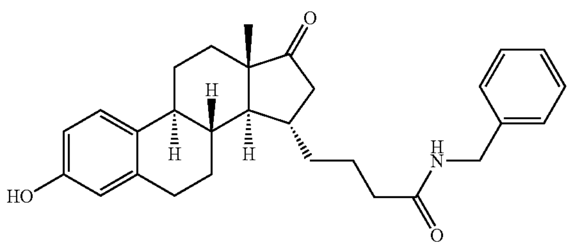 | 41.8 | 82.4 |
| 40 | 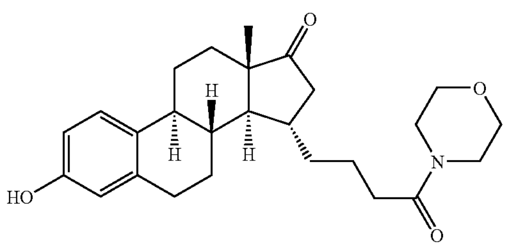 | 32.3 | 79.4 |
| 58 | 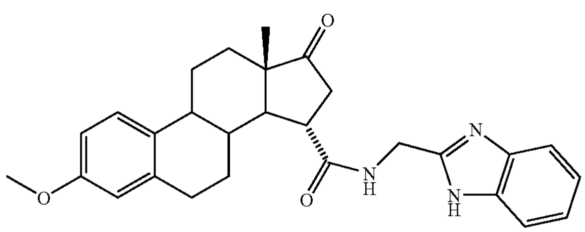 | 25.0 | 65.3 |
| 105 | 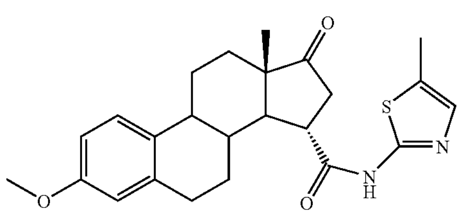 | 33.8 | 81.0 |
| 152 | 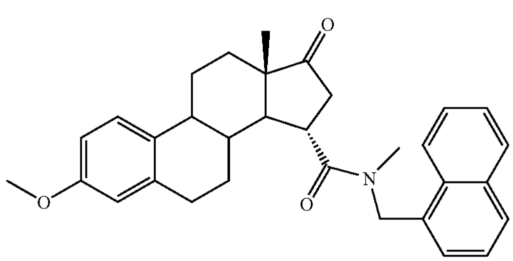 | 25.6 | 41.4 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 310 | 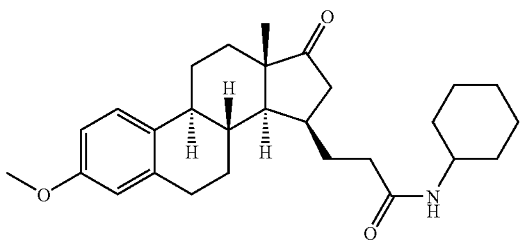 | 67.9 | 91.7 |
| 311 | 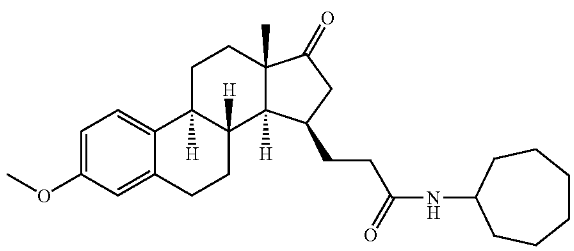 | 84.9 | 95.4 |
| 313 | 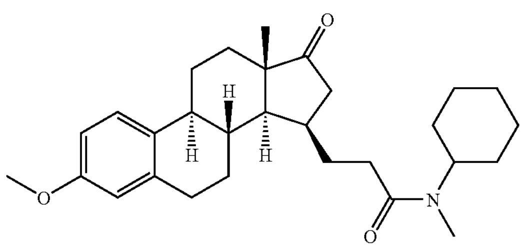 | 62.6 | 93.0 |
| 314 | 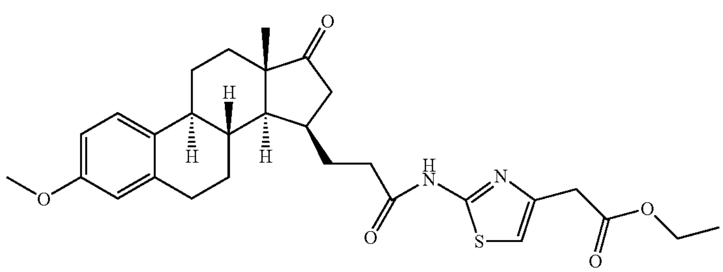 | 33.6 | 62.1 |
| 315 | 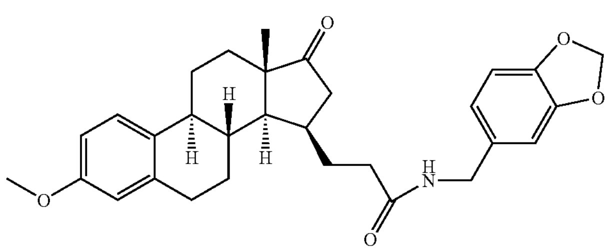 | 29.0 | 74.4 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 316 | | 25.3 | 74.5 |
| 322 | | 45.7 | 66.3 |
| 323 | | 28.5 | 72.7 |
| 324 | | 57.9 | 91.5 |
| 327 | | 28.7 | 77.0 |
| 329 | | 78.9 | 96.2 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 330 | | 25.2 | 75.9 |
| 331 | | 37.0 | 88.0 |
| 332 | | 42.2 | 85.4 |
| 333 | | 47.9 | 91.0 |
| 335 | | 59.0 | 90.5 |
| 338 | | 28.7 | 84.6 |

TABLE 42-continued
Inhibition of 17β-HSD enzyme type I
| Compound No. | Compound Structure | Inhibition of rec. 17β-HSD1 | |
|---|---|---|---|
| | | 100 nM | 1 μm |
| 339 | 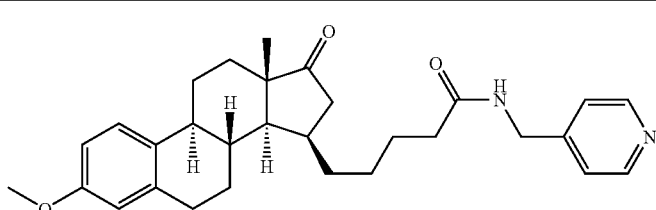 | 25.9 | 82.9 |
| 340 | 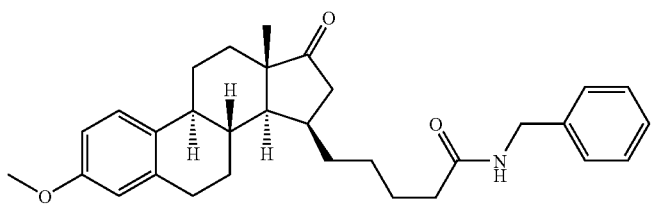 | 51.4 | 91.9 |
| 341 | 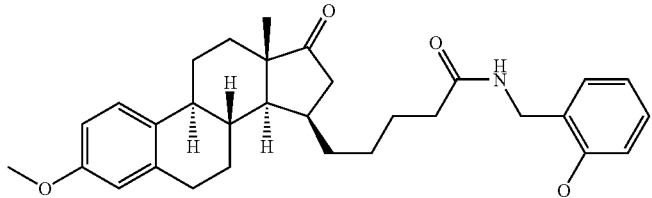 | 38.1 | 88.0 |
| 342 | 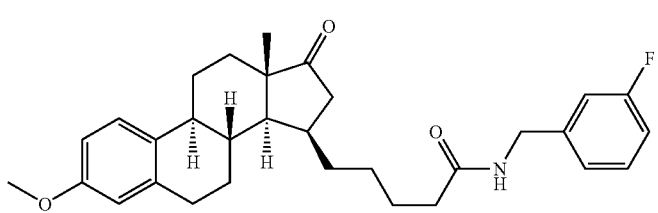 | 40.4 | 89.2 |
| 343 | 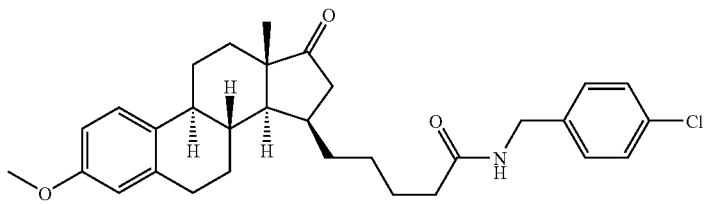 | 47.1 | 86.0 |
| 344 | 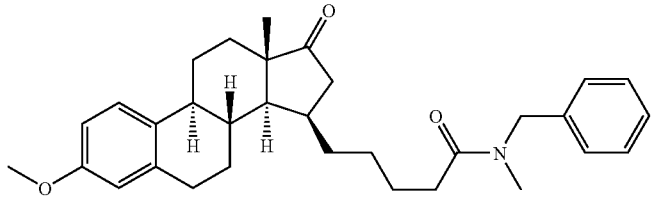 | 39.8 | 88.9 |

TABLE 42-continued
Inhibition of 17β-HSD enzyme type I
| Compound No. | Compound Structure | Inhibition of rec. 17β-HSD1 | |
|---|---|---|---|
| | | 100 nM | 1 μm |
| 345 | 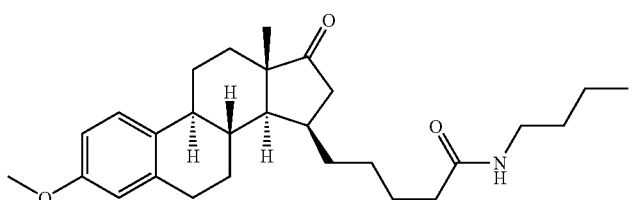 | 33.0 | 85.6 |
| 346 | 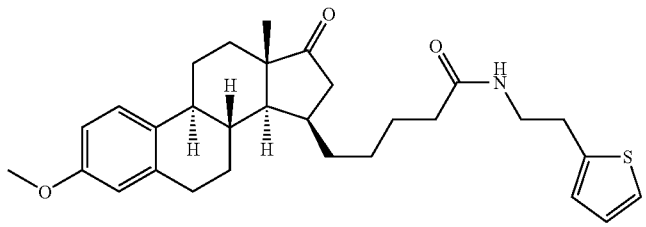 | 58.2 | 91.7 |
| 347 | 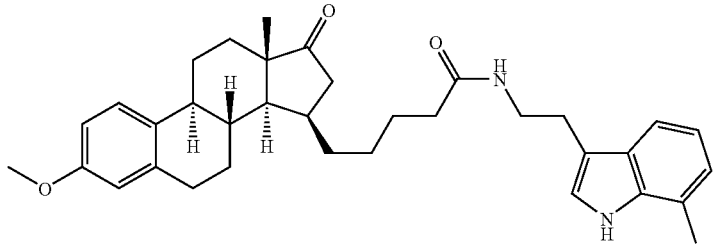 | 38.0 | 77.2 |
| 348 | 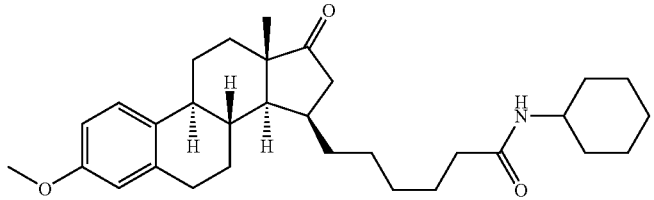 | 30.5 | 82.4 |
| 349 | 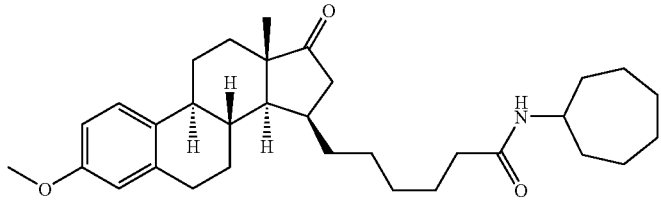 | 31.6 | 75.2 |
| 350 | 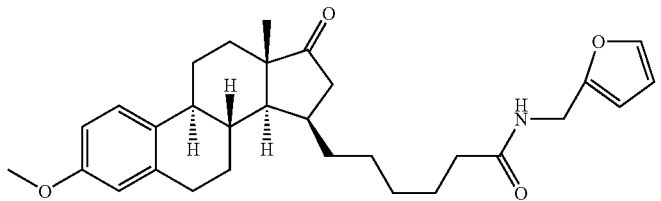 | 27.7 | 80.7 |

TABLE 42-continued
Inhibition of 17β-HSD enzyme type I
| Compound No. | Compound Structure | Inhibition of rec. 17β-HSD1 | |
|---|---|---|---|
| | | 100 nM | 1 μm |
| 353 | 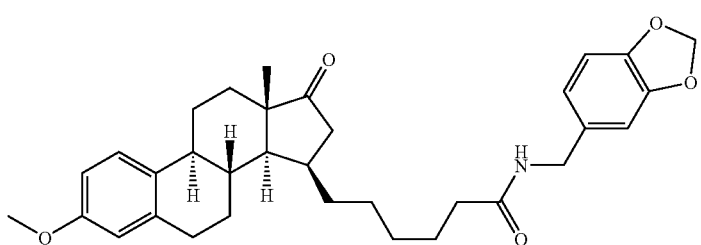 | 46.3 | 89.5 |
| 354 | 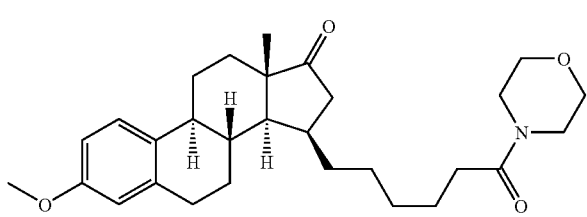 | 28.7 | 80.3 |
| 355 | 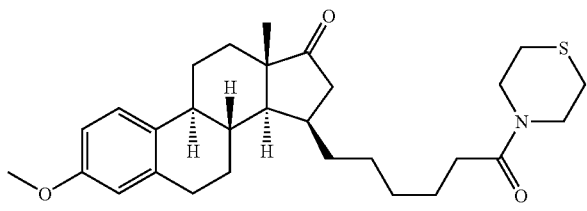 | 34.4 | 85.1 |
| 356 | 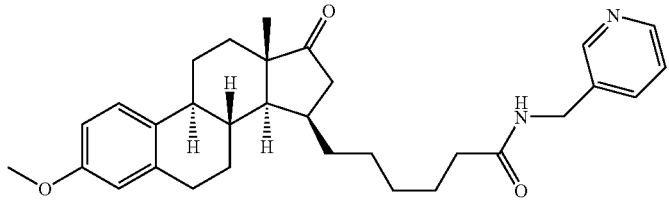 | 26.9 | 83.9 |
| 357 | 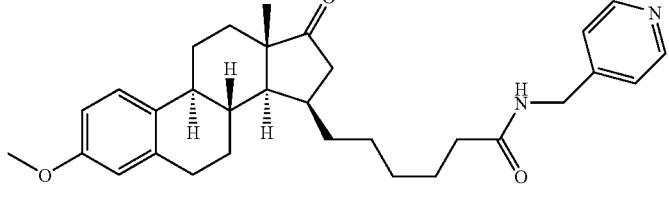 | 31.1 | 85.2 |
| 359 | 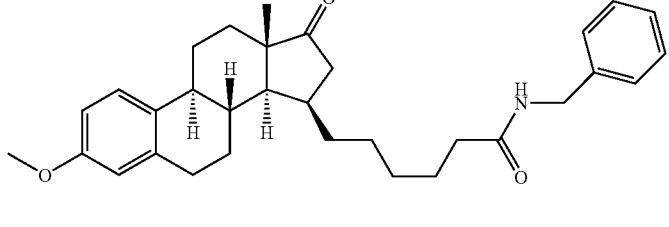 | 40.5 | 88.3 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 360 | | 41.5 | 85.6 |
| 361 | | 35.8 | 84.2 |
| 362 | | 35.1 | 75.1 |
| 363 | | 60.1 | 94.3 |
| 364 | | 48.7 | 90.8 |
| 365 | | 33.7 | 86.4 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 366 | 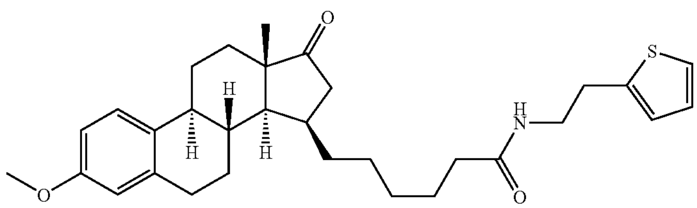 | 56.3 | 94.4 |
| 367 | 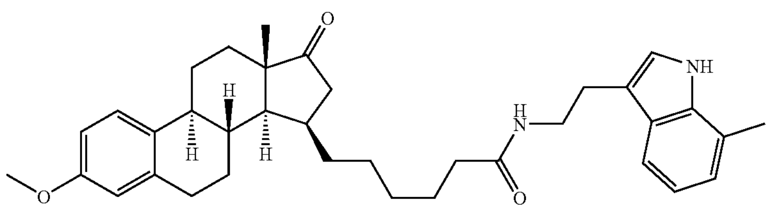 | 51.5 | 73.5 |
| 414 | 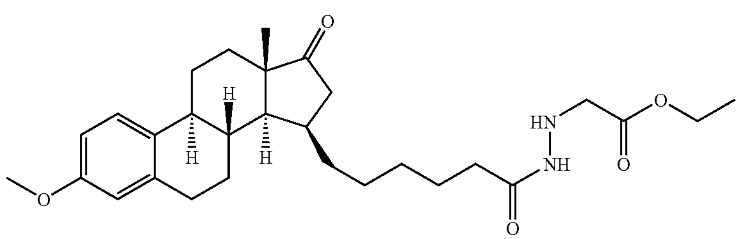 | 44.9 | 49.9 |
| 443 | 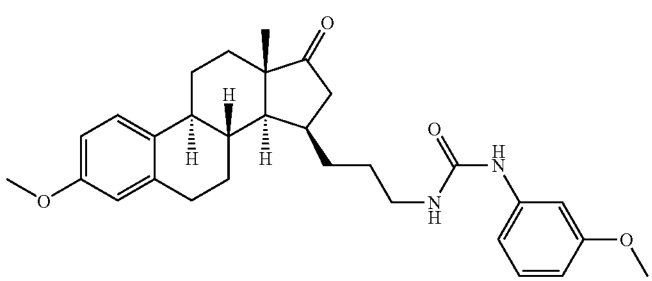 | 39.8 | 84.1 |
| 446 | 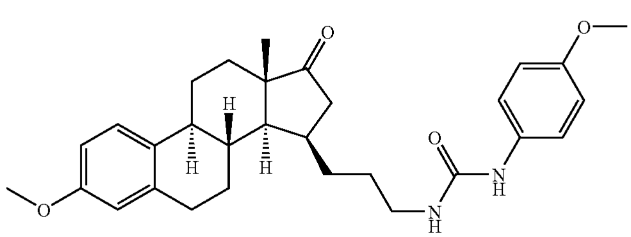 | 72.4 | 94.2 |
| 449 | 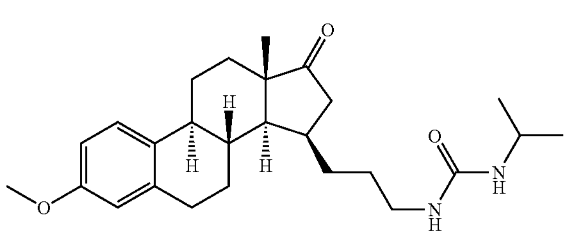 | 26.0 | 82.7 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 450 | 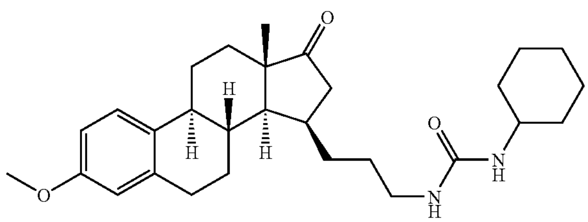 | 34.0 | 80.7 |
| 451 | 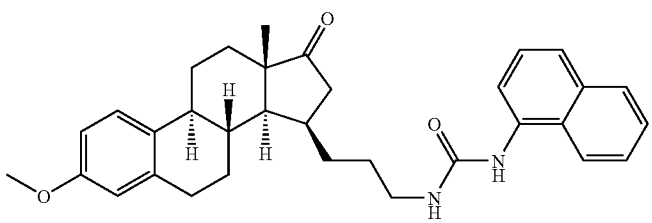 | 32.3 | 74.6 |
| 452 | 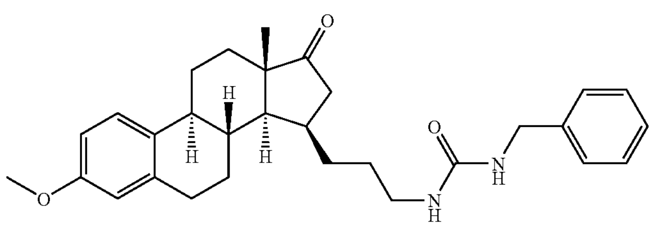 | 38.6 | 82.9 |
| 460 | 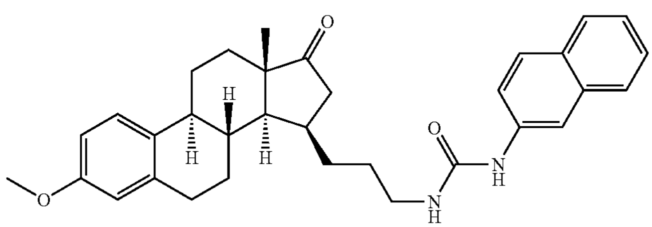 | 50.1 | 77.2 |
| 464 | 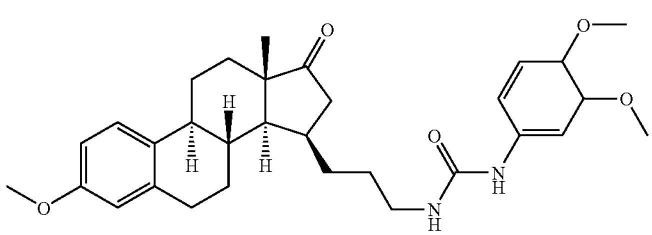 | 79.5 | 87.3 |
| 465 | 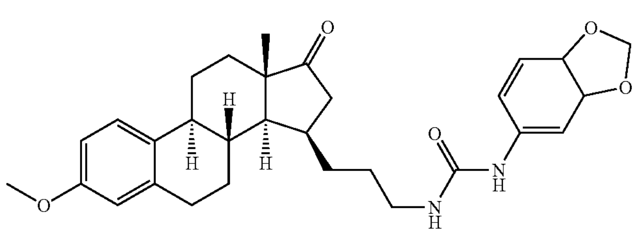 | 51.5 | 83.6 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 471 | 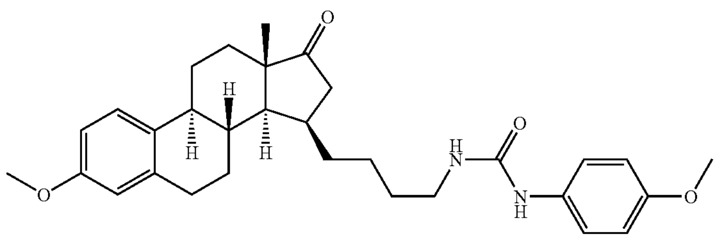 | 28.7 | 77.0 |
| 477 | 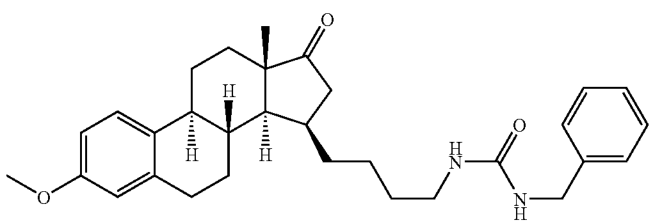 | 31.7 | 79.5 |
| 488 | 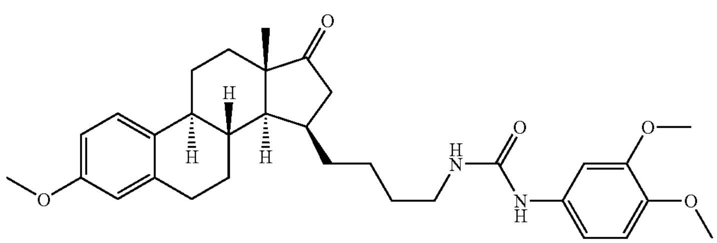 | 60.3 | 91.6 |
| 490 | 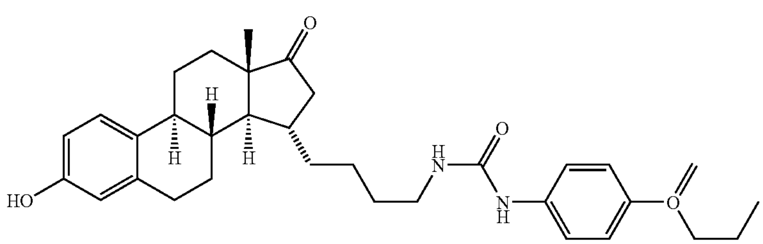 | 51.2 | 77.3 |
| 491 | 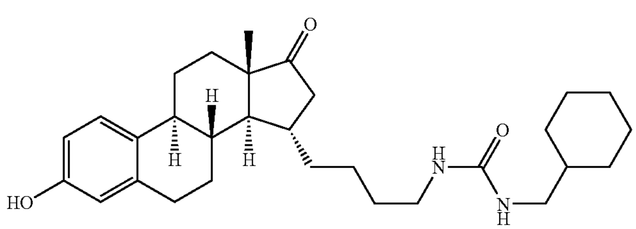 | 56.9 | 83.0 |
| 661 | 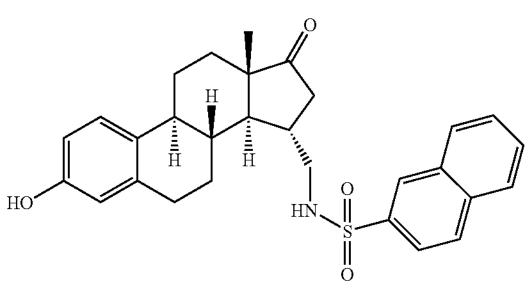 | 40.1 | 82.0 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 662 | 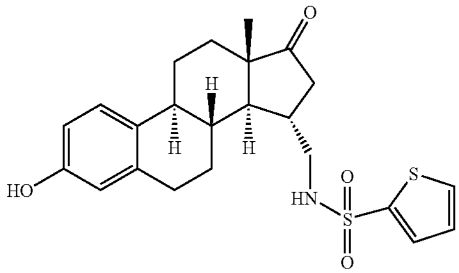 | 76.9 | 94.8 |
| 664 | 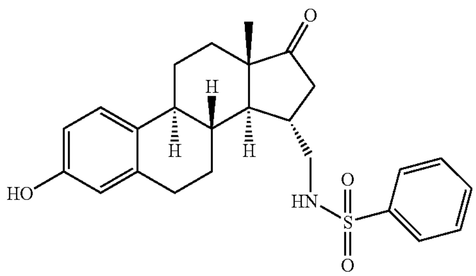 | 60.5 | 92.7 |
| 665 | 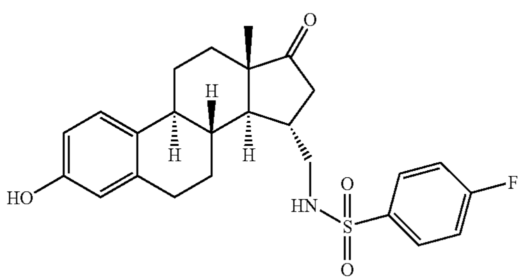 | 54.6 | 91.2 |
| 667 | 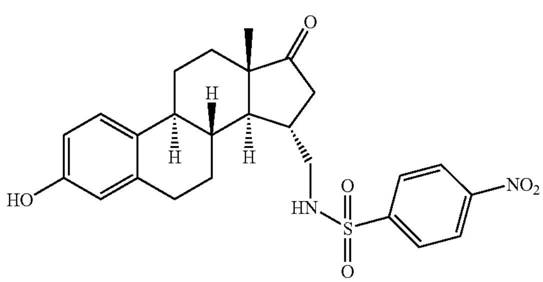 | 30.3 | 72.3 |
| 668 | 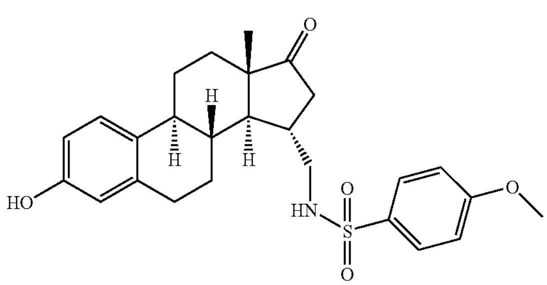 | 52.4 | 88.3 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 677 | 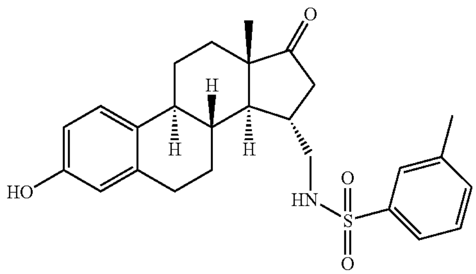 | 36.9 | 83.7 |
| 679 | 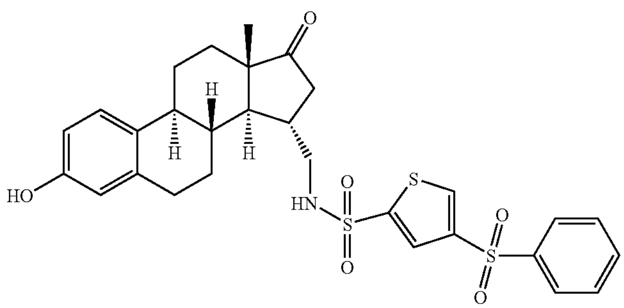 | 26.5 | 74.6 |
| 681 | 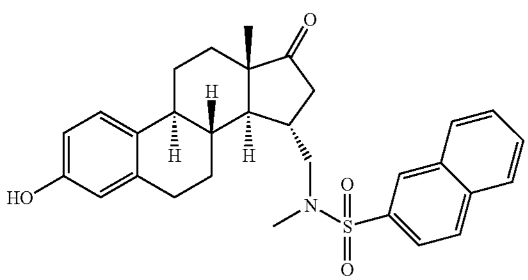 | 39.7 | 87.1 |
| 682 | 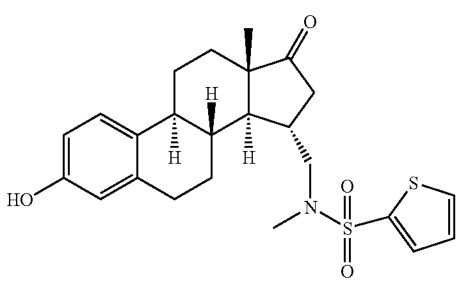 | 49.2 | 91.8 |
| 684 | 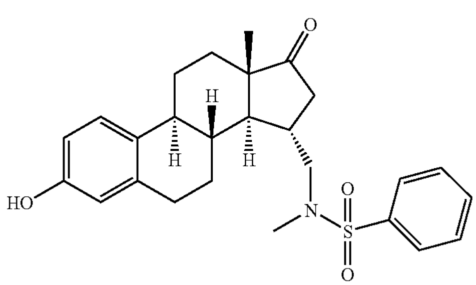 | 31.3 | 86.9 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 685 | | 36.0 | 85.6 |
| 688 | | 47.4 | 91.3 |
| 693 | | 25.8 | 80.1 |
| 694 | | 34.6 | 87.3 |
| 696 | | 35.7 | 80.5 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 744 | 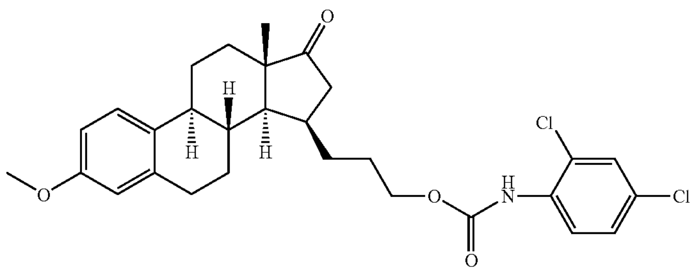 | 37.1 | 53.9 |
| 745 | 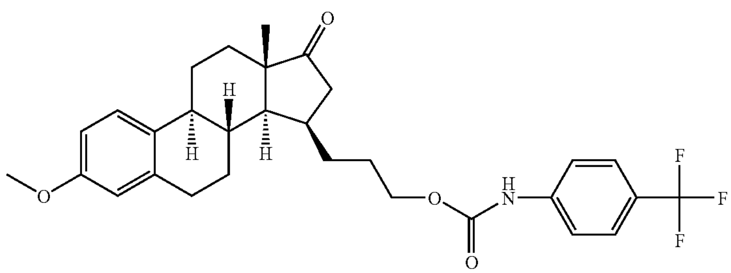 | 29.9 | 53.5 |
| 748 | 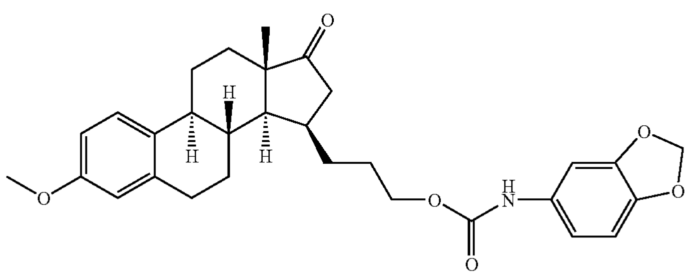 | 48.7 | 90.6 |
| 749 | 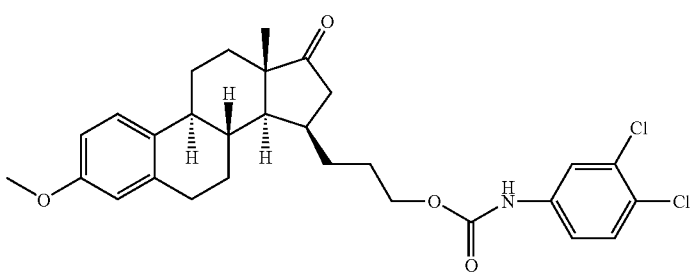 | 29.8 | 57.3 |
| 751 | 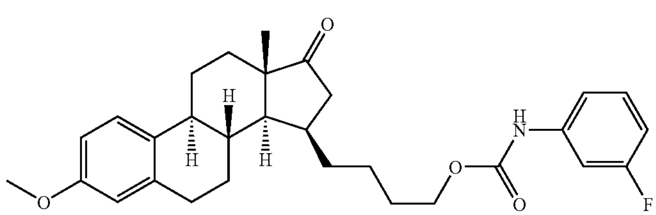 | 27.7 | 67.7 |

TABLE 42-continued

Inhibition of 17β-HSD enzyme type I

| Compound No. | Compound Structure | Inhibition of rec. 17β-HSD1 | |
|---|---|---|---|
| | | 100 nM | 1 μm |
| 754 | | 29.3 | 65.1 |
| 757 | | 33.5 | 50.3 |
| 760 | | 29.2 | 72.7 |
| 823 | | 76.1 | 97.0 |

2. Estrogen Receptor Binding Assay

The binding affinity of the compounds of the invention to the estrogen receptor α and to the estrogen receptor β may be determined according to the in vitro ER binding assays described by Koffmann et al. [Koffmann et al. (1991) J. Steroid. Biochem. Mol. Biol. 38:135]. Alternatively, an estrogen receptor binding assay may be performed according to international patent application PCT/US99/17799 (published as WO 00/07996).

3. Estrogen Receptor Transactivation Assays

Compounds of the invention showing binding affinity towards the estrogen receptor may be further tested with regard to their individual estrogenic or anti-estrogenic potential (agonistic binding or antagonistic binding to the ERα or ERβ). The determination of the estrogen receptor agonist activity may be performed according to an in vitro assay system using the MMTV-ERE-LUC reporter system which is for example described within U.S. patent application Ser. No. 10/289,079 (published as US 2003/0170292):

To assay estrogen receptor agonist activity, Hela cells are grown in 24-well microtiter plates and then transiently co-transfected with two plasmids using lipofectamine. The first plasmid comprises DNA encoding human estrogen receptor (either ER-alpha or ER-beta), and the second plasmid comprises an estrogen-driven reporter system comprising: a luciferase reporter gene (LUC) whose transcription is under the control of upstream regulatory elements comprising 4 copies of the vitellogenin estrogen response element (ERE) cloned into the mouse mammary tumor virus (MMTV) promoter (the full name for the reporter system being "MMTV-ERE-LUC"). Cells are exposed to the compounds of the invention in RPMI 1640 medium, supplemented with 10% charcoal-treated fetal calf serum, 2 mM L-glutamine, 0.1 mM non-essential amino acids and 1 mM sodium pyruvate for 42-48 hours at 37° C. in a 5% carbon dioxide incubator. Concurrently, cells exposed to estradiol (1 nM) serve as positive controls. Replicate wells exposed to the solvent in which the compounds of the invention are dissolved (i.e. ethanol or methanol) are used as negative controls. After the 42-48 hr incubation period, cells are rinsed with phosphate buffered saline (PBS), lysis buffer (Promega Corp) is added, and cell lysates are collected for measurement of luciferase activity with a luminometer. Estrogenic activity of the compounds of the invention is expressed as fold-increase in luciferase activity as compared to that observed in negative control cells.

Alternatively, the determination of the estrogen receptor transactivation activity (estrogenicity assay or agonist assay) and of the inhibitory potency of transactivation activity (antiestrogenicity assay or antagonist assay) may be performed according to international patent application PCT/US99/17799 (published as WO 00/07996).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

Cited Literature

Adamski J & Jakob F J (2001) "A guide to 17β-hydroxysteroid dehydrogenases", Molecular and Cellular Endocrinology, 171:1-4
Koffmann B et al. (1991) J. Steroid. Biochem. Mol. Biol. 38:135
Labaree D C et al. (2003) "Synthesis and Evaluation of B-, C- and D-ring substituted estradiol carboxylic acid esters as locally active estrogens" J. Med. Chem. 46:1886-1904
Labrie F et al. (2000) "Role of 17 beta-hydroxysteroid dehydrogenases in sex steroid formation in peripheral intracrine tissues" Trends Endocrinol Metab., 11:421-7
Labrie F et al. (1997) "The key role of 17 beta-hydroxysteroid dehydrogenases in sex steroid biology." Steroids, 62:148-58
Nambara T et al. (1976) "Synthesis of Estetrol Monoglucuronides" Steroids 27:111-122
Pelletier J D & Poirier D (1996) "Synthesis and evaluation of estradiol derivatives with 16α-(bromoalkylamide), 16α-(bromoalkyl) or 16α-(bromoalkynyl) side chain as inhibitors of 17β-hydroxysteroid dehydrogenase type 1 without estrogenic activity" Bioorg Med Chem, 4(10):1617-1628.
Poirier D (2003) "Inhibitors of 17 beta-hydroxysteroid dehydrogenases" Curr Med Chem. 10:453-77
Poirier D et al. (1998) "A 6β-(Thiaheptanamide) Derivative of Estradiol as inhibitor of 17β-Hydroxysteroid Dehydrogenase Type 1", J. Steroid Biochem. Molec. Biol., 64:83-90
Poirier D et al. (1996) "D-Ring alkylamine derivatives of estradiol: effect on ER-binding affinity and antiestrogenic activity" Bioorg Med Chem Lett 6(21):2537-2542.
Poirier D et al. (1991) "Synthesis of 17β-estradiol derivatives with N-Butyl, N-methyl alkylamide side chain at position 15." Tetrahedron, 47(37):7751-7766
Sam K M et al. (1998) "C16 and C17 Derivatives of Estradiol as Inhibitors of 17β-Hydroxysteroid Dehydrogenase Type 1: Chemical Synthesis and Structure-Activity Relationships", Drug Design and Discovery, 15:157-180
Tamaya et al. (1985) "Comparison of cellular levels of steroid receptors in uterine leiomyoma and myometrium." Acta Obstet Gynecol Scand., 64:307-9
Tremblay M R & Poirier D (1998) "Overview of a Rational Approach to Design Type I 17β-Hydroxysteroid Dehydrogenase Inhibitors Without Estrogenic Activity: Chemical Synthesis and Biological Evaluation", J. Steroid Biochem. Molec. Biol., 66:179-191
WO 03/017973—A METHOD OF TREATING BENIGN GYNECOLOGICAL DISORDERS AND A DRUG DELIVERY VEHICLE FOR USE IN SUCH A METHOD
WO 2004/080271—METHOD FOR PROGNOSTICATING THE PROGRESS OF BREAST CANCER AND COMPOUNDS USEFUL FOR PREVENTION OR TREATMENT THEREOF
WO 2004/085345—15α-SUBSTITUTED ESTRADIOL CARBOXYLIC ACID ESTERS AS LOCALLY ACTIVE ESTROGENS
WO 2004/085457—Compound

What is claimed is:
1. A compound corresponding to formula I,

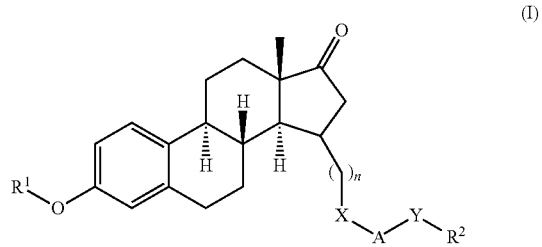

or a physiologically acceptable salt thereof, wherein
(i) X represents:
 (a) a bond,
 (b) —$NR^3$—, or
 (c) —O—;
A represents:
 (a) —CO—, or
 (b) if X represents —$NR^3$—, A may represent —$SO_2$—;
and
Y represents:
 (a) —$NR^4$—,
 (b) —O—, if X represents a bond or —$NR^3$—,
 (c) a bond,
 (d) —NH—$SO_2$—, if X represents —$NR^3$— and A represents —CO—,
 (e) —NH—$SO_2$—$NR^4$—, if X represents —O—, or
 (f) —NH—$NR^4$—, if X represents a bond;
or
(ii) —X-A-Y— together represent —O—;
and wherein
$R^1$ and $R^3$ are independently selected from:
 (a) —H,
 (b) —($C_1$-$C_6$)alkyl, which is optionally substituted with halogen, nitrile, —$OR^6$, —$SR^6$, or —$COOR^6$; the number of said substituents being up to three for halogen, and up to two for any combination of halogen, nitrile, —$OR^6$, —$SR^6$, or —$COOR^6$ moieties,
 (c) -phenyl, which is optionally substituted with halogen, nitrile, —$OR^6$, —$SR^6$, —$R^6$, or —$COOR^6$, the number of said substituents being up to perhalo for halogen, and up to two for any combination of halogen, nitrile, —$OR^6$, —$SR^6$, —$R^6$ or —$COOR^6$ moieties, and
 (d) —($C_1$-$C_4$)alkyl-phenyl, in which the alkyl portion is optionally substituted with up to three halogens; and the phenyl portion is optionally substituted with halogen, nitrile, —$OR^6$, —$SR^6$, —$R^6$ or —$COOR^6$, the number of substituents on the phenyl portion being up to perhalo for halogen, and up to two for any combination of halogen, nitrile, —$OR^6$, —$SR^6$, —$R^6$ or —$COOR^6$ moieties;

$R^2$ and $R^4$ are independently selected from:
(a) —H, wherein if X represents a bond, A represents —CO— and Y represents —O— or a bond, then $R^2$ is different from —H;
(b) —$(C_1-C_{12})$alkyl, optionally substituted with up to five substituents independently selected from the group consisting of halogen, hydroxyl, thiol, nitrile, alkoxy, aryloxy, arylalkyloxy, amino, amido, alkylthio, arylthio, arylalkylthio, sulfamoyl, sulfonamide, acyl, carboxyl, acylamino,
  aryl, which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, acylamino and heteroaryl; or which aryl is optionally substituted by two groups which are attached to adjacent carbon atoms and are combined into a saturated or partly unsaturated cyclic 5, 6, 7, or 8 membered ring system, optionally containing up to three heteroatoms selected from N, O and S, the number of N atoms being 0-3 and the number of O and S atoms each being 0-2;
  heteroaryl, which heteroaryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, acylamino, aryl-$(C_1-C_4)$-alkyl and aryl;
    whereby each aryl group is optionally substituted with up to three substituents independently selected from the group consisting of hydroxyl, halogen, $(C_1-C_6)$alkoxy, $(C_1-C_6)$alkyl, halogenated $(C_1-C_6)$alkyl and halogenated $(C_1-C_6)$alkoxy; and
  cycloheteroalkyl, which cycloheteroalkyl group is a four- to eight-membered heterocyclic ring consisting of carbon and at least one heteroatom, selected from N, O or S, the number of N atoms being 0-3 and the number of O and S atoms each being 0-1, which system may be saturated, partly saturated or hydroaromatic, and which ring is optionally part of a multiple condensed ring-system in which some rings are optionally aromatic and which cycloheteroaryl group is optionally substituted with up to three substituents independently selected from the group consisting of oxo, $(C_1-C_8)$-alkyl, aryl, aryl-$(C_1-C_4)$-alkyl, hydroxyl, $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, and acylamino,
    whereby each aryl group is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy);
(c) optionally substituted acyl if Y represents —NH—$NR^4$—,
(d) optionally substituted aryl,
(e) optionally substituted heteroaryl, and
(f) optionally substituted cycloheteroalkyl,
or, if Y represents —$NR^4$—, —NH—$NR^4$— or —NH—$SO_2$—$NR^4$—, then
$R^2$ and $R^4$ together with the nitrogen atom to which they are attached, may form a heterocyclic 4-, 5-, 6-, 7- or 8-membered ring, which is optionally saturated, partly unsaturated, or aromatic; which optionally contains up to three additional heteroatoms selected from N, O or S, the number of additional N atoms being 0, 1, 2 or 3 and the number of O and S atoms each being 0, 1 or 2; and which ring is optionally part of a multiple condensed ring-system, wherein the ring or the ring-system is optionally substituted;
$R^6$ represents H, —$(C_1-C_4)$alkyl or halogenated —$(C_1-C_4)$alkyl; and
n represents 1, 2, 3, 4, 5 or 6.

2. A compound according to claim 1, wherein $R^2$ and $R^4$ are independently selected from the group consisting of:
(a) —H, wherein if X represents a bond, A represents —CO— and Y represents —O— or a bond, then $R^2$ is different from —H,
(b) acyl —(C=O)—R', wherein R' represents hydrogen, $(C_1-C_4)$alkyl, aryl, or aryl-$(C_1-C_4)$alkyl, or heteroaryl-$(C_1-C_4)$alkyl;
  which aryl or aryl-$(C_1-C_4)$alkyl is optionally substituted in the aryl moiety with up to three substituents independently selected from the group consisting of hydroxyl, halogen, $(C_1-C_4)$alkoxy, $(C_1-C_4)$-alkyl or halogenated $(C_1-C_4)$alkyl;
(c) aryl
  which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, nitro, sulfamoyl, sulfonamide, carboxyl, aryloxy, arylalkyloxy, $(C_1-C_6)$alkylsulfonyl, arylsulfonyl, $(C_1-C_6)$alkylthio, arylthio, arylalkylthio, amino, amido, acyl, acylamino and heteroaryl; or
  which aryl is optionally substituted by two groups which are attached to adjacent carbon atoms and are combined into a saturated or partly unsaturated cyclic 5, 6, 7, or 8-membered ring system, optionally containing up to three heteroatoms selected from N, O and S, the number of N atoms being 0-3 and the number of O and S atoms each being 0-2;
(d) heteroaryl,
  which heteroaryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, carboxyl-$(C_1-C_6)$alkyl, thiol, nitrile, sulfamoyl, sulfonamide, arylsulfoxy, carboxyl, aryloxy, arylalkyloxy, $(C_1-C_6)$alkylsulfonyl, arylsulfonyl, $(C_1-C_6)$alkylthio, arylthio, arylalkylthio, amino, amido, acyl, acylamino, aryl-$(C_1-C_4)$-alkyl and aryl,
    whereby each aryl group is optionally substituted with up to three substituents independently selected from the group consisting of hydroxyl, halogen, $(C_1-C_6)$alkoxy, $(C_1-C_6)$alkyl, halogenated $(C_1-C_6)$alkyl and halogenated $(C_1-C_6)$alkoxy; or
(e) cycloheteroalkyl,
  which cycloheteroalkyl is optionally substituted with up to three substituents independently selected from the group consisting of oxo, $(C_1-C_{14})$-alkyl, aryl, aryl-$(C_1-C_4)$-alkyl, hydroxyl, $(C_1-C_6)$alkoxy, carboxyl-$(C_1-C_6)$alkyl, thiol, nitrile, sulfamoyl, sulfonamide, carboxyl, aryloxy, arylalkyloxy, $(C_1-C_6)$alkylthio, arylthio, arylalkylthio, amino, amido, acyl, and acylamino, whereby each aryl group is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy;

or wherein, if Y represents —$NR^4$—, —NH—$NR^4$— or —NH—$SO_2$—$NR^4$—, then $R^2$ and $R^4$ together with the nitrogen atom to which they are attached may form a heterocyclic 4-, 5-, 6-, 7- or 8-membered ring, which is optionally saturated or partly unsaturated; which optionally contains up to three additional heteroatoms selected from N, O or S, the number of additional N atoms being 0-3 and the number of O and S atoms each being 0-2; and which ring is optionally part of a multiple condensed ring-system, wherein the ring or the ring-system is optionally substituted (i) with up to three substituents independently selected from the group consisting of $(C_1-C_8)$-alkyl, halogen, hydroxyl, carboxyl, thiol, nitrile, $(C_1-C_6)$-alkoxy, carboxyl-$(C_1-C_6)$alkyl, aryloxy, arylalkyloxy, amino, amido, alkylthio, arylthio, arylalkylthio, sulfamoyl, sulfonamide, aryl, aryl-$(C_1-C_4)$-alkyl, heteroaryl, and cycloheteroalkyl, wherein the $(C_1-C_8)$-alkyl group is optionally substituted with up to three substituents independently selected from hydroxyl, halogen, $(C_1-C_4)$-alkoxy, or halogenated $(C_1-C_4)$-alkoxy, whereby the alkyl-chain of the $(C_1-C_4)$-alkoxy moiety is optionally substituted with hydroxyl;

wherein the aryl is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, halogenated $(C_1-C_4)$-alkoxy and carboxyl-$(C_1-C_6)$ alkyl, or wherein the aryl moiety is optionally substituted by two groups which are attached to adjacent carbon atoms and are combined into a saturated or partly unsaturated cyclic 5, 6, 7, or 8 membered ring system, optionally containing up to three heteroatoms selected from N, O and S, the number of N atoms being 0-3 and the number of O and S atoms each being 0-2;

wherein the heteroaryl is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, halogenated $(C_1-C_4)$-alkoxy) and carboxyl-$(C_1-C_6)$alkyl;

wherein the cycloheteroalkyl is optionally substituted with up to three substituents independently selected from the group consisting of oxo, $(C_1-C_8)$-alkyl, aryl, aryl-$(C_1-C_4)$-alkyl, hydroxyl, $(C_1-C_6)$ alkoxy, carboxyl-$(C_1-C_6)$alkyl, and carboxyl, whereby each aryl group is optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, and halogenated $(C_1-C_4)$-alkoxy); or (ii) by two groups which are attached to the same carbon atom and are combined into a saturated or partly unsaturated cyclic 4, 5, 6, 7, or 8-membered ring system, optionally containing up to three heteroatoms selected from N, O and S, the number of N atoms being 0-3 and the number of O and S atoms each being 0-2, whereby the cyclic ring system is optionally substituted by up to two substituents independently selected from oxo, $(C_1-C_6)$-alkyl, aryl and aryl-$(C_1-C_4)$-alkyl;

and wherein n represents (a) 1, 2, 3, 4, 5 or 6, if X represents —$NR^3$— or —O—, or (b) 1, 2, 3, 4, or 5, if X represents a bond.

3. A compound according to claim 1, wherein $R^2$ and $R^4$ are independently selected from:

(a) —H, wherein if X represents a bond, A represents —CO— and Y represents —O— or a bond, then $R^2$ is different from —H, (b) —$(C_1-C_{12})$alkyl, optionally substituted with up to five substituents independently selected from the group consisting of halogen, hydroxyl, nitrile, —O—$R^7$; —O—$Ar^1$, —O—$(C_1-C_4)$alkyl-$Ar^1$, alkylamino, alkylamido, —S—$R^7$, —S—$Ar^1$, —S—$(C_1-C_4)$alkyl-$Ar^1$, —(C=O)—$OR^8$, aryl, heteroaryl, and cycloheteroalkyl, wherein the aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-C_6)$alkoxy, —$(C_1-C_6)$alkyl-(C=O)—$OR^8$, nitrile, sulfamoyl, —(C=O)—$OR^8$, —O—$Ar^1$, —O—$(C_1-C_4)$alkyl-$Ar^1$, $(C_1-C_6)$alkylthio, —S—$Ar^1$, —S—$(C_1-C_4)$alkyl-$Ar^1$, alkylamino, and alkylamido; or wherein the aryl is optionally substituted by two groups which are attached to adjacent carbon atoms and are combined into a saturated cyclic 5 or 6 membered ring system, optionally containing up to three heteroatoms, such as N or O, the number of N atoms being 0-3 and the number of O atoms each being 0-2;

wherein the heteroaryl is optionally substituted with up to three substituents independently selected from the group consisting of halogen, hydroxyl, $(C_1-C_6)$ alkoxy, $(C_1-C_6)$alkyl, halogenated $(C_1-C_6)$alkyl, halogenated $(C_1-C_6)$alkoxy, —$(C_1-C_6)$alkyl-(C=O)—$OR^8$, nitrile, sulfamoyl, —(C=O)—$OR^8$, —O—$Ar^1$, —O—$(C_1-C_4)$alkyl-$Ar^1$, $(C_1-C_6)$alkylthio, —S—$Ar^1$, —S—$(C_1-C_4)$alkyl-$Ar^1$, alkylamino, alkylamido, —$(C_1-C_4)$alkyl-$Ar^1$ and $Ar^1$; and wherein the cycloheteroalkyl group is optionally substituted with up to three substituents independently selected from the group consisting of oxo, $(C_1-C_8)$-alkyl, $Ar^1$, —$(C_1-C_4)$alkyl-$Ar^1$, hydroxyl, $(C_1-C_6)$ alkoxy, —$(C_1-C_6)$alkyl-(C=O)—$OR^8$, nitrile, —(C=O)—$OR^8$, —O—$Ar^1$, —O—$(C_1-C_4)$alkyl-$Ar^1$, $(C_1-C_6)$alkylthio, —S—$Ar^1$, —S—$(C_1-C_4)$alkyl-$Ar^1$, alkylamino and alkylamido;

(c) aryl, which aryl is optionally substituted with up to three substituents independently selected from the group consisting of halogen, hydroxyl, $(C_1-C_6)$alkoxy, $(C_1-C_6)$alkyl, halogenated $(C_1-C_6)$alkyl, halogenated $(C_1-$ $C_6$)alkoxy, —($C_1$-$C_6$)alkyl-(C=O)—OR$^8$, nitro, nitrile, sulfamoyl, —(C=O)—OR$^8$, —(C=O)—R$^8$, —O—Ar$^1$, —O—($C_1$-$C_4$)alkyl-Ar$^1$, ($C_1$-$C_6$)alkylthio, —S—Ar$^1$, —S—($C_1$-$C_4$)alkyl-Ar$^1$, ($C_1$-$C_6$)alkylsulfonyl, —SO$_2$—Ar$^1$, alkylamino, alkylamide, —NH—CO—R$^8$, Ar$^1$ and heteroaryl; or which aryl is optionally substituted by two groups which are attached to adjacent carbon atoms and are combined into a saturated cyclic 5 or 6 membered ring system, optionally containing up to three heteroatoms, such as N or O, the number of N atoms being 0-3 and the number of O atoms each being 0-2;

(d) heteroaryl, which heteroaryl is optionally substituted with up to three substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$)alkoxy, —($C_1$-$C_6$)alkyl-(C=O)—OR$^8$, nitrile, sulfamoyl, —(C=O)—OR$^8$, —O—Ar$^1$, —O—($C_1$-$C_4$)alkyl-Ar$^1$, ($C_1$-$C_6$)alkylthio, —S—Ar$^1$, —S—($C_1$-$C_4$)alkyl-Ar$^1$, ($C_1$-$C_6$)alkylsulfonyl, —SO$_2$—Ar$^1$, alkylamino, alkylamido, —($C_1$-$C_4$)alkyl-Ar$^1$ and Ar$^1$; or (e) cycloheteroalkyl, which cycloheteroalkyl group is optionally substituted with up to three substituents independently selected from the group consisting of oxo, ($C_1$-$C_8$)-alkyl, Ar$^1$, —($C_1$-$C_4$)alkyl-Ar$^1$, hydroxyl, ($C_1$-$C_6$)alkoxy, —($C_1$-$C_6$)alkyl-(C=O)—OR$^8$, nitrile, —(C=O)—OR$^8$, —O—Ar$^1$, —O—($C_1$-$C_4$)alkyl-Ar$^1$, ($C_1$-$C_6$)alkylthio, —S—Ar$^1$, —S—($C_1$-$C_4$)alkyl-Ar$^1$, alkylamino and alkylamido;

wherein

R$^7$ represents ($C_1$-$C_6$)alkyl, optionally substituted with up to three hydroxy groups in the alkyl chain or halogenated ($C_1$-$C_6$)alkyl, R$^8$ represents hydrogen, ($C_1$-$C_4$)alkyl, phenyl, or ($C_1$-$C_4$)alkyl-phenyl, wherein the phenyl-moiety is optionally substituted with up to three substituents independently selected from the group consisting of hydroxyl, halogen, ($C_1$-$C_4$)alkoxy, ($C_1$-$C_4$)-alkyl, halogenated ($C_1$-$C_4$)alkyl and halogenated ($C_1$-$C_4$)alkoxy;

R$^{8'}$ represents hydrogen, ($C_1$-$C_4$)alkyl or ($C_1$-$C_2$)alkyl-phenyl; and Ar$^1$ represents phenyl or naphthyl, which are optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy;

or wherein, if Y represents —NR$^4$—, —NH—NR$^4$— or —NH—SO$_2$—NR$^4$—, then the ring or ringsystem formed by R$^2$ and R$^4$ together with the nitrogen atom to which R$^2$ and R$^4$ are attached, is selected from the group consisting of

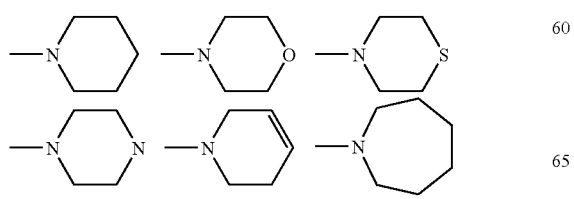

wherein the ring or the ring-system is optionally substituted (i) with up to three substituents independently selected from the group consisting of ($C_1$-$C_8$)-alkyl, oxo, hydroxyl, ($C_1$-$C_6$)alkoxy, —($C_1$-$C_6$)alkyl—(C=O)—OR$^{8'}$, nitrile, —(C=O)—OR$^{8'}$, —O—Ar$^2$, —O—($C_1$-$C_4$)alkyl-Ar$^2$, ($C_1$-$C_6$)alkylthio, alkylamino, alkylamido, aryl, aryl-($C_1$-$C_4$)alkyl, heteroaryl, and cycloheteroalkyl, wherein the aryl and aryl-($C_1$-$C_4$)alkyl group are optionally substituted in the aryl moiety with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, halogenated ($C_1$-$C_4$)-alkoxy and carboxyl-($C_1$-$C_4$) alkyl, or wherein the aryl moiety is optionally substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2; and wherein the ($C_1$-$C_8$)-alkyl group is optionally substituted with up to three substituents independently selected among hydroxyl, halogen, halogenated ($C_1$-$C_4$)-alkoxy or ($C_1$-$C_4$)-alkoxy, whereby the alkyl-chain of the ($C_1$-$C_4$)-alkoxy moiety is optionally substituted with up to three hydroxyl groups;

wherein the heteroaryl is optionally substituted with up to three substituents independently selected from the group consisting of hydroxyl, halogen, ($C_1$-$C_4$)-alkyl, ($C_1$-$C_4$)-alkoxy, halogenated ($C_1$-$C_4$)-alkyl, halogenated ($C_1$-$C_4$)-alkoxy) and carboxyl-($C_1$-$C_6$)alkyl; and wherein the cycloheteroalkyl is optionally substituted with up to three substituents independently selected from the group consisting of oxo, ($C_1$-$C_8$)-alkyl, hydroxyl, ($C_1$-$C_6$)alkoxy, —(C=O)—OR$^9$, and —($C_1$-$C_6$)alkyl—(C=O)—OR$^9$; or (ii) by two groups which are attached to the same carbon atom and are combined into a saturated or partly unsaturated cyclic 4, 5, 6, 7, or 8-membered ring system, optionally containing up to three heteroatoms selected from N, O and S, the number of N atoms being 0-3 and the number of O and S atoms each being 0-2, whereby the cyclic ring system is optionally substituted by up to three substituents independently selected from oxo, $(C_1-C_6)$-alkyl, aryl and aryl-$(C_1-C_4)$-alkyl;
wherein
Ar² represents phenyl or naphthyl, which are optionally substituted with up to three substituents independently selected from the group consisting of hydroxyl, halogen, $(C_1-C_4)$-alkyl, $(C_1-C_4)$-alkoxy, halogenated $(C_1-C_4)$-alkyl, or halogenated $(C_1-C_4)$-alkoxy
R⁹ represents hydrogen, $(C_1-C_4)$alkyl, phenyl, or $(C_1-C_4)$ alkyl-phenyl; whereby the phenyl is optionally substituted with up to three substituents independently selected from the group consisting of hydroxyl, halogen, $(C_1-C_4)$alkoxy, $(C_1-C_4)$-alkyl, halogenated $(C_1-C_4)$ alkyl and halogenated $(C_1-C_4)$alkoxy.

4. A compound according to claim 3, wherein R² and R⁴ are independently selected from:
(a) —H, wherein if X represents a bond, A represents —CO— and Y represents —O— or a bond, then R² is different from —H,
(b) an alkyl group selected from
  (i) —$(C_1-C_8)$alkyl, optionally substituted with substituents independently selected from the group consisting of hydroxyl, nitrile, —O—R⁷ʼ; —O-phenyl, —O—$(C_1-C_4)$alkyl-phenyl, alkylamino, alkylamido, —S—R⁷ʼ, and —(C=O)—OR⁸ʼ, the number of substituents on said alkyl being up to five for hydroxyl and one, two or three for any combination of the other substituents;
  (ii) —$(C_1-C_4)$alkyl, optionally substituted with one or two substituents independently selected from the group consisting of aryl, heteroaryl, and cycloheteroalkyl,
    which aryl is optionally substituted with halogen, hydroxyl, $(C_1-C_6)$alkoxy, $(C_1-C_6)$alkyl, halogenated $(C_1-C_4)$alkyl, halogenated $(C_1-C_4)$alkoxy, sulfamoyl, or alkylamido, the number of substituents on said aryl being up to three for halogen and one or two for any combination of the other substituents; or which aryl is optionally substituted by two groups which are attached to adjacent carbon atoms and are combined into a saturated cyclic 5 or 6 membered ring system, optionally containing up to three heteroatoms selected from N and O, the number of N atoms being 0-3 and the number of O atoms being 0-2;
    which heteroaryl is optionally substituted with one or two substituents independently selected from the group consisting of $(C_1-C_4)$alkoxy and $(C_1-C_4)$alkyl;
  (iii) -cyclo$(C_3-C_8)$alkyl, optionally substituted with hydroxyl;
  (iv) —$(C_1-C_4)$alkyl-cyclo$(C_3-C_8)$alkyl, optionally substituted with hydroxyl;
  (v) a bicyclic ring system of 6 to 10 carbon atoms selected from the group consisting of bicyclo[2.1.1]hexyl, bicyclo[2.2.1]heptyl, bicyclo[3.2.1]octyl, bicyclo[2.2.2]octyl, bicyclo[3.2.2]nonanyl, bicyclo[3.3.1]nonanyl, and bicyclo[3.3.2]decanyl; and
  (vi) adamantyl;
(c) aryl,
  which aryl is optionally substituted with halogen, $(C_1-C_6)$alkoxy, halogenated $(C_1-C_4)$alkyl, halogenated $(C_1-C_6)$alkoxy, nitro, nitrile, —CO—$(C_1-C_4)$alkyl, —CO—O—$(C_1-C_4)$alkyl, —NH—CO—$(C_1-C_4)$ alkyl, $(C_1-C_4)$alkyl-sulfonyl, phenyl or heteroaryl, the number of substituents on said aryl being up to three for halogen, and one or two for any combination of the other substituents; or which aryl is optionally substituted by two groups which are attached to adjacent carbon atoms and are combined into a saturated cyclic 5 or 6 membered ring system, optionally containing up to three heteroatoms selected from N and O, the number of N atoms being 0-3 and the number of O atoms being 0-2;
(d) heteroaryl,
  which heteroaryl is optionally substituted with up to two substituents independently selected from the group consisting of halogen, $(C_1-C_4)$alkyl, halogenated $(C_1-C_4)$alkyl, —$(C_1-C_4)$alkyl-(C=O)—OR⁸ʼ, —O—Ar¹ʼ, —SO₂—Ar¹ʼ and phenyl; or
(e) cycloheteroalkyl,
  which cycloheteroalkyl group is optionally substituted with one or two substituents independently selected from the group consisting of oxo, $(C_1-C_4)$alkyl, and $(C_1-C_4)$alkyl-phenyl;
wherein
R⁷ʼ represents $(C_1-C_4)$alkyl, optionally substituted in the alkyl chain with one or two hydroxyl groups; and
Ar¹ʼ represents phenyl optionally substituted with up to three halogen atoms;
or wherein, if Y represents —NR⁴—, —NH—NR⁴— or —NH—SO₂—NR⁴—,
  then the ring or ringsystem formed by R² and R⁴ together with the nitrogen atom to which R² and R⁴ are attached, is selected from the group consisting of

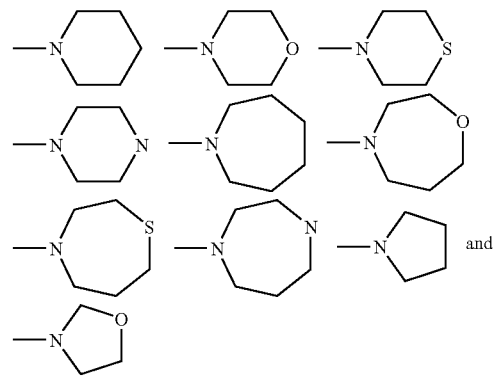

wherein the ring or the ring-system is optionally substituted
(i) with up to three substituents independently selected from the group consisting of
  (a) hydroxyl,
  (b) oxo,
  (c) $C_1-C_4$-alkyl optionally substituted with up to two hydroxyl and/or $(C_1-C_4)$-alkoxy groups,
    whereby the alkyl-chain of the $(C_1-C_4)$-alkoxy moiety may optionally be further substituted with one or two hydroxyl group;
  (d) cyclo$(C_3-C_8)$alkyl;
  (e) —(C=O)—O—$(C_1-C_4)$-alkyl;
  (f) phenyl, optionally substituted with halogen, $(C_1-C_4)$-alkyl, $(C_1-C_4)$-alkoxy, or halogenated $(C_1-C_4)$-alkyl, the number of said substituents on the phenyl moiety being up to three for halogen, and one or two for any combination of said other substituents;

(g) phenyl-($C_1$-$C_4$)alkyl, optionally substituted in the phenyl group by up three halogen, or optionally substituted in the phenyl group by two groups which are attached to adjacent carbon atoms and are combined into a saturated or partly unsaturated cyclic 5 or 6-membered ring system, optionally containing up to two O atoms;

(h) alkylamido;

(i) heteroaryl, wherein the heteroaryl is selected from the group consisting of pyridinyl, furyl, thienyl, thiazolyl, imidazolyl, pyrazolyl, indolyl, quinolinyl, benzoimidazolyl and benzo[b]thiophene; and (j) cycloheteroalkyl, wherein the cycloheteroalkyl is selected from the group consisting of pyrrolidinyl, 1,3-dihydro-benzoimidazolyl, morpholinyl, tetrahydrofuranyl, piperidinyl or azepanyl,
which cycloheteroalkyl group is optionally substituted with oxo; or (ii) by two groups which are attached to the same carbon atom and are combined into a saturated or partly unsaturated cyclic 5, 6, or 7-membered ring system, optionally containing up to three heteroatoms selected from N and O, the number of N atoms being 0-3 and the number of O atoms being 0-2,
whereby the cyclic ring system may optionally be further substituted with up to two substituents independently selected from oxo and phenyl.

5. A compound according to claim 1, which is an optically pure enantiomer corresponding to formula (II)

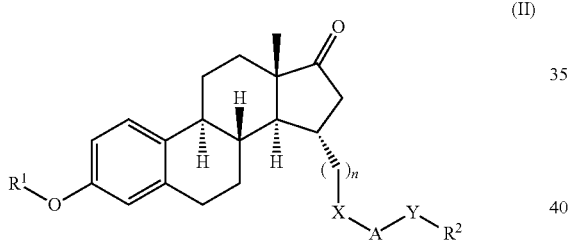

(II)

or a physiologically acceptable salt thereof.

6. A compound according to claim 1, which is an optically pure enantiomer corresponding to formula (III)

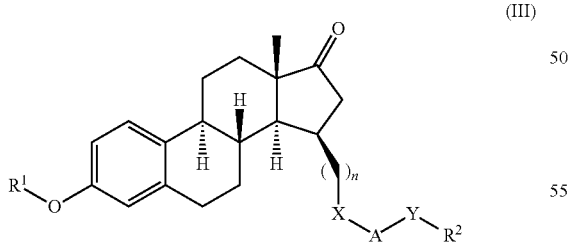

(III)

or a physiologically acceptable salt thereof.

7. A compound according to claim 1, wherein $R^1$ represents H, ($C_1$-$C_4$)alkyl or phenyl($C_1$-$C_4$)alkyl.

8. A compound according to claim 7, wherein $R^1$ represents H, methyl or benzyl.

9. A compound according to claim 1, wherein $R^3$ represents H, ($C_1$-$C_4$)alkyl or phenyl($C_1$-$C_4$)alkyl.

10. A compound according to claim 9, wherein $R^3$ represents H, methyl or benzyl.

11. A compound according to claim 1, wherein $R^4$ represents
(a) —H,
(b) an alkyl group selected from
  (i) —($C_1$-$C_6$)alkyl, optionally substituted with substituents independently selected from the group consisting of hydroxyl, nitrile, alkylamino, ($C_1$-$C_4$)-alkoxy, the number of substituents on the alkyl being up to five for hydroxyl and up to two for any combination of the other substituents;
  (ii) aryl-($C_1$-$C_4$)alkyl or heteroaryl-($C_1$-$C_4$)alkyl, wherein the aryl is phenyl or naphthyl and the heteroaryl is pyridinyl;
  (iii) cyclo($C_3$-$C_6$)alkyl;
  (iv) cyclo($C_3$-$C_6$)alkyl-($C_1$-$C_2$)alkyl-; or
(c) piperidinyl, which is optionally substituted with a ($C_1$-$C_4$)alkyl group.

12. A compound according to claim 11, wherein, if X represents —$NR^3$— or —O— and Y represents —$NR^4$—, then $R^4$ is —H.

13. A compound according to claim 1, wherein
X represents a bond;
A represents —CO—,
Y represents
  (a) —$NR^4$—,
  (b) —O—,
  (c) a bond, or
  (d) —NH—$NR^4$—;
and n represents 1, 2, 3, 4, or 5.

14. A compound according to claim 13, wherein Y represents —$NR^4$—, and n represents 1, 2, 3, 4 or 5.

15. A compound according to claim 14, wherein $R^2$ represents
(i) —($C_1$-$C_4$)alkyl,
(ii) —($C_3$-$C_8$)cycloalkyl
(iii) —($C_1$-$C_4$)alkyl-aryl, wherein the aryl is phenyl or naphthyl,
  which phenyl is optionally substituted with one or two substituents independently selected from the group consisting of hydroxyl, halogen, and ($C_1$-$C_4$)alkoxy; or
  which phenyl is optionally substituted by two groups which are attached to adjacent carbon atoms and are combined into a saturated cyclic 5 or 6-membered ring system, containing 1 or 2 O atoms; or
(iv) heteroaryl or —($C_1$-$C_4$)alkyl-heteroaryl, wherein the heteroaryl is furyl, thienyl, thiazolyl, pyridinyl, indolyl or benzoimidazolyl;
  which heteroaryl is optionally substituted with one or two substituents independently selected from the group consisting of ($C_1$-$C_4$)alkyl and —($C_1$-$C_4$)alkyl-(C=O)—O—($C_1$-$C_4$)alkyl;
  and $R^4$ is independently selected from H and —($C_1$-$C_4$)-alkyl; or
$R^2$ and $R^4$ together with the nitrogen atom to which $R^2$ and $R^4$ are attached, form a ring or ringsystem, which is selected from the group consisting of morpholine, thiomorpholine and piperazyl.

16. A compound according to claim 1, wherein
X represents —NH—;
A represents —CO—;
Y represents:
  (a) —NH—,
  (b) —O—, or
  (c) a bond,
and n represents 1, 2, 3, 4, 5 or 6.

17. A compound according to claim 16, wherein
X represents —NH—,
Y represents —NH— or a bond, and
n represents 1, 2, 3 or 4.

18. A compound according to claim 17, wherein Y represents —NH—.

19. A compound according to claim 18, wherein $R^2$ represents
(i) —$(C_1-C_4)$alkyl,
(ii) —$(C_3-C_8)$cycloalkyl,
(iii) —$(C_1-C_4)$alkyl-$(C_3-C_8)$cycloalkyl,
(iv) aryl, wherein the aryl is phenyl or naphthyl,
which phenyl is optionally substituted with one or two substituents independently selected from the group consisting of hydroxyl, halogen, —CO—O$(C_1-C_4)$alkyl and $(C_1-C_4)$alkoxy; or
which phenyl is optionally substituted by two groups which are attached to adjacent carbon atoms and are combined into a saturated cyclic 5 or 6-membered ring system, containing 1 or 2 O atoms, or
(v) —$(C_1-C_4)$alkyl-phenyl.

20. A compound according to claim 17, wherein Y represents a bond.

21. A compound according to claim 20, wherein $R^2$ represents:
(i) —$(C_1-C_4)$alkyl,
(ii) —$(C_3-C_8)$cycloalkyl,
(iii) —$(C_1-C_4)$alkyl-$(C_3-C_8)$cycloalkyl,
(iv) —$(C_1-C_4)$alkyl, substituted with one or two substituents independently selected from the group consisting of —O—$(C_1-C_4)$alkyl and —O—$(C_1-C_4)$alkyl-phenyl,
(v) phenyl,
which phenyl is optionally substituted with one, two or three substituents independently selected from the group consisting of halogen and $(C_1-C_4)$alkoxy;
(vi) —$(C_1-C_4)$alkyl-phenyl; or
(vii) adamantyl.

22. A compound according to claim 1, wherein
X represents —$NR^3$—;
A represents —$SO_2$—;
Y represents —NH—, —O— or a bond; and
n represents 1, 2, 3, or 4.

23. A compound according to claim 22, wherein Y represents a bond, and $R^3$ represents H or —$(C_1-C_4)$alkyl.

24. A compound according to claim 23, wherein $R^2$ represents
(i) aryl selected from phenyl and naphthyl,
which aryl is optionally substituted with one or two substituents independently selected from the group consisting of halogen, nitro, $(C_1-C_4)$alkoxy, and —$(C_1-C_4)$alkyl; or
(ii) heteroaryl selected from furyl, thienyl, thiazolyl and indolyl,
which heteroaryl is optionally substituted with one or two substituents independently selected from the group consisting of —$SO_2$-phenyl and $(C_1-C_4)$alkyl.

25. A compound according to claim 1, wherein
X represents —O—;
A represents —CO—;
Y represents —NH—, a bond or —NH—$SO_2$—$NR^4$—; and
n represents 1, 2, 3, 4, 5 or 6.

26. A compound according to claim 25, wherein Y represents —NH—, and n represents 3, 4, 5 or 6.

27. A compound according to claim 26, wherein $R^2$ represents phenyl or naphthyl,
which phenyl is optionally substituted with one or two substituents independently selected from the group consisting of hydroxyl, halogen, nitro, —CO—O$(C_1-C_4)$alkyl, $(C_1-C_4)$alkoxy and halogenated $(C_1-C_4)$alkyl; or
which phenyl is optionally substituted by two groups which are attached to adjacent carbon atoms and combined into a saturated cyclic 5 or 6-membered ring system containing 1 or 2 O atoms.

28. A compound according to claim 25, wherein Y represents —NH—$SO_2$—$NR^4$—.

29. A compound according to claim 28, wherein
$R^2$ represents
(i) —$(C_1-C_4)$alkyl,
(ii) —$(C_3-C_8)$cycloalkyl,
(iii) —$(C_1-C_4)$alkyl-phenyl,
(iv) phenyl, or
(v) heteroaryl or —$(C_1-C_4)$alkyl-heteroaryl, wherein the heteroaryl is furyl, thienyl, thiazolyl, pyridinyl, indolyl, or benzoimidazolyl; and
$R^4$ is independently selected from the group consisting of H, —$(C_1-C_4)$-alkyl and —$(C_1-C_4)$alkyl-phenyl; or
$R^2$ and $R^4$ together with the nitrogen atom to which $R^2$ and $R^4$ are attached, form a ring selected from the group consisting of morpholine, thiomorpholine and piperazyl, which ring is optionally substituted with $(C_1-C_4)$-alkyl.

30. A compound according to claim 1, wherein —X-A-Y— represent —O—, and wherein $R^2$ represents —H, and n represents 1, 2, 3, 4, 5 or 6.

31. A compound according to claim 1, selected from the group consisting of:
3-hydroxy-15β-(4-morpholin-4-yl-4-oxo-butyl)-estra-1,3,5(10)-trien-17-one;
3-methoxy-15β-(4-morpholin-4-yl-4-oxo-butyl)-estra-1,3,5(10)-trien-17-one;
N-benzyl-4-(3-methoxy-17-oxo-estra-1,3,5(10)-trien-15β-yl)-butyramide;
N-benzyl-4-(3-Hydroxy-17-oxo-estra-1,3,5(10)-trien-15β-yl)-butyramide;
4-(3-methoxy-17-oxo-estra-1,3,5(10)-trien-15β-yl)-N-[2-(7-methyl-1H-indol-3-yl)-ethyl]-butyramide;
4-(3-hydroxy-17-oxo-estra-1,3,5(10)-trien-15β-yl)-N-[2-(7-methyl-1H-indol-3-yl)-ethyl]-butyramide;
N-(2,4-difluoro-benzyl)-4-(3-hydroxy-17-oxo-estra-1,3,5(10)-trien-15β-yl)-butyramide;
N-benzyl-4-(3-hydroxy-17-oxo-estra-1,3,5(10)-trien-15β-yl)-N-methyl-butyramide;
N-benzyl-4-(3-hydroxy-17-oxo-estra-1,3,5(10)-trien-15α-yl)-butyramide;
3-hydroxy-15α-(4-morpholin-4-yl-4-oxo-butyl)-estra-1,3,5(10)-trien-17-one;
N-cyclohexyl-3-(3-methoxy-17-oxo-estra-1,3,5(10)-trien-15β-yl)-propionamide;
N-cyclooctyl-3-(3-methoxy-17-oxo-estra-1,3,5(10)-trien-15β-yl)-propionamide;
N-cyclohexyl-3-(3-methoxy-17-oxo-estra-1,3,5(10)-trien-15β-yl)-N-methyl-propionamide;
N-[2-(4-hydroxy-phenyl)-ethyl]-3-(3-methoxy-17-oxo-estra-1,3,5(10)-trien-15β-yl)-propionamide;
3-(3-methoxy-17-oxo-estra-1,3,5(10)-trien-15β-yl)-N-(5-methyl-thiazol-2-yl)-propionamide;
5-(3-methoxy-17-oxo-estra-1,3,5(10)-trien-15β-yl)-pentanoic acid cyclohexylamide;
5-(3-methoxy-17-oxo-estra-1,3,5(10)-trien-15β-yl)-pentanoic acid cyclooctylamide;
5-(3-methoxy-17-oxo-estra-1,3,5(10)-trien-15β-yl)-pentanoic acid (furan-2-ylmethyl)-amide;

5-(3-methoxy-17-oxo-estra-1,3,5(10)-trien-15β-yl)-pentanoic acid (benzo[1,3]dioxol-5-ylmethyl)-amide;
5-(3-methoxy-17-oxo-estra-1,3,5(10)-trien-15β-yl)-pentanoic acid (pyridin-3-ylmethyl)-amide;
5-(3-methoxy-17-oxo-estra-1,3,5(10)-trien-15β-yl)-pentanoic acid (pyridin-4-ylmethyl)-amide;
5-(3-methoxy-17-oxo-estra-1,3,5(10)-trien-15β-yl)-pentanoic acid benzylamide;
5-(3-methoxy-17-oxo-estra-1,3,5(10)-trien-15β-yl)-pentanoic acid 2-methoxy-benzylamide;
5-(3-methoxy-17-oxo-estra-1,3,5(10)-trien-15β-yl)-pentanoic acid 3-fluoro-benzylamide;
5-(3-methoxy-17-oxo-estra-1,3,5(10)-trien-15β-yl)-pentanoic acid 4-chloro-benzylamide;
5-(3-methoxy-17-oxo-estra-1,3,5(10)-trien-15β-yl)-pentanoic acid benzyl-methyl-amide;
5-(3-methoxy-17-oxo-estra-1,3,5(10)-trien-15β-yl)-pentanoic acid butylamide;
5-(3-methoxy-17-oxo-estra-1,3,5(10)-trien-15β-yl)-pentanoic acid (2-thiophen-2-yl-ethyl)-amide;
5-(3-methoxy-17-oxo-estra-1,3,5(10)-trien-15β-yl)-pentanoic acid [2-(7-methyl-1H-indol-3-yl)-ethyl]-amide;
6-(3-methoxy-17-oxo-estra-1,3,5(10)-trien-15β-yl)-hexanoic acid cyclohexylamide;
6-(3-methoxy-17-oxo-estra-1,3,5(10)-trien-15β-yl)-hexanoic acid (furan-2-ylmethyl)-amide;
6-(3-methoxy-17-oxo-estra-1,3,5(10)-trien-15β-yl)-hexanoic acid (benzo[1,3]dioxol-5-ylmethyl)-amide;
3-methoxy-15β-(6-morpholin-4-yl-6-oxo-hexyl)-estra-1,3,5(10)-trien-17-one;
3-methoxy-15β-(6-oxo-6-thiomorpholin-4-yl-hexyl)-estra-1,3,5(10)-trien-17-one;
6-(3-methoxy-17-oxo-estra-1,3,5(10)-trien-15β-yl)-hexanoic acid (pyridin-3-ylmethyl)-amide;
6-(3-methoxy-17-oxo-estra-1,3,5(10)-trien-15β-yl)-hexanoic acid (pyridin-4-ylmethyl)-amide;
6-(3-methoxy-17-oxo-estra-1,3,5(10)-trien-15β-yl)-hexanoic acid benzylamide;
6-(3-methoxy-17-oxo-estra-1,3,5(10)-trien-15β-yl)-hexanoic acid 2-methoxy-benzylamide;
6-(3-methoxy-17-oxo-estra-1,3,5(10)-trien-15β-yl)-hexanoic acid 3-fluoro-benzylamide;
6-(3-methoxy-17-oxo-estra-1,3,5(10)-trien-15β-yl)-hexanoic acid [2-(4-hydroxy-phenyl)-ethyl]-amide;
6-(3-methoxy-17-oxo-estra-1,3,5(10)-trien-15β-yl)-hexanoic acid benzyl-methyl-amide;
6-(3-methoxy-17-oxo-estra-1,3,5(10)-trien-15β-yl)-hexanoic acid butylamide;
6-(3-methoxy-17-oxo-estra-1,3,5(10)-trien-15β-yl)-hexanoic acid (2-thiophen-2-yl-ethyl)-amide;
1-[3-(3-methoxy-17-oxo-estra-1,3,5(10)-trien-15β-yl)-propyl]-3-(3-methoxy-phenyl)-urea;
1-[3-(3-methoxy-17-oxo-estra-1,3,5(10)-trien-15β-yl)-propyl]-3-(4-methoxy-phenyl)-urea;
1-isopropyl-3-[3-(3-methoxy-17-oxo-estra-1,3,5(10)-trien-15β-yl)-propyl]-urea;
1-cyclohexyl-3-[3-(3-methoxy-17-oxo-estra-1,3,5(10)-trien-15β-yl)-propyl]-urea;
1-benzyl-3-[3-(3-methoxy-17-oxo-estra-1,3,5(10)-trien-15β-yl)-propyl]-urea;
1-(3,4-dimethoxy-phenyl)-3-[3-(3-methoxy-17-oxo-estra-1,3,5(10)-trien-15β-yl)-propyl]-urea;
1-benzo[1,3]dioxol-5-yl-3-[3-(3-methoxy-17-oxo-estra-1,3,5(10)-trien-15β-yl)-propyl]-urea;
1-benzyl-3-[4-(3-methoxy-17-oxo-estra-1,3,5(10)-trien-15β-yl)-butyl]-urea;
1-(3,4-dimethoxy-phenyl)-3-[4-(3-methoxy-17-oxo-estra-1,3,5(10)-trien-15β-yl)-butyl]-urea;
4-{3-[4-(3-hydroxy-17-oxo-estra-1,3,5(10)-trien-15α-yl)-butyl]-ureido}-benzoic acid ethylester;
1-cyclohexylmethyl-3-[4-(3-hydroxy-17-oxo-estra-1,3,5(10)-trien-15α-yl)-butyl]-urea;
naphthalene-2-sulfonic acid (3-hydroxy-17-oxo-estra-1,3,5(10)-trien-15α-ylmethyl)-amide;
thiophene-2-sulfonic acid (3-hydroxy-17-oxo-estra-1,3,5(10)-trien-15α-ylmethyl)-amide;
N-(3-hydroxy-17-oxo-estra-1,3,5(10)-trien-15α-ylmethyl)-benzenesulfonamide;
4-fluoro-N-(3-hydroxy-17-oxo-estra-1,3,5(10)-trien-15α-ylmethyl)-benzenesulfonamide;
N-(3-hydroxy-17-oxo-estra-1,3,5(10)-trien-15α-ylmethyl)-4-methoxy-benzenesulfonamide;
N-(3-hydroxy-17-oxo-estra-1,3,5(10)-trien-15α-ylmethyl)-3-methyl-benzenesulfonamide;
naphthalene-2-sulfonic acid (3-hydroxy-17-oxo-estra-1,3,5(10)-trien-15α-ylmethyl)-methyl-amide;
thiophene-2-sulfonic acid (3-hydroxy-17-oxo-estra-1,3,5(10)-trien-15α-ylmethyl)-methyl-amide;
N-(3-hydroxy-17-oxo-estra-1,3,5(10)-trien-15α-ylmethyl)-N-methyl-benzenesulfonamide;
4-fluoro-N-(3-hydroxy-17-oxo-estra-1,3,5(10)-trien-15α-ylmethyl)-N-benzenesulfonamide;
N-(3-hydroxy-17-oxo-estra-1,3,5(10)-trien-15α-ylmethyl)-4-methoxy-N-benzenesulfonamide;
3-chloro-N-(3-hydroxy-17-oxo-estra-1,3,5(10)-trien-15α-ylmethyl)-N-methyl-benzenesulfonamide;
N-(3-hydroxy-17-oxo-estra-1,3,5(10)-trien-15α-ylmethyl)-3, N-dimethyl-benzenesulfonamide;
4-benzenesulfonyl-thiophene-2-sulfonic acid (3-hydroxy-17-oxo-estra-1,3,5(10)-trien-15α-ylmethyl)-methyl-amide;
benzo[1,3]dioxol-5-yl-carbamic acid 3-(3-methoxy-17-oxo-estra-1,3,5(10)-trien-15β-yl)-propylester;
3-hydroxy-15β-(3-hydroxypropyl)-estra-1,3,5(10)-trien-17-one;
and physiologically acceptable salts thereof.

32. A pharmaceutical composition comprising a compound according to claim 1, and at least one pharmaceutically acceptable carrier, diluent or adjuvant.

33. A method of treating a steroid hormone dependent disease or disorder in a mammal, said method comprising administering to said mammal a pharmaceutically effective amount of a compound according to claim 1, wherein
(a) the steroid hormone dependent disease or disorder is an estradiol dependent disease or disorder and
(i) is malign and is selected from the group consisting of breast cancer, ovarian cancer, uterine cancer, endometrial cancer, and endometrial hyperplasia; or
(ii) is benign and is selected from the group consisting of endometriosis, uterine fibroids, uterine leiomyoma, adenomyosis, dysmenorrheal, menorrhagia, and metrorrhagia; or
(b) the steroid hormone dependent disease or disorder is selected from the group consisting of prostate carcinoma prostadynia, benign prostatic hyperplasia, and colon cancer.

34. A method according to claim 33, wherein the estradiol dependent disease or disorder is breast cancer, and the mammal is a post-menopausal human female.

35. A method according to claim 33, wherein said mammal is a human pre- or peri-menopausal female.

36. A method according to claim 33, wherein said treatment requires lowering the endogenous 17β-estradiol concentration in a generalized or tissue specific manner.

37. A method of treating a benign estradiol dependent disease or disorder selected from the group consisting of endometriosis, uterine fibroids, uterine leiomyoma, adenomyosis, dysmenorrheal, menorrhagia, and metrorrhagia, in a mammal, said method comprising administering to said mammal a pharmaceutically effective amount of a compound according to claim 1, wherein said compound is a selective inhibitor of type 1, 17β-hydroxysteroid dehydrogenase enzyme.

38. A method according to claim 37, wherein the selective inhibitor shows no or only pure antagonistic binding affinities to estrogen receptors.

39. A method according to claim 37, wherein said mammal is a human female.

40. A method according to claim 39, wherein said human female is a pre- or peri-menopausal female.

41. A method according to claim 33, for treating breast cancer in a post-menopausal female, said method comprising administering to said female a pharmaceutically effective amount of a selective inhibitor of the type 1, 17β-hydroxysteroid dehydrogenase enzyme showing no or only pure antagonistic binding affinities to estrogen receptors.

* * * * *

UNITED STATES PATENT AND TRADEMARK OFFICE
CERTIFICATE OF CORRECTION

| | | |
|---|---|---|
| PATENT NO. | : 8,088,758 B2 | |
| APPLICATION NO. | : 10/983887 | |
| DATED | : January 3, 2012 | |
| INVENTOR(S) | : Messinger et al. | |

It is certified that error appears in the above-identified patent and that said Letters Patent is hereby corrected as shown below:

Title Page, Item (75), inventor address: "Munich, DE (US)" to read as --Munich (DE)--

In the Specification

Column 01, line 66, background: "etc" to read as --etc.--

Column 03, line 63, background: "a subtype," to read as --α subtype,--

Column 05, line 08, background: "estron" to read as --estrone--

Column 09, line 28, summary: "alkoxy);" to read as --alkoxy;--

Column 10, line 60, summary: "alkoxy)" to read as --alkoxy--

Column 11, line 04, summary: "alkoxy);" to read as --alkoxy;--

Column 16, line 63, summary: "$C_1$-$C_4$)" to read as -- -($C_1$-$C_4$)--

Column 22, line 42, summary: "at lease" to read as --at least--

Column 24, line 60, detailed description: "steroide" to read as --steroid--

Column 25, line 39, detailed description: "(J, lodo-)" to read as --(I, lodo-)--

Column 26, line 28, detailed description: "Bicyclo[3.2.1 ]octyl," to read as --Bicyclo[3.2.1]octyl,--

Column 26, line 29, detailed description: "Bicyclo[3.3.1 ]nonanyl," to read as --Bicyclo[3.2.1] nonanyl,--

Signed and Sealed this
Fifteenth Day of July, 2014

Michelle K. Lee
*Deputy Director of the United States Patent and Trademark Office*

CERTIFICATE OF CORRECTION (continued)
U.S. Pat. No. 8,088,758 B2

Column 27, line 08, detailed description: "N or 0," to read as --N or O,--

Column 27, line 67, detailed description: "alkoxy)," to read as --alkoxy,--

Column 28, line 28, detailed description: "alkoxy)," to read as --alkoxy,--

Column 28, line 63, detailed description: "alkoxy)," to read as --alkoxy,--

Column 29, line 63, detailed description: "alkoxy)," to read as --alkoxy,--

Column 30, line 15, detailed description: "alkoxy)," to read as --alkoxy,--

Column 36, line 03, detailed description: "elixiers," to read as --elixirs,--

Column 37, line 41, detailed description: "estron" to read as --estrone--

Column 41, line 36, detailed description: "carbodiimid" to read as --carbodiimide--

Column 42, line 42, detailed description: "triphosghen" to read as --triphosgene--

Column 49, line 57, detailed description: "estron" to read as --estrone--

Column 49, line 63, detailed description: "estron" to read as --estrone--

Column 51, line 57, detailed description: "Benzylbromid" to read as --Benzylbromide--

Column 58, line 08, detailed description: "020 C." to read as --0° C.--

Column 60, line 64, detailed description: "estron" to read as --estrone--

Column 63, line 66, detailed description: "estron" to read as --estrone--

Column 65, line 25, detailed description: "α a Stereochemistry" to read as --α stereochemistry--

Column 68, line 37, detailed description: "Estron" to read as --Estrone--

Column 70, line 46, detailed description: "estron" to read as --estrone--

Column 72, line 57, detailed description: "estron" to read as --estrone--

Column 74, line 67, detailed description: "estron" to read as --estrone--

Column 75, line 32, detailed description: "estron" to read as --estrone--

Column 75, line 55, detailed description: "estron" to read as --estrone--

CERTIFICATE OF CORRECTION (continued)
U.S. Pat. No. 8,088,758 B2

Column 77, line 60, detailed description: "estron" to read as --estrone--

Column 79, line 45, detailed description: "estron" to read as --estrone--

Column 90, line 38, detailed description: "methansulfonic" to read as --methanesulfonic--

Column 90, line 40, detailed description: "methansulfonic" to read as --methanesulfonic--

Column 118, line 07, detailed description: "tetramethyldiaminoethan" to read as --tetramethyldiaminoethane--

Column 119, line 21, detailed description: "carbodiimid" to read as --carbodiimide--

Column 123, line 21, detailed description: "carbaxylic" to read as --carboxylic--

Column 124, line 56, detailed description: "polymere" to read as --polymer--

Column 125, line 26, detailed description: "aenzyl" to read as --Benzyl--

Column 138, line 23, detailed description: "isocyanat" to read as --isocyanate--

Column 149, line 60, detailed description: "estron-alcohol" to read as --estrone-alcohol--

Column 152, line 48, detailed description: "Estron-alcohol" to read as --Estrone-alcohol--

Column 152, line 66, detailed description: "estron-alcohol" to read as --estrone-alcohol--

Column 155, line 55, detailed description: "pheneyl" to read as --phenyl--

Column 156, line 24, detailed description: "pheneyl" to read as --phenyl--

Column 159, line 39, detailed description: "estron" to read as --estrone--

Column 160, line 21, detailed description: "estron" to read as --estrone--

In the Claims

Column 199, line 64, claim 1: "alkoxy);" to read as --alkoxy;--

Column 201, line 58, claim 2: "alkoxy)" to read as --alkoxy--

Column 202, line 03, claim 2: "alkoxy);" to read as --alkoxy;--

Column 204, line 54, claim 3: "alkoxy)" to read as --alkoxy--

Column 205, line 02, claim 3: "substitutents" to read as --substituents--

Column 205, line 10, claim 3: "alkoxy" to read as --alkoxy;--

Column 206, line 56, claim 4: "$C_1$-$C_4$) alkyl" to read as --($C_1$-$C_4$) alkyl--

Column 206, line 60, claim 4: "one or two hydroxyl group;" to read as --one or two hydroxyl groups;--

Column 207, line 02, claim 4: "by up three" to read as --by up to three--

Column 212, line 28, claim 31: "N-benzenesulfonamide;" to read as --N-methyl-benzenesulfonamide;--

Column 212, line 30, claim 31: "N-benzenesulfonamide;" to read as --N-methyl-benzenesulfonamide;--

Column 212, line 57, claim 33: "dysmenorrheal," to read as --dysmenorrhea,--

Column 212, line 60, claim 33: "prostate carcinoma prostadynia," to read as --prostate carcinoma, prostadynia,--

Column 213, line 07, claim 37: "dysmenorrheal," to read as --dysmenorrhea,--